(12) United States Patent
Pickford et al.

(10) Patent No.: US 10,953,100 B2
(45) Date of Patent: Mar. 23, 2021

(54) COMPOUNDS AND THERAPEUTIC USES THEREOF

(71) Applicant: Centauri Therapeutics Limited (GB/GB), London (GB)

(72) Inventors: Christopher Pickford, Sandwich (GB); Christine Watson, Sandwich (GB); Melanie Glossop, Sandwich (GB)

(73) Assignee: CENTUARI THERAPEUTICS LIMITED (GB/GB), London (GB)

( * ) Notice: Subject to any disclaimer, the term of this patent is extended or adjusted under 35 U.S.C. 154(b) by 178 days.

(21) Appl. No.: 15/766,193

(22) PCT Filed: Oct. 7, 2016

(86) PCT No.: PCT/GB2016/053134
§ 371 (c)(1),
(2) Date: Apr. 5, 2018

(87) PCT Pub. No.: WO2017/060729
PCT Pub. Date: Apr. 13, 2017

(65) Prior Publication Data
US 2018/0280521 A1    Oct. 4, 2018

(30) Foreign Application Priority Data
Oct. 8, 2015   (GB) ..................... 1517859

(51) Int. Cl.
*A61K 47/54*   (2017.01)
(52) U.S. Cl.
CPC ......... *A61K 47/549* (2017.08); *A61K 47/542* (2017.08); *A61K 47/545* (2017.08)
(58) Field of Classification Search
CPC ... A61K 47/542; A61K 47/545; A61K 47/549
USPC ........... 435/91.1, 455, 458; 536/23.1
See application file for complete search history.

(56) References Cited

U.S. PATENT DOCUMENTS

| | | |
|---|---|---|
| 2010/0285052 A1 | 11/2010 | Mullis et al. |
| 2012/0003251 A1 | 1/2012 | Mautino et al. |
| 2015/0190529 A1 | 7/2015 | Peterson et al. |
| 2017/0130226 A1* | 5/2017 | Hall .................. C12N 15/115 |

FOREIGN PATENT DOCUMENTS

| | | | | |
|---|---|---|---|---|
| WO | 1997/046098 A1 | 12/1997 | | |
| WO | 2004/017810 A2 | 3/2004 | | |
| WO | WO-2004022565 A1 * | 3/2004 | ........... | C07H 15/203 |
| WO | 2005/014008 A2 | 2/2005 | | |
| WO | 2005/079423 A2 | 9/2005 | | |
| WO | 2015/198024 A1 | 12/2015 | | |

OTHER PUBLICATIONS

Kristian et al, J. Mol. Med (Berl), vol. 93, No. 6, pp. 619-631 (Year: 2015).*
Angus et al, Bioorganic and Medicinal Chemistry, vol. 8, No. 12, pp. 2709-2718 (Year: 2000).*
Sascha A. Kristian et al: "Retargeting pre-existing human antibodies to a bacterial pathogen with an alpha-Gal conjugated aptamer", Journal of Molecular Medince., vol. 93, No. 6, May 5, 205 (May 5, 2015), pp. 619-631, XP055327406, DE ISSN: 0946-2716, DOI: 10.1007/s00109-015-1280-4 abstract.
G. E. Winter et al: "Phthalimide conjugation as a strategy for in vivo target protein degradation", Science, vol. 348, No. 6241, Jun. 19, 2015 (Jun. 19, 2015), pp. 1376-1381, XP055328122, ISSN: 0036-8075, DOI: 10.1126/science. aab1433 abstract: figure 2c.
Adam D. Friedman et al: "Highly stable aptamers selected from a 2'-fully modified fGmH RNA library for targeting biomaterials", Biomaterials., vol. 36, Jan. 1, 2015 (Jan. 1, 2015), pp. 110-123, XP055330159, GB ISSN: 0142-9612, DOI: 10.1016/j. biomaterials. 2014.08.046 abstract; figure 3.
PCT/GB2016/053134—International Search Report, dated Jan. 3, 2017.
V.L. Sousa et al: "Localization, purification and specificity of the full length membrane bound form of human recombinant alpha-1,3/4-fucosyltransferase from BHK-21B cells", The Biochemical Journal, 2001, 357(3), 803-810, whole document, in particular the abstract.

* cited by examiner

Primary Examiner — Jane J Zara
(74) Attorney, Agent, or Firm — Aura IP Law, PC

(57) ABSTRACT

The invention relates to novel compounds with the ability to link an immune response to a defined therapeutic target, to the use of said compounds in treating cancer and a disease or disorder mediated and/or caused by an infective agent, to compositions containing said compounds, processes for their preparation and to novel intermediates used in said process.

23 Claims, 11 Drawing Sheets
Specification includes a Sequence Listing.

A

B

FIGURE 1 (ctd)

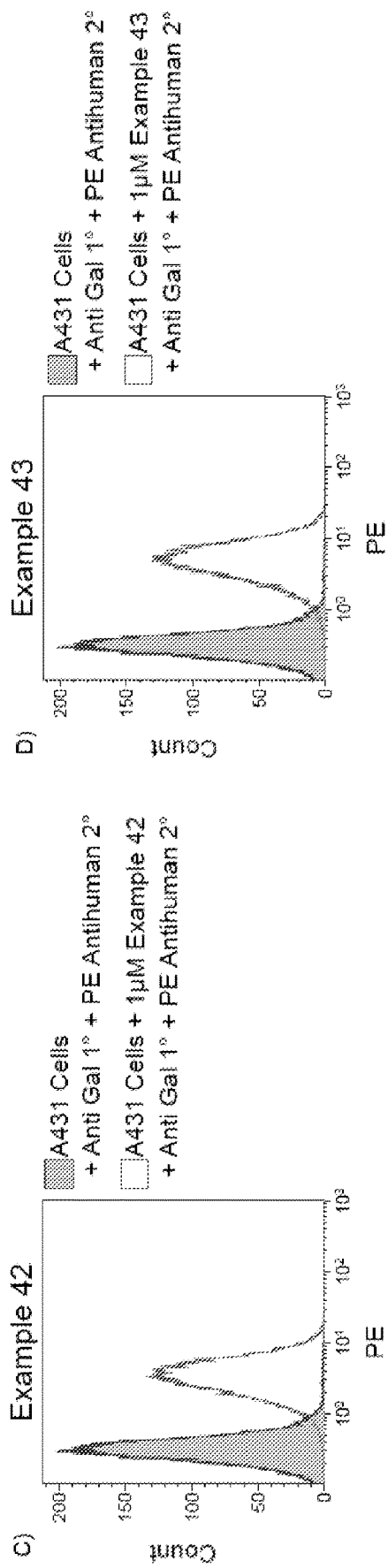
FIGURE 3 (ctd)

A

B

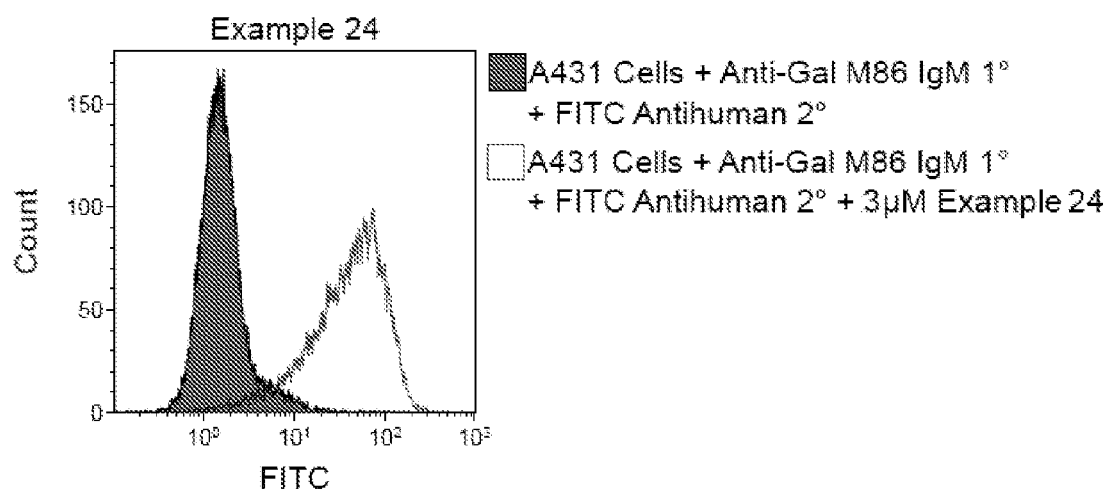
FIGURE 6 (ctd)

COMPOUNDS AND THERAPEUTIC USES THEREOF

CROSS-REFERENCE TO RELATED APPLICATIONS

The present application is a U.S. National Stage entry under 35 U.S.C. § 371 of International Application No. PCT/GB2016/053134 filed on Oct. 7, 2016, designating the United States of America and published in English on Apr. 13, 2017, which in turn claims priority to Great Britain Patent Application 1517859.3 filed on Oct. 8, 2015, each of which is hereby incorporated by reference in its entirety.

FIELD OF THE INVENTION

The invention relates to novel compounds with the ability to link an immune response to a defined therapeutic target, to the use of said compounds in treating cancer and a disease or disorder mediated and/or caused by an infective agent, to compositions containing said compounds, processes for their preparation and to novel intermediates used in said process.

BACKGROUND OF THE INVENTION

There is a need to find novel ways to recruit an individual's immune system to fight disease. The human immune system continually surveys the body seeking foreign signals to identify potentially harmful pathogens or mutated human cells (that could become a cause of cancerous growth) and target them for elimination. Natural antibodies exist that can be recruited to said pathogens or mutated human cells to drive the immune system to eliminate the threat.

Cancer is a group of diseases involving abnormal cell growth with the potential to invade or spread to other parts of the body. In 2012, cancer occurred in about 14.1 million people. It caused about 8.2 million deaths or 14.6% of all human deaths. The most common types of cancer in males are lung cancer, prostate cancer, colorectal cancer and stomach cancer. In females the most common types are breast cancer, colorectal cancer, lung cancer, and cervical cancer. It is well established that the immune response plays a vital role in the identification and elimination of cancerous cells. Drugs exist that fight cancer by boosting an individual's immune system to help fight the cancer. There is a need to be able to better target the immune response specifically to the cancer cell and to generate a broader range of the patient's own tumour associated antigens. Targeting pre-existing natural antibodies to the patient's own tumour could meet this need. There is an urgent need to identify novel ways of treating bacterial, viral and fungal infections. Antimicrobial drug resistance is becoming a major global health threat. For example, it is estimated that more than 2 million people in the US are infected with bacteria resistant to one class of antibiotics every year (Centers for Disease Control and Prevention, 2013).

An innovative approach to the treatment of infectious disease or cancer was disclosed in WO 2005/079423 which describes an immunity linker which contains two binding moieties. The first binding moiety is capable of binding to an immune response component of an individual. The second binding moiety is capable of binding to any compound or foreign material such as antigens, pathogens, chemicals, or endogenous materials such as altered cells found in cancer. The resultant effect of said immunity linker molecule is that the pre-existing immune response of the individual is diverted towards the target, i.e. the cancer cell or specific pathogen. Examples of said first binding moieties include compounds or agents which are recognised by the immune system of said individual as foreign and which would therefore trigger an immune response. One example of a first binding moiety is a carbohydrate molecule capable of binding to a human serum antibody anti-alpha-galactosyl (i.e. galactosyl-alpha-1,3-galactosyl-beta-1,4-N-acetylglucosamine). Examples of said second binding moieties include antibodies and nucleic acid aptamer molecules that bind to a specific target molecule. The principle of the method disclosed in WO 2005/079423 is that the second binding moiety (e.g. nucleic acid aptamer) of the linker molecule will bind to a cancer cell and the presence of the first binding moiety (i.e. the carbohydrate molecule capable of binding to a human anti-alpha-galactosyl antibody) on the linker molecule will divert an immune response to the cancer cell resulting in effective destruction of the cancer cell. A similar approach may be used in the treatment of diseases or disorders mediated and/or caused by an infective agent wherein the second binding moiety (i.e. nucleic acid aptamer) of the linker molecule will bind to the infective agent.

There is therefore a great need for linker molecules which contain spacer groups which have been optimised to control the number and position of first binding moieties (i.e. the carbohydrate molecule capable of binding to a human anti-alpha-galactosyl antibody) relative to the position of the second binding moiety (i.e. the nucleic acid aptamer). Such linker molecules are designed to attract natural antibodies in such a way as to be able to maximise the efficacy of immune recruitment while minimising potential side effects and therefore have great utility in the provision of effective anti-cancer therapies and therapies against infective agents.

SUMMARY OF THE INVENTION

According to a first aspect of the invention, there is provided a compound of formula (I) or a pharmaceutically acceptable salt thereof:

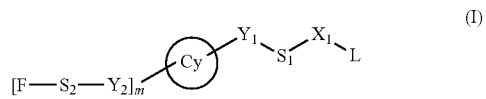

wherein:

L represents a binding moiety selected from a nucleic acid aptamer or biotin;

$S_1$ represents a spacer selected from a —$(CH_2)_a$— or —$(CH_2)_b$—$(CH_2$—$CH_2$—$O)_c$—$(CH_2)_d$— group, wherein one to five of said —$CH_2$— groups may optionally be substituted by one or more groups selected from —O—, —C(O)NH—, —NHC(O)— and phenyl;

a represents an integer selected from 1 to 35;
b represents an integer selected from 0 to 5;
c represents an integer selected from 1 to 20;
d represents an integer selected from 1 to 20;

$S_2$ represents a spacer selected from a —$(CH_2)_e$— or —$(CH_2)_f$—$(CH_2$—$CH_2$—$O)_g$—$(CH_2)_h$— group, wherein one to three of said —$CH_2$— groups may optionally be substituted by one or more groups selected from —N(H)—, —C(O)NH— and —NHC(O)—;

e represents an integer selected from 1 to 15;
f represents an integer selected from 1 to 10;
g represents an integer selected from 1 to 20;

h represents an integer selected from 1 to 5;

$X_1$ represents —O— or —NH—, such that when L represents a nucleic acid aptamer, $X_1$ represents —O— and when L represents biotin, $X_1$ represents —NH—;

$Y_1$ and $Y_2$ independently represent a bond, —O—, —S—, —NH—, —NHC(O)—, —C(O)NH—, —OC(O)—, —C(O)O—, —SC(O)—, —C(O)S—, —NHSO$_2$—, —SO$_2$NH— or —NHC(O)NH— group;

F represents a carbohydrate molecule capable of binding to a human anti-alpha-galactosyl antibody;

m represents an integer selected from 1 to 5; and

Cy represents phenyl, biphenyl, triphenyl or a bicyclic heteroaromatic ring system, such that when Cy represents biphenyl or triphenyl, said —$Y_1$—$S_1$—$X_1$-L group may be present on any of said phenyl rings and said [F—$S_2$—$Y_2$]$_m$— group or groups may be present on any of said phenyl rings.

DETAILED DESCRIPTION OF THE INVENTION

Figure 1:
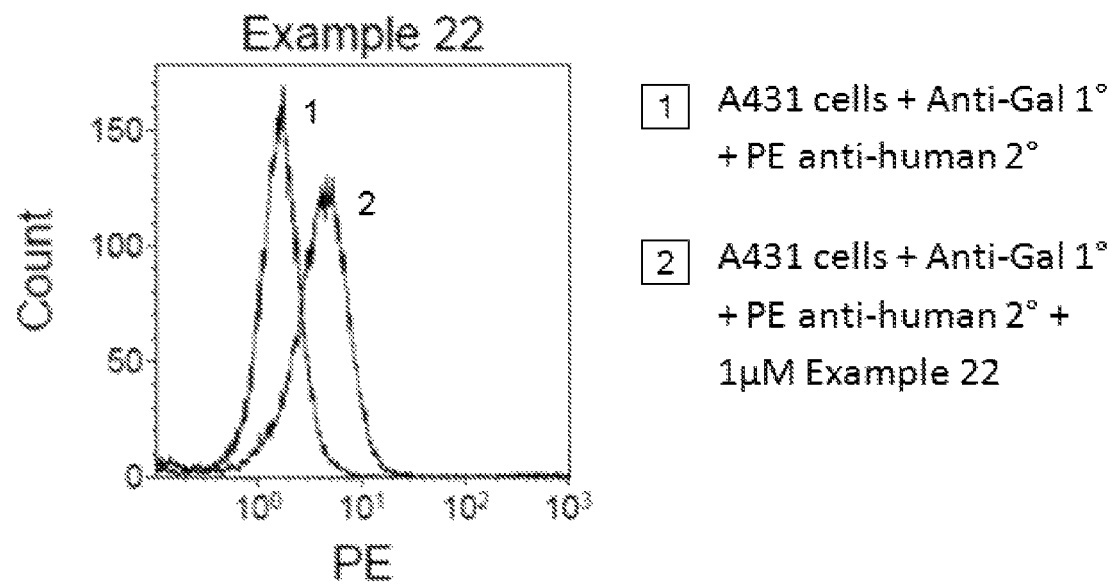
FIG. 1: Flow cytometry assay results which demonstrate the capture of anti-alpha galactosyl IgG antibodies to the cell surface using Example 22 (FIG. 1A), Example 23 (FIG. 1B) and Example 24 (FIG. 1C).
Figure 1:
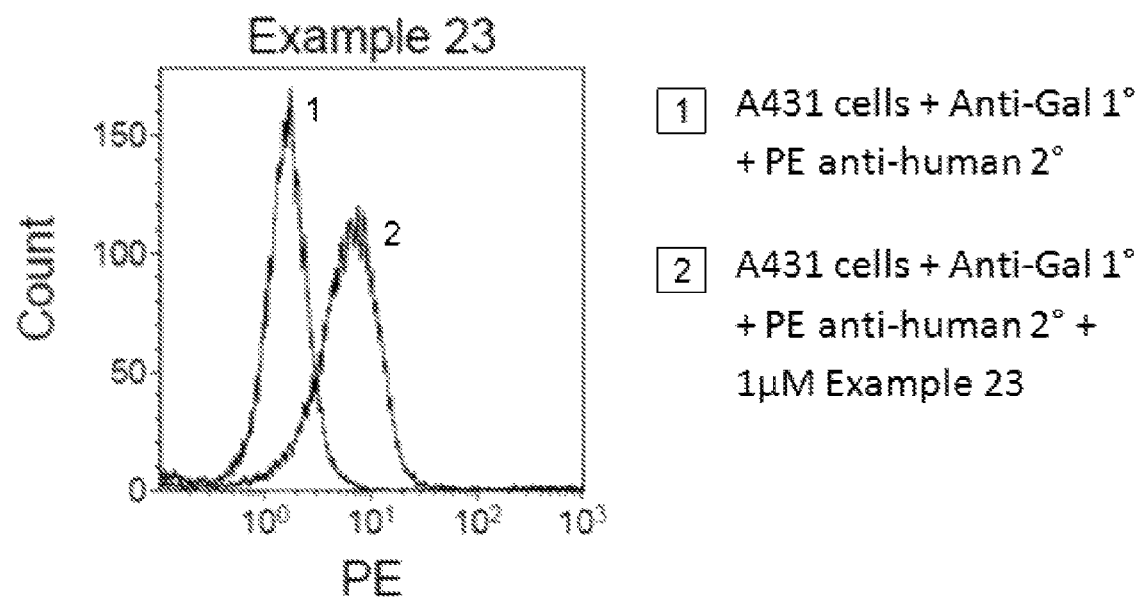

According to one particular aspect of the invention which may be mentioned, there is provided a compound of formula (I) or a pharmaceutically acceptable salt thereof:

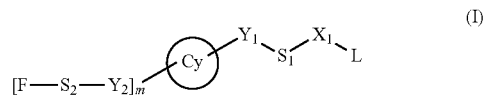

(I)

wherein:

L represents a binding moiety selected from a nucleic acid aptamer or biotin;

$S_1$ represents a spacer selected from a —(CH$_2$)$_a$— or —(CH$_2$)$_b$—(CH$_2$—CH$_2$—O)$_c$—(CH$_2$)$_d$— group, wherein one or two of said —CH$_2$— groups may optionally be substituted by a —C(O)NH— or —NHC(O)— group;

a represents an integer selected from 1 to 15;
b represents an integer selected from 1 to 5;
c represents an integer selected from 1 to 20;
d represents an integer selected from 1 to 5;

$S_2$ represents a spacer selected from a —(CH$_2$)$_e$— or —(CH$_2$)$_f$—(CH$_2$—CH$_2$—O)$_g$—(CH$_2$)$_h$— group, wherein one or two of said —CH$_2$— groups may optionally be substituted by a —C(O)NH— or —NHC(O)— group;

e represents an integer selected from 1 to 15;
f represents an integer selected from 1 to 10;
g represents an integer selected from 1 to 10;
h represents an integer selected from 1 to 5;

$X_1$ represents —O— or —NH—, such that when L represents a nucleic acid aptamer, $X_1$ represents —O— and when L represents biotin, $X_1$ represents —NH—;

$Y_1$ and $Y_2$ independently represent a bond, —O—, —S—, —NH—, —NHC(O)—, —C(O)NH—, —OC(O)—, —C(O)O—, —SC(O)—, —C(O)S—, —NHSO$_2$—, —SO$_2$NH— or —NHC(O)NH— group;

F represents a carbohydrate molecule capable of binding to a human anti-alpha-galactosyl antibody;

m represents an integer selected from 1 to 5; and

Cy represents phenyl, biphenyl or a bicyclic heteroaromatic ring system, such that when Cy represents biphenyl, said —$Y_1$—$S_1$—$X_1$-L group may be present on either of said phenyl rings and said [F—$S_2$—$Y_2$]$_m$— group or groups may be present on either or both of said phenyl rings.

The compounds of the present invention comprise linker molecules (i.e. —$S_2$—$Y_2$-Cy-$Y_1$—$S_1$—$X_1$—) which have been optimised to control the number and position of F groups (i.e. the carbohydrate molecule capable of binding to a human anti-alpha-galactosyl antibody) relative to the position of the binding moiety L (i.e. the nucleic acid aptamer). For example, a rigid cyclic group has the advantage of providing a scaffold for the optimal positioning of one or more F groups relative to L. It will be appreciated that the exact number and orientation of F groups relative to L will vary depending on the nature of the L group. Furthermore, the presence of the cyclic group, which contains a single phenyl ring, a biphenyl ring, a triphenyl ring or a bicyclic heteroaryl ring, provides the significant advantage of presenting multiple F groups (i.e. the carbohydrate molecule capable of binding to a human anti-alpha-galactosyl antibody) to enhance the resultant immune response from the host. Chemical presentation of multiple binding groups was previously known in the art, however, this has been achieved using one or more amino acid groups (for example see WO 2014/178878) or branching linker groups (for example see US 2014/0112975) by contrast to the present invention which uses either a single 6 membered ring system (i.e. phenyl), two 6 membered ring systems fused (i.e quinolinyl) or joined by a bond (biphenyl) or three membered ring systems joined by 2 bonds (triphenyl). The technical effect of this distinction is that the compounds of the present invention may be prepared more easily than the linkers previously known in art which typically require "click chemistry" (see Kolb et al (2001) *Angewandte Chemie International Edition* 40(11); 2004-2021). Furthermore, the compounds of the present invention advantageously avoid the presence of chiral centres. Synthesis of the compounds of the present invention also do not make use of resins and therefore provide the advantage of being suitable for scaling for large scale pharmaceutical manufacture. Therefore, the compounds of the invention are not only therapeutically effective but provide the advantage of enhancing the immune response from the host and ease and efficiency of synthesis in high yields with scalability. In addition, the linkers of the present invention are not labile, therefore, do not typically comprise "cleavable linker" components as required by many compounds previously known in the art (see U.S. Pat. No. 8,828,956 for example). Furthermore, the linkers of the present invention allowed the person skilled in the art to choose specific left and right hand combinations of groups with synthetic ease and efficiency.

In one embodiment, $S_1$ represents a spacer selected from:
—$(CH_2)_a$—, wherein one to four of said —$CH_2$— groups are optionally substituted by one or more groups selected from —C(O)NH— and —NHC(O)— (such as —$(CH_2)_2$—, —$CH_2$—CONH—$(CH_2)_2$—, —$CH_2$—NHCO—$(CH_2)_4$—CONH—$(CH_2)_2$—, —$(CH_2)_6$—, —$(CH_2)_5$—CONH—$(CH_2)_5$—CONH—$(CH_2)_6$— or —$(CH_2)_5$—CONH—$(CH_2)_5$—CONH—$(CH_2)_5$—CONH—$(CH_2)_5$—CONH—$(CH_2)_6$—); or
—$(CH_2)_b$—$(CH_2$—$CH_2$—O$)_c$—$(CH_2)_d$—, wherein one to five of said —$CH_2$— groups are optionally substituted by one or more groups selected from —O—, —C(O)NH—, —NHC(O)— and phenyl (such as —$(CH_2)_2$—NHCO—$(CH_2CH_2O)_{12}$—$(CH_2)_2$—, —$(CH_2)_2$—NHCO—$(CH_2CH_2O)_4$—$(CH_2)_2$—NHCO—$CH_2$—O-phenyl-CONH—$(CH_2)_6$—, —$(CH_2)_2$—NHCO—$(CH_2CH_2O)_{12}$—$(CH_2)_2$—NHCO—$CH_2$—O— phenyl-CONH—$(CH_2)_6$— or —$(CH_2CH_2O)_4$—$(CH_2)_2$—CONH—$(CH_2)_2$—).

In a further embodiment, $S_1$ represents a spacer selected from —$(CH_2)_a$—, wherein one or two of said —$CH_2$— groups are optionally substituted by a —C(O)NH— or —NHC(O)— group (such as —$(CH_2)_2$—, —$CH_2$—CONH—$(CH_2)_2$—, —$CH_2$—NHCO—$(CH_2)_4$—CONH—$(CH_2)_2$— or —$(CH_2)_6$—) or —$(CH_2)_b$—$(CH_2$—$CH_2$—O$)_c$—$(CH_2)_d$—, wherein one or two of said —$CH_2$— groups are optionally substituted by a —C(O)NH— or —NHC(O)— group (such as —$(CH_2)_2$—NHCO—$(CH_2CH_2O)_{12}$—$(CH_2)_2$—).

In a yet further embodiment, $S_1$ represents a spacer selected from:
—$(CH_2)_a$—, wherein two or four of said —$CH_2$— groups are optionally substituted by —C(O)NH— (such as —$(CH_2)_6$—, —$(CH_2)_5$—CONH—$(CH_2)_5$—CONH—$(CH_2)_6$— or —$(CH_2)_5$—CONH—$(CH_2)_5$—CONH—$(CH_2)_5$—CONH—$(CH_2)_6$—); or
—$(CH_2)_b$—$(CH_2$—$CH_2$—O$)_c$—$(CH_2)_d$—, wherein five of said —$CH_2$— groups are optionally substituted by one or more groups selected from —O—, —C(O)NH—, —NHC(O)— and phenyl (such as —$(CH_2)_2$—NHCO—$(CH_2CH_2O)_4$—$(CH_2)_2$—NHCO—$CH_2$—O-phenyl-CONH—$(CH_2)_6$— or —$(CH_2)_2$—NHCO—$(CH_2CH_2O)_{12}$—$(CH_2)_2$—NHCO—$CH_2$—O-phenyl-CONH—$(CH_2)_6$—).

It will be appreciated that a, b, c, d, e, f, g and h are selected to maintain a suitable linker length between groups F and L. Examples of suitable linker lengths between F and L range from about 5 Å to about 50 Å or more in length, about 6 Å to about 45 Å, about 7 Å to about 40 Å, about 8 Å to about 35 Å, about 9 Å to about 30 Å, about 10 Å to about 25 Å, about 11 Å to about 20 Å, about 12 Å to about 15 Å. Thus, in one embodiment, a, b, c, d, e, f, g and h represent a total integer of no more than 45, such as between 5 and 45, such as between 7 and 42, such as no more than 30, such as between 5 and 30, such as between 7 and 29.

In one embodiment, a represents an integer selected from 1 to 30. In a further embodiment, a represents an integer selected from 2 to 30. In a further embodiment, a represents an integer selected from 2, 4, 6, 9, 18 or 30. In a further embodiment, a represents an integer selected from 6, 18 or 30. In a further embodiment, a represents an integer selected from 1 to 10. In a further embodiment, a represents an integer selected from 2 to 9. In a yet further embodiment, a represents an integer selected from 2, 4, 6 or 9.

In one embodiment, b represents an integer selected from 0 to 3. In a further embodiment, b represents an integer selected from 0 or 3. In a further embodiment, b represents an integer selected from 1 to 3. In a further embodiment, b represents an integer selected from 2 or 3. In a yet further embodiment, b represents an integer selected from 3.

In one embodiment, c represents an integer selected from 1 to 15. In a further embodiment, c represents an integer selected from 1 to 12. In a further embodiment, c represents an integer selected from 4 to 12. In a yet further embodiment, c represents an integer selected from 4 or 12. In a yet further embodiment, c represents an integer selected from 12.

In one embodiment, d represents an integer selected from 1 to 15. In a further embodiment, d represents an integer selected from 2 to 13. In a further embodiment, d represents an integer selected from 2, 5 or 13. In a further embodiment, d represents an integer selected from 13. In a further embodiment, d represents an integer selected from 1 to 3. In a further embodiment, d represents an integer selected from 1 or 2. In a yet further embodiment, d represents an integer selected from 2.

In one embodiment, $Y_1$ represents a bond, —C(O)NH— or —O—. In a further embodiment, $Y_1$ represents —C(O)NH—.

In one embodiment, $S_2$ represents a spacer selected from:
—$(CH_2)_e$—, wherein one or two of said —$CH_2$— groups are optionally substituted by one or two groups selected from —N(H)—, —C(O)NH— and —NHC(O)— (such as —$(CH_2)_3$—NHCO—$CH_2$—, —$(CH_2)_3$—, —$(CH_2)_3$—NHCO—$(CH_2)_4$—CONH—$CH_2$—, —$(CH_2)_3$—NH—$CH_2$— or —$(CH_2)_3$—NHCO—$(CH_2)_3$—NHCO—$CH_2$—); or
—$(CH_2)_f$—$(CH_2$—$CH_2$—O$)_g$—$(CH_2)_h$—, wherein one to three of said —$CH_2$— groups are optionally substituted by one to three —NHC(O)— groups (such as —$(CH_2)_3$—NHCO—$(CH_2CH_2O)_4$—$(CH_2)_2$—NHCO—$CH_2$—, —$(CH_2)_3$—NHCO—$(CH_2CH_2O)_{12}$—$(CH_2)_2$—NHCO—$CH_2$— or —$(CH_2)_3$—NHCO—$(CH_2)_3$—NHCO—$(CH_2CH_2O)_4$—$(CH_2)_2$—NHCO—$CH_2$—).

In a further embodiment, $S_2$ represents a spacer selected from —$(CH_2)_e$—, wherein one or two of said —$CH_2$— groups are optionally substituted by a —C(O)NH— or —NHC(O)— group (such as —$(CH_2)_3$—NHCO—$CH_2$—, —$(CH_2)_3$—NHCO—, —$(CH_2)_3$—, —$(CH_2)_3$—NHCO—$(CH_2)_4$—CONH—$CH_2$— or —$(CH_2)_3$—NH—$CH_2$—) or —$(CH_2)_f$—$(CH_2$—$CH_2$—O$)_g$—$(CH_2)_h$—, wherein one or two of said —$CH_2$— groups are optionally substituted by a —C(O)NH— or —NHC(O)— group (such as —$(CH_2)_3$—NHCO—$(CH_2)_2$—$(OCH_2CH_2)_4$—NHCO—$CH_2$— or —$(CH_2)_4$—NHCO—$(CH_2)_2$—$(OCH_2CH_2)_4$—NHCO—$CH_2$—).

In a yet further embodiment, $S_2$ represents a spacer selected from:
—$(CH_2)_e$—, wherein one or two of said —$CH_2$— groups are optionally substituted by one or two —NHC(O)— groups (such as —$(CH_2)_3$—NHCO—$CH_2$— or —$(CH_2)_3$—NHCO—$(CH_2)_3$—NHCO—$CH_2$—); or
—$(CH_2)_f$—$(CH_2$—$CH_2$—O$)_g$—$(CH_2)_h$—, wherein one to three of said —$CH_2$— groups are optionally substituted by one to three —NHC(O)— groups (such as —(CH$_2$)$_3$—NHCO—(CH$_2$CH$_2$O)$_4$—(CH$_2$)$_2$—NHCO—CH$_2$—, —(CH$_2$)$_3$—NHCO—(CH$_2$CH$_2$O)$_{12}$—(CH$_2$)$_2$—NHCO—CH$_2$— or —(CH$_2$)$_3$—NHCO—(CH$_2$)$_3$—NHCO—(CH$_2$CH$_2$O)$_4$—(CH$_2$)$_2$—NHCO—CH$_2$—).

In one embodiment, e represents an integer selected from 1 to 10. In a further embodiment, e represents an integer selected from 3 to 10. In a further embodiment, e represents an integer selected from 3, 5, 9 or 10. In a further embodiment, e represents an integer selected from 5 or 9. In a further embodiment, e represents an integer selected from 4 to 10. In a yet further embodiment, e represents an integer selected from 4, 5 or 10.

In one embodiment, f represents an integer selected from 1 to 8. In a further embodiment, f represents an integer selected from 2 to 8. In a further embodiment, f represents an integer selected from 2 to 6. In a yet further embodiment, f represents an integer selected from 4 to 8. In a yet further embodiment, f represents an integer selected from 4 or 8.

In one embodiment, g represents an integer selected from 1 to 15. In a further embodiment, g represents an integer selected from 4 to 12. In a further embodiment, g represents an integer selected from 4 or 12. In a further embodiment, g represents an integer selected from 1 to 5. In a further embodiment, g represents an integer selected from 1 to 4. In a yet further embodiment, g represents an integer selected from 4.

In one embodiment, h represents an integer selected from 1 to 4. In a further embodiment, h represents an integer selected from 4.

In one embodiment, Y$_2$ represents a bond, —O— or —NHC(O)—. In a further embodiment, Y$_2$ represents a bond or —O—. In a yet further embodiment, Y$_2$ represents —O—.

In one embodiment, m represents an integer selected from 1 to 4. In a further embodiment, m represents an integer selected from 3 or 4. In a further embodiment, m represents an integer selected from 1 to 3. In a yet further embodiment, m represents an integer selected from 2 or 3. In a yet further embodiment, m represents an integer selected from 1 or 2. In a yet further embodiment, m represents an integer selected from 1.

References herein to the term "bicyclic heteroaromatic ring system" refer to a bicyclic ring system containing two fused six membered rings and comprising at least one heteroatom selected from N. Particular examples of bicyclic heteroaryl groups containing two fused six membered rings include but are not limited to quinoline, isoquinoline, pyridopyridine, quinoxaline, quinazoline, cinnoline, phthalazine, naphthyridine and pteridine groups. In one embodiment, said bicyclic heteroaromatic ring system is quinolinyl.

In one embodiment, Cy represents phenyl, biphenyl, triphenyl or quinolinyl. In a further embodiment, Cy represents phenyl, biphenyl or triphenyl. In a further embodiment, Cy represents phenyl, biphenyl or quinolinyl. In a further embodiment, Cy represents phenyl or biphenyl. In a yet further embodiment, Cy represents biphenyl.

According to a further aspect of the invention, there is provided a compound of formula (I)$^a$ or a pharmaceutically acceptable salt thereof:

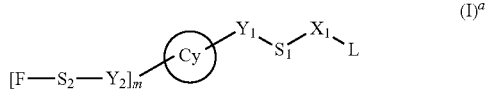

(I)$^a$ wherein:
L represents a binding moiety selected from a nucleic acid aptamer or biotin;
S$_1$ represents a spacer selected from a —(CH$_2$)$_a$— or —(CH$_2$)$_b$—(CH$_2$—CH$_2$—O)$_c$—(CH$_2$)$_d$— group, wherein one or two of said —CH$_2$— groups may optionally be substituted by a —C(O)NH— or —NHC(O)— group;
  a represents an integer selected from 2 to 9;
  b represents an integer selected from 1 to 3;
  c represents an integer selected from 1 to 15;
  d represents an integer selected from 1 to 3;
S$_2$ represents a spacer selected from a —(CH$_2$)$_e$— or —(CH$_2$)$_f$—(CH$_2$—CH$_2$—O)$_g$—(CH$_2$)$_h$— group, wherein one or two of said —CH$_2$— groups may optionally be substituted by a —C(O)NH— or —NHC(O)— group;
  e represents an integer selected from 1 to 10;
  f represents an integer selected from 1 to 8;
  g represents an integer selected from 1 to 5;
  h represents an integer selected from 1 to 3;
X$_1$ represents —O— or —NH—, such that when L represents a nucleic acid aptamer, X$_1$ represents —O— and when L represents biotin, X$_1$ represents —NH—;
Y$_1$ and Y$_2$ independently represent a bond, —O— or —C(O)NH— group;
F represents a carbohydrate molecule capable of binding to a human anti-alpha-galactosyl antibody;
m represents an integer selected from 1 to 4; and
Cy represents phenyl, biphenyl or quinolinyl, such that when Cy represents biphenyl, said —Y$_1$—S$_1$—X$_1$-L group may be present on either of said phenyl rings and said [F—S$_2$—Y$_2$]$_m$— group or groups may be present on either or both of said phenyl rings.

According to a further aspect of the invention, there is provided a compound of formula (I)$^b$ or a pharmaceutically acceptable salt thereof:

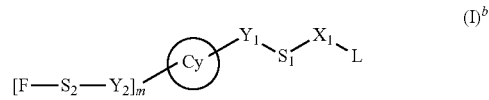

(I)$^b$ wherein:
L represents a binding moiety selected from a nucleic acid aptamer or biotin;
S$_1$ represents a spacer selected from a —(CH$_2$)$_a$— or —(CH$_2$)$_b$—(CH$_2$—CH$_2$—O)$_c$—(CH$_2$)$_d$— group, wherein one to five of said —CH$_2$— groups may optionally be substituted by one or more groups selected from —O—, —C(O)NH—, —NHC(O)— and phenyl;
  a represents an integer selected from 2 to 30;
  b represents an integer selected from 0 to 3;
  c represents an integer selected from 4 to 12;
  d represents an integer selected from 2 to 13;
S$_2$ represents a spacer selected from a —(CH$_2$)$_e$— or —(CH$_2$)$_f$—(CH$_2$—CH$_2$—O)$_g$—(CH$_2$)$_h$— group, wherein one to three of said —CH$_2$— groups may optionally be substituted by one or more groups selected from —N(H)—, —C(O)NH— and —NHC(O)—;
  e represents an integer selected from 3 to 10;
  f represents an integer selected from 4 to 8;
  g represents an integer selected from 4 to 12;
  h represents an integer selected from 1 to 4;
X$_1$ represents —O— or —NH—, such that when L represents a nucleic acid aptamer, X$_1$ represents —O— and when L represents biotin, X$_1$ represents —NH—;

$Y_1$ and $Y_2$ independently represent a bond, —O—, —C(O)NH— or —NHC(O)— group;

F represents a carbohydrate molecule capable of binding to a human anti-alpha-galactosyl antibody;

m represents an integer selected from 1 to 4; and

Cy represents phenyl, biphenyl, triphenyl or quinolinyl, such that when Cy represents biphenyl or triphenyl, said —$Y_1$—$S_1$—$X_1$-L group may be present on any of said phenyl rings and said [F—$S_2$—$Y_2$]$_m$— group or groups may be present on any of said phenyl rings.

References herein to the term "carbohydrate molecule capable of binding to a human anti-alpha-galactosyl antibody" include sugar (i.e. carbohydrate) moieties capable of binding to an immune response component (i.e. an anti-alpha-galactosyl antibody) of said human and consequently eliciting an immune response in a human. In one embodiment, said anti-alpha-galactosyl antibody is an anti-alpha-galactosyl IgG antibody or an anti-alpha-galactosyl IgM antibody. Data is presented herein in FIGS. 1 and 6 which demonstrates the capture of anti-alpha galactosyl IgG and IgM antibodies, respectively. Examples of such carbohydrate molecules include alpha-galactosyl compounds and modified derivatives thereof. Further examples of suitable carbohydrate molecules include the alpha-gal epitopes listed in US 2012/0003251 as being suitable for use in the selective targeting and killing of tumour cells, the epitopes of which are herein incorporated by reference. In one embodiment, F is selected from galactosyl-alpha-1,3-galactosyl-beta-1,4-N-acetylglucosamine, alpha1-3 galactobiose, alpha1-3-beta1-4-galactotriose or galilipentasaccharide.

In one particular embodiment, F has a structure as shown in one of the following formulae:

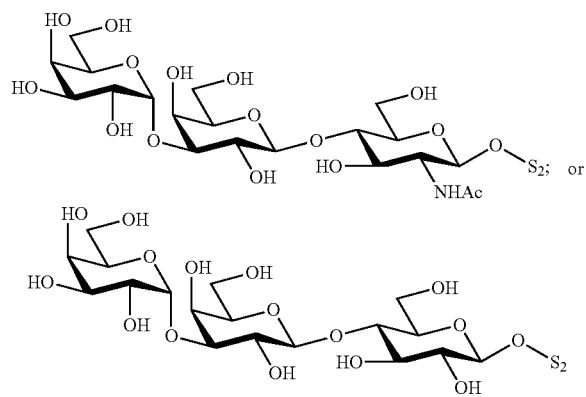

wherein $S_2$ refers to the point of attachment to the $S_2$ group.

In one particular embodiment, F has a structure as shown in the following formula:

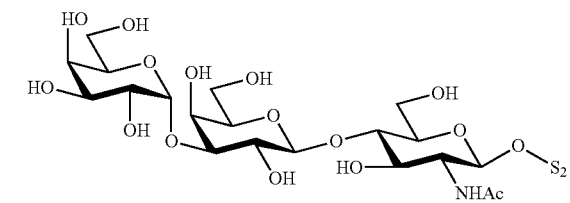

wherein $S_2$ refers to the point of attachment to the $S_2$ group.

References herein to the term "binding moiety" refer to any suitable moiety which is capable of binding to a further component. The invention requires the binding moiety to be either a nucleic acid aptamer or biotin.

In one embodiment, L represents a therapeutic target binding moiety selected from a nucleic acid aptamer.

References herein to "nucleic acid aptamer" refer to an oligonucleotide molecule that binds to a specific target molecule, such as a therapeutic target molecule. Nucleic acid aptamers are typically identified by selecting them from a large random sequence pool. In one embodiment, the nucleic acid aptamer is a DNA aptamer, an RNA aptamer or a nucleic acid analogue aptamer. In a further embodiment, the nucleic acid aptamer is an RNA aptamer. In one embodiment, the nucleic acid aptamer is an oligonucleotide comprising more than 5 but less than 100 nucleic acid molecules. It will be appreciated that the nucleic acid aptamer may contain natural and non-natural nucleotides, such as modified nucleotides which may have a fluorine or methoxy substituent at the 2' position. Examples of suitable non-natural nucleotides are described in Table 9.6.1 of Stovall et al (2014). *In Vitro Selection Using Modified or Unnatural Nucleotides*. doi:10.1002/0471142700.nc0906s56, the non-natural nucleotides of which are herein incorporated by reference.

When L represents a therapeutic target binding moiety selected from a nucleic acid aptamer, L represents the following structure:

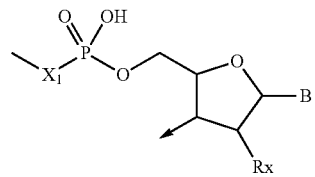

wherein B represents a natural base (i.e. adenine, thymine/uracil, guanine or cytosine) or non-natural base, the arrow represents the next nucleotide in the aptamer sequence, Rx represents hydrogen, a hydroxyl group or a 2' modification such as fluorine or methoxy and $X_1$ refers to the point of attachment to the $X_1$ group which is required by the invention to be —O— when L represents a nucleic acid aptamer.

It will be apparent to the skilled person that a nucleic acid aptamer directed to a specific therapeutic target may easily be prepared in accordance with known procedures, such as Selective systematic Evolution of Ligands by EXponential enrichment (SELEX).

It will be appreciated that the nucleic acid aptamers of the present invention will be configured to bind to a therapeutic target which is either a cancer cell or a specific pathogen.

In one embodiment, the nucleic acid aptamer is configured to bind to a cancer cell. In a further embodiment, the nucleic acid aptamer specifically binds to a tumour-associated antigen whose cell surface expression on a tumour cell is different to its expression on a healthy cell. In a further embodiment, the nucleic acid aptamer is an Epidermal Growth Factor Receptor (EGFR) binding nucleic acid aptamer. EGFR is well known to be over-expressed in several human cancer types.

In one embodiment, the EGFR binding nucleic acid aptamer is an aptamer which binds to any of the EGFR subfamily selected from: EGFR (ErbB-1), HER2/c-neu (ErbB-2), Her 3 (ErbB-3) and Her 4 (ErbB-4).

Examples of suitable EGFR binding nucleic acid aptamers include those described in Li et al (2011) PLoS One 6(6), 1-9 which describes a series of anti-EGFR aptamers, including E07. A dissertion was presented by Viswatej Avutu in 2011:

(https://repositories.lib.utexas.edu/bitstream/handle/2152/13407/Avutu-Bioch_10.pdf?sequence=2)

which describes a minimised variant of E07 known as MinE07 which has the following sequence:

5'-rGrGrA fCrGrG rAfUfU fUrArA fUfCrG fCfCrG fUrArG rArArA rArGfC rAfUrG fUfCrA rArArG fCfCrG rGrArA fCfCrG fUfCfC-3' (SEQ ID NO: 4), wherein "r" represents a natural 2'-OH (RNA) nucleotide and "f" represents a modified 2'-fluoro nucleotide. Thus, in one embodiment, the EGFR binding nucleic acid aptamer comprises an aptamer having the sequence of SEQ ID NO: 4 or a sequence having at least 90% sequence identity to said sequence (such as at least 95, 96, 97, 98 or 99% sequence identity). In a further embodiment, the EGFR binding nucleic acid aptamer comprises an aptamer having the sequence of SEQ ID NO: 4.

Examples of further suitable EGFR binding nucleic acid aptamers include the nucleic acid aptamers of SEQ ID NOS: 1 to 84 described in International Patent Application No. PCT/GB2015/051812. In one embodiment, the nucleic acid aptamer is selected from SEQ ID NO: 79 described in International Patent Application No. PCT/GB2015/051812 which has the following sequence:

```
                                            (SEQ ID NO: 5)
5'-mGmGmG mAfUfU fUAA fUfCmG fCfCmG fUmAmG AmAmA

AmGfC mAfUmG fUfCmA AAmG fCfCmG mGmAA fCfCfC-3';
``` wherein m is 2'-OMe and f is 2'-F. Thus, in one embodiment, the EGFR binding nucleic acid aptamer comprises an aptamer having the sequence of SEQ ID NO: 5 or a sequence having at least 90% sequence identity to said sequence (such as at least 95, 96, 97, 98 or 99% sequence identity). In a further embodiment, the EGFR binding nucleic acid aptamer comprises an aptamer having the sequence of SEQ ID NO: 5.

In a further embodiment, the nucleic acid aptamer comprises a 5' and 3' modified derivative of SEQ ID NO: 5 having the following sequence:

$H_2N$—$(CH_2)_6$-5'-(SEQ ID NO: 5)-3'-idT (hereinafter referred to as SEQ ID NO: 1) or a sequence having at least 90% sequence identity to said sequence (such as at least 95, 96, 97, 98 or 99% sequence identity).

In a further embodiment, the EGFR binding nucleic acid aptamer comprises an aptamer having the sequence of SEQ ID NO: 1.

In one embodiment, the nucleic acid aptamer is other than an Epidermal Growth Factor Receptor (EGFR) binding nucleic acid aptamer.

In an alternative embodiment, the nucleic acid aptamer is configured to bind to a specific pathogen. In a further embodiment, the nucleic acid aptamer is configured to bind to Streptococcus bacteria, such as group A Streptococcus (GAS) bacteria. Examples of suitable nucleic acid aptamers configured to bind to group A Streptococcus bacteria include the nucleic acid aptamers described in Kristian et al (2015) J. Mol. Med. (2015) 93, 619-631, the nucleic acid aptamers of which (specifically those described in Table 1 of Kristian et al, supra) are herein incorporated by reference. In one embodiment, the nucleic acid aptamer is selected from GAS aptamer 20A24P described in, Kristian et al (2015) J. Mol. Med. (2015) 93, 619-631 which has the following sequence:

5'-AGCAGCACAGAGGTCAGATGGGGGGAA-GACACAGAGAAAGGCCGGGGTGAAGTGTAG AGGCCTATGCGTGCTACCGTGAA-3' (SEQ ID NO: 6). Thus, in one embodiment, the nucleic acid aptamer comprises an aptamer having the sequence of SEQ ID NO: 6 or a sequence having at least 90% sequence identity to said sequence (such as at least 95, 96, 97, 98 or 99% sequence identity). In a further embodiment, the nucleic acid aptamer comprises an aptamer having the sequence of SEQ ID NO: 6.

In a further embodiment, the nucleic acid aptamer comprises a 5' modified derivative of SEQ ID NO: 6 having the following sequence:

$H_2N$—$(CH_2)_6$-5'-(SEQ ID NO: 6)-3' (hereinafter referred to as SEQ ID NO: 2) or a sequence having at least 90% sequence identity to said sequence (such as at least 95, 96, 97, 98 or 99% sequence identity). In a further embodiment, the nucleic acid aptamer comprises an aptamer having the sequence of SEQ ID NO: 2.

In an alternative embodiment, the nucleic acid aptamer is configured to bind to Staphylococcus bacteria, such as Staphylococcus aureus bacteria, in particular protein A (SpA). Examples of suitable nucleic acid aptamers configured to bind to Staphylococcus aureus bacteria, in particular protein A (SpA) include the nucleic acid aptamers described in Friedman et al (2015) Biomaterials 36, 110-123, the nucleic acid aptamers of which are herein incorporated by reference. In one embodiment, the nucleic acid aptamer is selected from Staphylococcus aureus aptamer SEQ ID fmA12Δ9 described in Friedman et al (2015) Biomaterials 36, 110-123 which has the following sequence:

5'-mUfGmUfGmUmAmAmUmUmCmUfGmCmCmA-mUmUmCmUmUmUmUfGfGfGfGmCfG fGmAmA-mUmAmCmAfGfGmAmUfGmUfGmAfGmUfGmCmA-mUmUfGmCmAmUmCmAmCf GmUmC-3' (SEQ ID NO: 7); wherein m is 2'-OMe and f is 2'-F. Thus, in one embodiment, the nucleic acid aptamer comprises an aptamer having the sequence of SEQ ID NO: 7 or a sequence having at least 90% sequence identity to said sequence (such as at least 95, 96, 97, 98 or 99% sequence identity). In a further embodiment, the nucleic acid aptamer comprises an aptamer having the sequence of SEQ ID NO: 7.

In a further embodiment, the nucleic acid aptamer comprises a 5' and 3' modified derivative of SEQ ID NO: 7 having the following sequence:

$H_2N$—$(CH_2)_6$-5'-(SEQ ID NO: 7)-3'-idT (hereinafter referred to as SEQ ID NO: 3) or a sequence having at least 90% sequence identity to said sequence (such as at least 95, 96, 97, 98 or 99% sequence identity). In a further embodiment, the nucleic acid aptamer comprises an aptamer having the sequence of SEQ ID NO: 3.

In an alternative embodiment, L represents a binding moiety selected from biotin.

When the binding moiety represents biotin, L represents the following structure:

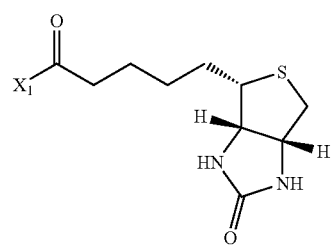

wherein $X_1$ refers to the point of attachment to the $X_1$ group which is required by the invention to be —NH— when L represents biotin.

In a further embodiment, the invention provides a compound of formula (I) which comprises a compound of Examples 1-62 or a pharmaceutically acceptable salt thereof. In a further embodiment, the invention provides a compound of formula (I) which comprises a compound of Examples 1-25 or a pharmaceutically acceptable salt thereof. It will be appreciated that the compounds of Examples 1-21 and 48-62 comprise compounds where L represents biotin. The compounds of Examples 1-21 and 48-62 find particular utility as tool compounds, reference or test compounds. The compounds of Examples 1-21 and 48-62 having L representing biotin assist with confirming proof of concept of binding, however, it will be appreciated that each of the biotin molecules may be substituted for a nucleic acid aptamer specific for a cancer cell or infective agent for therapeutic utility.

In a further embodiment, the invention provides a compound of formula (I) which comprises a compound of Examples 22-47 or a pharmaceutically acceptable salt thereof. In a yet further embodiment, the invention provides a compound of formula (I) which comprises a compound of Examples 22-25 or a pharmaceutically acceptable salt thereof.

In a further embodiment, the invention provides a compound of formula (I) which comprises a compound of Examples 22-24 and 26-43 or a pharmaceutically acceptable salt thereof. In a yet further embodiment, the invention provides a compound of formula (I) which comprises a compound of Examples 22-24 or a pharmaceutically acceptable salt thereof. It will be appreciated that the compounds of Examples 22-24 and 26-43 comprise compounds where L represents an EGFR nucleic acid aptamer and therefore have specific therapeutic utility in the treatment of cancer which can be inferred from the approach demonstrated for nucleic acid aptamers directed to group A *Streptococcus* (GAS) bacteria described in Kristian et al (2015) (supra).

In one embodiment, the compound of formula (I) is other than a compound of Examples 22-24 and 26-43 or a pharmaceutically acceptable salt thereof.

In a further embodiment, the invention provides a compound of formula (I) which comprises a compound of Example 25 or a pharmaceutically acceptable salt thereof. It will be appreciated that the compound of Example 25 comprises a compound where L represents a nucleic acid aptamer directed to group A *Streptococcus* (GAS) bacteria and therefore has specific therapeutic utility in the treatment of infection as described in Kristian et al (2015) (supra).

In a further embodiment, the invention provides a compound of formula (I) which comprises a compound of Examples 44-47 or a pharmaceutically acceptable salt thereof. It will be appreciated that the compounds of Examples 44-47 comprise a compound where L represents a nucleic acid aptamer directed to *Staphylococcus aureus* bacteria and therefore has specific therapeutic utility in the treatment of infection as described in Friedman et al (2015) (supra).

In one embodiment, the invention provides a compound of formula (I) which is the free base of a compound of Examples 1-62 (in particular Examples 22-47).

In a further embodiment, the invention provides a compound of formula (I) which is the free base of a compound of Examples 1-25 (in particular Examples 22-25).

A reference to a compound of formula (I) and sub-groups thereof also includes ionic forms, salts, solvates, isomers (including geometric and stereochemical isomers), tautomers, N-oxides, esters, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, isotopes and protected forms thereof as defined in any aspect of the invention (except intermediate compounds in chemical processes) are referred to as "compounds of the invention".

Compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds. In one embodiment, the compound of formula (I) exists as the phosphate salt.

The salts of the present invention can be synthesized from the parent compound that contains a basic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate salt, also known as a hemisulfate salt.

Salts further include, by way of example only, sodium, potassium, calcium, magnesium, ammonium, tetraalkylammonium, and the like.

It will be appreciated that when the target binding moiety represents a nucleic acid aptamer that the compound of formula (I) will desirably be present as a salt free form to avoid any potential degradation of the nucleic acid aptamer.

Where the compounds of formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

Compounds of formula (I) containing an amine function may also form N-oxides. A reference herein to a compound of formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention.

Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of formula (I) may exist in a number of different geometric isomeric, and tautomeric forms and references to compounds of formula (I) include all such forms. For the avoidance of doubt, where a compound can exist in one of several geometric isomeric or tautomeric forms and only one is specifically described or shown, all others are nevertheless embraced by formula (I).

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, fluorine, such as $^{18}$F, nitrogen, such as $^{13}$N and $^{15}$N, oxygen, such as $^{15}$O, $^{17}$O and $^{18}$O.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

Methods for the Preparation of Compounds of Formula (I)

In this section, as in all other sections of this application unless the context indicates otherwise, references to formula (I) also include all other sub-groups and examples thereof as defined herein.

The compounds pertaining to the invention described herein may be prepared in a stepwise synthetic sequence as illustrated in the Processes and Schemes below. The syntheses involve the preparation of various central constructs which then enable the choice of branching and length of linker with which to connect the two binding moieties. Compounds of the formula (I) can be prepared in accordance with synthetic methods well known to the skilled person. For example, one skilled in the art will appreciate that the chemical steps and choice of protecting groups may be managed in any order to enable synthetic success.

According to a further aspect of the invention there is provided a process for preparing a compound of formula (I) as hereinbefore defined which comprises:

(a) preparing a compound of formula (I) wherein Y$_1$ represents —CONH— (i.e. a compound of formula (IA)) by reacting a compound of formula (II) with a compound of formula (III):

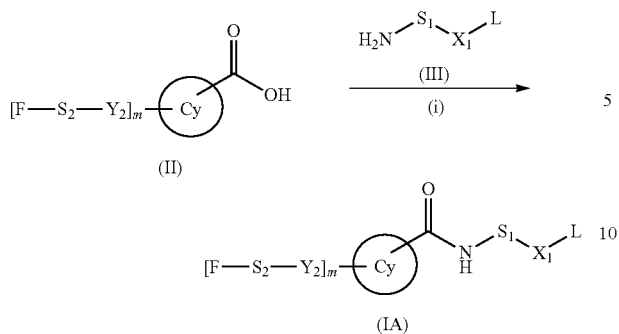
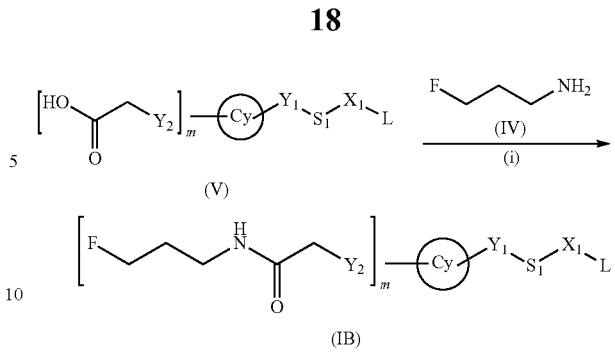

wherein $S_2$, $Y_2$, m, Cy, $S_1$, $X_1$, L and F are as defined hereinbefore; or (b) preparing a compound of formula (I) wherein $S_2$ represents —$(CH_2)_3$—NHCO—$CH_2$— and $Y_2$ represents —O— (i.e. a compound of formula (IB)) by reacting a compound of formula (IV) with a compound of formula (V):

wherein $Y_2$, m, Cy, $Y_1$, $S_1$, $X_1$, L and F are as defined hereinbefore; or (c) preparing a compound of formula (I) wherein $S_2$ represents —$(CH_2)_3$—NHCO—$(CH_2)_2$—$(OCH_2CH_2)_4$—NHCO—$CH_2$— and $Y_2$ represents —O— (i.e. a compound of formula (IC)) by reacting a compound of formula (IV) with a compound of formula (VI):

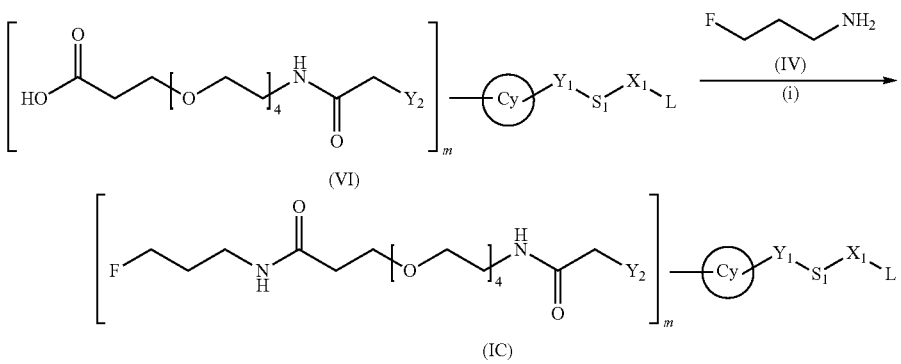

wherein $Y_2$, m, Cy, $Y_1$, $S_1$, $X_1$, L and F are as defined hereinbefore; or (d) preparing a compound of formula (I) wherein $S_2$ represents —$(CH_2)_3$—NH—$CH_2$— and $Y_2$ represents a bond (i.e. a compound of formula (ID)) by reacting a compound of formula (IV) with a compound of formula (VII):

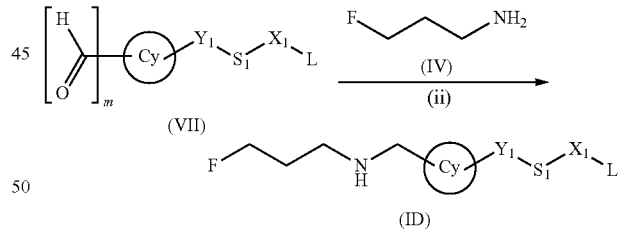

wherein m, Cy, $Y_1$, $S_1$, $X_1$, L and F are as defined hereinbefore; or (e) preparing a compound of formula (I) wherein $S_2$ represents —$(CH_2)_3$—NHCO—$(CH_2)_4$—CONH—$CH_2$— and $Y_2$ represents a bond (i.e. a compound of formula (IE)) by reacting a compound of formula (IV) with a compound of formula (VIII):

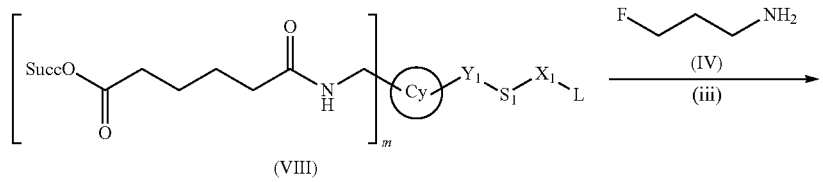

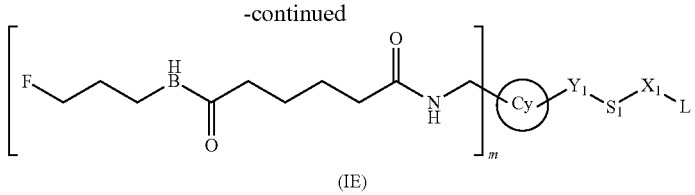

(IE)

wherein m, Cy, $Y_1$, $S_1$, $X_1$, L and F are as defined hereinbefore and Succ represents succinimide; or (f) preparing a compound of formula (I) wherein $S_2$ represents —$(CH_2)_3$—NHCO— and $Y_2$ represents a bond (i.e. a compound of formula (IF)) by reacting a compound of formula (IV) with a compound of formula (IX):

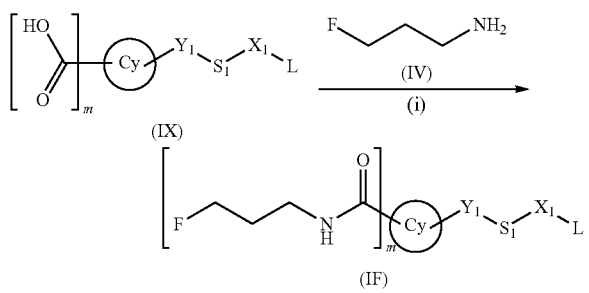

wherein m, Cy, $Y_1$, $S_1$, $X_1$, L and F are as defined hereinbefore; or (g) preparing a compound of formula (I) wherein $Y_1$ represents —CONH— and $S_1$ contains a —CONH— group (i.e. a compound of formula (IG)) by reacting a compound of formula (IIA) with a compound of formula (III):

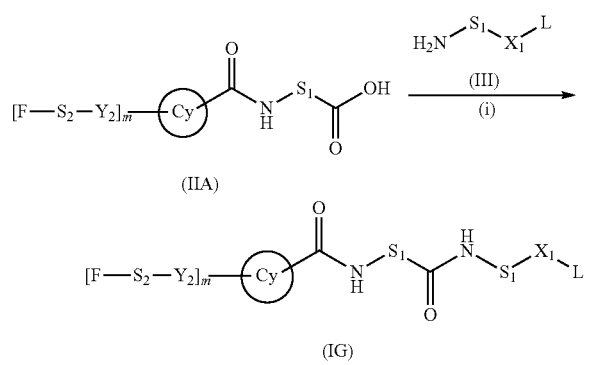

wherein $S_2$, $Y_2$, m, Cy, $S_1$, $X_1$, L and F are as defined hereinbefore; and/or (h) deprotection of a protected derivative of a compound of formula (I); and/or (i) interconversion of a compound of formula (I) or protected derivative thereof to a further compound of formula (I) or protected derivative thereof.

Processes (a), (b), (c), (f) and (g) typically comprise an amide bond formation reaction which comprises activation of the carboxylic acid with either phosphate containing reagents, triazine-based reagents or carbodiimide containing reagents in the presence of an organic base in an organic solvent. Preferred conditions comprise HATU ((1-[bis(dimethylamino)methylene]-1H-1,2,3-triazolo[4,5-b]pyridinium 3-oxid hexafluorophosphate) with either triethylamine or diisopropylethylamine in DMF or a mixture of DMF and DMSO; DMTMM (4-(4,6-dimethoxy-1,3,5-triazin-2-yl)-4-methylmorpholin-4-ium chloride or tetrafluoroborate salt) with an inorganic base in DMF, or with HBTU with triethylamine in DMF.

Process (d) typically comprises a reductive amination reaction which comprises stirring a solution of an amine of general formula (IV) and aldehyde of general formula (VII) in an inert solvent together with a suitable reducing reagent. An aldehyde derivative such as an acetal or hemi-acetal may be employed rather than its parent. Suitable reducing reagents include sodium cyanoborohydride, sodium triacetoxyborohydride, or picoline borane in the presence of inert solvents such as dichloromethane, methanol, or THF with the optional addition of acetic acid. Preferred conditions comprise picoline borane with acetic acid in MeOH at room temperature.

Process (e) typically comprises an amide bond formation reaction from pre-prepared activated esters of formula (VIII) and amines of formula (IV). Preferred conditions comprise stirring both components at room temperature in DMF either with or without the addition of an organic base such as triethylamine (e.g. Example 13, Preparation 14) or diisopropylcarbodiimide and aqueous carbonate base in DMF at room temperature or DIPEA/TEA in DMF/chloroform/DMSO.

Process (h) typically comprises any suitable deprotection reaction, the conditions of which will depend upon the nature of the protecting group. When the protecting group represents tBoc, such a deprotection reaction will typically comprise the use of a suitable acid in a suitable solvent. For example, the acid may suitably comprise trifluoroacetic acid or hydrogen chloride and the solvent may suitably comprise dichloromethane ethyl acetate, 1,4-dioxane, methanol or water. Optionally a mixture of solvents may be used, for example aqueous methanol or ethyl acetate/1,4-dioxane.

Process (i) typically comprises interconversion procedures known by one skilled in the art. For example, in compounds of formula (I), a first substituent may be converted by methods known by one skilled in the art into a second, alternative substituent. A wide range of well known functional group interconversions are known by a person skilled in the art for converting a precursor compound to a compound of formula (I) and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described in processes (a), (b), (c), (d), (e), (f) and (g) are followed or preceded by one or more reactions known to the skilled in the art and are performed in an appropriate order to achieve the requisite substitutions on $S_2$, $Y_2$, m, Cy, $S_1$, $X_1$, $Y_1$, L and F defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation and arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

Compounds of formula (II), (V) (VI) and (IX) may be prepared according to the methods described in Scheme 1 from compounds of formula (X), that are key intermediates of the linker molecules.

wherein m, Cy, $Y_1$, $S_1$, $X_1$, $S_2$, $Y_2$, F and L are as defined hereinbefore, $PG^1$ is a protecting group comprising either allyl, tert-butyl, methyl, ethyl or benzyl and $PG^2$ is an orthogonal protecting group comprising either methyl, ethyl or tert-butyl.

Compounds of formula (II) may be prepared from compounds of formula (X) according to process step (iv) a deprotection reaction mediated by catalytic hydrogenation. Preferred conditions comprise 10% Pd/C in MeOH/EtOH or water or any combination thereof under an atmosphere of hydrogen (from between 15-70 psi). Alternatively deprotection may be mediated by a phase transfer reaction. Preferred conditions comprise TEA and water at room temperature for 16 hours.

Compounds of formula (V) may be prepared from compounds of formula (X) according to process step (v), an acid or base mediated deprotection reaction as required by the protecting group employed. Wherein acid mediated deprotection conditions are required, preferred conditions comprise TFA, 4M HCl in dioxane, or 37% HCl in water with a co-solvent of DCM or water as necessary. Wherein base mediated conditions are required, preferred conditions comprise either sodium or lithium hydroxide in aqueous media such as methanol or THF with water. When $PG^1$ represents allyl, a palladium catalyst mediated deprotection may be employed. Preferred conditions comprise tetrakistriphenylphosphine palladium (0) with piperidine in THF.

Compounds of formula (VI) may be prepared from compounds of formula (X) according to a sequence of processes using reaction steps (v) and (i). Compounds of formula (VI) may be prepared firstly by utilising a suitable deprotection step according to process step (v) as previously described, secondly by an amide bond reaction with a suitable amine according to process step (i) as described in process (a) above, and thirdly by another suitable deprotection according to process step (v).

Compounds of formula (IX) may be prepared from compounds of formula (X) according to process steps (iv) or (v) as described above.

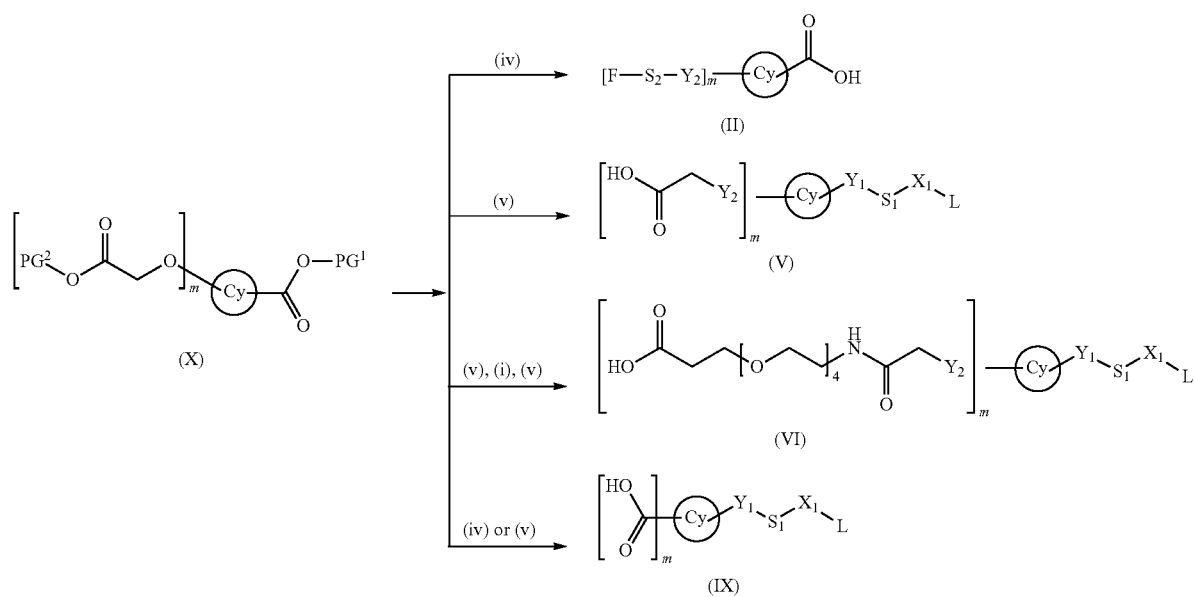

Scheme 1

Compounds of formula (IIA) may be prepared according to the methods described in Scheme 1A from compounds of formula (II) and compounds of formula (XIII):

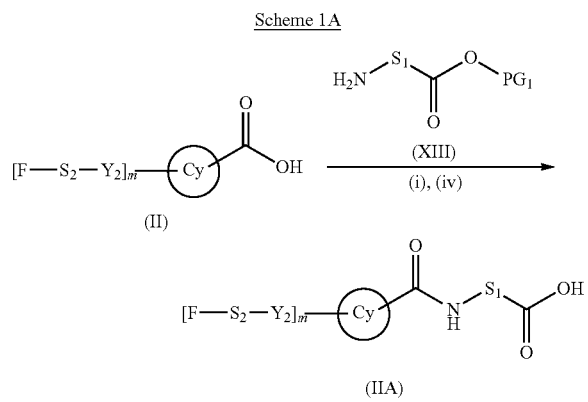

Scheme 1A (II)

(XIII)

(IIA)

wherein F, $S_2$, $Y_2$, Cy and $S_1$ are as defined herein before and $PG_1$ is a protecting group comprising benzyl.

Compounds of formula (X) may be prepared according to the methods described in Scheme 2 from compounds of formula (XI).

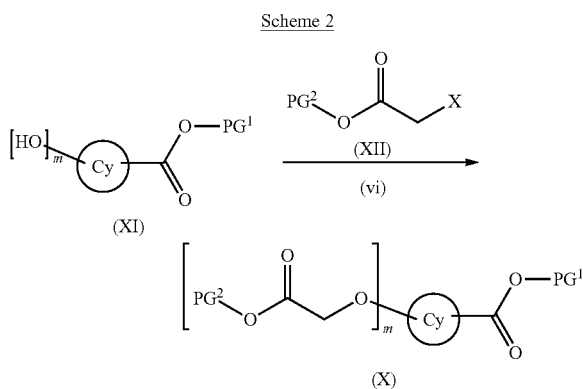

Scheme 2

(XI)

(XII)

(X)

wherein m and Cy are as defined hereinbefore, $PG^1$ is a protecting group comprising either allyl, tert-butyl, methyl, ethyl or benzyl, $PG^2$ is an orthogonal protecting group comprising either methyl, ethyl or tert-butyl and X is Cl, Br or I.

Compounds of formula (X) may be prepared from compounds of formula (XI) and (XII) according to process step (vi), an alkylation reaction. Typical conditions comprise an inorganic base in a polar organic solvent at room temperature. Preferred conditions comprise potassium carbonate in DMF.

When Cy is bi-phenyl, or triphenyl, compounds of formula (XI) may be prepared by employment of a Suzuki reaction to construct the bi/tri-phenyl unit. Preferred conditions comprise tetrakistriphenyl phosphine palladium (0) or [1,1'-bis(diphenylphosphino)ferrocene]dichloropalladium (II) complex with dichloromethane with sodium carbonate, potassium acetate or sodium bicarbonate in dioxane and water at 100-110° C. When suitable required protecting groups are employed, such as TBS, such protecting groups may be deprotected using a fluoride mediated deprotection. Preferred conditions comprise TBAF in THF at room temperature.

Alternatively, wherein Cy is bi/tri-phenyl, compounds of formula (X) may be prepared directly by employment of a Suzuki reaction to construct the bi/tri-phenyl unit using conditions as described above and herein.

Compounds of formula (III), (XII) and (XIII) are either commercially available or prepared according to the methods described herein.

Compounds of formula (IV) and (VIII) are either prepared according to the literature or prepared according to the methods described herein.

Compounds of formula (VII) are either prepared according to the literature or prepared according to the methods described herein (e.g. Preparation 35).

One skilled in the art will appreciate that one may choose the appropriate combination of steps described in processes (a) to (f) or Schemes 1 and 2 to generate the highest yields for the Examples and Preparations described herein.

It will be appreciated that certain intermediates described herein represent novel compounds not previously known in the art. Thus, according to a further aspect of the invention there is provided an intermediate compound selected from a compound of formula (II), (IIA), (V), (VI), (VII), (VIII), (IX), (X) or (XI) as defined hereinbefore.

Pharmaceutical Compositions

While it is possible for the compound of formula (I) to be administered alone, it is preferable to present it as a pharmaceutical composition (e.g. formulation).

Thus, according to a further aspect, the invention provides a pharmaceutical composition, and methods of making a pharmaceutical composition comprising (e.g admixing) at least one compound of the invention where L represents a nucleic acid aptamer, together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity (i.e. generally recognised as safe (GRAS)), irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the invention can be formulated in accordance with known techniques, see for example, Remington's Pharmaceutical Sciences, Mack Publishing Company, Easton, Pa., USA.

The pharmaceutical compositions can be in any form suitable for parenteral, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a compound of the invention. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various anti-bacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous or subcutaneous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for subcutaneous (s.c.) administration.

The compound of the invention may be formulated with a carrier and administered in the form of nanoparticles, the increased surface area of the nanoparticles assisting their absorption. In addition, nanoparticles offer the possibility of direct penetration into the cell.

Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% (w/w) of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral or subcutaneous formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. One example of a patient pack includes a prefilled syringe. Such pre-filled syringes already contain the drug substance. The front end portion of a pre-filled syringe to which a needle is to be attached is sealed with a nozzle cap. Prior to injection, the nozzle cap is removed from the front end portion and a needle is attached thereto. A gasket is then slid by pushing a plunger rod toward the front end portion so that the drug is expelled.

Compositions for nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compound of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect.

Therapeutic Uses

According to a further aspect of the invention, there is provided a compound of formula (I) as defined herein where L represents a nucleic acid aptamer for use in therapy.

According to a further aspect of the invention, there is provided a compound of formula (I) as defined herein where L represents a nucleic acid aptamer for use in the treatment of cancer or a disease mediated by an infective agent.

According to a further aspect of the invention, there is provided the use of a compound of formula (I) as defined herein where L represents a nucleic acid aptamer in the manufacture of a medicament for use in the treatment of cancer or a disease mediated by an infective agent.

According to a further aspect of the invention, there is provided a method of treating cancer or a disease mediated by an infective agent which comprises administering to an individual in need thereof a compound of formula (I) as defined herein where L represents a nucleic acid aptamer.

The compound of the invention is generally administered to a subject in need of such administration, for example a human or animal patient, preferably a human.

The compound of the invention will typically be administered in amounts that are therapeutically or prophylactically useful and which generally are non-toxic. However, in certain situations (for example in the case of life threatening diseases), the benefits of administering a compound of the invention may outweigh the disadvantages of any toxic effects or side effects, in which case it may be considered desirable to administer a compound of the invention in amounts that are associated with a degree of toxicity.

The compound of the invention may be administered over a prolonged term (i.e. chronic administration) to maintain beneficial therapeutic effects or may be administered for a short period only (i.e. acute administration). Alternatively they may be administered in a continuous manner or in a manner that provides intermittent dosing (e.g. a pulsatile manner).

A typical daily dose of the compound of the invention can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the invention can either be administered on a daily basis or on a repeat basis every 2, or 3, or 4, or 5, or 6, or 7, or 10 or 14, or 21, or 28 days for example. Alternatively, the compound of the invention can be administered by infusion, multiple times per day.

The compound of the invention may be administered in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound of the invention may be administered once or more than once each day. The compound of the invention can be administered continuously (i.e. taken every day without a break for the duration of the treatment regimen). Alternatively, the compound of the invention can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the invention for periods of one hour daily for up to ten days in particular up to five days for one week, and the treatment repeated at a desired interval such as two to four weeks, in particular every three weeks.

More particularly, a patient may be given an infusion of a compound of the invention for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, and in particular a continuous infusion of 24 hours to 72 hours.

Ultimately, however, the quantity of compound of the invention administered and the type of composition used will be commensurate with the nature of the disease or physiological condition being treated and will be at the discretion of the physician.

It will be appreciated that the compound of the invention can be used as a single agent or in combination with other therapeutic agents. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

Where the compound of the invention is administered in combination therapy with one, two, three, four or more other therapeutic agents (preferably one or two, more preferably one), the agents can be administered simultaneously or sequentially. In the latter case, the two or more agents will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and compound of the invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound of the invention and the one or more other therapeutic agent(s) when given as a combination may be determined by the person skilled in the art. Said ratio and the exact dosage and frequency of administration depends on the particular compound of the invention and the other therapeutic agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compound of present invention. A particular weight ratio for the compound of the invention and another therapeutic agent may range from 1/10 to 10/1, more in particular from 1/5 to 5/1, even more in particular from 1/3 to 3/1.

Anti-Cancer Therapy

According to a further aspect of the invention, there is provided a compound of formula (I) as defined herein where L represents a nucleic acid aptamer for use in the treatment of cancer.

According to a further aspect of the invention, there is provided the use of a compound of formula (I) as defined herein where L represents a nucleic acid aptamer in the manufacture of a medicament for use in the treatment of cancer.

According to a further aspect of the invention, there is provided a method of treating cancer which comprises administering to an individual in need thereof a compound of formula (I) as defined herein where L represents a nucleic acid aptamer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and pre-malignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In one embodiment, the cancer is selected from lung, head and neck as well as colorectal cancer.

Examples of other anticancer therapeutic agents or treatments that may be administered together (whether concurrently or at different time intervals) with the compound of the invention include but are not limited to:

Topoisomerase I inhibitors;
Antimetabolites;
Tubulin targeting agents;
DNA binder and topoisomerase II inhibitors;
Alkylating Agents;
Monoclonal Antibodies;
Anti-Hormones;
Signal Transduction Inhibitors;
Proteasome Inhibitors;
DNA methyl transferases;
Cytokines and retinoids;
Chromatin targeted therapies;
Radiotherapy; and
Other therapeutic or prophylactic agents, such as immunotherapy agents.

The compound of the invention may also be administered in conjunction with non-chemotherapeutic treatments such as radiotherapy, photodynamic therapy, gene therapy; surgery and controlled diets.

For use in combination therapy with another chemotherapeutic agent, the compound of the invention and one, two, three, four or more other therapeutic agents can be, for example, formulated together in a dosage form containing two, three, four or more therapeutic agents i.e. in a unitary pharmaceutical composition containing all components. In an alternative embodiment, the individual therapeutic agents may be formulated separately and presented together in the form of a kit, optionally with instructions for their use.

Anti-Infective Therapy

According to a further aspect of the invention, there is provided a compound of formula (I) as defined herein where L represents a nucleic acid aptamer for use in the treatment of a disease or disorder mediated by and/or caused by an infective agent.

According to a further aspect of the invention, there is provided the use of a compound of formula (I) as defined herein where L represents a nucleic acid aptamer in the manufacture of a medicament for use in the treatment of a disease or disorder mediated by and/or caused by an infective agent.

According to a further aspect of the invention, there is provided a method of treating a disease or disorder mediated by and/or caused by an infective agent which comprises administering to an individual in need thereof a compound of formula (I) as defined herein where L represents a nucleic acid aptamer.

Examples of infective agents include any pathogen such as a bacteria, fungus, parasite or virus. Thus, in one embodiment, the disease or disorder mediated by and/or caused by an infective agent is bacterial infection.

Examples of such as bacterial infection include infection by the following bacteria: *Staphylococcus* sp. such as *Staphylococcus aureus* (including methicillin resistant *Staphylococcus aureus* (MRSA)), Clostridia sp (e.g. *Clostridium difficile, Clostridium tetani* and *Clostridium botulinum*), *Enterobacter* species, *Mycobacterium tuberculosis*, *Shigella* sp. such as *Shigelladysenteriae*, *Campylobacter* sp. such as *Campylobacter jejuni*, *Enterococcus* sp. such as *Enterococcus faecalis, Bacillus anthracis, Yersinia pestis, Bordetella pertussis, Streptococcal species, Salmonella thyphimurim, Salmonella enterica, Chlamydia* species, *Treponemapallidum, Neisseria gonorrhoeae, Borreliaburgdorferi, Vibrio cholerae, Corynebacterium diphtheriae, Helicobacter pylori*, Gram-negative pathogens, such as *Acinetobacter baumannii, Pseudomonas aeruginosa, Klebsiella pneumoniae*, and *Escherichia coli* (and including strains that are resistant to one or more classes of anti-biotics, especially multi-drug resistant (MDR) strains).

EXAMPLES

The invention will now be illustrated, but not limited, by reference to the specific embodiments described in the following examples. Compounds are named using an automated naming package such as AutoNom (MDL) or ChemDraw or are as named by the chemical supplier.

The following synthetic procedures are provided for illustration of the methods used; for a given preparation or step the precursor used may not necessarily derive from the individual batch synthesised according to the step in the description given.

Analytical Methods
LCMS
System: LCMS Agilent 1100 (quaternary pump); mass spectrometer: Waters Micromass ZQ
Column: XBridge C18 4.6×50 mm, 5 μm.
Solvent: A=water; B=acetonitrile, C=10 mm ammonium formate in water; D=0.05% formic acid in acetonitrile
Column temperature: 25° C., injection volume: 5 μL
LCMS Method A: 4.5 Minute Acidic Run

| Time (mins) | A (%) | B (%) | C (%) | D (%) | Flow (mL/min) |
|---|---|---|---|---|---|
| 0 | 95 | 0 | 0 | 5 | 2.0 |
| 3.5 | 0 | 95 | 0 | 5 | 2.0 |
| 4.5 | 0 | 95 | 0 | 5 | 2.0 |
| 4.6 | 95 | 0 | 0 | 5 | 2.0 |

LCMS Method B: 4.5 Minute Buffered Run

| Time (mins) | A (%) | B (%) | C (%) | D (%) | Flow (mL/min) |
|---|---|---|---|---|---|
| 0 | 0 | 5 | 95 | 0 | 2.0 |
| 3.5 | 0 | 95 | 5 | 0 | 2.0 |
| 4.5 | 0 | 95 | 5 | 0 | 2.0 |
| 4.6 | 0 | 5 | 95 | 0 | 2.0 |

LCMS Method C: 8 Minute Acidic Run

| Time (mins) | A (%) | B (%) | C (%) | D (%) | Flow (mL/min) |
|---|---|---|---|---|---|
| 0 | 95 | 0 | 0 | 5 | 2.0 |
| 3.5 | 5 | 90 | 0 | 5 | 2.0 |
| 8.0 | 5 | 90 | 0 | 5 | 2.0 |
| 8.10 | 95 | 0 | 0 | 5 | 2.0 |

LCMS Method D: 8 Minute Buffered Run

| Time (mins) | A (%) | B (%) | C (%) | D (%) | Flow (mL/min) |
|---|---|---|---|---|---|
| 0 | 0 | 5 | 95 | 0 | 2.0 |
| 3.5 | 0 | 95 | 5 | 0 | 2.0 |
| 8.0 | 0 | 95 | 5 | 0 | 2.0 |
| 8.10 | 0 | 5 | 95 | 0 | 2.0 |

System: LCMS Agilent 1100 (quaternary pump); mass spectrometer: PE SCIEX API 2000 MS/MS Column: Agilent Poroshell 120 column, SB-C18, 4.6 mm×30 mm, 2.7 μm Solvent: A=water; B=0.1% formic acid in acetonitrile Column temperature: 20° C., injection volume: 5 μL LCMS Method E: 4.5 Minute Acidic Run

| Time (mins) | A (%) | B (%) | C (%) | D (%) | Flow (mL/min) |
|---|---|---|---|---|---|
| 0.5 | 95 | 5 | 0 | 5 | 2.0 |
| 1.5 | 0 | 100 | 0 | 5 | 2.0 |
| 4.0 | 0 | 100 | 0 | 5 | 2.0 |
| 4.3 | 95 | 5 | | | |
| 4.5 | 95 | 5 | 0 | 5 | 2.0 |

NMR

NMR details were recorded on either an Oxford Instruments AS400 or Bruker Avance III Ultrashield plus 400 MHz.

Reverse Phase HPLC

Wherein examples and preparations have been purified using reverse phase HPLC, the following conditions may apply:

System:

Gilson TRILUTION™ comprising: Gilson 215 liquid handler; Gilson 811C dynamic mixer; Gilson 306 pumps, Gilson manometric module; Gilson 155 UV/Vis detector, Gilson 819 injection value actuator and a Gilson valvemate II value actuator.

Method:

Methods were run as specified in the individual experimental using either a Phenomenex Luna C-18, 5 μm, 150× 21.20 mm, 100 Å (product number 00F-4041-P0) column or Phenomenex Magellen C-18, 5 μm, 150×10.00 mm (product number 00F-4118-NO) column and collecting at the $\lambda_{max}$ in 2 mL fractions.

Alternatively, preparative HPLC may be performed at room temperature using a Varian auto-purification system with an Agilent Pursuit 5 Column (C18, 5 μm, 21.2 mm×250 mm), controlled by Varian Star software (version 6.41)

Mobile phases consisted of acetonitrile and water, both containing 0.1% v/v formic acid.

Method:

| | Time (min) | | | | | | | |
|---|---|---|---|---|---|---|---|---|
| | 0 | 2 | 3 | 13 | 14 | 21 | 22 | 25 |
| Water (%) | 95 | 95 | 50 | 10 | 5 | 5 | 95 | 95 |
| Acetonitrile (%) | 5 | 5 | 50 | 90 | 95 | 95 | 5 | 5 |

Flow rate: 20 mL/min

MALDI-ToF

Wherein the molecular weight of the Examples exceeds 1500 Da, MALDI-ToF data was obtained using a Bruker ultrafleXtreme.

Abbreviations

Wherein the following abbreviations have been used, the following meanings apply:

AcOH is acetic acid;
aq. is aqueous;
BBr$_3$ is boron tribromide;
Boc is tert-butyloxycarbonyl;
br s is broad singlet;
δ is chemical shift in ppm;
d is doublet;
dd is doublet of doublets;
ddd is doublet of doublets of doublets;
DCM is dichloromethane;
DIPEA is diisopropylethylamine;
DMF is dimethylformamide;
DMTMM is 4-(4,6-Dimethoxy-1,3,5-triazin-2-yl)-4-methylmorpholinium chloride or tetrafluoroborate;
DMSO is dimethylsulphoxide;
DMSO-d$_6$ is perdeuterated dimethylsulphoxide NMR solvent;
DNA is deoxyribonucleic acid;
ES is electrospray ionisation technique;
EtOH is ethanol;
EtOAc is ethyl acetate;
HATU is O-(7-azabenzotriazol-1-yl)-N,N,N',N'-tetramethyluronium hexafluorophosphate;
HBTU is O-(benzotriazol-1-yl)-N,N,N',N'-tetramethyluronium hexafluorophosphate;
HFIP is hexafluoroisopropanol;
HPLC is high pressure liquid chromatography;
IMS is industrial methylated spirit (typically 5%-10% MeOH in EtOH);
μ is micro;
m is multiplet;
MALDI-ToF is matrix assisted laser desorption ionisation-time of flight;
MeCN is acetonitrile;
MeOH is methanol;
mins is minutes;
mL is millilitre;
MS is mass spectrometry;
NH$_3$ is ammonia or ammonium hydroxide (28% aqueous solution);
NMR is nuclear magnetic resonance;
OD is optical density;
Pd/C is (typically 5%-10%) palladium on charcoal hydrogenation catalyst (water-wet);
Pd(PPh$_3$)$_4$ is tetrakis triphenylphosphine palladium (0);
ppm is parts per million;
q is quartet;
RNA is ribonucleic acid;
RP is reverse phase;
Rt is retention time;
r.t. is room temperature;
s is singlet;
t is triplet;
TBAF is tetra-n-butylammonium fluoride;
TBME is tert-butyl methyl ether;
TEA is triethylamine;
TEAA is triethylammonium acetate;
TBS is tert-butyldimethylsilyloxy;
TBTU is O-(benzotriazol-1-yl)-N,N,N',N'-tetramethyluronium tetrafluoroborate;
TFA is trifluoroacetic acid;
TFAA is trifluoroacetic anhydride; and
THF is tetrahydrofuran Wherein alpha-Gal is referred to, the following intermediate applies:

3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amine

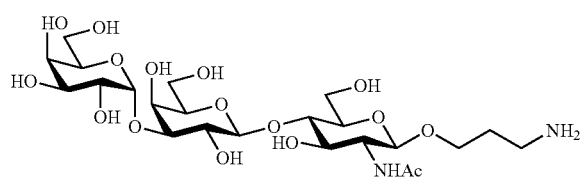

This intermediate may be prepared according to the methods described by Bovin et al (Mendeleev Communications (2002), (4), 143-145).

Preparations 1-137 describe the methods used to prepare intermediates from the key linker molecules required for conjugation into the Examples, as described by Processes (a) to (g) and Schemes 1-2 as described hereinbefore.

Preparation 1

1-(2-{3-[(2-{5-[(3aS,4S,6aR)-2-Oxo-hexahydro-1H-thieno[3,4-d]imidazolidin-4-yl]pentanamido}ethyl)carbamoyl]-5-[3,5-bis({[(14-carboxy-3,6,9,12-tetraoxatetradecan-1-yl)carbamoyl]methoxy})phenyl]phenoxy}acetamido)-3,6,9,12-tetraoxapentadecan-15-oic acid

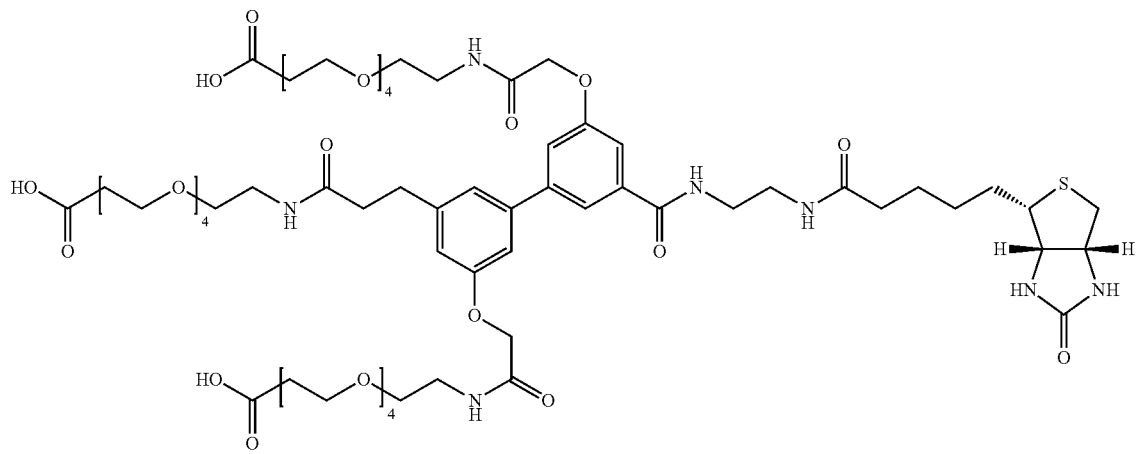

A solution of tert-butyl 1-(2-{3-[(2-{5-[(3aS,4S,6aR)-2-oxo-hexahydro-1H-thieno[3,4-d]imidazolidin-4-yl]pentanamido}ethyl)carbamoyl]-5-[3,5-bis({[15-(tert-butoxy)-15-oxo-3,6,9,12-tetraoxapentadecan-1-yl]carbamoyl}methoxy)phenyl]phenoxy}acetamido)-3,6,9,12-tetraoxapentadecan-15-oate (Preparation 30, 30.9 mg, 19.3 µmol) dissolved in DCM:TFA:H$_2$O (10:10:1 v/v/v, 5 mL) was stirred at room temperature for 1 hour. The reaction was concentrated in vacuo and azeotroped with toluene/dioxane (1:1 v/v, 3×5 mL), to afford the title compound as an off white solid. The solid was dissolved in DMF (1 mL) to afford a stock solution that was used directly in the next step.

LCMS Method A: Rt=1.88 mins, ES$^+$ MS m/z 1431.4 [M+H]$^+$

Preparation 2

1-[2-(3-{[2-(1-{5-[(3aS,4S,6aR)-2-Oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}phenoxy)acetamido]-3,6,9,12-tetraoxapentadecan-15-oic acid

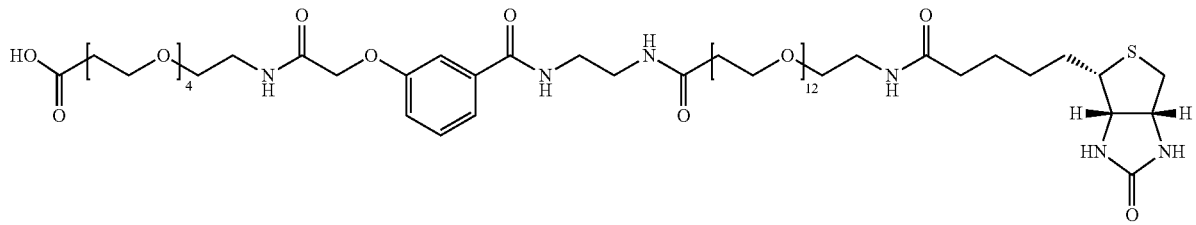

37

The title compound was prepared according to the method described for Preparation 1.

LCMS Method A: Rt=1.97 mins, ES⁻ MS m/z 1310.2 [M−H]⁻

Precursor: Preparation 21

Preparation 3

3-(2-Oxo-2-((2-(5-(((3aS,4S,6aR)-2-oxohexahydro-1H-thieno[3,4-d]imidazol-4-yl)pentanamido)ethyl)amino)ethoxy)benzoic acid

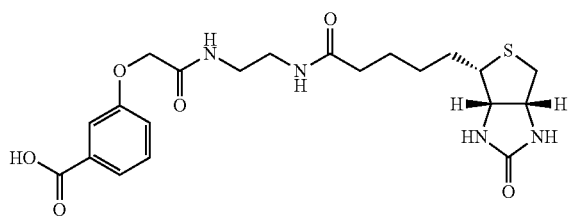 [SMILES: O=C(CCCC[C@@H]1SC[C@@H]2NC(=O)N[C@@H]21)NCCNC(=O)COc1cccc(C(=O)O)c1]

The title compound was prepared according to the method described for Preparation 10, using Preparation 44 and taken on directly to the next step.

38

Preparation 4

2-(4-((2-(5-(((3aS,4S,6aR)-2-Oxohexahydro-1H-thieno[3,4-d]imidazol-4-yl)pentanamido)ethyl)carbamoyl)phenoxy)acetic acid

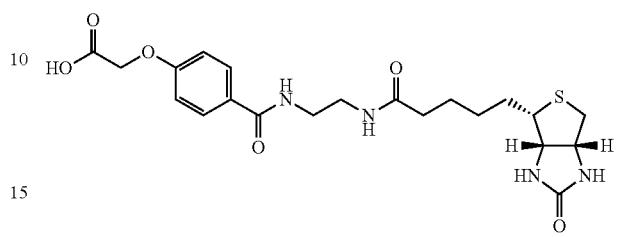

The title compound was prepared according to the method described for Preparation 1 using Preparation 26.

LCMS Method A: Rt=1.52 mins, ES⁺ MS m/z 465.3 [M+H]⁺

Preparation 5

2,2',2''-((5'-((2-(5-(((3aS,4S,6aR)-2-Oxohexahydro-1H-thieno[3,4-d]imidazol-4-yl)pentanamido)ethyl)carbamoyl)-[1,1'-biphenyl]-3,3',5-triyl)tris(oxy))triacetic acid

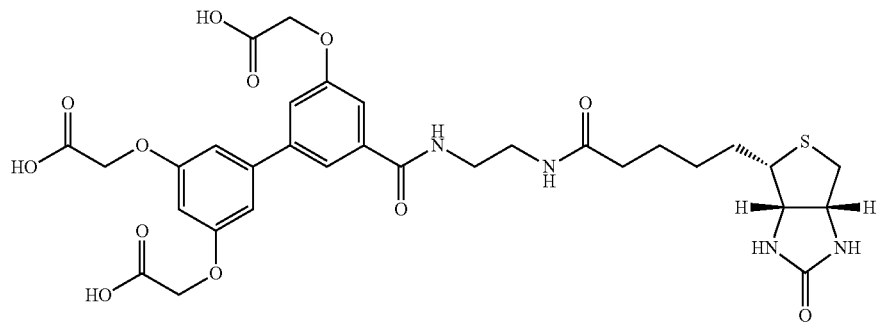 [SMILES: O=C(O)COc1cc(OCC(=O)O)cc(-c2cc(OCC(=O)O)cc(C(=O)NCCNC(=O)CCCC[C@@H]3SC[C@@H]4NC(=O)N[C@@H]43)c2)c1]

The title compound was prepared according to the method described for Preparation 1 using Preparation 29.

LCMS Method A: Rt=1.66 mins, ES⁺ MS m/z 689.4 [M+H]⁺

Preparation 6

1-[2-(3-{[2-(1-{5-[(3aS,4S,6aR)-2-Oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}-5-{[(14-carboxy-3,6,9,12-tetraoxatetradecan-1-yl)carbamoyl]methoxy}phenoxy)acetamido]-3,6,9,12-tetraoxapentadecan-15-oic acid

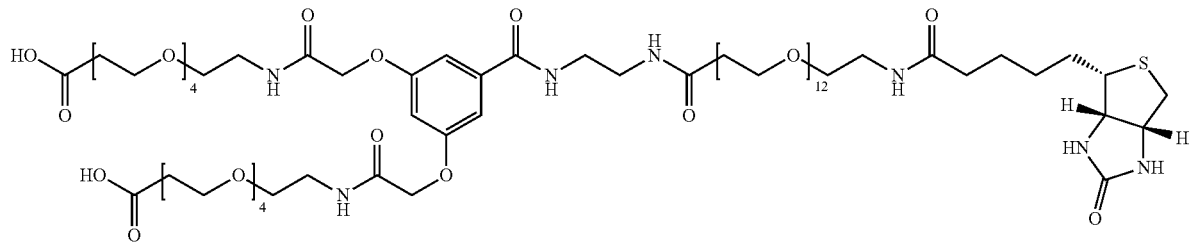

A solution of tert-butyl 1-[2-(3-{[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}-5-({[15-(tert-butoxy)-15-oxo-3,6,9,12-tetraoxapentadecan-1-yl]carbamoyl}methoxy)phenoxy)acetamido]-3,6,9,12-tetraoxapentadecan-15-oate (Preparation 27, 10.0 mg, 5.7 μmol) dissolved in dioxane (1 mL) and aqueous HCl (37% in water, 1 mL) was stirred at room temperature for 2 hours. The reaction was concentrated in vacuo and azeotroped with toluene (2×5 mL) to afford the title compound as a colourless oil that was used directly in the next step.

LCMS Method A: Rt=1.93 mins, ES$^+$ MS m/z 1633.8 [M+H]$^+$

Preparation 7

2,2',2'',2'''-((5-((2-(5-((3aS,4S,6aR)-2-Oxohexahydro-1H-thieno[3,4-d]imidazol-4-yl)pentanamido)ethyl)carbamoyl)-[1,1'-biphenyl]-2,3',4,5'-tetrayl)tetrakis(oxy))tetraacetic acid

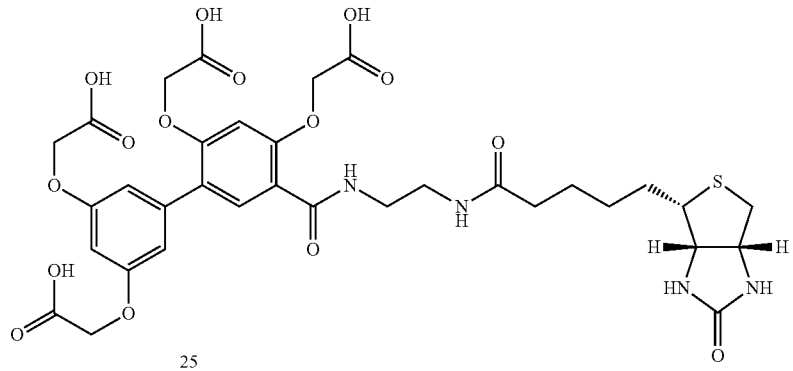

The title compound was prepared according to the method described for Preparation 1 using Preparation 28 and taken on directly to the next step.

LCMS Method A: Rt=1.52 mins, ES$^+$ MS m/z 465.3 [M+H]$^+$

Preparation 8

2-((2-((2-(5-((3aS,4S,6aR)-2-Oxohexahydro-1H-thieno[3,4-d]imidazol-4-yl)pentanamido)ethyl)carbamoyl)quinolin-4-yl)oxy)acetic acid

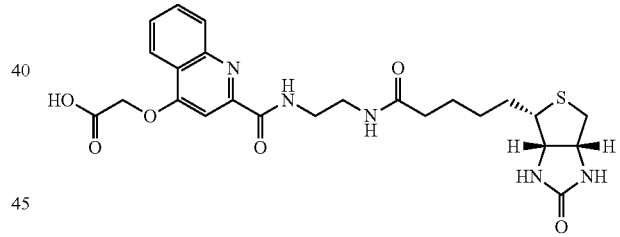

The title compound was prepared according to the method described for Preparation 1 using Preparation 32.

LCMS Method E: Rt=2.99 mins, ES$^+$ MS m/z 516.0 [M+H]$^+$

Preparation 9

2-((3'-((2-(5-((3aS,4S,6aR)-2-Oxohexahydro-1H-thieno[3,4-d]imidazol-4-yl)pentanamido)ethyl)carbamoyl)-[1,1'-biphenyl]-4-yl)oxy)acetic acid

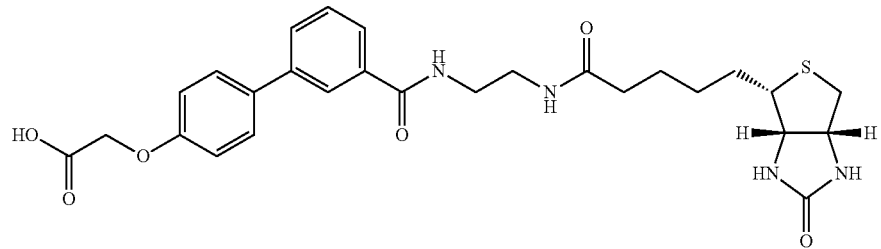 [SMILES: O=C(O)COc1ccc(-c2cccc(C(=O)NCCNC(=O)CCCC[C@@H]3SC[C@@H]4NC(=O)N[C@@H]43)c2)cc1]

The title compound was prepared according to the method described for Preparation 1 using Preparation 33.

LCMS Method E: Rt=3.00 mins, ES+ MS m/z 541.0 [M+H]+

Preparation 10

2-(3-{[2-(1-{5-[(3aS,4S,6aR)-2-Oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}-5-(carboxymethoxy)phenoxy)acetic acid

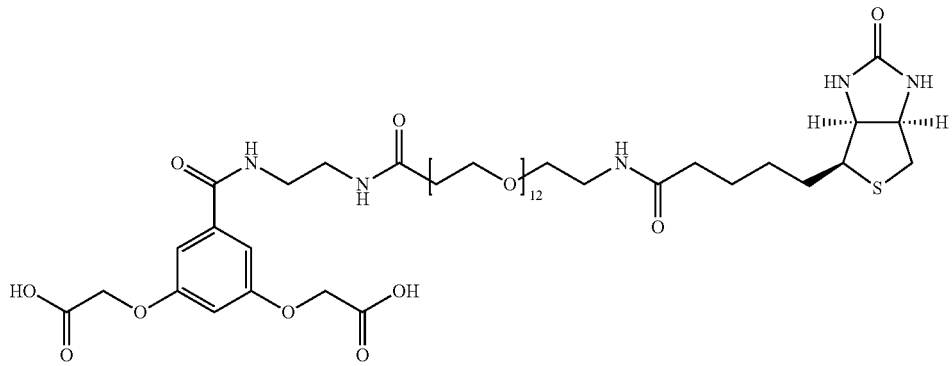

To a solution of ethyl 2-(3-{[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}-5-(2-ethoxy-2-oxoethoxy)phenoxy)acetate in MeOH/water (Preparation 23, 1:1 v/v, 1 mL, 10.0 µmol) was added 2M aqueous NaOH (30 µL, 60 µmol) and the reaction was stirred at room temperature for 1 hour. The reaction was acidified with 2M aqueous HCl and concentrated in vacuo. The residue was azeotroped with toluene (3×4 mL) to afford the title compound as a cream solid that was used directly in the next step.

LCMS Method B: Rt=1.58 mins, ES+ MS m/z 1139.1 [M+H]+

Preparation 11

2-(3-((2-(5-((3aS,4S,6aR)-2-Oxohexahydro-1H-thieno[3,4-d]imidazol-4-yl)pentanamido)ethyl)carbamoyl)phenoxy)acetic acid

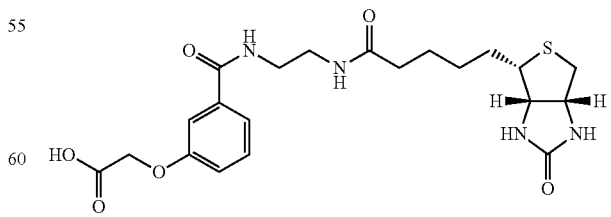

The title compound was prepared according to the method described for Preparation 10 using Preparation 19.

LCMS Method A: Rt=1.71 mins, ES+ MS m/z 465.2 [M+H]+

Preparation 12

2-(3-{[2-(1-{5-[(3aS,4S,6aR)-2-Oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}phenoxy)acetic acid

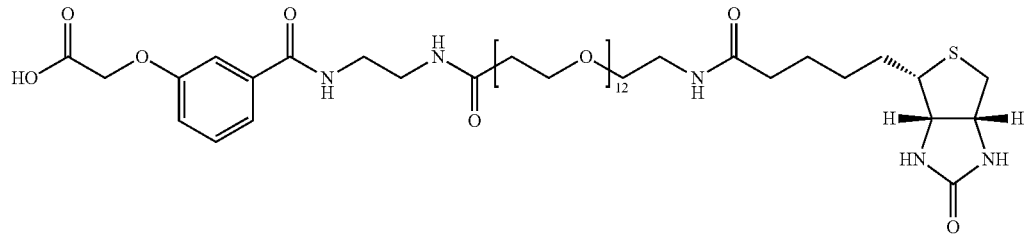

The title compound was prepared according to the method described for Preparation 10 using Preparation 20.
LCMS Method A: Rt=1.89 mins, ES$^+$ MS m/z 1062.8 [M+H]$^+$

Preparation 13

2,2'-((5-((2-(5-((3aS,4S,6aR)-2-Oxohexahydro-1H-thieno[3,4-d]imidazol-4-yl)pentanamido)ethyl)carbamoyl)-1,3-phenylene)bis(oxy))diacetic acid

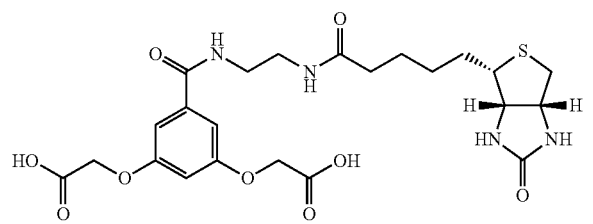 [SMILES: O=C(O)COc1cc(OCC(=O)O)cc(C(=O)NCCNC(=O)CCCC[C@@H]2SC[C@@H]3NC(=O)N[C@@H]32)c1]

The title compound was prepared according to the method described for Preparation 10 using Preparation 22 and taken on directly to the next step.

Preparation 14

2,5-Dioxopyrrolidin-1-yl 6-oxo-6-((3-((2-(5-((3aS,4S,6aR)-2-oxohexahydro-1H-thieno[3,4-d]imidazol-4-yl)pentanamido)ethyl)carbamoyl)benzyl)amino)hexanoate

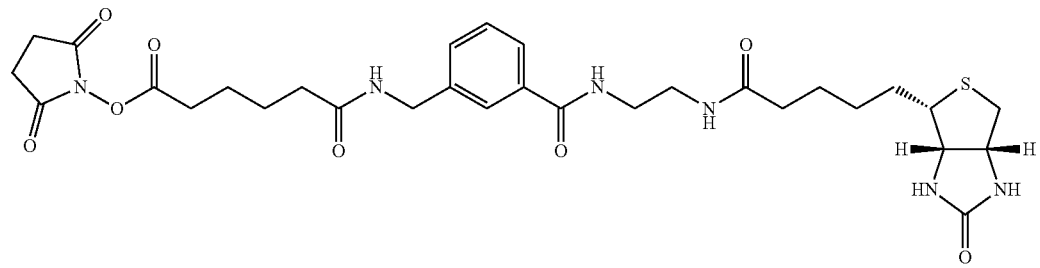 [SMILES: O=C(CCCC[C@@H]1SC[C@@H]2NC(=O)N[C@@H]21)NCCNC(=O)c1cccc(CNC(=O)CCCCC(=O)ON2C(=O)CCC2=O)c1]

To a suspension of di(N-succinimidyl)adipate (Preparation 34, 187 mg, 0.55 mmol) in dimethylformamide (4 mL) and chloroform (4 mL) was added 6-(3-(2-(5-((3aS,4S,6aR)-2-oxohexahydro-1H-thieno[3,4-d]imidazol-4-yl)pentanamido)ethyl)carbamoyl)benzylamine (Preparation 48, 50 mg, 0.11 mmol) and triethylamine (0.016 mL, 0.12 mmol) and the reaction mixture was stirred at room temperature for 20 hours. The reaction was concentrated in vacuo and purified using silica gel column chromatography eluting with 2.5-25% methanol in dichloromethane. The resulting solid was triturated with DCM and filtered to afford the title compound as a white solid (27 mg, 38%). Taken on directly to the next step.

Preparation 15

2-(3-((6-Oxo-6-((2-(5-((3aS,4S,6aR)-2-oxohexahydro-1H-thieno[3,4-d]imidazol-4-yl)pentanamido)ethyl)amino)hexanamido)methyl)phenoxy)acetic acid

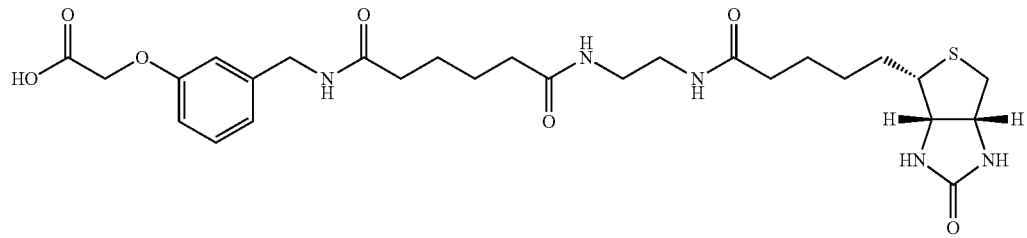 [SMILES: O=C(O)COc1cccc(CNC(=O)CCCCC(=O)NCCNC(=O)CCCC[C@@H]2SC[C@@H]3NC(=O)N[C@@H]32)c1]

To a solution of methyl 2-(3-((6-oxo-6-((2-(5-((3aS,4S,6aR)-2-oxohexahydro-1H-thieno[3,4-d]imidazol-4-yl)pentanamido)ethyl)amino)hexanamido)methyl) phenoxy)acetate (Preparation 38, 35 mg, 0.06 mmol) dissolved in MeOH (1 mL), THF (2 mL) and water (1 mL) was added LiOH monohydrate (5 mg, 0.1 mmol). The reaction was stirred at room temperature for 6 hours before concentrating in vacuo. The residue was acidified by the addition of 1M HCl and concentrated in vacuo to afford the title compound (17 mg, 59%), that was taken on directly to the next step.

LCMS Method E: Rt=3.02 mins, ES$^+$ MS m/z 578 [M+H]$^+$

Preparation 16

3',5-Bis(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid

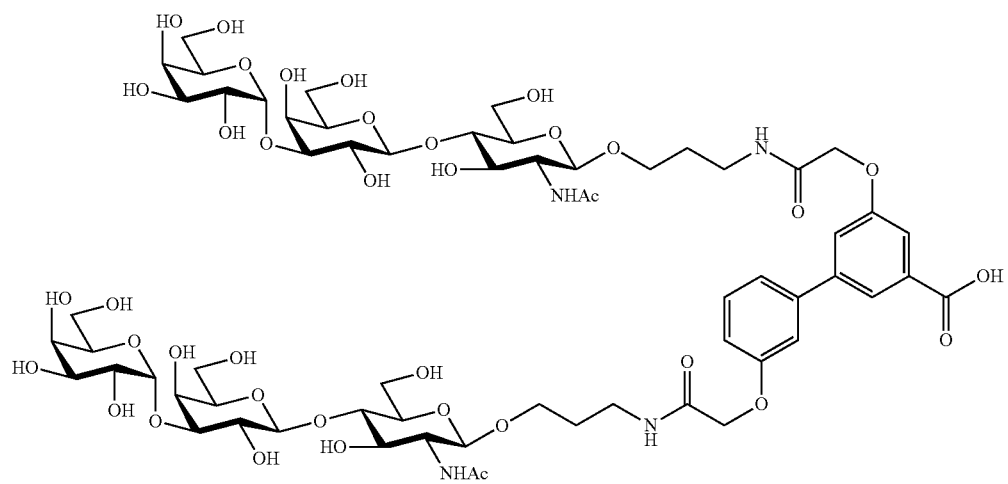

To benzyl 3',5-bis(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate (Preparation 36, 34 mg, 21.2 μmol) dissolved in IMS (3.4 mL) was added 10% Pd/C (3.40 mg). The reaction was put under an atmosphere of hydrogen (50 psi) and stirred for 3 hours at room temperature. The catalyst was removed by filtration using a syringe filter and concentrated in vacuo to afford the title compound as a colourless solid (33 mg, >99%).

LCMS Method A: Rt=1.53 mins, ES$^+$ MS m/z 757.0 [M+2H]$^+$/2, theoretical mass: 1512.4

Preparation 17

3',5-Bis(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid

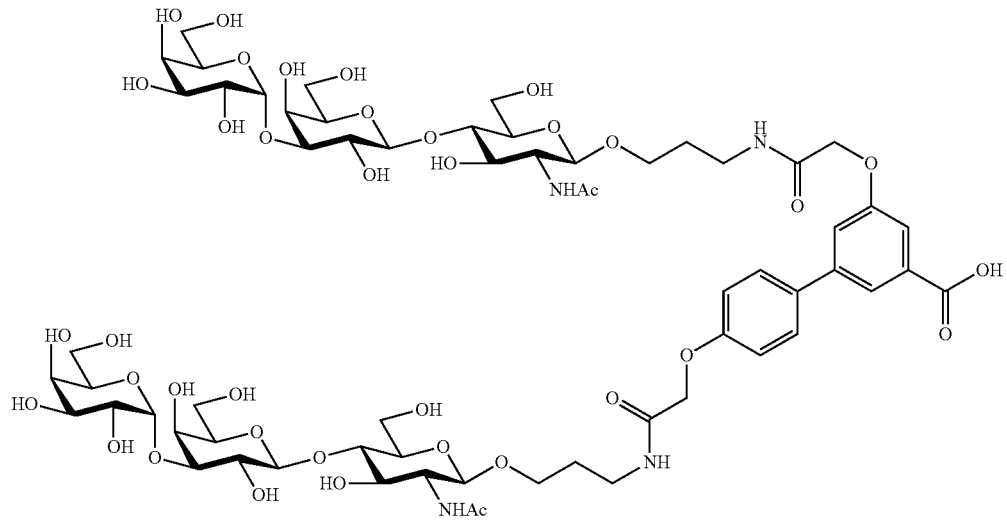

To benzyl 4',5-bis(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate (Preparation 49, 73.0 mg, 45.5 µmol) dissolved in MeOH/water (1:1 v/v, 10 mL) was added 10% Pd/C (20 mg). The reaction was put under an atmosphere of hydrogen (70 psi) and stirred for 3 hours at room temperature. The catalyst was removed by filtration through Dicalite and concentrated in vacuo. The residue was purified using reverse phase column chromatography (Biotage SP1, 4 g, C-18 column, eluting with 2-30% MeCN/water with 0.1% NH$_3$) to afford the title compound as a colourless solid (64.1 mg, 93%).

LCMS Method A: Rt=1.32 mins, ES$^+$ MS m/z 1513.5 [M+H]$^+$

Preparation 18

1-[2-(4-{3-[(2-{5-[(3aS,4S,6aR)-2-Oxo-hexahydro-1H-thieno[3,4-d]imidazolidin-4-yl]pentanamido}ethyl)carbamoyl]-5-{[(14-carboxy-3,6,9,12-tetraoxatetradecan-1-yl)carbamoyl]methoxy}phenyl}phenoxy)acetamido]-3,6,9,12-tetraoxapentadecan-15-oic acid

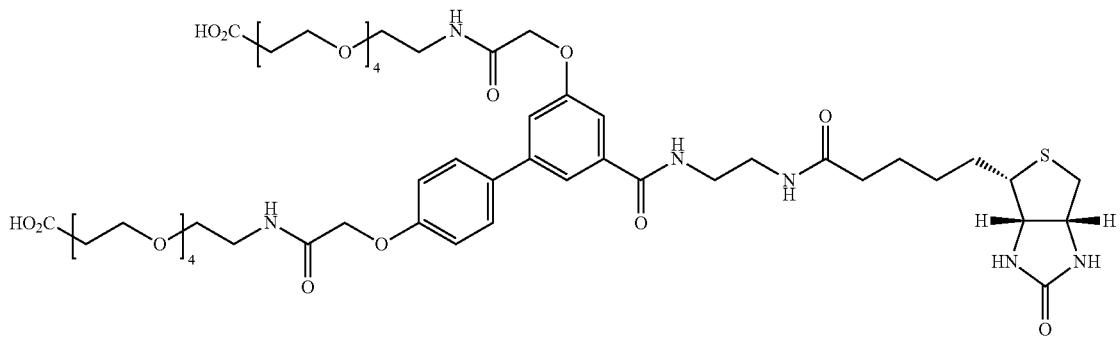

The title compound was prepared according to the method described for Preparation 1 using tert-butyl 1-[2-(4-{3-[(2-{5-[(3aS,4S,6aR)-2-oxo-hexahydro-1H-thieno[3,4-d]imidazolidin-4-yl]pentanamido}ethyl)carbamoyl]-5-({[15-(tert-butoxy)-15-oxo-3,6,9,12-tetraoxapentadecan-1-yl]carbamoyl}methoxy)phenyl}phenoxy)acetamido]-3,6,9,12-tetraoxapentadecan-15-oate (Preparation 25, 10.0 mg, 5.7 μmol).

LCMS Method B: Rt=1.93 mins, ES⁻ MS m/z 1108.2 [M−H]⁻

Preparation 19

Ethyl 2-(3-((2-(5-((3aS,4S,6aR)-2-oxohexahydro-1H-thieno[3,4-d]imidazol-4-yl)pentanamido)ethyl)carbamoyl)phenoxy)acetate

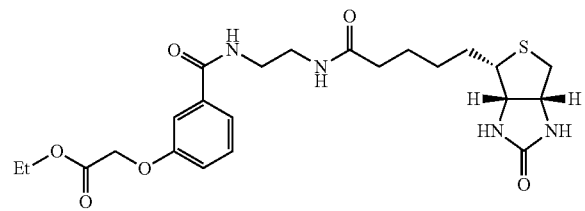 [SMILES: CCOC(=O)COc1cccc(C(=O)NCCNC(=O)CCCC[C@@H]2SC[C@@H]3NC(=O)N[C@@H]32)c1]

To ethyl 2-(3-((2-aminoethyl)carbamoyl)phenoxy)acetate trifluroacetic acid salt (Preparation 50, 87.0 mg, 229 μmol) dissolved in DMF (1 mL) was added 2,5-dioxopyrrolidin-1-yl 5-((3aS,4S,6aR)-2-oxohexahydro-1H-thieno[3,4-d]imidazol-4-yl)pentanoate (85.9 mg, 252 μmol) and TEA (95.7 μL, 686 μmol). The reaction was stirred at room temperature for 1 hour before concentrating in vacuo. The residue was dissolved in DMF (1 mL) and NH₄OH (2 drops) was added with stirring at room temperature for 10 minutes. The resulting precipitate was filtered, and washed with DMF (2×2 mL). The combined organic extracts were concentrated in vacuo and the residue was purified by silica gel column chromatography eluting with 5-15% MeOH in DCM to afford the title compound as a colourless glass (47.5 mg, 42%).

LCMS Method A: Rt=2.03 mins, ES⁺ MS m/z 493.4 [M+H]⁺

¹H NMR (400 MHz, DMSO-d₆): δ ppm 8.50 (1H, t), 7.95 (1H, t), 7.45-7.35 (3H, m), 7.10 (1H, dd), 6.40 (1H, s), 6.35 (1H, s), 5.75 (1H, s), 4.85 (2H, s), 4.30-4.25 (1H, m), 4.15 (2H, q), 4.10-4.05 (1H, m), 3.25-3.15 (2H, m), 3.10-3.05 (1H, m), 2.80 (1H, dd), 2.60-2.55 (1H, m), 2.10-2.05 (3H, m), 1.65-1.55 (1H, m), 1.55-1.40 (3H, m), 1.35-1.25 (2H, m), 1.20 (3H, t).

Preparation 20

Ethyl 2-(3-{[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}phenoxy)acetate

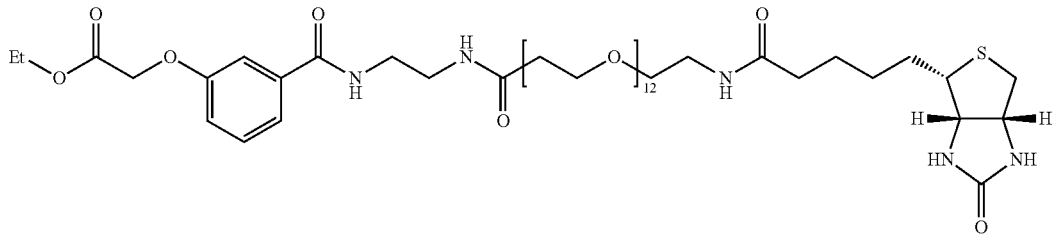

The title compound was prepared according to the method described by Example 1 using ethyl 2-(3-((2-aminoethyl)carbamoyl)phenoxy)acetate trifluroacetic acid salt (Preparation 50, 87.0 mg, 229 μmol) and 2,5-dioxopyrrolidin-1-yl 1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-oate (35.0 mg, 37.0 μmol) and isolated as a colourless oil (29.2 mg, 66%).

LCMS Method A: Rt=2.11 mins, ES⁺ MS m/z 1092.9 [M+H]⁺

Preparation 21 tert-Butyl 1-[2-(3-{[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}phenoxy)acetamido]-3,6,9,12-tetraoxapentadecan-15-oate

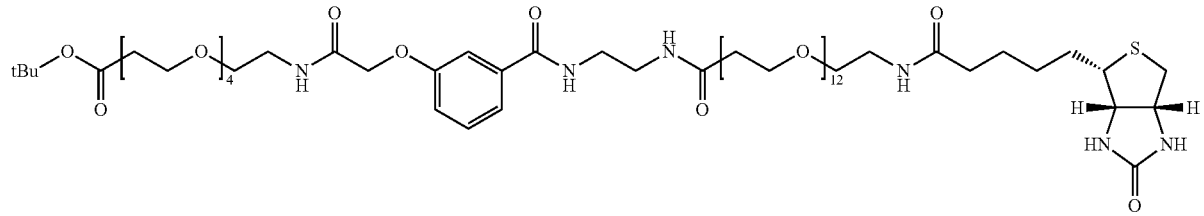

The title compound was prepared according to the method described for Example 1 using 2-(3-{[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}phenoxy)acetic acid in DMF (Preparation 12, 500 µL, 17.4 µmol) and tert-butyl 1-amino-3,6,9,12-tetraoxapentadecan-15-oate (5.3 µL, 17.4 µmol) and isolated as a colourless oil (14.5 mg, 61%).

LCMS Method A: Rt=2.26 mins, ES⁻ MS m/z 1366.3 [M−H]⁻

Preparation 22

Diethyl 2,2'-((5-((2-(5-(((3aS,4S,6aR)-2-oxohexahydro-1H-thieno[3,4-d]imidazol-4-yl)pentanamido)ethyl)carbamoyl)-1,3-phenylene)bis(oxy))diacetate

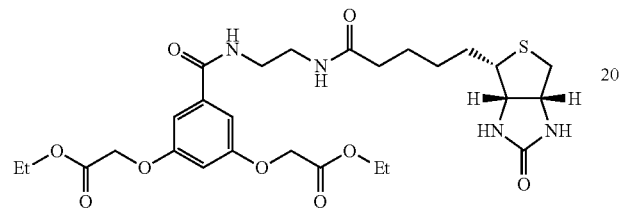

The title compound was prepared according to the method described for Example 1 using ethyl 2-{3-[(2-aminoethyl)carbamoyl]-5-(2-ethoxy-2-oxoethoxy)phenoxy}acetate trifluoroacetic acid salt (146 mg, 426 µmol) and 2,5-dioxopyrrolidin-1-yl 5-((3aS,4S,6aR)-2-oxohexahydro-1H-thieno[3,4-d]imidazol-4-yl)pentanoate (Preparation 64) and isolated as a colourless film (117 mg, 46%).

LCMS Method B: Rt=2.23 mins, ES⁺ MS m/z 595.2 [M+H]⁺

Preparation 23

Ethyl 2-(3-{[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}-5-(2-ethoxy-2-oxoethoxy)phenoxy)acetate

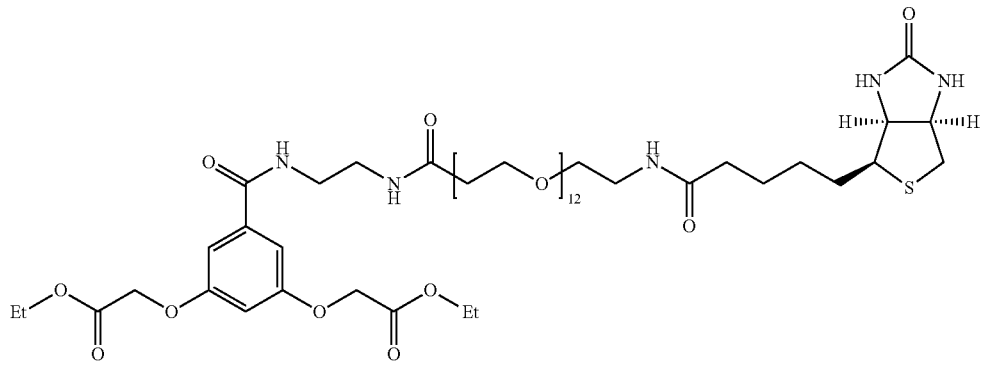

The title compound was prepared according to the method described for Example 1 using ethyl 2-{3-[(2-aminoethyl)carbamoyl]-5-(2-ethoxy-2-oxoethoxy)phenoxy}acetate trifluoroacetic acid salt (Preparation 64, 41.2 mg, 85.0 µmol) and 2,5-dioxopyrrolidin-1-yl 1-{5-[(3aS,4S,6aR)-2-oxohexahydro-1H-thieno[3,4-d]imidazolidin-4-yl]pentanamido}-3,6,9,12,15,18,21,24,27,30,33,36-dodecaoxanonatriacontan-39-oate. The reaction was concentrated in vacuo and purified using reverse phase column chromatography (Biotage SP1, 12 g, C-18 column, eluting with 2-25% MeCN/water with 0.1% NH₃) to afford the title compound as a clear oil (55 mg, 60%), that was dissolved in MeOH/H₂O (1:1 v/v, 4.6 mL) to make a stock solution for the next step.

LCMS Method B: Rt=2.26 mins, ES⁺ MS m/z 1195.1 [M+H]⁺

Preparation 24

Di-tert-butyl 2,2'-((5-((2-(5-((3aS,4S,6aR)-2-oxo-hexahydro-1H-thieno[3,4-d]imidazol-4-yl)pentana-mido)ethyl)carbamoyl)-[1,1'-biphenyl]-3,4'-diyl)bis(oxy))diacetate

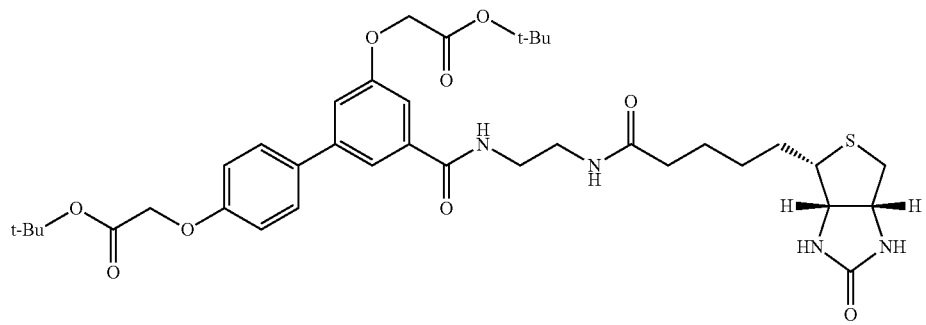 [SMILES: CC(C)(C)OC(=O)COc1ccc(-c2cc(OCC(=O)OC(C)(C)C)cc(C(=O)NCCNC(=O)CCCC[C@@H]3SC[C@@H]4NC(=O)N[C@@H]43)c2)cc1]

The title compound was prepared according to the method described by Example 1 using 4',5-bis(2-(tert-butoxy)-2-oxoethoxy)-[1,1'-biphenyl]-3-carboxylic acid (Preparation 63, 174 mg, 378 μmol) and N-(2-aminoethyl)-5-((3aS,4S,6aR)-2-oxohexahydro-1H-thieno[3,4-d]imidazol-4-yl)pentanamide (163 mg, 568 μmol) and isolated as a colourless solid (181 mg, 66%).

LCMS Method A: Rt=3.03 mins, ES$^+$ MS m/z 728.4 [M+H]$^+$ $^1$H NMR (400 MHz, DMSO-d$_6$): δ ppm 7.75-7.70 (1H, m), 7.65-7.60 (2H, m), 7.35-7.30 (2H, m), 7.05-7.00 (2H, m), 4.75 (2H, s), 4.65 (2H, s), 4.40 (1H, dd), 4.15 (1H, dd), 3.55-3.45 (4H, m), 3.35-3.30 (2H, m) 3.05-3.00 (1H, m), 2.85-2.80 (1H, m), 2.65-2.60 (1H, m), 2.30, (1H, s), 2.20 (2H, td), 1.65-1.60 (2H, m), 1.50 (18H, s), 1.50-1.45 (2H, m), 1.40-1.35 (3H, m).

Preparation 25

Tert-butyl 1-[2-(4-{3-[(2-{5-[(3aS,4S,6aR)-2-oxo-hexahydro-1H-thieno[3,4-d]imidazolidin-4-yl]pentanamido}ethyl)carbamoyl]-5-({[15-(tert-butoxy)-15-oxo-3,6,9,12-tetraoxapentadecan-1-yl]carbamoyl}methoxy)phenyl}phenoxy)acetamido]-3,6,9,12-tetraoxapentadecan-15-oate

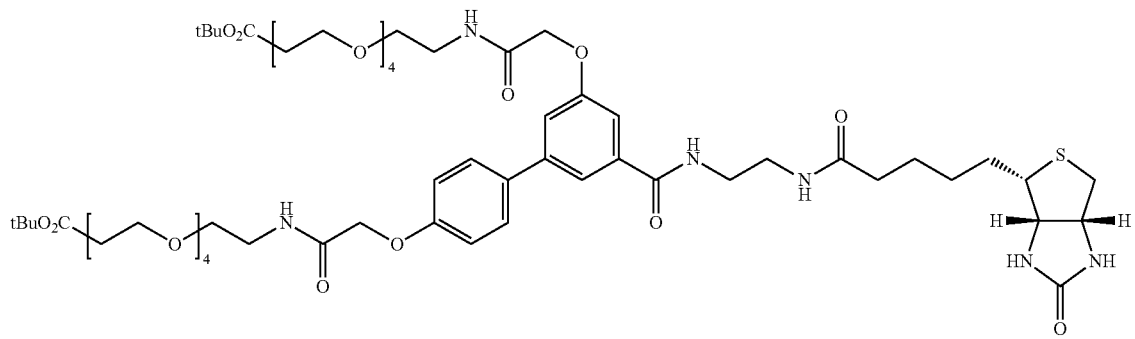

The title compound was prepared according to the method described for Example 1 using 2,2'-((5-((2-(5-((3aS,4S,6aR)-2-oxohexahydro-1H-thieno[3,4-d]imidazol-4-yl)pentanamido)ethyl)carbamoyl)-[1,1'-biphenyl]-3,4'-diyl)bis(oxy))diacetic acid (Preparation 39, 20.0 mg, 32.6 μmol) and tert-butyl 1-amino-3,6,9,12-tetraoxapentadecan-15-oate (24.7 μL, 81.5 μmol) and isolated as a colourless oil (21.8 mg, 55%).

LCMS Method A: Rt=2.70 mins, ES$^+$ MS m/z 1222.0 [M+H]$^+$

Preparation 26 tert-Butyl 2-(4-((2-(5-((3aS,4S,6aR)-2-oxohexa-hydro-1H-thieno[3,4-d]imidazol-4-yl)pentanamido)ethyl)carbamoyl)phenoxy)acetate

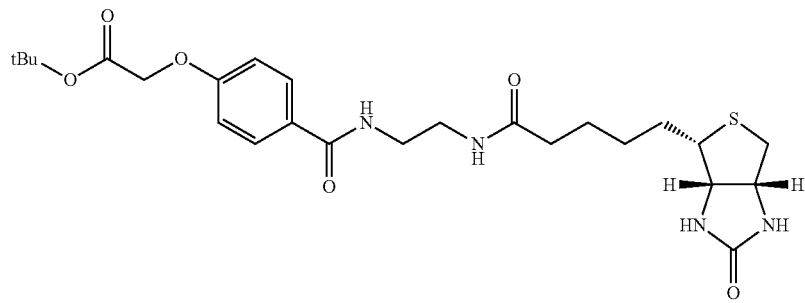 [SMILES: CC(C)(C)OC(=O)COc1ccc(C(=O)NCCNC(=O)CCCC[C@@H]2SC[C@@H]3NC(=O)N[C@@H]32)cc1]

The title compound was prepared according to the method described for Example 1 using 4-(2-(tert-butoxy)-2-oxoethoxy)benzoic acid (WO 2011/71570 A1, 137 mg, 543 µmol) and N-(2-aminoethyl)-5-((3aS,4S,6aR)-2-oxohexahydro-1H-thieno[3,4-d]imidazol-4-yl)pentanamide (155 mg, 543 µmol) and isolated as a colourless solid (205 mg, 72%).

LCMS Method B: Rt=2.30 mins, ES+ MS m/z 521.3 [M+H]+

Preparation 27 tert-Butyl 1-[2-(3-{[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dode-caoxanonatriacontan-39-amido)ethyl]carbamoyl}-5-({[15-(tert-butoxy)-15-oxo-3,6,9,12-tetraoxapentadecan-1-yl]carbamoyl}methoxy)phenoxy)acetamido]-3,6,9,12-tetraoxapentadecan-15-oate

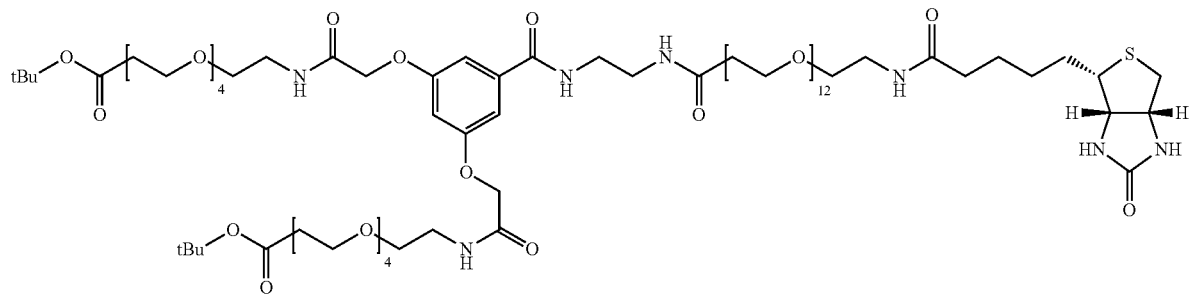

The title compound was prepared according to the method described for Example 1 using 2-(3-{[2-(1-{5-[(3aS,6aR)-2-oxo-hexahydro-1H-thieno[3,4-d]imidazolidin-4-yl]pentanamido}-3,6,9,12,15,18,21,24,27,30,33,36-dode-caoxanonatriacontan-39-amido)ethyl]carbamoyl}-5-(carboxymethoxy)phenoxy)acetic acid (Preparation 10, 19 mg, 15 µmol) and tert-butyl 1-amino-3,6,9,12-tetraoxapentadecan-15-oate (11.4 µL, 37.5 µmol) and isolated as a colourless oil (10.0 mg, 38%).

LCMS Method A: Rt=2.60 mins, ES+ MS m/z 1746.8 [M+H]+

Preparation 28

Tetra-tert-butyl 2,2',2'',2'''-((5-((2-(5-((3aS,4S,6aR)-2-oxohexahydro-1H-thieno[3,4-d]imidazol-4-yl)pentanamido)ethyl)carbamoyl)-[1,1'-biphenyl]-2,3',4,5'-tetrayl)tetrakis(oxy))tetraacetate

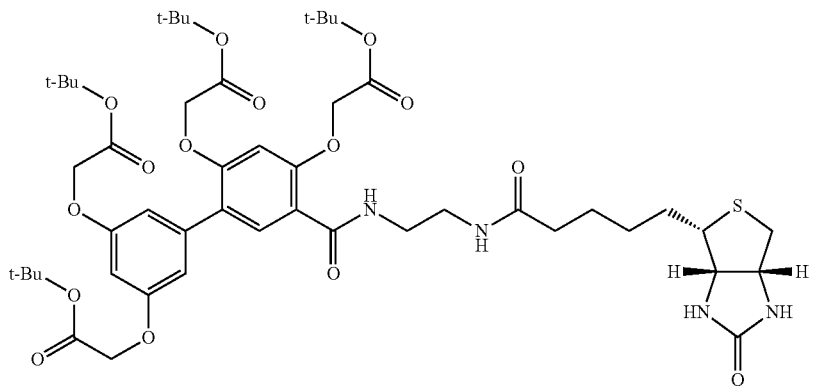 [SMILES: CC(C)(C)OC(=O)COc1cc(OCC(=O)OC(C)(C)C)cc(-c2cc(C(=O)NCCNC(=O)CCCC[C@@H]3SC[C@@H]4NC(=O)N[C@@H]43)c(OCC(=O)OC(C)(C)C)cc2OCC(=O)OC(C)(C)C)c1]

The title compound was prepared according to the method described for Example 1 using 3',4,5',6-tetrakis(2-(tert-butoxy)-2-oxoethoxy)-[1,1'-biphenyl]-3-carboxylic acid (Preparation 77, 130 mg, 177 μmol) and N-(2-aminoethyl)-5-((3aS,4S,6aR)-2-oxohexahydro-1H-thieno[3,4-d]imidazol-4-yl)pentanamide (50.7 mg, 177 μmol) and isolated as a colourless solid (81 mg, 46%).

LCMS Method B: Rt=3.61 mins, ES$^+$ MS m/z 987.8 [M+H]$^+$ $^1$H NMR (400 MHz, CDCl$_3$): δ ppm 8.70 (1H, t), 8.20 (1H, s), 7.10-7.05 (1H, m), 6.80 (2H, d), 6.45 (1H, s), 6.30 (1H, s), 5.80 (1H, s), 5.10 (1H, s), 4.60 (2H, s), 4.50 (4H, s), 4.45 (2H, s), 4.40-4.35 (1H, m), 4.20-4.15 (1H, m), 3.70-3.55 (1H, m), 3.55-3.40 (1H, m), 3.05-3.00 (1H, m), 2.80 (1H, dd), 2.60 (1H, d), 2.25-2.10 (2H, m), 1.70-1.55 (3H, m), 1.55 (9H, s), 1.50 (18H, s), 1.45 (9H, s), 1.40-1.30 (3H, m).

Preparation 29

Tri-tert-butyl-2,2',2''-((5'-((2-(5-((3aS,4S,6aR)-2-oxohexahydro-1H-thieno[3,4-d]imidazol-4-yl)pentanamido)ethyl)carbamoyl)-[1,1'-biphenyl]-3,3',5-triyl)tris(oxy))triacetate

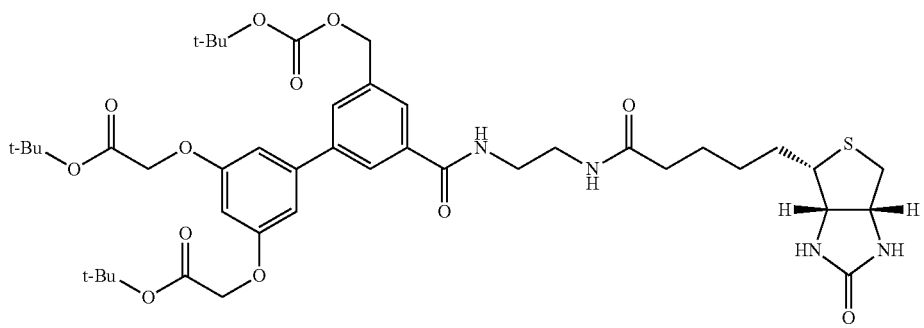 [SMILES: CC(C)(C)OC(=O)COc1cc(OCC(=O)OC(C)(C)C)cc(-c2cc(COC(=O)OC(C)(C)C)cc(C(=O)NCCNC(=O)CCCC[C@@H]3SC[C@@H]4NC(=O)N[C@@H]43)c2)c1]

The title compound was prepared according to the method described for Example 1 using 3',5,5'-tris(2-(tert-butoxy)-2-oxoethoxy)-[1,1'-biphenyl]-3-carboxylic acid (Preparation 71, 152 mg, 258 μmol) and N-(2-aminoethyl)-5-((3aS,4S,6aR)-2-oxohexahydro-1H-thieno[3,4-d]imidazol-4-yl)pentanamide (79.3 mg, 258 μmol) as a yellow film (166 mg, 75%). LCMS Method B: Rt=3.30 mins, ES$^+$ MS m/z 857.7 [M+H]$^+$ ¹H NMR (400 MHz, CDCl₃): δ ppm 8.00 (1H, t), 7.65 (1H, s), 7.40 (1H, s), 7.20 (1H, s), 6.90-6.85 (1H, m), 6.80 (2H, d), 6.45 (1H, t), 6.20 (1H, s), 5.45 (1H, s), 4.60 (2H, s), 4.50 (4H, s), 4.45-4.40 (1H, m), 4.20-4.15 (1H, m), 3.55 (2H, m), 3.50-3.40 (2H, m), 3.05-3.00 (1H, m), 2.80 (1H, dd), 2.60 (1H, d), 2.15 (2H, t), 1.70-1.55 (4H, m), 1.45 (27H, s), 1.30 (2H, s).

Preparation 30 tert-Butyl 1-(2-{3-[(2-{5-[(3aS,4S,6aR)-2-oxo-hexahydro-1H-thieno[3,4-d]imidazolidin-4-yl]pentanamido}ethyl)carbamoyl]-5-[3,5-bis({[15-(tert-butoxy)-15-oxo-3,6,9,12-tetraoxapentadecan-1-yl]carbamoyl}methoxy)phenyl]phenoxy}acetamido)-3,6,9,12-tetraoxapentadecan-15-oate

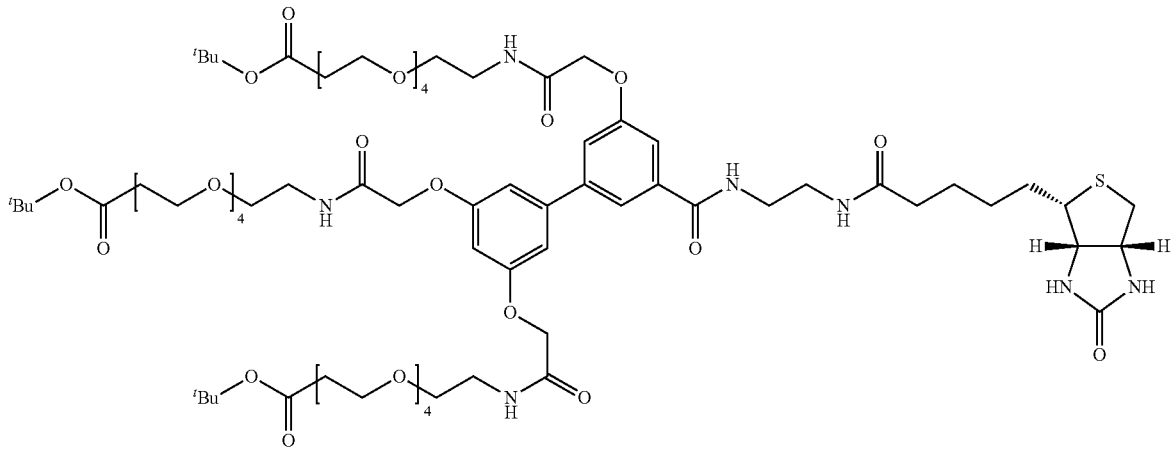

To 2-{3-[(2-{5-[(3aS,4S,6aR)-2-oxo-hexahydro-1H-thieno[3,4-d]imidazolidin-4-yl]pentanamido}ethyl)carbamoyl]-5-[3,5-bis(carboxymethoxy)phenyl]phenoxy}acetic acid (Preparation 5, 20.0 mg, 29.0 μmol) dissolved in DMF (500 μL) was added HATU (44.0 mg, 116 μmol) and DIPEA (40.5 μL, 232 μmol). After 1 minute tert-butyl 1-amino-3,6,9,12-tetraoxapentadecan-15-oate (35.0 μL, 116 μmol) was added and the reaction was stirred at room temperature under nitrogen for 3 hours. The reaction was concentrated in vacuo and purified using reverse phase column chromatography (Biotage SP1, 4 g, C-18 column, eluting with 5-40% MeCN in water with 0.1% NH₃) to afford the title compound as a colourless oil (30.9 mg, 67%).

LCMS Method B: Rt=2.96 mins, ES⁺ MS m/z 599.7 [M+H]⁺

Preparation 31

4-Hydroxy-N-(2-(5-((3aS,4S,6aR)-2-oxohexahydro-1H-thieno[3,4-d]imidazol-4-yl)pentanamido)ethyl)quinoline-2-carboxamide

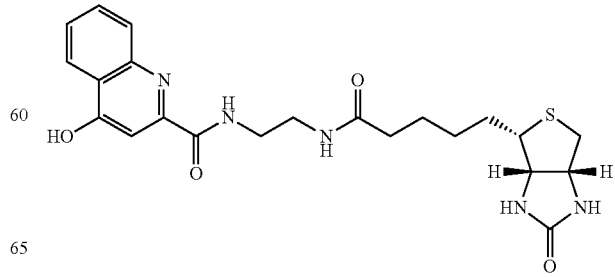

The title compound was prepared according to the method described for Example 1 using 4-hydroxyquinoline-2-carboxylic acid (200 mg, 1.06 mmol) and N-(2-aminoethyl)-5-((3aS,4S,6aR)-2-oxohexahydro-1H-thieno[3,4-d]imidazol-4-yl)pentanamide (303 mg, 1.06 mmol) and isolated as an off-white solid (196 mg, 40%). Taken on directly to the next step.

Preparation 32 tert-Butyl 2-((2-((2-(5-((3aS,4S,6aR)-2-oxohexahydro-1H-thieno[3,4-d]imidazol-4-yl)pentanamido)ethyl)carbamoyl)quinolin-4-yl)oxy)acetate

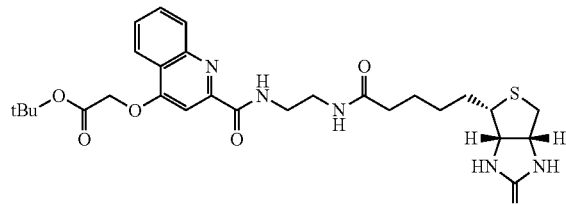

The title compound was prepared according to the method described for Preparation 57 using 4-hydroxy-N-(2-(5-((3aS,4S,6aR)-2-oxohexahydro-1H-thieno[3,4-d]imidazol-4-yl)pentanamido)ethyl)quinoline-2-carboxamide (Preparation 31,196 mg, 0.43 mmol) and isolated as a green solid (167 mg, 68%).

LCMS Method E: Rt=3.14 mins, ES+ MS m/z 572.0 [M+H]+

Preparation 33 tert-Butyl 2-((3'-((2-(5-((3aS,4S,6aR)-2-oxohexahydro-1H-thieno[3,4-d]imidazol-4-yl)pentanamido)ethyl)carbamoyl)-[1,1'-biphenyl]-4-yl)oxy)acetate

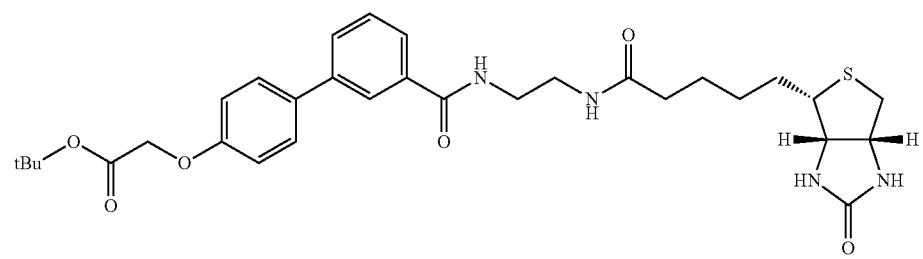 [SMILES: CC(C)(C)OC(=O)COc1ccc(-c2cccc(C(=O)NCCNC(=O)CCCC[C@@H]3SC[C@@H]4NC(=O)N[C@@H]43)c2)cc1]

The title compound was prepared according to the method described for Example 1 using 4'-(2-(tert-butoxy)-2-oxoethoxy)-[1,1'-biphenyl]-3-carboxylic acid (Preparation 60, 226 mg, 0.69 mmol) and N-(2-aminoethyl)-5-((3aS,4S,6aR)-2-oxohexahydro-1H-thieno[3,4-d]imidazol-4-yl)pentanamide (197 mg, 0.69 mmol) and isolated as a green solid (511 mg, >100%).

LCMS Method E: Rt=3.21 mins, ES+ MS m/z 597.0 [M+H]+

Preparation 34

Di(N-succinimidyl)adipate

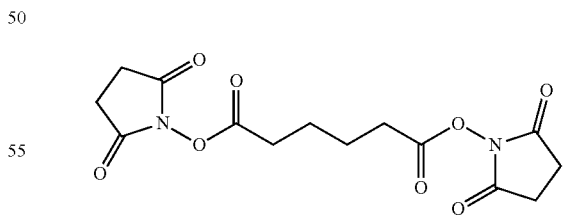

Trifluoroacetic anhydride (3.80 mL, 27.3 mmol) was added to a suspension containing adipic acid (2.0 g, 13.70 mmol), N-hydroxysuccinimide (3.15 g, 27.3 mmol) and pyridine (4.4 mL, 54.7 mmol) in chlorobenzene (17 mL) at 0° C. The reaction mixture was stirred for 15 minutes at 0° C. and then at room temperature for 20 hours. The product was filtered and washed with ethanol to afford a white solid. The solid was re-crystallised from acetonitrile to afford the title compound (2.45 g, 52%).

LCMS Method E: Rt=3.00 mins, ES+ MS m/z 341.0 [M+H]+

$^1$H NMR (400 MHz, DMSO-d$_6$): δ ppm 2.81 (8H, s), 2.77-2.70 (4H, m), 1.78-1.62 (4H, m).

Preparation 35

3-Formyl-N-(2-(5-((3aS,4S,6aR)-2-oxohexahydro-1H-thieno[3,4-d]imidazol-4-yl)pentanamido)ethyl)benzamide

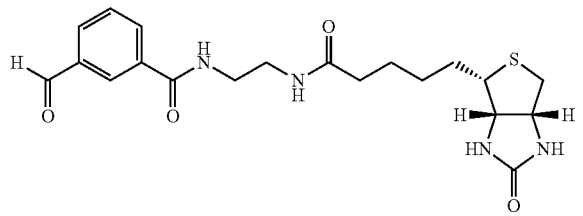 [SMILES: O=Cc1cccc(C(=O)NCCNC(=O)CCCC[C@@H]2SC[C@@H]3NC(=O)N[C@@H]32)c1]

The title compound was prepared according to the method described for Example 1 using 3-carboxybenzaldehyde (100 mg, 0.67 mmol) and N-(2-aminoethyl)-5-((3aS,4S,6aR)-2-oxohexahydro-1H-thieno[3,4-d]imidazol-4-yl)pentanamide (190 mg, 0.67 mmol) and isolated as a yellow solid (168 mg, 60%).

LCMS Method E: Rt=2.90 mins, ES+ MS m/z 419.0 [M+H]+

$^1$H NMR (400 MHz, DMSO-d$_6$): δ ppm 10.08 (1H, s), 8.74 (1H, t), 8.37 (1H, s), 8.15 (1H, dt), 8.07 (1H, dt), 7.94 (1H, t), 7.71 (1H, t), 6.42 (1H, s), 6.36 (1H, s), 4.30-4.28 (1H, m), 4.10-4.08 (1H, m), 3.26-3.24 (2H, m), 3.09-3.00 (1H, m), 2.85-2.75 (1H, dd), 2.62-2.50 (3H, m), 2.07 (2H, t), 1.67-1.18 (6H, m).

Preparation 36

Benzyl 3',5-bis(2-((3-(((2R,3R,4R,5S,6R)-3-acetamido-5-((((2S,3R,4S,5S,6R)-3,5-dihydroxy-6-(hydroxymethyl)-4-((((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate

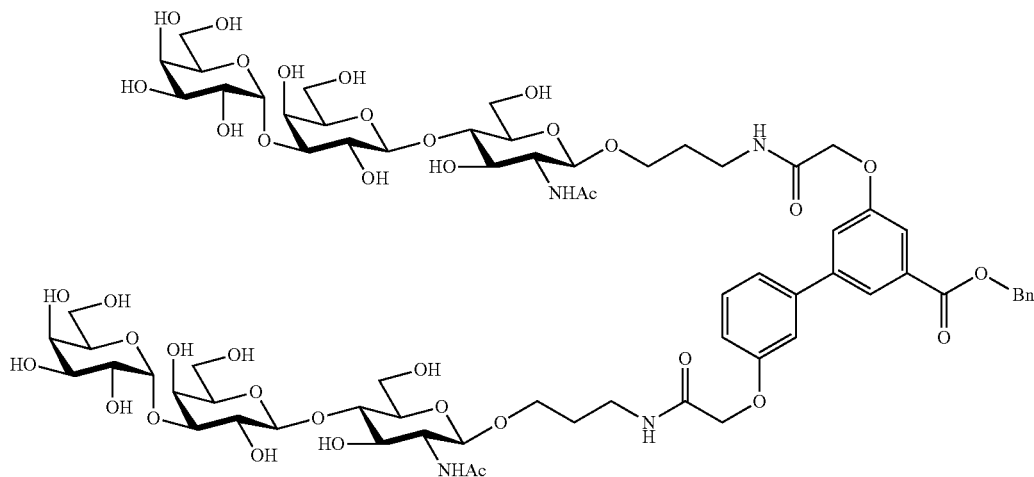

The title compound was prepared according to the method described for Example 1 using a solution of 2,2'-((5-((benzyloxy)carbonyl)-[1,1'-biphenyl]-3,3'-diyl)bis(oxy))diacetic acid (Preparation 61, 13.9 mg, 31.9 μmol) in DMF (2 mL) with triethylamine (26.7 μL, 191 μmol) and alpha-Gal (50 mg, 83 μmol) and isolated as a colourless solid (34 mg, 66%).

LCMS Method B: Rt=2.08 mins, ES+ MS m/z 1607.4 [M+H]+

Preparation 37

2,5-Dioxopyrrolidin-1-yl 6-((3-(2-methoxy-2-oxoethoxy)benzyl)amino)-6-oxohexanoate

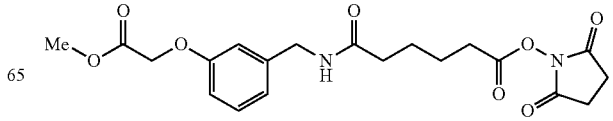

To a solution of di(N-succinimidyl)adipate (Preparation 34, 495 mg, 1.46 mmol) in DMF (32 mL) was added a solution of methyl 2-[3-(aminomethyl)phenoxy]acetate (90 mg, 0.29 mmol) and DIPEA (0.15 mL, 0.87 mmol) in chloroform (14.5 mL). The reaction mixture was stirred at room temperature for 3 hours, concentrated in vacuo and azeotroped with a mixture of toluene and acetonitrile. The residue was triturated several times with 1:1 acetonitrile:methanol followed by hexane and diethyl ether to afford the title compound as a brown oil (160 mg, >100%, contains 1 equivalent of diisopropylethylamine trifluoroacetate and 1 equivalent of N-hydroxysuccinimide).

$^1$H NMR (400 MHz, CDCl$_3$): δ ppm 7.25 (1H, t), 6.92 (1H, d), 6.84 (1H, br s), 6.80 (1H, dd), 4.64 (2H, s), 4.41 (2H, d), 3.81 (3H, s), 2.83 (4H, br s), 2.67-2.63 (2H, m), 2.32 (2H, t), 1.85-1.78 (4H, m).

Preparation 38

Methyl 2-(3-((6-oxo-6-((2-(5-((3aS,4S,6aR)-2-oxo-hexahydro-1H-thieno[3,4-d]imidazol-4-yl)pentanamido)ethyl)amino)hexanamido)methyl)phenoxy)acetate

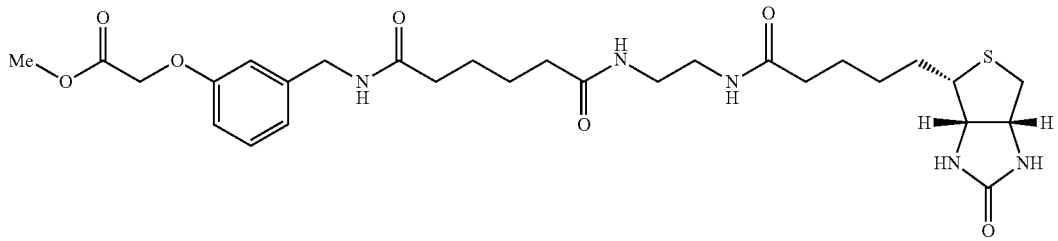 [SMILES: COC(=O)COc1cccc(CNC(=O)CCCCC(=O)NCCNC(=O)CCCC[C@@H]2SC[C@@H]3NC(=O)N[C@@H]32)c1]

To a solution of 2,5-dioxopyrrolidin-1-yl 6-((3-(2-methoxy-2-oxoethoxy)benzyl)amino)-6-oxohexanoate (Preparation 37, 160 mg, 0.29 mmol) in DMF (12 mL) was added a slurry of N-(2-aminoethyl)-5-((3aS,4S,6aR)-2-oxo-hexahydro-1H-thieno[3,4-d]imidazol-4-yl)pentanamide (83 mg, 0.29 mmol) in DMF (2 mL) and chloroform (2 mL) and the reaction mixture was stirred at room temperature for 20 hours. The reaction was concentrated in vacuo and purified using silica gel column chromatography eluting with 2-4% ammonium hydroxide in 0-20% methanol in dichloromethane to afford the title compound as an off-white solid (60 mg, 53%).

LCMS Method E: Rt=3.04 mins, ES$^+$ MS m/z 592.0 [M+H]$^+$

Preparation 39

2,2'-((5-((2-(5-((3aS,4S,6aR)-2-Oxohexahydro-1H-thieno[3,4-d]imidazol-4-yl)pentanamido)ethyl)carbamoyl)-[1,1'-biphenyl]-3,4'-diyl)bis(oxy))diacetic acid

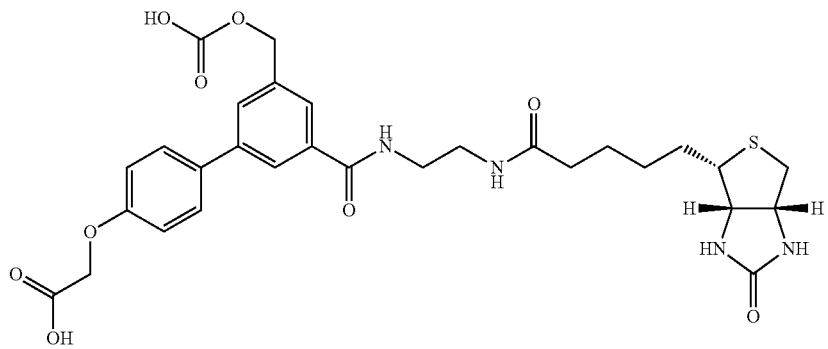 [SMILES: O=C(O)COc1ccc(-c2cc(COC(=O)O)cc(C(=O)NCCNC(=O)CCCC[C@@H]3SC[C@@H]4NC(=O)N[C@@H]43)c2)cc1]

The title compound was prepared according to the method described by Preparation 1 using di-tert-butyl 2,2'-((5-((2-(5-((3aS,4S,6aR)-2-oxohexahydro-1H-thieno[3,4-d]imidazol-4-yl)pentanamido)ethyl)carbamoyl)-[1,1'-biphenyl]-3,4'-diyl)bis(oxy))diacetate (Preparation 24, 181 mg, 249 µmol) and isolated as a colourless solid (147 mg, 96%).

LCMS Method A: Rt=1.77 mins, ES$^+$ MS m/z 615.4 [M+H]$^+$ $^1$H NMR (400 MHz, DMSO-d$_6$): δ ppm 8.60 (1H, t), 7.95 (1H, t), 7.70 (2H, d), 7.65 (1H, s), 7.30 (2H, dd) 7.05 (2H, d), 6.40 (2H, br s), 4.80 (2H, s), 4.75 (2H, s), 4.30 (1H, dd), 4.10 (1H, dd), 3.35-3.30 (2H, m), 3.25-3.20 (2H, m), 2.80 (1H, dd), 2.55 (1H, d), 2.05 (2H, t), 1.60-1.40 (4H, m), 1.35-1.25 (3H, m).

Preparation 40

Tert-butyl N-[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamate

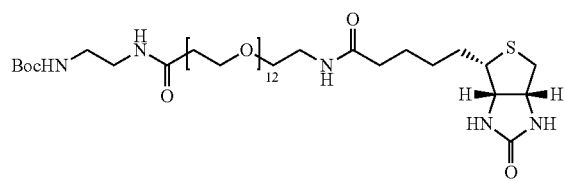

The title compound was prepared according to the method described by Example 1 using tert-butyl (2-aminoethyl)carbamate (11.9 mg, 74.4 μmol) and a solution of 2,5-dioxopyrrolidin-1-yl 1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-oate (70 mg, 70.4 μmol) in DMF and used directly in the next step.

Preparation 41

1-{5-[(3aS,4S,6aR)-2-Oxo-hexahydro-1H-thieno[3,4-d]imidazolidin-4-yl]pentanamido}-N-(2-aminoethyl)-3,6,9,12,15,18,21,24,27,30,33,36-dodecaoxanonatriacontan-39-amide hydrochloride

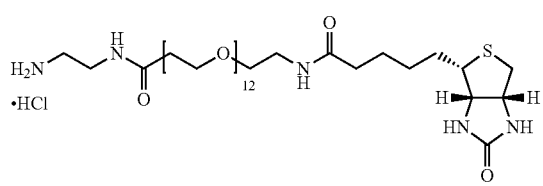

The title compound was prepared according to the method described by Preparation 48 using tert-butyl N-[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamate (Preparation 40, 79 mg, 70.4 μmol) and isolated as a colourless gum (39 mg, 56% over 2 steps).

LCMS Method B: Rt=1.64 mins, ES$^+$ MS m/z 886.8 [M+H]$^+$ $^1$H NMR (400 MHz, CD$_3$OD): δ ppm 4.50 (1H, s), 4.30 (1H, s), 3.70 (2H, t), 3.75-3.55 (48H, m), 3.50 (2H, t), 3.25-3.20 (1H, m), 2.90 (1H, dd), 2.80 (2H, t), 2.70 (1H, d), 2.45 (2H, t), 2.20 (2H, t), 1.80-1.55 (4H, m), 1.50-1.40 (2H, m).

Preparation 42

3',5,5'-Tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid

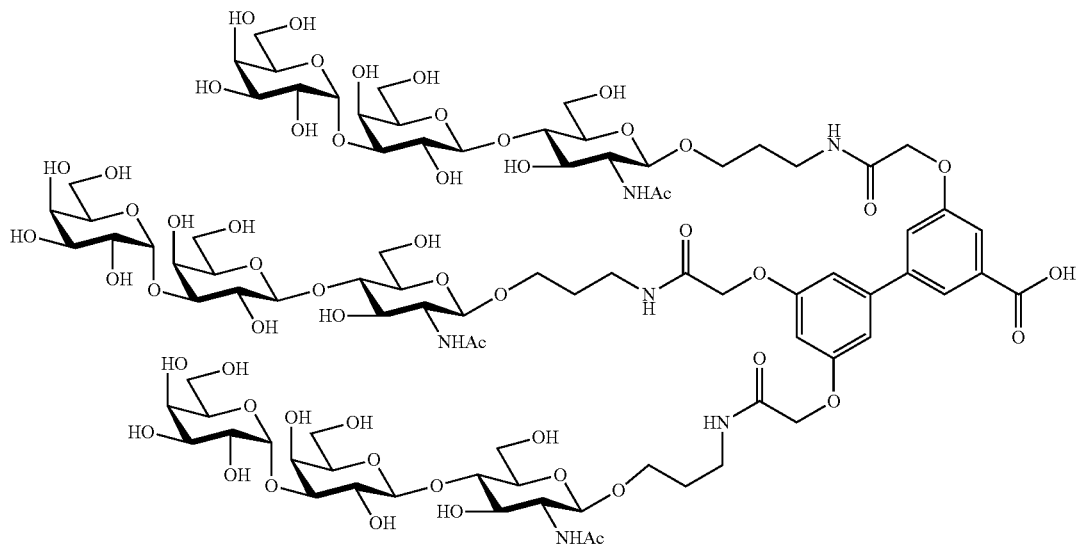

Method A

The title compound was prepared according to the method described by Preparation 16 using benzyl 3',5,5'-tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate (Preparation 43, 71.2 mg, 31.4 μmol) and isolated as a colourless solid (61.2 mg 89%).

LCMS Method B: Rt=1.27 mins, ES$^+$ MS m/z 1088.4 [M+2H]$^+$/2, theoretical mass: 2174.4

Preparation 42 may also be prepared according to the following Method:

Method B

To benzyl 3',5,5'-tris(2-((3-(((2R,3R,4R,5S,6R)-3-acet-amido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate (Preparation 43, 278 mg, 123 μmol) dissolved in water (7 mL) was added TEA (7 mL) and the reaction was stirred vigorously for 16 hours at room temperature. The reaction was concentrated in vacuo and purified using reverse phase column chromatography (Biotage Isolera, 30 g, C-18 column, eluting with 5-40% MeCN/water with 0.1% $NH_3$) to afford the title compound as a colourless solid (224 mg, 83%).

LCMS Method B: Rt=1.27 mins, 97%, $ES^+$ MS m/z 1088.4 $[M+2H]^+/2$, theoretical mass: 2174.4

Preparation 43

Benzyl 3',5,5'-tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate The title compound was prepared according to the method described by Example 1 using alpha-Gal (100 mg, 166 μmol) and 2,2',2''-((5'-((benzyloxy)carbonyl)-[1,1'-biphenyl]-3,3',5-triyl)tris(oxy))triacetic acid (Preparation 73, 21.2 mg, 41.5 μmol) and isolated as a colourless solid (71.2 mg, 76%).

LCMS Method B: Rt=1.80 mins, $ES^+$ MS m/z 1313.3 $[M+2H]^+/2$, theoretical mass: 2624.3

Preparation 44

Methyl 3-(2-oxo-2-((2-(5-((3aS,4S,6aR)-2-oxohexahydro-1H-thieno[3,4-d]imidazol-4-yl)pentanamido)ethyl)amino)ethoxy)benzoate

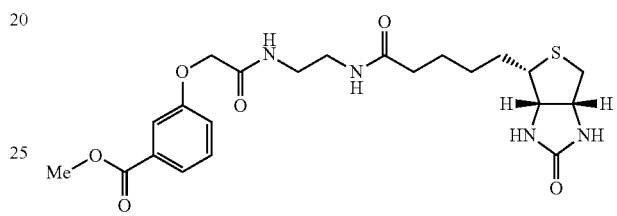

The title compound was prepared according to the method described by Example 1 using 2-(3-(methoxycarbonyl)phenoxy)acetic acid (Preparation 51, 100 mg, 475 μmol) and N-(2-aminoethyl)-5-((3aS,4S,6aR)-2-oxohexahydro-1H-thieno[3,4-d]imidazol-4-yl)pentanamide (136 mg, 475 μmol) and isolated as a colourless solid (135 mg, 59%).

LCMS Method B: Rt=1.98 mins, $ES^+$ MS m/z 479.3 $[M+H]^+$ $^1$H NMR (400 MHz, DMSO-$d_6$): δ ppm 8.20 (1H, t), 7.85 (1H, t), 7.60-7.55 (1H, m), 7.55-7.50 (1H, m), 7.45 (1H, t), 7.25-7.20 (1H, m), 6.40 (1H, s), 6.35 (1H, s), 4.50 (2H, s), 4.30-4.25 (1H, m), 4.10-4.05 (1H, m), 3.85 (3H, s), 3.20-3.10 (4H, m), 3.10-3.05 (1H, m), 2.80 (1H, dd), 2.55 (1H, d), 2.05 (2H, t), 1.65-1.50 (1H, m), 1.50-1.35 (3H, m), 1.30-1.20 (2H, m).

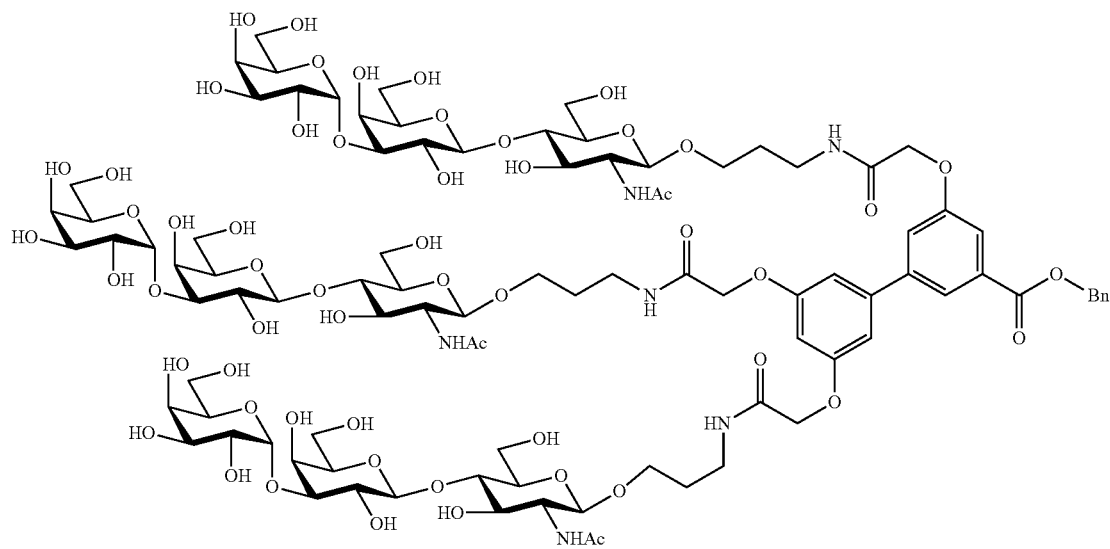

Preparation 45

Benzyl 3-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)benzoate

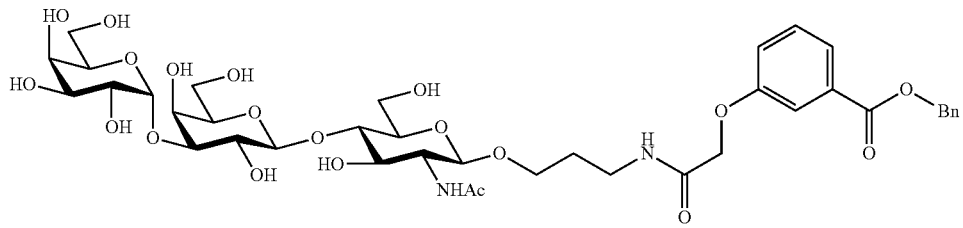

To alpha-Gal (50.0 mg, 83.0 µmol) dissolved in DMSO (250 µL) with DMF (2.5 mL) was added TEA (167 µL, 1.20 mmol) and 2-(3-((benzyloxy)carbonyl)phenoxy)acetic acid (Preparation 56, 68.6 mg, 240 µmol). A solution of HATU (137 mg, 360 µmol) in DMF (750 µL) was added and the reaction stirred at room temperature under nitrogen for 16 hours. The reaction was concentrated in vacuo and purified using reverse phase column chromatograhy (Biotage SP1, 12 g, C-18 column, eluting with 7-60% MeCN/water with 0.1% $NH_3$). The desired residue was freeze-dried and further purified (Biotage SP1, 12 g, C-18 column, eluting with 7-60% MeCN/water with 0.1% $NH_3$). The residue was freeze-dried to afford the title compound as a colourless solid (99 mg 47%).

LCMS Method B: Rt=2.22 mins, $ES^+$ MS m/z 871.6 $[M+H]^+$

Preparation 46

3-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)benzoic acid

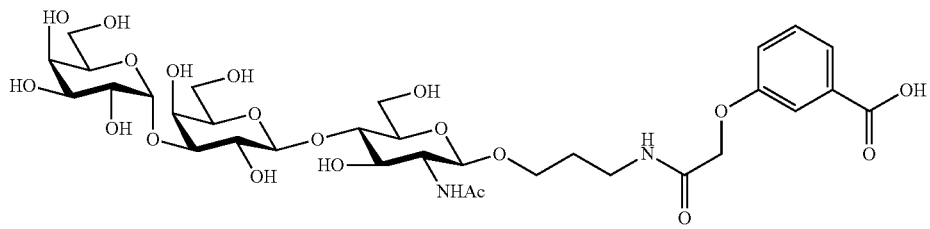

To benzyl 3-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)benzoate (Preparation 45, 99.0 mg, 113 µmol) dissolved in MeOH/water (1:1 v/v, 10 mL) was added 10% Pd/C (9.9 mg). The reaction was put under an atmosphere of hydrogen (50 psi) and stirred for 3 hours at room temperature. The reaction was filtered using a syringe filter and concentrated in vacuo to afford the title compound as a colourless solid (98 mg, 100%).

LCMS Method A: Rt=1.43 mins, $ES^+$ MS m/z 781.6 $[M+H]^+$

Preparation 47 tert-Butyl 3-((2-(5-((3aS,4S,6aR)-2-oxohexahydro-1H-thieno[3,4-d]imidazol-4-yl)pentanamido)ethyl)carbamoyl)benzylcarbamate

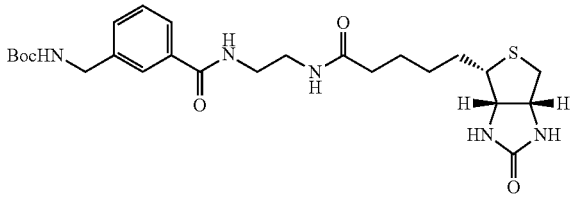 [SMILES: CC(C)(C)OC(=O)NCc1cccc(C(=O)NCCNC(=O)CCCC[C@@H]2SC[C@@H]3NC(=O)N[C@@H]32)c1]

To a solution of 3-(tert-butyloxycarbonyl-aminomethyl)benzoic acid (200 mg, 0.80 mmol) and HBTU (364 mg, 0.96 mmol) in DMF (16 mL) was added TEA (0.33 mL, 2.40 mmol) and N-(2-aminoethyl)-5-((3aS,4S,6aR)-2-oxohexahydro-1H-thieno[3,4-d]imidazol-4-yl)pentanamide (228 mg, 0.80 mmol) and the reaction mixture was stirred at room temperature for 20 hours.

The reaction was concentrated in vacuo and purified using silica gel column chromatography eluting with 5-10% MeOH in DCM to afford the title compound as a beige solid (360 mg, 84%).

LCMS Method E: Rt=2.98 mins, ES+ MS m/z 520.3 [M+H]+

$^1$H NMR (400 MHz, DMSO-$d_6$): δ ppm 8.47 (1H, t), 7.93 (1H, t), 7.71 (1H, br s), 7.68 (1H, d), 7.43 (1H, t), 7.42-7.36 (2H, m), 6.41 (1H, br s), 6.35 (1H, br s), 4.29 (1H, dd), 4.16 (2H, d), 4.09 (1H, ddd), 3.29 (2H, t), 3.21 (2H, t), 3.09-3.03 (1H, m), 2.80 (1H, dd), 2.56 (1H, d), 2.06 (2H, t), 1.64-1.43 (4H, m), 1.39 (9H, s), 1.33-1.26 (2H, m).

Preparation 48

3-(Aminomethyl)-N-(2-(5-((3aS,4S,6aR)-2-oxohexahydro-1H-thieno[3,4-d]imidazol-4-yl)pentanamido)ethyl)benzamide hydrochloride salt

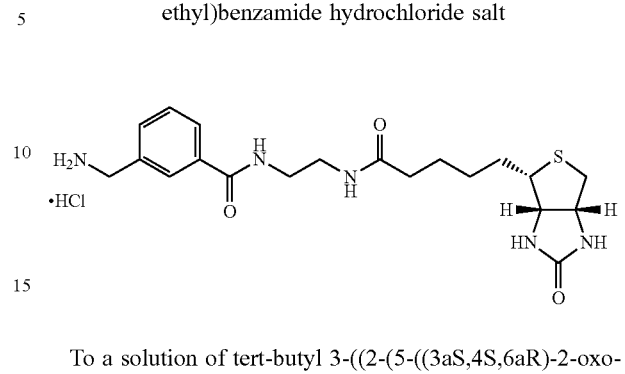

To a solution of tert-butyl 3-((2-(5-((3aS,4S,6aR)-2-oxohexahydro-1H-thieno[3,4-d]imidazol-4-yl)pentanamido)ethyl)carbamoyl)benzylcarbamate (Preparation 47, 355 mg, 0.68 mmol) in dioxane (2.7 mL) and MeOH (2.7 mL) was added 4M HCl in dioxane (0.85 mL, 3.40 mmol) and the reaction mixture was stirred at room temperature for 20 hours. The reaction was concentrated in vacuo. The resulting solid was triturated with DCM, MeOH and TBME, and dried at 50° C. under vacuum for 3 hours to afford the title compound as a white solid (378 mg, 53%).

LCMS Method A: Rt=2.28 mins, ES+ MS m/z 420.5 [M+H]+

$^1$H NMR (400 MHz, DMSO-$d_6$): δ ppm 8.63 (1H, t), 8.50 (3H, br s), 8.06 (1H, t), 8.04 (1H, s), 7.85 (1H, d), 7.64 (1H, d), 7.49 (1H, t), 4.29 (1H, dd), 4.10 (2H, dd), 4.06 (2H, q), 3.30-3.28 (2H, m), 3.22-3.20 (2H, m), 3.10-3.05 (1H, m), 2.80 (1H, dd), 2.57 (1H, d), 2.08 (2H, t), 1.64-1.39 (4H, m), 1.37-1.24 (2H, m).

Preparation 49

Benzyl 4',5-bis(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate

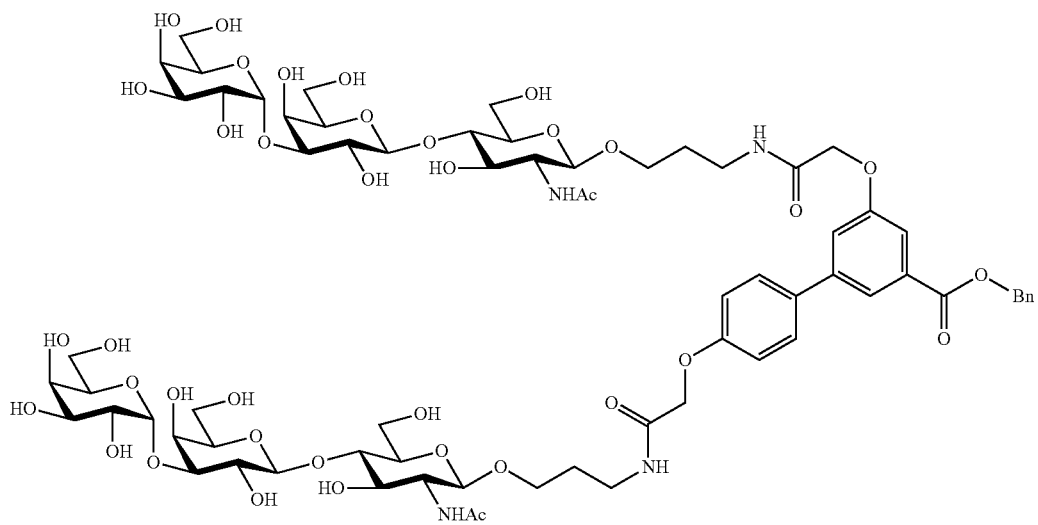

To alpha-Gal (109 mg, 182 μmol) dissolved in DMSO (500 μL) with DMF (7 mL) was added DIPEA (76.0 μL, 437 μmol) and 2,2'-((5-((benzyloxy)carbonyl)-[1,1'-biphenyl]-3,4'-diyl)bis(oxy))diacetic acid (Preparation 62, 31.8 mg, 72.9 μmol). HATU (82.9 mg, 219 μmol) was added as a solution in DMF (500 μL) was added and the reaction stirred for 2 hours at room temperature under nitrogen. The reaction was concentrated in vacuo and purified using reverse phase column chromatography (Biotage SP1, 12 g, C-18 column, eluting with 5-40% MeCN in water with 0.1% NH$_3$) to afford the title compound as a colourless solid (73.0 mg, 62%).

LCMS Method B: Rt=2.03 mins, ES$^+$ MS m/z 1606.6 [M+H]$^+$

The following Preparations describe the methods used to prepare the linker molecules key to the presentation of one or more F groups.

Preparations to Enable One F Group

Preparation 50

Ethyl 2-(3-((2-aminoethyl)carbamoyl)phenoxy)acetate trifluroacetic acid salt

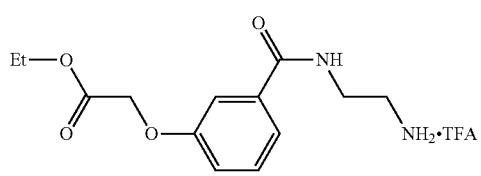

Ethyl 2-(3-((2-((tert-butoxycarbonyl)amino)ethyl)carbamoyl)phenoxy)acetate (Preparation 54, 100 mg, 273 μmol) dissolved in DCM (1 mL) was added TFA (209 μL, 2.73 mmol). The reaction was stirred at room temperature for 1 hour. The reaction was concentrated in vacuo and azeotroped with toluene/dioxane (1:1 v/v, 2×1 mL) to afford the title compound as a gum (107 mg, >99%).

LCMS Method A: Rt=1.70 mins, ES$^+$ MS m/z 267.2 [M+H]$^+$ $^1$H NMR (400 MHz, CD$_3$OD): δ ppm 8.70 (1H, m), 7.50-7.40 (3H, m), 7.15 (1H, dd), 4.80 (2H, s), 4.25 (2H, q), 3.70-3.65 (4H, m), 3.20 (2H, t), 1.30 (3H, t).

Preparation 51

2-(3-(Methoxycarbonyl)phenoxy)acetic acid

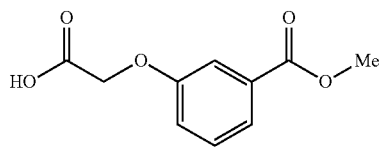 [SMILES: COC(=O)c1cccc(OCC(=O)O)c1]

The title compound was prepared according to the method described for Preparation 1 using methyl 3-(2-(tert-butoxy)-2-oxoethoxy)benzoate (Preparation 55). Taken on directly to the next step.

Preparation 52

Ethyl (3-allyloxycarbonyl)phenoxyacetate

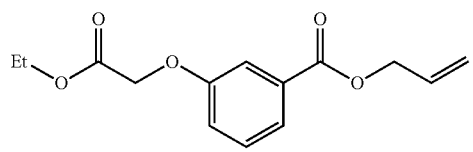 [SMILES: C=CCOC(=O)c1cccc(OCC(=O)OCC)c1]

To a solution of allyl 3-hydroxybenzoate (Preparation 82, 17.82 g, 0.1 mol) in DMF (100 mL) was added K$_2$CO$_3$ (18.0 g, 0.13 mol) and ethyl bromoacetate (98%, 14.7 mL, 0.13 mol). The reaction was stirred at 40° C. for 24 hours. Water (500 mL) was added and the product extracted with EtOAc (2×200 mL). The combined organic extracts were washed with brine (3×200 mL), concentrated in vacuo and purified using silica gel column chromatography eluting with 10-30% EtOAc in heptane to afford the title compound as a clear oil (24.3 g, 92% yield over 2 steps).

LCMS Method B: Rt=2.93 mins, ES$^+$ MS m/z 265.1 [M+H]$^+$ $^1$H NMR (400 MHz, CDCl$_3$): δ ppm 7.72-7.70 (1H, m), 7.59-7.57 (1H, m), 7.40-7.35 (1H, m), 7.22 (1H, m), 6.10-5.99 (1H, m), 5.39 (1H, dd), 5.27 (1H, dd), 4.80 (2H, d), 4.66 (2H, s), 4.28 (2H, q), 1.19 (3H, t).

Preparation 53

Ethyl (3-carboxy)phenoxyacetate

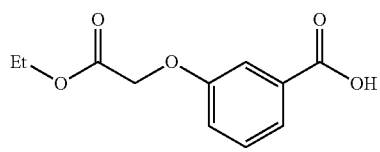 [SMILES: CCOC(=O)COc1cccc(C(=O)O)c1]

Tetrakis-(triphenylphosphine)palladium (0.35 g, 0.3 mmol) was added to a stirred solution of allyl 3-ethoxycarbonylmethoxybenzoate (Preparation 52, 2.64 g, 10 mMol) and piperidine (10 mL, 0.1 mol) in anhydrous THF (50 mL). The reaction mixture was stirred under nitrogen at room temperature for 2 hours. To the reaction was added silica gel (5 g) and the reaction was concentrated in vacuo. The solid residue was purified using silica gel column chromatography eluting with EtOAc:heptane:AcOH (30:60:1 to 50:50:1) to afford the title compound as an off-white solid (1.0 g, 45%). Trituration with heptane afforded a colourless solid (566 mg, 25%).

LCMS Method A: Rt=2.26 mins, no mass ion detected $^1$H NMR (400 MHz, CDCl$_3$): δ ppm 7.79-7.74 (1H, m), 7.62-7.59 (1H, m), 7.43-7.39 (1H, m), 7.22-7.19 (1H, m), 4.69 (2H, s), 4.30 (2H, q), 1.30 (3H, t).

Preparation 54

Ethyl 2-(3-((2-((tert-butoxycarbonyl)amino)ethyl) carbamoyl)phenoxy)acetate

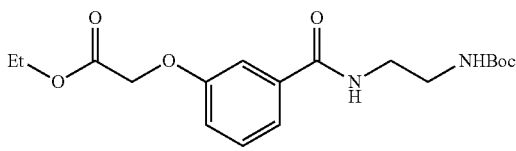 [SMILES: CCOC(=O)COc1cccc(C(=O)NCCNC(=O)OC(C)(C)C)c1]

To a solution of ethyl (3-carboxy)phenoxyacetate (Preparation 53, 448 mg, 2 mmol) in DMF (6 mL) was added a solution of boc-ethylenediamine (384 mg, 2.4 mmol) in DMF (2 mL), followed by DIEA (1.04 mL, 6 mmol). The resulting suspension was cooled in an ice-bath and a solution of HATU (824 mg, 2.1 mmol) in DMF (2 mL) added dropwise to give a yellow solution. The ice-bath was removed and the reaction mixture stirred at room temperature for 16 hours. An equal volume of water was added and the product was extracted with EtOAc (2×30 mL). The combined organic extracts were washed with water (3×30 mL), concentrated in vacuo and purified using silica gel column chromatography eluting with EtOAc:heptane (1:1 to 3:2) to afford the title compound as an oil (830 mg, >100%).

LCMS Method B: Rt=2.73 mins, ES+ MS m/z 367.3 [M+H]+

$^1$H NMR (400 MHz, CDCl$_3$): δ ppm 7.43-7.32 (3H, m), 7.16 (1H, br s), 7.10-7.04 (1H, m), 4.96 (1H, br s), 4.64 (2H, s), 4.27 (2H, q), 3.59-3.52 (2H, m), 3.46-3.35 (2H, m), 1.42 (9H, s), 1.28 (3H, t).

Preparation 55

Methyl 3-(2-(tert-butoxy)-2-oxoethoxy)benzoate

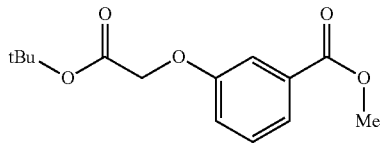 [SMILES: COC(=O)c1cccc(OCC(=O)OC(C)(C)C)c1]

The title compound was prepared according to the method described by Preparation 57 using methyl 3-hydroxybenzoate (1.00 gm 6.57 mmol) and isolated as a yellow oil (1.55 g. 89%).

LCMS Method A: Rt=2.95 mins, no mass ion observed $^1$H NMR (400 MHz, CDCl$_3$): δ ppm 7.65 (1H, d), 7.50 (1H, s), 7.35 (1H, t), 7.10 (1H, d), 4.55 (2H, s), 3.90 (3H, s), 1.45 (9H, s).

Preparation 56

2-(3-((Benzyloxy)carbonyl)phenoxy)acetic acid

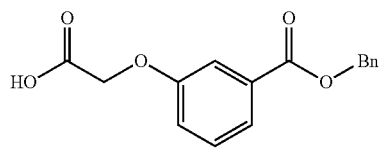

To benzyl 3-(2-(tert-butoxy)-2-oxoethoxy)benzoate (Preparation 57, 2.42 g, 7.07 mmol) dissolved in DCM (10 mL) was added TFA (1.08 mL, 14.1 mmol). After stirring for 16 hours at room temperature, further TFA (1.08 mL, 14.1 mmol) was added and the reaction stirred for a further 24 hours. The reaction was concentrated in vacuo and the residue azeotroped with toluene/dioxane (1:1 v/v, 10 mL). The residue was dissolved in DCM (10 mL), filtered, and concentrated in vacuo. The residue was dissolved in DCM a second time and washed with 2M aqueous HCl (20 mL). The organic layer was dried over MgSO$_4$ and concentrated in vacuo to afford the title compound as a pale brown oil (1.91 g, 94%).

LCMS Method A: Rt=3.92 mins, no mass ion observed $^1$H NMR (400 MHz, CDCl$_3$): δ ppm 7.75 (1H, d), 7.60 (1H, s), 7.45-7.25 (6H, m), 7.10-7.05 (1H, m), 5.40 (2H, s), 4.70 (2H, s), 3.40 (1H, br s).

Preparation 57

Benzyl 3-(2-(tert-butoxy)-2-oxoethoxy)benzoate

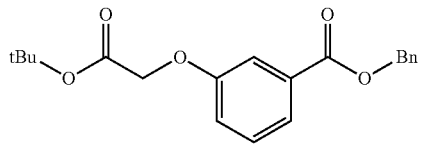 [SMILES: CC(C)(C)OC(=O)COc1cccc(C(=O)OCc2ccccc2)c1]

To benzyl 3-hydroxybenzoate (3.12 g, 13.7 mmol) dissolved in DMF (10 mL) was added tert-butyl bromoacetate (2.02 mL, 13.7 mmol) and potassium carbonate (4.16 g, 30.1 mmol) and the reaction was stirred for 16 hours at room temperature under nitrogen. The reaction was concentrated in vacuo, dissolved in water (10 mL) and extracted with EtOAc (2×10 mL). The combined organic layers were washed with brine (10 mL), 2M aqueous NaOH solution (10 mL), dried over MgSO$_4$ and concentrated in vacuo to afford the title compound as a pale yellow oil (2.42 g, 51%).

LCMS Method B: Rt=3.74 mins, no mass ion observed $^1$H NMR (400 MHz, CDCl$_3$): δ ppm 7.70 (1H, d), 7.60 (1H, s), 7.45-7.30 (6H, m), 7.10 (1H, dd), 5.35 (2H, s), 4.55 (2H, s), 1.45 (9H, s).

Preparation 58

Benzyl 4'-hydroxy-[1,1'-biphenyl]-3-carboxylate

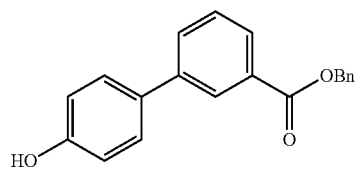 [SMILES: O=C(OCc1ccccc1)c1cccc(-c2ccc(O)cc2)c1]

To a solution of benzyl chloride (295 µL, 2.56 mmol) in DMF (5 mL) was added 4'-hydroxybiphenyl-4-carboxylic acid (500 mg, 2.33 mmol) and potassium carbonate (322 mg, 2.33 mmol). The reaction mixture was stirred at room temperature for 20 hours before concentrating in vacuo. The residue was partitioned between water (20 mL) and diethyl ether (20 mL). The organic layer was separated and the aqueous layer extracted again with diethyl ether (20 mL). The combined organic extracts were washed with water (10 mL), dried over sodium sulphate and concentrated in vacuo. The residue was purified by silica gel column chromatography eluting with 0-30% EtOAc in hexane to afford the title compound as a white solid (378 mg, 53%).

LCMS Method E: Rt=3.48 mins, ES+ MS m/z 305.0 [M+H]+

$^1$H NMR (400 MHz, CDCl$_3$): δ ppm 8.26-8.24 (1H, m), 8.03-7.98 (1H, m), 7.75-7.71 (1H, m), 7.51-7.43 (5H, m), 7.42-7.31 (3H, m), 6.95-6.90 (2H, m), 5.40 (2H, s).

Preparation 59

Benzyl 4'-(2-(tert-butoxy)-2-oxoethoxy)-[1,1'-biphenyl]-3-carboxylate

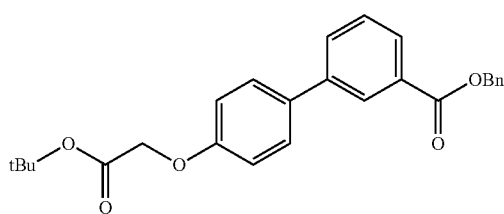 [SMILES: CC(C)(C)OC(=O)COc1ccc(-c2cccc(C(=O)OCc3ccccc3)c2)cc1]

To a solution of benzyl 4'-hydroxy-[1,1'-biphenyl]-3-carboxylate (Preparation 58, 368 mg, 1.21 mmol) and tert-butyl bromoacetate (178 μL, 1.21 mmol) in DMF (5 mL) was added potassium carbonate (200 mg, 1.45 mmol) and the reaction was stirred at room temperature for 20 hours followed by 50° C. for 2 hours. The reaction was concentrated in vacuo and the resulting residue partitioned between water (20 mL) and DCM (20 mL). The organic layer was separated and the aqueous layer extracted again with DCM (20 mL). The combined organic extracts were washed with water (10 mL), dried over sodium sulphate and concentrated in vacuo. The residue was purified by silica gel column chromatography eluting with 0-15% EtOAc in hexane to afford the title compound as an oil (510 mg, 100%).

LCMS Method E: Rt=3.85 mins, no mass ion observed $^1$H NMR (400 MHz, CDCl$_3$): δ ppm 8.25 (1H, t), 8.03-7.99 (1H, dt), 7.76-7.71 (1H, m), 7.58-7.31 (8H, m), 7.06-6.95 (2H, m), 5.39 (2H, s), 4.56 (2H, s), 1.50 (9H, s).

Preparation 60

4'-(2-(tert-Butoxy)-2-oxoethoxy)-[1,1'-biphenyl]-3-carboxylic acid

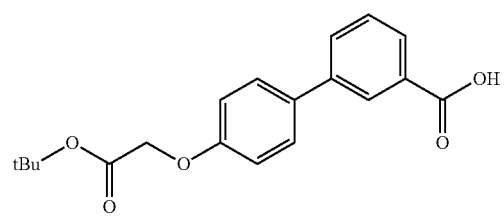 [SMILES: CC(C)(C)OC(=O)COc1ccc(-c2cccc(C(=O)O)c2)cc1]

To a solution of benzyl 4'-(2-(tert-butoxy)-2-oxoethoxy)-[1,1'-biphenyl]-3-carboxylate (Preparation 59, 420 mg, 1.0 mmol) in ethanol (10 mL) was added 10% Pd/C (11.0 mg). The reaction was placed under an atmosphere of hydrogen (15 psi) and stirred for 20 hours at room temperature. The catalyst was removed by filtration through Celite and the reaction was concentrated in vacuo to afford the title compound as a white solid (286 mg, 87%).

LCMS Method E: Rt=3.37 mins, no mass ion observed $^1$H NMR (400 MHz, CDCl$_3$): δ ppm 8.31 (1H, t), 8.08-8.03 (1H, m), 7.82-7.77 (1H, m), 7.60-7.49 (3H, m), 7.03-6.96 (2H, m), 4.57 (2H, s), 1.50 (9H, s).

Preparations to Enable Two F Groups

Preparation 61

2,2'-((5-((Benzyloxy)carbonyl)-[1,1'-biphenyl]-3,3'-diyl)bis(oxy))diacetic acid

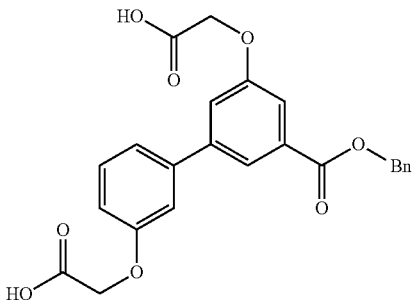 [SMILES: O=C(O)COc1cccc(-c2cc(OCC(=O)O)cc(C(=O)OCc3ccccc3)c2)c1]

A solution of di-tert-butyl 2,2'-((5-((benzyloxy)carbonyl)-[1,1'-biphenyl]-3,3'-diyl)bis(oxy))diacetate (Preparation 66, 100 mg, 182 μmol) dissolved in DCM/TFA/water (10:10:1 v/v/v, 5 mL) was stirred for 16 hours at room temperature. The reaction was concentrated in vacuo and the residue was dissolved in MeOH (1 mL). The solution was treated with water (10 mL) and concentrated in vacuo. The residue was dissolved in MeCN, the resulting particulates were filtered and the filtrate was concentrated in vacuo to afford the title compound as a gummy solid (42.0 mg. 53%).

LCMS Method A: Rt=2.81 mins, ES– MS m/z 435.3 [M–H]–

$^1$H NMR (400 MHz, CDCl$_3$): δ ppm 7.95 (1H, t), 7.60-7.55 (1H, m), 7.45-7.40 (2H, m), 7.40-7.35 (4H, m), 7.35-7.30 (1H, m), 7.25-7.20 (1H, m), 7.10 (1H, t), 6.95 (1H, dd), 5.40 (2H, s), 4.80 (2H, s), 4.75 (2H, s).

Preparation 62

2,2'-((5-((Benzyloxy)carbonyl)-[1,1'-biphenyl]-3,4'-diyl)bis(oxy))diacetic acid

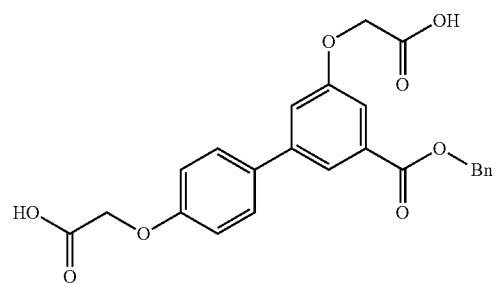 [SMILES: O=C(O)COc1ccc(-c2cc(OCC(=O)O)cc(C(=O)OCc3ccccc3)c2)cc1]

A solution of di-tert-butyl 2,2'-((5-((benzyloxy)carbonyl)-[1,1'-biphenyl]-3,4'-diyl)bis(oxy))diacetate (Preparation 68, 200 mg, 365 µmol) dissolved in DCM/TFA/water (10:10:1 v/v/v, 10 mL) was stirred for 3 hours at room temperature. The reaction was concentrated in vacuo and azeotroped with dioxane/toluene (1:1, v/v, 2×10 mL) before freeze-drying overnight to afford the title compound as a colourless solid (101 mg, 64%).

LCMS Method A: Rt=1.83 mins, ES⁻ MS m/z 435.3 [M−H]⁻

¹H NMR (400 MHz, CD₃OD): δ ppm 7.90 (1H, t), 7.65-7.55 (2H, m), 7.55-7.50 (1H, m), 7.50-7.45 (2H, m) 7.45-7.35 (4H, m), 7.10-7.00 (2H, m), 5.40 (2H, s), 4.80 (2H, s), 4.70 (2H, s).

Preparation 63

4',5-bis(2-(tert-Butoxy)-2-oxoethoxy)-[1,1'-biphenyl]-3-carboxylic acid

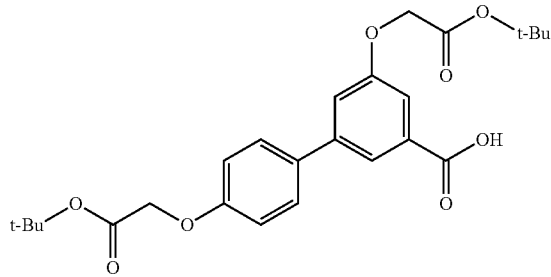 [SMILES: CC(C)(C)OC(=O)COc1ccc(-c2cc(OCC(=O)OC(C)(C)C)cc(C(=O)O)c2)cc1]

To a solution of di-tert-butyl 2,2'-((5-((benzyloxy)carbonyl)-[1,1'-biphenyl]-3,4'-diyl)bis(oxy))diacetate (Preparation 68, 210 mg, 383 µmol) in IMS (5 mL) was added 10% Pd/C (20 mg). The reaction was put under an atmosphere of hydrogen (70 psi) and stirred for 5 hours at room temperature. The catalyst was removed by filtration using Dicalite and the reaction was concentrated in vacuo to afford the title compound as a yellow oil (174 mg, 99%).

LCMS Method A: Rt=3.45 mins, ES⁻ MS m/z 457.3 [M−H]⁻

¹H NMR (400 MHz, CDCl₃): δ ppm 7.95-7.90 (1H, m), 7.55-7.50 (2H, m), 7.50-7.45 (1H, m), 7.35 (1H, t), 7.00-6.95 (2H, m), 4.60 (2H, s), 4.55 (2H, s), 1.50 (9H, s), 1.50 (9H, s).

Preparation 64

Ethyl 2-{3-[(2-aminoethyl)carbamoyl]-5-(2-ethoxy-2-oxoethoxy)phenoxy}acetate trifluoroacetic acid salt

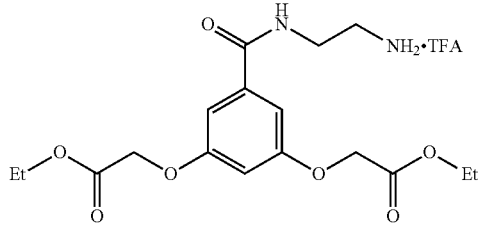

The title compound was prepared according to the method described by Preparation 1 using diethyl 2,2'-((5-((2-((tert-butoxycarbonyl)amino)ethyl)carbamoyl)-1,3-phenylene)bis(oxy))diacetate (J. Am. Chem. Soc. 2006, 128, 10362) as a colourless solid (207 mg, >99%).

LCMS Method B: Rt=2.09 mins, ES⁺ MS m/z 369.2 [M+H]⁺

¹H NMR (400 MHz, DMSO-d₆): δ ppm 8.55-8.50 (1H, m), 7.75 (2H, br s), 7.00 (2H, s), 6.70 (1H, s), 4.80 (4H, s), 4.15 (4H, q), 3.45-3.40 (2H, m), 3.00-2.95 (2H, m), 1.20 (6H, t).

Preparation 65

Benzyl 3',5-dihydroxy-[1,1'-biphenyl]-3-carboxylate

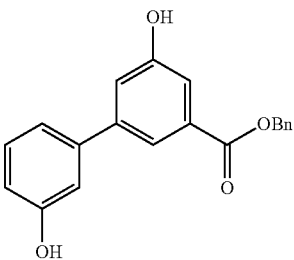 [SMILES: O=C(OCc1ccccc1)c1cc(O)cc(-c2cccc(O)c2)c1]

A mixture of benzyl 3-bromo-5-hydroxybenzoate (Preparation 78, 1.00 g, 3.26 mmol), sodium carbonate (1.21 g, 11.4 mmol) and 3-(4,4,5,5-tetramethyl-1,3,2-dioxaborolan-2-yl)phenol (860 mg, 3.91 mmol) dissolved in dioxane/water (30 mL, 5:1 v/v) was degassed for 30 minutes with nitrogen. Pd(PPh₃)₄ (284 mg, 246 µmol) was added and the reaction heated to 100° C. for 16 hours under nitrogen. After cooling to room temperature, EtOAc (50 mL) and water (25 mL) were added. The layers were separated and the aqueous phase was extracted with EtOAc (2×15 mL). The combined organic phases were dried over MgSO₄ and concentrated in vacuo. The residue was purified using silica gel column chromatography eluting with 5-40% EtOAc in heptane to afford the title compound as a colourless oil (860 mg, 82%).

LCMS Method A: Rt=3.03 mins, ES⁻ MS m/z 319.2 [M−H]⁻

¹H NMR (400 MHz, DMSO-d₆): δ ppm 10.0 (1H, s), 9.60 (1H, s), 7.60 (1H, s), 7.50-7.45 (2H, m), 7.40 (2H, t), 7.30-7.25 (2H, m), 7.25 (1H, t), 7.25-7.20 (1H, m), 7.05-7.00 (1H, m), 6.95 (1H, s), 5.30 (2H, s).

Preparation 66

Di-tert-butyl 2,2'-((5-((benzyloxy)carbonyl)-[1,1'-biphenyl]-3,3'-diyl)bis(oxy))diacetate

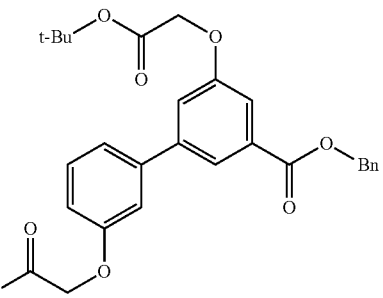

To benzyl 3',5-dihydroxy-[1,1'-biphenyl]-3-carboxylate (Preparation 65, 860 mg, 2.68 mmol) dissolved in DMF (30 mL) was added tert-butyl bromoacetate (1.19 mL, 8.05 µmol) and potassium carbonate (2.23 g, 16.1 mmol). The resulting suspension was stirred for 16 hours under nitrogen before concentration in vacuo. The residue was dissolved in water (10 mL) and extracted with EtOAc (2×10 mL). The combined organic layers were washed with brine (10 mL), 2M aqueous NaOH (10 mL) dried over MgSO₄ and concentrated in vacuo. The residue was purified using silica gel column chromatography eluting with 5-40% EtOAc in heptane to afford the title compound as a colourless gum (1.29 g, 89%).

LCMS Method B: Rt=4.22 mins, no mass ion observed
¹H NMR (400 MHz, CDCl₃): δ ppm 7.90 (1H, t), 7.55-7.50 (1H, m), 7.45-7.30 (7H, m), 7.20-7.15 (1H, m), 7.15-7.10 (1H, m), 6.90 (1H, dd), 5.40 (2H, s), 4.60 (2H, s), 4.55 (2H, s), 1.50 (9H, s), 1.45 (9H, s).

Preparation 67

Benzyl 4',5-dihydroxy-[1,1'-biphenyl]-3-carboxylate

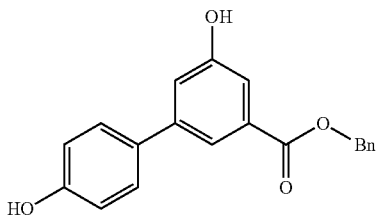 [SMILES: O=C(OCc1ccccc1)c1cc(O)cc(-c2ccc(O)cc2)c1]

A mixture of benzyl 3-bromo-5-hydroxybenzoate (Preparation 78, 1.05 g, 3.42 mmol), sodium carbonate (1.27 g, 12.0 mmol) and (4-hydroxyphenyl)boronic acid (565 mg, 4.10 mmol) dissolved in dioxane/water (3:1 v/v, 30 mL) were deoxygenated for 30 minutes with nitrogen. Pd(PPh₃)₄ (395 mg, 341 μmol) was added and the reaction was heated to 100° C. for 5 hours under nitrogen. After cooling to room temperature, EtOAc (50 mL) and water (30 mL) were added and the layers were separated. The aqueous layer was extracted with EtOAc (2×50 mL) and the combined organic layers washed with brine (50 mL). The organic layer was dried over MgSO₄ and concentrated in vacuo. The residue was purified using silica gel column chromatography eluting with 5-40% EtOAc/heptane) to afford the title compound as a yellow solid (815 mg, 74%).

LCMS Method A: Rt=2.94 mins, ES⁻ MS m/z 319.3 [M−H]⁻
¹H NMR (400 MHz, CD₃OD): δ ppm 7.70 (1H, t), 7.50-7.35 (8H, m), 7.20 (1H, t), 6.85-6.80 (2H, m), 5.35 (2H, s).

Preparation 68

Di-tert-butyl 2,2'-((5-((benzyloxy)carbonyl)-[1,1'-biphenyl]-3,4'-diyl)bis(oxy))diacetate

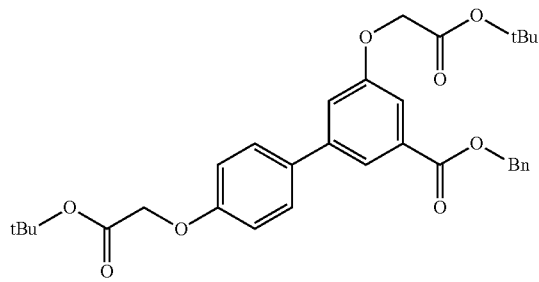 [SMILES: CC(C)(C)OC(=O)COc1ccc(-c2cc(OCC(=O)OC(C)(C)C)cc(C(=O)OCc3ccccc3)c2)cc1]

To benzyl 4',5-dihydroxy-[1,1'-biphenyl]-3-carboxylate (Preparation 67, 815 mg, 2.54 mmol) dissolved in DMF (10 mL) was added tert butyl bromoacetate (752 μL, 5.09 μmol) and potassium carbonate (1.58 g, 11.5 mmol). The resulting suspension was stirred for 5 hours at room temperature under nitrogen. The reaction was concentrated in vacuo and the resulting residue was dissolved in water (30 mL) and extracted with EtOAc (2×30 mL). The combined organic layers were washed with brine (30 mL), 2M aqueous NaOH (30 mL), dried over MgSO₄ and concentrated in vacuo to afford the title compound as a yellow oil that solidified over time (1.49 g, >99%) and was used directly in the next step.

LCMS Method C: Rt=4.23 mins, no mass ion observed.
¹H NMR (400 MHz, CD₃OD): δ ppm 7.85 (1H, t), 7.60-7.55 (2H, m), 7.50-7.35 (7H, m), 7.05-6.95 (2H, m), 5.40 (2H, s), 4.70 (2H, s), 4.65 (2H, s), 1.50 (9H, s), 1.45 (9H, s).

Preparations to Enable Three F Groups

Preparation 69

Benzyl 3',5'-bis((tert-butyldimethylsilyl)oxy)-5-hydroxy-[1,1'-biphenyl]-3-carboxylate

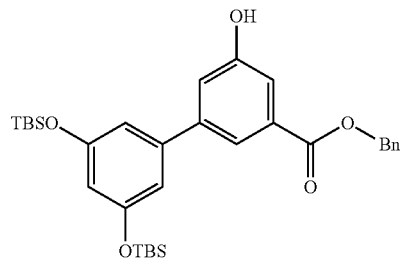 [SMILES: CC(C)(C)[Si](C)(C)Oc1cc(O[Si](C)(C)C(C)(C)C)cc(-c2cc(O)cc(C(=O)OCc3ccccc3)c2)c1]

A mixture of benzyl 3-bromo-5-hydroxybenzoate (Preparation 78, 755 mg, 2.46 mmol), sodium carbonate (912 mg, 8.60 mmol) and ((5-(4,4,5,5-tetramethyl-1,3,2-dioxaborolan-2-yl)-1,3-phenylene)bis(oxy))bis(tert-butyldimethylsilane) (Preparation 80, 1.87 g, 2.95 mmol) dissolved in dioxane/water (30 mL, 5:1 v/v) was degassed for 30 minutes with nitrogen. Pd(PPh₃)₄ (284 mg, 246 μmol) was added and the reaction heated to 100° C. for 90 minutes under nitrogen. After cooling to room temperature, EtOAc (100 mL) and water (50 mL) were added. The layers were separated and the aqueous phase was backwashed with EtOAc (2×25 mL). The combined organic phases were dried over MgSO₄ and concentrated in vacuo. The residue was treated with heptane (100 mL) and the resulting mixture sonicated for 5 minutes, before filtering to remove the solid. The filtrate was concentrated in vacuo to afford the crude title compound as a clear brown oil (1.27 g) that was used directly in the next step.

LCMS Method C: Rt=5.47 mins, ES⁺ MS m/z 565.4 [M+H]⁺

Preparation 70

Benzyl 3',5,5'-trihydroxy-[1,1'-biphenyl]-3-carboxylate

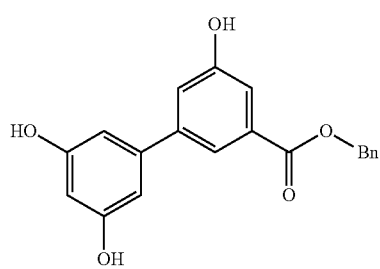 [SMILES: O=C(OCc1ccccc1)c1cc(O)cc(-c2cc(O)cc(O)c2)c1]

To a solution of crude benzyl 3',5'-bis((tert-butyldimethylsilyl)oxy)-5-hydroxy-[1,1'-biphenyl]-3-carboxylate (Preparation 69, 1.27 g, 2.46 mmol) dissolved in THF (12 mL) was added TBAF solution (1M in THF, 6.15 mL, 6.15 mmol) dropwise. The reaction was stirred at room temperature under nitrogen for 90 minutes before diluting with EtOAc (100 mL). The organic phase was washed with water (2×50 mL), dried over MgSO$_4$ and concentrated in vacuo. The residue was purified using silica gel column chromatography eluting with 5% MeOH in DCM to afford the title compound as a pale brown solid (356 mg, 43% over 3 steps).

LCMS Method A: Rt=2.66 mins, ES$^-$ MS m/z 335.3 [M−H]$^-$ $^1$H NMR (400 MHz, CD$_3$OD): δ ppm 7.60 (1H, t), 7.45-7.40 (2H, m), 7.40-20 (4H, m), 7.15-7.10 (1H, m), 6.45 (2H, d), 6.20 (1H, t), 5.30 (2H, s).

Preparation 71

3',5,5'-Tris(2-(tert-butoxy)-2-oxoethoxy)-[1,1'-biphenyl]-3-carboxylic acid

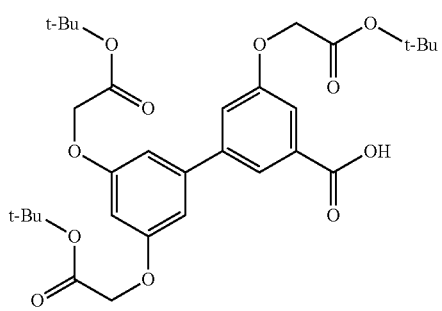 [SMILES: CC(C)(C)OC(=O)COc1cc(OCC(=O)OC(C)(C)C)cc(-c2cc(OCC(=O)OC(C)(C)C)cc(C(=O)O)c2)c1]

To tri-tert-butyl 2,2',2''-((5'-((benzyloxy)carbonyl)-[1,1'-biphenyl]-3,3',5-triyl)tris(oxy))triacetate (Preparation 72, 267 mg, 393 μmol) dissolved in IMS (2.7 mL) was added 10% Pd/C (2.7 mg). The reaction was put under an atmosphere of hydrogen (50 psi) and stirred for 3 hours at room temperature. The catalyst was removed by filtration through Dicalite with MeOH and concentrated in vacuo to afford the title compound as a pale yellow gum (152 mg, 66%).

LCMS Method A: Rt=3.72 mins, ES$^-$ MS m/z 587.4 [M−H]$^-$ $^1$H NMR (400 MHz, CDCl$_3$): δ ppm 7.90 (1H, s), 7.55-7.50 (1H, m), 7.35-7.30 (1H, m), 6.75 (2H, d), 6.50 (1H, t), 4.60 (2H, s), 4.50 (4H, s), 1.50 (27H, s).

Preparation 72

Tri-tert-butyl 2,2',2''-((5'-((benzyloxy)carbonyl)-[1,1'-biphenyl]-3,3',5-triyl)tris(oxy))triacetate

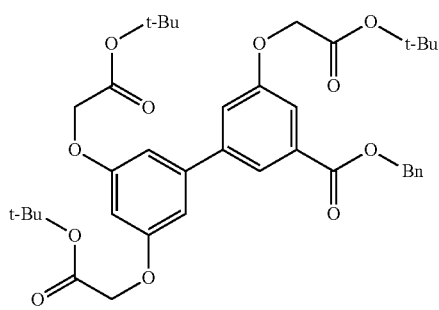 [SMILES: CC(C)(C)OC(=O)COc1cc(OCC(=O)OC(C)(C)C)cc(-c2cc(OCC(=O)OC(C)(C)C)cc(C(=O)OCc3ccccc3)c2)c1]

To benzyl 3',5,5'-trihydroxy-[1,1'-biphenyl]-3-carboxylate (Preparation 70, 356 mg, 1.06 mmol) dissolved in DMF (10 mL) was added tert-butyl bromoacetate (625 μL, 4.23 mmol) and potassium carbonate (1.17 g, 8.47 mmol). The resulting suspension was stirred for 16 hours under nitrogen before concentration in vacuo. The resulting residue was dissolved in water (10 mL) and extracted with EtOAc (2×10 mL). The combined organic layers were washed with brine (10 mL), 2M aqueous NaOH (10 mL), dried over MgSO$_4$ and concentrated in vacuo. The residue was purified using silica gel column chromatography eluting with 7-60% EtOAc/heptane to afford the title compound as a clear colourless gum (618 mg, 86%).

LCMS Method C: Rt=4.34 mins, no mass ion observed $^1$H NMR (400 MHz, CDCl$_3$): δ ppm 7.85 (1H, s), 7.55-7.50 (1H, m), 7.45-7.25 (6H, m), 6.70 (2H, d), 6.45-6.40 (1H, m), 5.35 (2H, s), 4.55 (2H, s), 4.50 (4H, s), 1.45 (27H, s)

Preparation 73

2,2',2''-((5'-((Benzyloxy)carbonyl)-[1,1'-biphenyl]-3,3',5-triyl)tris(oxy))triacetic acid

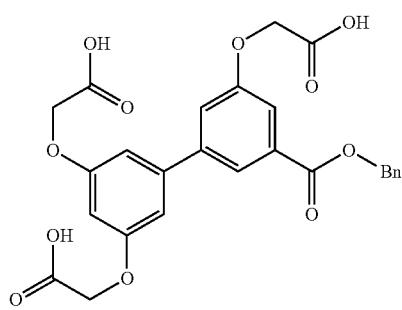 [SMILES: O=C(O)COc1cc(OCC(=O)O)cc(-c2cc(OCC(=O)O)cc(C(=O)OCc3ccccc3)c2)c1]

A solution of tri-tert-butyl 2,2',2''-((5'-((benzyloxy)carbonyl)-[1,1'-biphenyl]-3,3',5-triyl)tris(oxy))triacetate (Preparation 72, 100 mg, 147 μmol) dissolved in DCM/TFA/water (10:10:1 v/v/v, 5 mL) was stirred for 16 hours at room temperature. The reaction was concentrated in vacuo, dissolved in MeOH (1 mL) and precipitated with water (10 mL). The precipitate was collected by filtration, washed with water and dried under vacuum to afford the title compound as a colourless solid (57.8 mg, 77%).

LCMS Method A: Rt=2.48 mins, ES⁻ MS m/z 509.3 [M−H]⁻

¹H NMR (400 MHz, DMSO-$d_6$): δ ppm 13.05 (3H, br s), 7.90 (1H, s), 7.55-7.45 (3H, m), 7.45-7.30 (4H, m), 6.80 (2H, d), 6.50 (1H, t), 5.40 2H, s), 4.85 (2H, s). 4.75 (4H, s).

Preparations to Enable Four F Groups

Preparation 74

Benzyl 3',5'-bis((tert-butyldimethylsilyl)oxy)-4,6-dihydroxy-[1,1'-biphenyl]-3-carboxylate

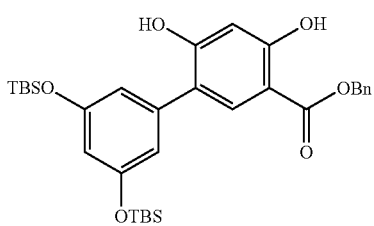 [SMILES: CC(C)(C)[Si](C)(C)Oc1cc(O[Si](C)(C)C(C)(C)C)cc(-c2cc(C(=O)OCc3ccccc3)c(O)cc2O)c1]

A mixture of benzyl 5-bromo-2,4-dihydroxybenzoate (Preparation 79, 1.59 g, 4.93 mmol), sodium carbonate (1.83 g, 17.2 mmol) and ((5-(4,4,5,5-tetramethyl-1,3,2-dioxaborolan-2-yl)-1,3-phenylene)bis(oxy))bis(tert-butyldimethylsilane) (Preparation 80, 2.59 g, 5.91 mmol) dissolved in dioxane/water (60 mL, 5:1 v/v) was degassed for 30 minutes with nitrogen. Pd(PPh₃)₄ (569 mg, 493 μmol) was added and the reaction heated to 100° C. for 5 hours under nitrogen. After cooling to room temperature, EtOAc (100 mL) and water (50 mL) were added.

The layers were separated and the aqueous phase was extracted with EtOAc (2×25 mL).

The combined organic phases were dried over MgSO₄ and concentrated in vacuo to afford the crude title compound that was used directly in the next step.

Preparation 75

Benzyl 3',4,5',6-tetrahydroxy-[1,1'-biphenyl]-3-carboxylate

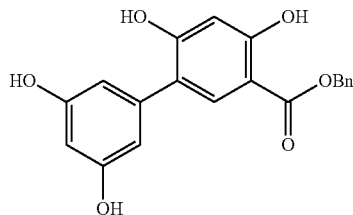 [SMILES: O=C(OCc1ccccc1)c1cc(-c2cc(O)cc(O)c2)c(O)cc1O]

To a solution of crude benzyl 3',5'-bis((tert-butyldimethylsilyl)oxy)-4,6-dihydroxy-[1,1'-biphenyl]-3-carboxylate (Preparation 74, 4.50 g, 4.93 mmol) dissolved in THF (25 mL) was added TBAF solution (1M in THF, 12.3 mL, 12.3 mmol) dropwise. The reaction was stirred for 90 minutes at room temperature under nitrogen before diluting with EtOAc (100 mL). The organic phase was washed with water (2×50 mL), dried over MgSO₄ and concentrated in vacuo. The residue was purified using silica gel column chromatography (Biotage Isolera, 45 g, eluting with 0-20% MeOH in EtOAc) followed by a second silica gel column chromatography (Biotage Isolera, 45 g, eluting with 10-50% MeOH in EtOAc) to afford the title compound as an orange solid (306 mg, 18% over 3 steps).

LCMS Method A: Rt=2.81 mins, ES⁻ MS m/z 351.2 [M−H]⁻

¹H NMR (400 MHz, CDCl₃): δ ppm 10.80 (1H, s), 7.65 (1H, s), 7.35-7.20 (5H, m), 6.45 (1H, s), 6.35 (1H, d), 6.30 (1H, t), 5.25 (2H, s).

Preparation 76

Tetra-tert-butyl 2,2',2'',2'''-((5-((benzyloxy)carbonyl)-[1,1'-biphenyl]-2,3',4,5'-tetrayl)tetrakis(oxy))tetraacetate

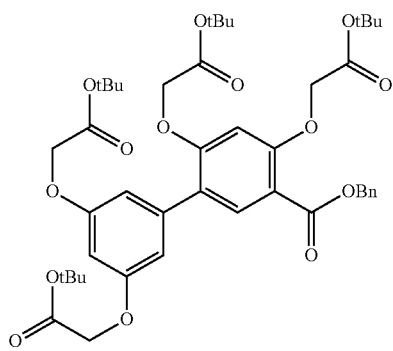 [SMILES: CC(C)(C)OC(=O)COc1cc(OCC(=O)OC(C)(C)C)cc(-c2cc(C(=O)OCc3ccccc3)c(OCC(=O)OC(C)(C)C)cc2OCC(=O)OC(C)(C)C)c1]

To benzyl 3',4,5',6-tetrahydroxy-[1,1'-biphenyl]-3-carboxylate (Preparation 75, 306 mg, 868 μmol) dissolved in DMF (10 mL) was added tert-butyl bromoacetate (770 μL, 5.21 μmol) and potassium carbonate (1.17 g, 8.47 mmol) to give a suspension, which was stirred for 16 hours at room temperature under nitrogen. Further tert-butyl bromoacetate (770 μL, 5.21 μmol) and potassium carbonate (1.17 g, 8.47 mmol) were added and the reaction stirred for 4 hours before concentrating in vacuo. The resulting residue was dissolved in water (10 mL) and extracted with EtOAc (2×10 mL). The combined organic layers were then washed with brine (10 mL), 2M aqueous NaOH solution (10 mL), dried over MgSO₄ and concentrated in vacuo. The residue was purified using silica gel column chromatography (Biotage SP1, 30 g column, eluting with 2-50% EtOAc/heptane) followed by a second silica gel column chromatography (Biotage Isolera, 45 g column, eluting with 5-40% EtOAc in heptane) to afford the title compound as a colourless gum (286 mg, 41%).

LCMS Method C: Rt=4.36 mins, ES⁺ MS m/z 809.6 [M+H]⁺

¹H NMR (400 MHz, CDCl₃): δ ppm 7.90 (1H, s), 7.45-7.40 (2H, m), 7.40-7.25 (3H, m), 6.75 (2H, d), 6.45 (1H, t), 6.35 (1H, s), 5.35 (2H, s), 4.60 (2H, s), 4.50 (4H, s), 4.45 (2H, s), 1.50 (9H, s), 1.45 (18H, s), 1.45 (9H, s).

Preparation 77

3',4,5',6-Tetrakis(2-(tert-butoxy)-2-oxoethoxy)-[1,1'-biphenyl]-3-carboxylic acid

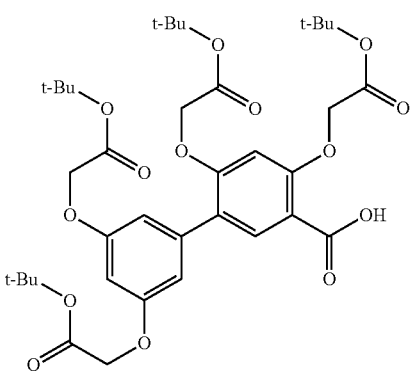 [SMILES: CC(C)(C)OC(=O)COc1cc(OCC(=O)OC(C)(C)C)cc(-c2cc(C(=O)O)c(OCC(=O)OC(C)(C)C)cc2OCC(=O)OC(C)(C)C)c1]

To tetra-tert-butyl 2,2',2",2'"-((5-((benzyloxy)carbonyl)-[1,1'-biphenyl]-2,3',4,5'-tetrayl)tetrakis(oxy))tetraacetate (Preparation 76, 143 mg, 177 µmol) dissolved in IMS (1.4 mL) was added 10% Pd/C (14.3 mg). The reaction was put under an atmosphere of hydrogen (50 psi) and stirred for 3 hours at room temperature. The catalyst was removed by filtration through Dicalite with MeOH and the reaction was concentrated in vacuo to afford the title compound as a pale yellow gum (130 mg, >99%).

LCMS Method A: Rt=3.97 mins, ES⁻ MS m/z 717.6 [M-H]⁻

$^1$H NMR (400 MHz, CD$_3$OD): δ ppm 7.90 (1H, s), 6.80 (2H, s), 6.60 (1H, s), 6.45 (1H, s), 4.80 (2H, s), 4.65 (2H, s), 4.60 (4H, s), 1.50 (9H, s), 1.50 (9H, s), 1.45 (18H, s).

Preparations of Key Building Blocks

Preparation 78

Benzyl 3-bromo-5-hydroxybenzoate

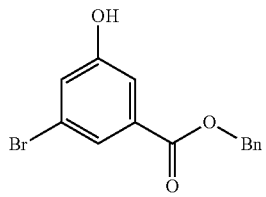 [SMILES: O=C(OCc1ccccc1)c1cc(O)cc(Br)c1]

To a solution of 3-bromo-5-hydroxybenzoic acid (4.08 g, 18.8 mmol) dissolved in DMF (25 mL) was added K$_2$CO$_3$ (2.60 g, 18.8 mmol) and after 5 minutes benzyl bromide (2.24 mL, 18.8 mmol) was added dropwise over 10 minutes. The reaction was stirred at room temperature under nitrogen for 16 hours overnight. Additional K$_2$CO$_3$ (520 mg, 3.76 mmol) and benzyl bromide (450 µL, 3.79 mmol) were added and the reaction stirred for 3 hours. The reaction was concentrated in vacuo and the residue was partitioned between EtOAc (30 mL) and water (30 mL). The aqueous layer was extracted with EtOAc (2×20 mL) and the combined organic layers washed with brine (30 mL). The organic layer was dried over MgSO$_4$ and concentrated in vacuo. The residue was purified by silica gel column chromatography eluting with 5% EtOAc in heptane to afford the title compound as a colourless solid (3.88 g, 67%).

LCMS Method A: Rt=3.36 mins, ES⁻ MS m/z 307.2 [M-H]⁻

$^1$H NMR (400 MHz, CDCl$_3$): δ ppm 7.75 (1H, t), 7.50-7.45 (1H, m), 7.45-7.30 (5H, m), 7.20 (1H, t), 5.30 (2H, s), 5.30 (1H, br s).

Preparation 79

Benzyl 5-bromo-2,4-dihydroxybenzoate

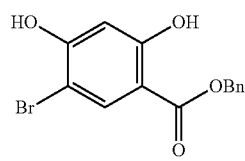

To 5-bromo-2,4-dihydroxybenzoic acid (2.50 g, 10.7 mmol) dissolved in DMF (25 mL) was added KHCO$_3$ (1.07 g, 10.7 mmol) and benzyl bromide (1.30 mL, 10.7 mmol), before stirring for 16 hours at room temperature under nitrogen. The reaction was concentrated in vacuo and the residue was partitioned between EtOAc (20 mL) and water (20 mL). The layers were separated and the organic layer was washed with 1M aqueous citric acid (20 mL), saturated, aqueous NaHCO$_3$ (20 mL) and brine (20 mL). The organic layer was dried over MgSO$_4$ and concentrated in vacuo. The residue was purified using silica gel column chromatography (Biotage Isolera, 45 g column, eluting with 0-40% EtOAc/heptane) to afford the title compound as a colourless solid (2.36 g, 68%).

LCMS Method A: Rt=3.37 mins, no mass ion observed.

$^1$H NMR (400 MHz, CDCl$_3$): δ ppm 10.80 (1H, s), 8.00 (1H, s), 7.45-7.35 (5H, m), 6.60 (1H, s), 5.90 (1H, s), 5.35 (2H, s).

Preparation 80

((5-(4,4,5,5-Tetramethyl-1,3,2-dioxaborolan-2-yl)-1,3-phenylene)bis(oxy))bis(tert-butyldimethylsilane)

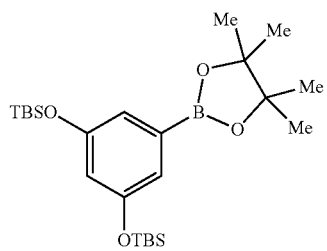 [SMILES: CC1(C)OB(c2cc(O[Si](C)(C)C(C)(C)C)cc(O[Si](C)(C)C(C)(C)C)c2)OC1(C)C]

A solution of 1,3-bis((tert-butyldimethylsilyl)oxy)benzene (Preparation 81, 1.00 g, 2.95 mmol and bis(pinacolato)diboron (750 mg, 2.95 mmol) dissolved in isohexane (15 mL) were degassed for 1 hour using nitrogen. [Ir(OMe)(COD)]$_2$ (19.6 mg, 59.1 µmol) and 4,4'-di-tert-butyl-2,2'-bipyridine (15.9 mg, 59.0 µmol) were added and the reaction sealed and heated to 110° C. for 16 hours. The reaction was cooled, concentrated in vacuo and used directly in the next step (1.87 g).

LCMS Method C: Rt=6.19 mins, ES+MS m/z 465.4 [M+H]+

¹H NMR (400 MHz, CDCl₃): δ ppm 6.85 (2H, d), 6.40 (1H, t), 1.25 (12H, s), 0.95 (18H, s), 0.15 (12H, s).

Preparation 81

1,3-Bis((tert-butyldimethylsilyl)oxy)benzene

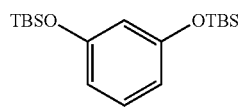 [SMILES: CC(C)(C)[Si](C)(C)Oc1cccc(O[Si](C)(C)C(C)(C)C)c1]

To resorcinol (2.00 g, 18.2 mmol) and imidazole (3.71 g, 54.5 mmol) dissolved in DCM (40 mL) was added tert-butyldimethylchlorosilane (8.21 g, 54.5 mmol). A precipitate formed and further DCM (40 mL) was added, before stirring for 16 hours at room temperature under nitrogen. The reaction was filtered and the filtrate was concentrated in vacuo. The residue was purified using silica gel column chromatography (Biotage SP1, 120 g silica column, eluting with 0-10% EtOAc in heptane) to afford the title compound as a colourless oil (6.18 g, >99%).

LCMS Method C: Rt=5.39 mins, ES+ MS m/z 339.3 [M+H]+

¹H NMR (400 MHz, CDCl₃): δ ppm 6.95 (1H, t), 6.35 (2H, dd), 6.25 (1H, t), 1.85 (18H, s), 0.10 (12H, s).

Preparation 82

Allyl 3-hydroxybenzoate

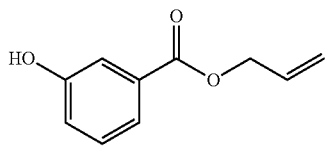

Allyl bromide (97%, 13.1 g, 0.105 mol) was added slowly to a stirred suspension of 3-hydroxybenzoic acid (99%, 13.95 g, 0.1 mol) and Na₂CO₃ (11.66 g, 0.11 mol) in anhydrous DMF (200 mL) and the reaction mixture stirred at room temperature for 48 hours. Water (500 mL) was added and the product was extracted with EtOAc (3×250 mL). The combined organic extracts were concentrated in vacuo to afford a crude residue that was used directly in the next step.

LCMS Method B: Rt=2.53 mins, no mass ion detected

Preparations 83-139 further exemplify the intermediates and key linker molecules that enable single or multiple display of F, and are used for conjugation into Examples 26-62, as described by Schemes 1-8.

Preparation 83

3',5,5'-Tris((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxylic acid

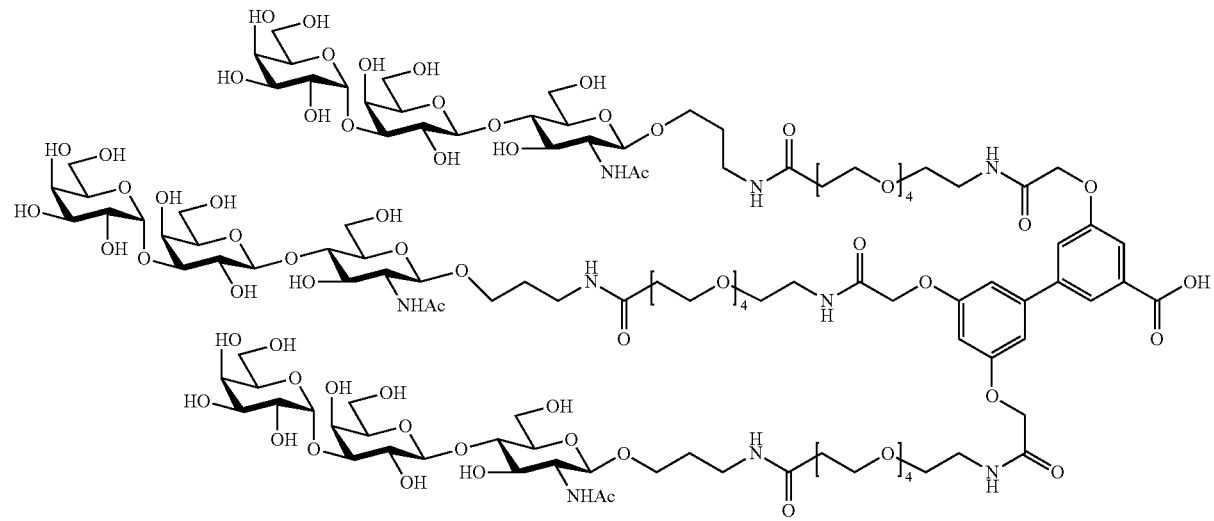

Step 1

To 1,1',1''-((5'-((benzyloxy)carbonyl)-[1,1'-biphenyl]-3,3',5-triyl)tris(oxy))tris(2-oxo-6,9,12,15-tetraoxa-3-azaoctadecan-18-oic acid) (Preparation 111, 48.0 mg, 38.3 μmol) in DMF (4 mL) was added TEA (48.1 μL, 345 μmol) followed by alpha-Gal (92.4 mg, 153 μmol) in DMSO (500 μL). HATU (58.3 mg, 153 μmol) was added and the reaction was left to stir for 1 hour under nitrogen at room temperature. The reaction was concentrated in vacuo and purified using reverse phase column chromatography (Biotage SP1, 10 g, C-18 column, eluting with 5-40% MeCN/water with 0.1% NH₃).

Step 2

To the residue (94.0 mg, 31.3 μmol) dissolved in MeOH/water (1:1 v/v, 10 mL) was added Pd/C (10%, 10 mg). The reaction was put under an atmosphere of hydrogen (50 psi) and stirred for 3 hours at room temperature. The catalyst was removed by filtration through a syringe filter and the reaction was concentrated in vacuo to afford the title compound as a colourless solid (92 mg, 81% over two steps).

LCMS Method A: Rt=1.58 mins ES⁻ MS m/z 1457.2 [M−2H]⁻/2, theoretical mass: 2915.9

Preparations 84-101 were prepared according to the method described for Preparation 83, a two-step reaction protocol comprising: Step 1) addition of aminopropyl-linked alpha-Gal employing a standard amide bond forming step, followed by: Step 2) deprotection of the benzyl protected benzoic/carboxylic acid intermediate, starting from the appropriate carboxylic acid precursor as described below. The reactions were stirred from between 1-24 hours for Step 1, hydrogenated for between 1-3 hours at from 50-80 psi for Step 2, and purified using the reverse-phase purification conditions as described below unless otherwise specified:

Purification Method 1: Biotage SP1 (10 g, C-18 column, eluting with 5-40% MeCN/water with 0.1% NH₃).

Preparation 84

4',5-Bis((46-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,42-dioxo-6,9,12,15,18,21,24,27,30,33,36,39-dodecaoxa-3,43-diazahexatetracontyl)oxy)-[1,1'-biphenyl]-3-carboxylic acid

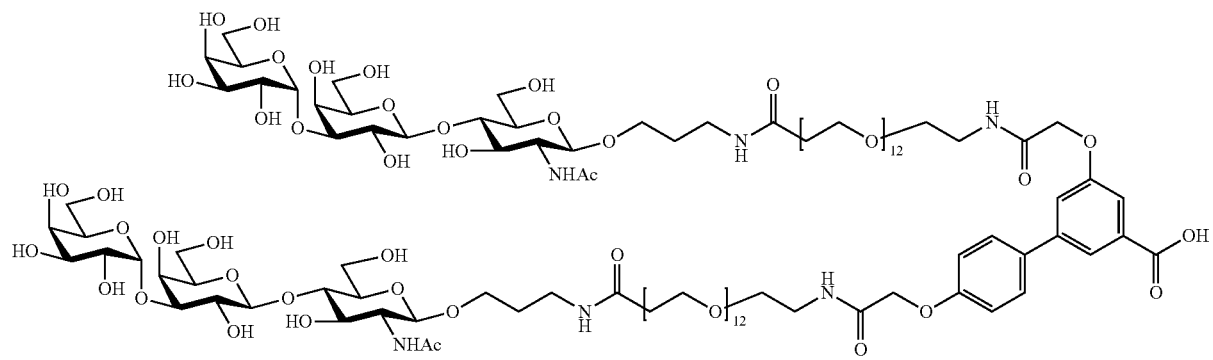

Method: Preparation 83 using 2.5 eq alpha-Gal, 4 eq DIPEA and 3 eq HATU.

Isolated yield: 50% over 2 steps, Purification Method 1 with 10-80% MeCN in water with 0.1% NH₃

LCMS Method A: Rt=1.68 mins, ES⁻ MS m/z 1357.2 [M−2H]⁻/2, theoretical mass: 2714.8

Precursor: Preparation 113

Preparation 85

4'-((22-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxylic acid

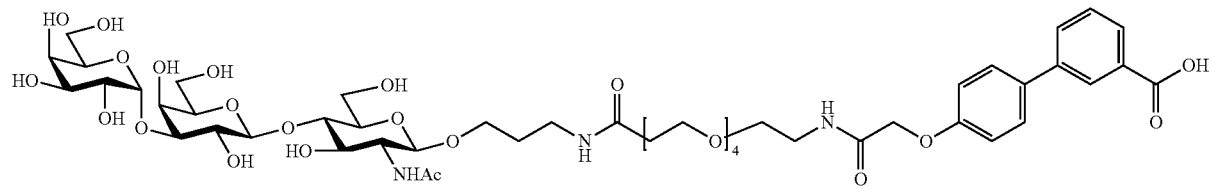

Method: Preparation 83 using 1.3 eq alpha-Gal, 3 eq TEA and 1.3 eq HATU.

Isolated yield: 78% over 2 steps, Purification Method 1 with 5-80% MeCN in water with 0.1% NH₃

LCMS Method B: Rt=1.55 mins, ES⁻ MS m/z 1102.7 [M−H]⁻, theoretical mass: 1104.1

Precursor: Preparation 114

Preparation 86

4',5-Bis((22-((((2R,3R,4R,5S,6R)-3-acetamido-5-
(((2S,3R,4S,5S,6R)-3,5-dihydroxy-6-(hydroxym-
ethyl)-4-(((2R,3R,4S,5R,6R)-3,4,5-trihydroxy-6-
(hydroxymethyl)tetrahydro-2H-pyran-2-yl)oxy)
tetrahydro-2H-pyran-2-yl)oxy)-4-hydroxy-6-
(hydroxymethyl)tetrahydro-2H-pyran-2-yl)oxy)-2,
18-dioxo-6,9,12,15-tetraoxa-3,19-diazadocosyl)
oxy)-[1,1'-biphenyl]-3-carboxylic acid

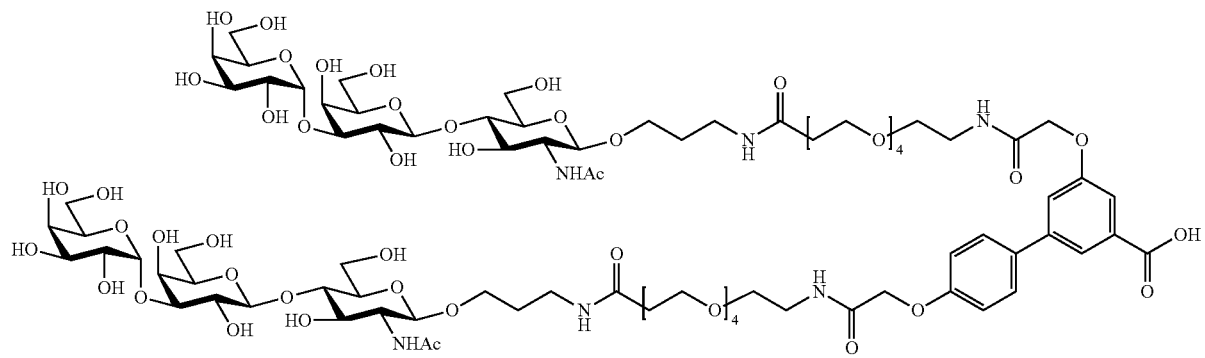

Method: Preparation 83 using 2.5 eq alpha-Gal, 3.5 eq TEA and 2.6 eq HATU.

Isolated yield: 58% over 2 steps, Purification Method 1 with 5-70% MeCN in water with 0.1% $NH_3$ and following hydrogenation, the residue was purified using reverse phase column chromatography (Biotage SP1, 10 g, C-18 column, eluting with 2-20% MeCN/water with 0.1% $NH_3$).

LCMS Method B: Rt=1.49 mins, $ES^+$ MS m/z 1006.0 $[M+2H]^+/2$, theoretical mass: 2010.0

Precursor: Preparation 115

Preparation 87

3',5,5'-Tris((46-((((2R,3R,4R,5S,6R)-3-acetamido-5-
(((2S,3R,4S,5S,6R)-3,5-dihydroxy-6-(hydroxym-
ethyl)-4-(((2R,3R,4S,5R,6R)-3,4,5-trihydroxy-6-
(hydroxymethyl)tetrahydro-2H-pyran-2-yl)oxy)
tetrahydro-2H-pyran-2-yl)oxy)-4-hydroxy-6-
(hydroxymethyl)tetrahydro-2H-pyran-2-yl)oxy)-2,
42-dioxo-6,9,12,15,18,21,24,27,30,33,36,39-
dodecaoxa-3,43-diazahexatetracontyl)oxy)-[1,1'-
biphenyl]-3-carboxylic acid

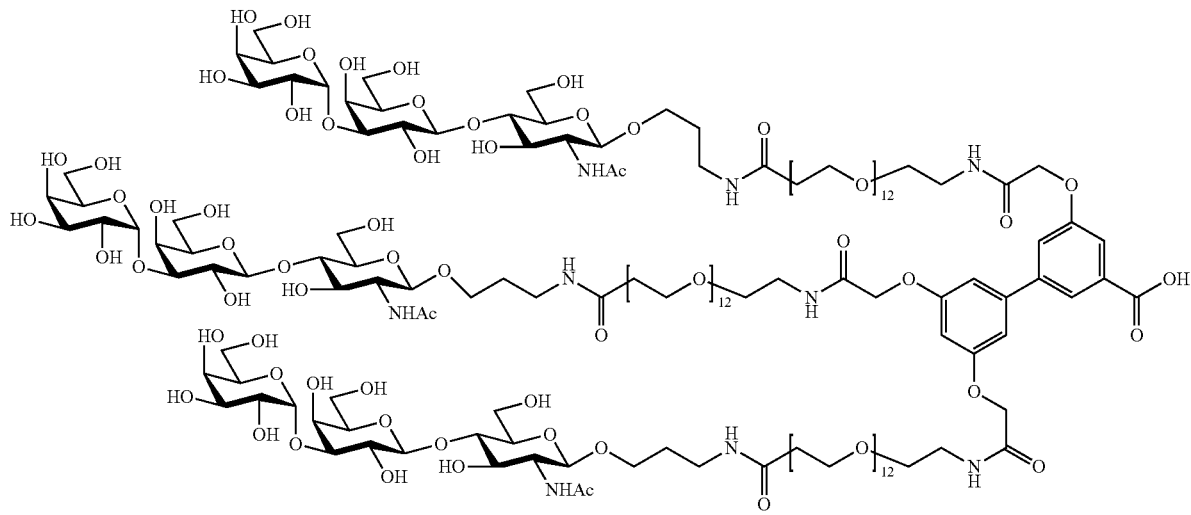

Method: Preparation 83 using 4 eq alpha-Gal, 9 eq TEA and 4 eq HATU.

Isolated yield: 45% over 2 steps, Purification Method 1 with 5-70% MeCN in water with 0.1% $NH_3$ LCMS Method B: Rt=1.68 mins, $ES^-$ MS m/z 1985.4 $[M-2H]^-/2$, theoretical mass: 3973.2

Precursor: Preparation 116

Preparation 88

3',5,5'-Tris((27-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18,23-trioxo-6,9,12,15-tetraoxa-3,19,24-triazaheptacosyl)oxy)-[1,1'-biphenyl]-3-carboxylic acid

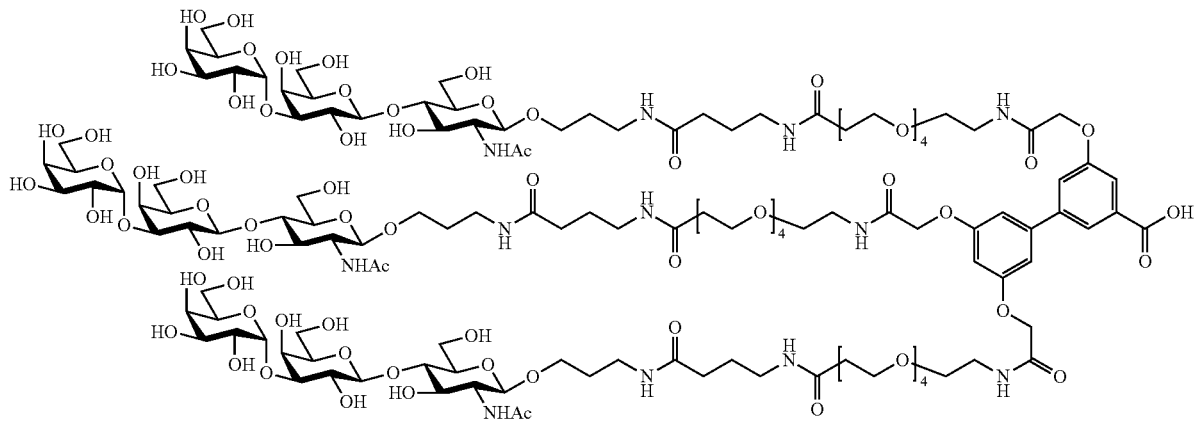

Method: Preparation 83 using 4 eq alpha-Gal, 10 eq TEA and 4 eq HATU.

Isolated yield: 48% over 2 steps, Purification Method 1 with 7-60% MeCN in water with 0.1% $NH_3$ and following hydrogenation, the residue was purified using reverse phase column chromatography (Biotage SP1, 10 g, C-18 column, eluting with 5-40% MeCN/water with 0.1% $NH_3$).

LCMS Method A: Rt=1.56 mins, $ES^+$ MS m/z 1058.2 $[M+3H]^+/3$, theoretical mass: 3171.2

Precursor: Preparation 117

Preparation 89

3',5,5'-Tris(2-((4-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-4-oxobutyl)amino)-2-oxoethoxy)-[1,1'-biphenyl]-3-carboxylic acid

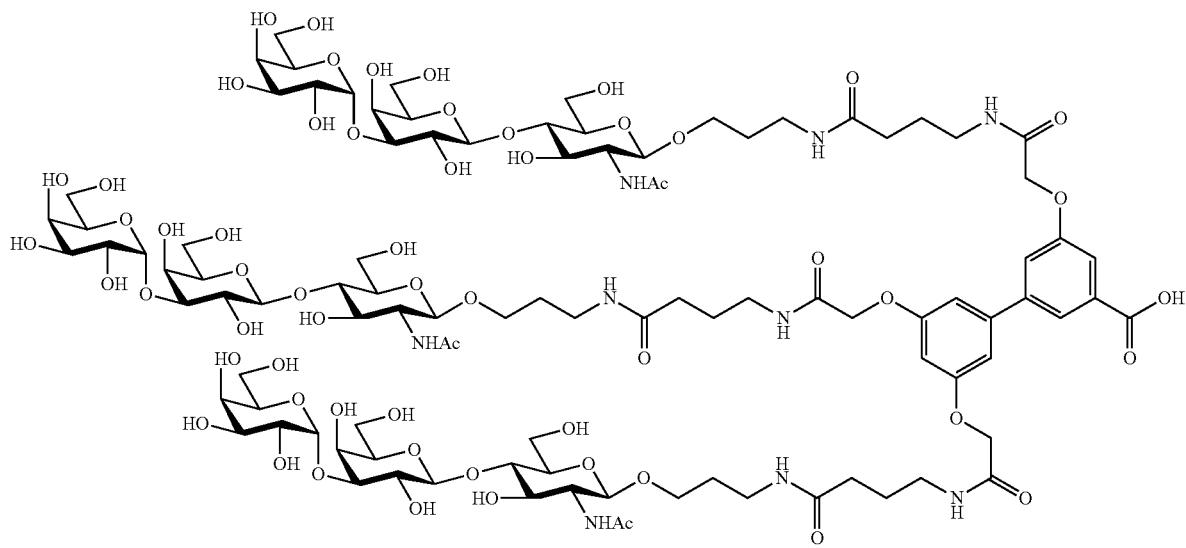

Method: Preparation 83 using 4 eq alpha-Gal, 10 eq TEA and 4 eq HATU.

Isolated yield: 65% over 2 steps, Purification Method 1 with 7-60% MeCN in water with 0.1% $NH_3$ and following hydrogenation, the residue was purified using reverse phase column chromatography (Biotage SP1, 4 g, C-18 column, eluting with 5-40% MeCN/water with 0.1% $NH_3$).

LCMS Method A: Rt=1.39 mins, $ES^+$ MS m/z 1215.6 $[M+2H]^+/2$, theoretical mass: 2429.3

Precursor: Preparation 118

Preparation 90

4'-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid

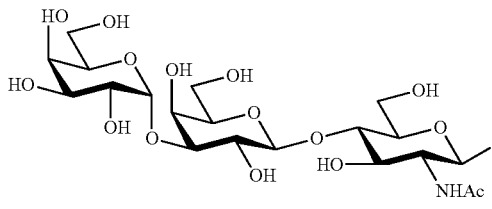
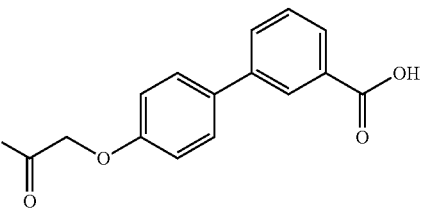

Method: Preparation 83 using 1.3 eq alpha-Gal, 3 eq TEA and 1.5 eq HATU.

Isolated yield: 55% over 2 steps, Purification Method 1 with 7-60% MeCN in water with 0.1% $NH_3$ and following hydrogenation, the residue was purified using reverse phase column chromatography (Biotage SP1, 4 g, C-18 column, eluting with 5-40% MeCN/water with 0.1% $NH_3$).

LCMS Method A: Rt=1.83 mins, $ES^+$ MS m/z 857.6 $[M+H]^+$, theoretical mass: 856.8

Precursor: Preparation 121

Preparation 91

3",5"-Bis(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1':3',1"-terphenyl]-3-carboxylic acid

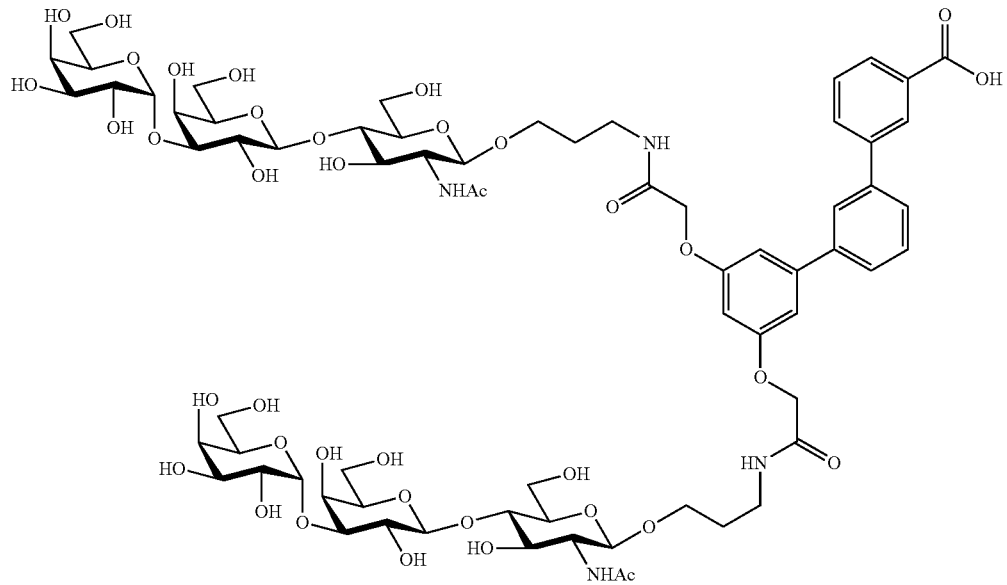

Method: Preparation 83 using 2.4 eq alpha-Gal, 5 eq TEA and 2.5 eq HATU.

Isolated yield: 83% over 2 steps, Purification Method 1 with 7-60% MeCN in water with 0.1% $NH_3$ LCMS Method B: Rt=1.60 mins, $ES^+$ MS m/z 1591.8 $[M]^+$, theoretical mass: 1591.5

Precursor: Preparation 119

Preparation 92

3,3'',5,5''-Tetrakis(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1':3',1''-terphenyl]-5'-carboxylic acid

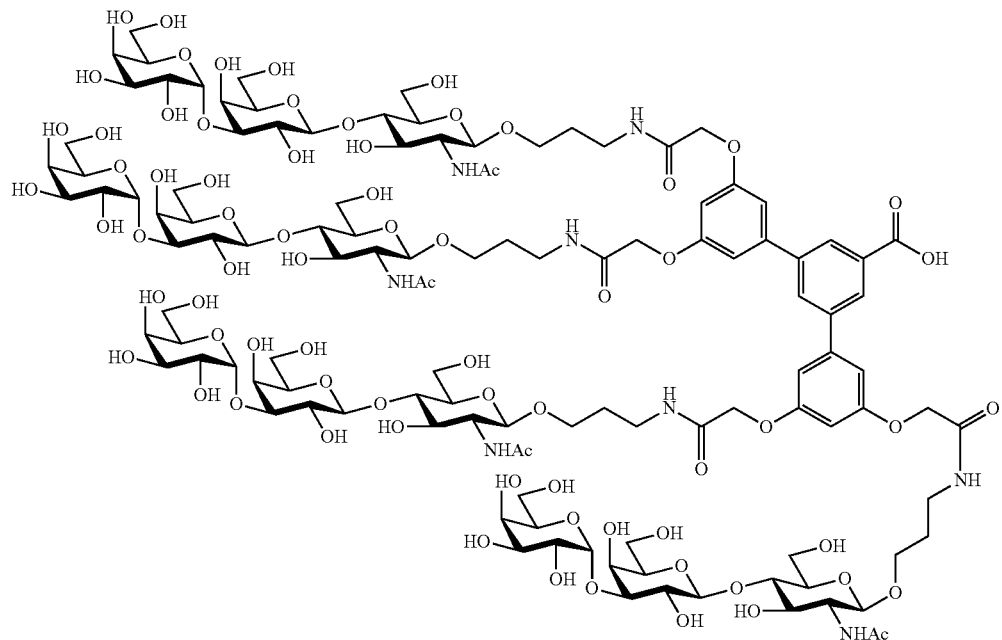

Method: Preparation 83 using 5.2 eq alpha-Gal, 11 eq TEA and 5 eq HATU.

Isolated yield: 64% over 2 steps, Purification Method 1 with 5-40% MeCN in water with 0.1% $NH_3$ LCMS Method B: Rt=1.35 mins, $ES^-$ MS m/z 1453.5 $[M-2H]^-/2$, theoretical mass: 2908.7

Precursor: Preparation 120

Preparation 93

3,3",5,5"-Tetrakis((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1':3',1"-terphenyl]-5'-carboxylic acid

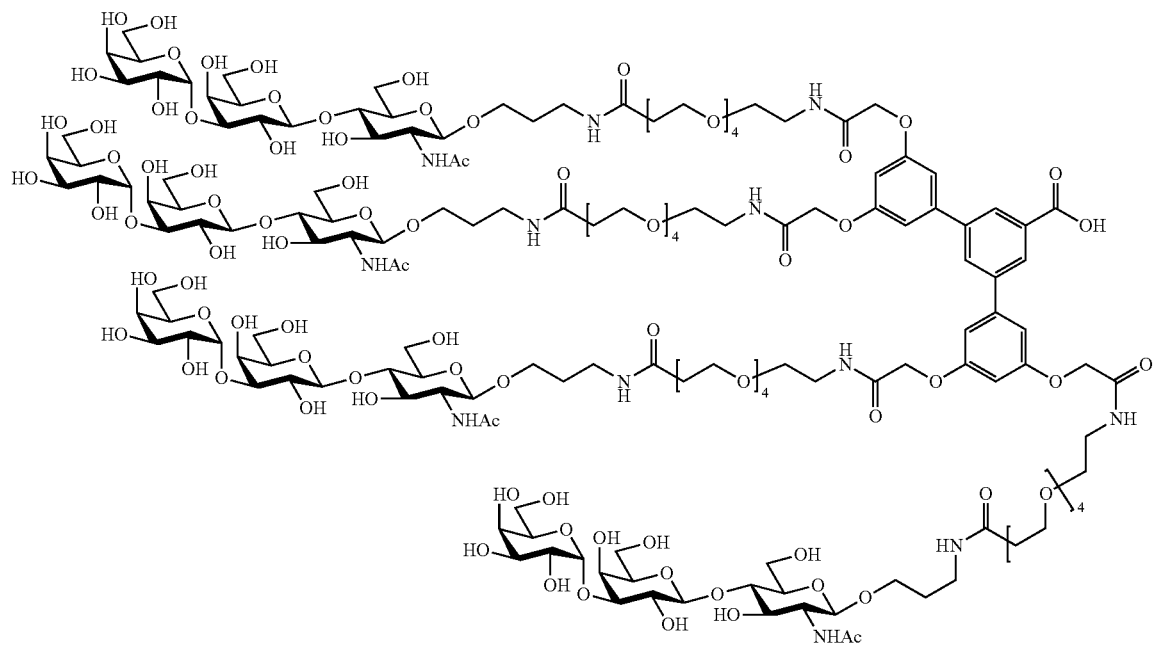

Method: Preparation 83 using 6 eq alpha-Gal, 13 eq TEA and 6 eq HATU.

Isolated yield: 73% over 2 steps, Purification Method 1 with 7-60% MeCN in water with 0.1% $NH_3$ LCMS Method B: Rt=1.41 mins, $ES^+$ MS m/z 1300.8 $[M+3H]^+/3$, theoretical mass: 3897.9

Precursor: Preparation 112

Preparation 94

3',4',5'-Tris(2-((3-(((2R,3R,4R,5S,6R)-3-acetamido-5-((((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid

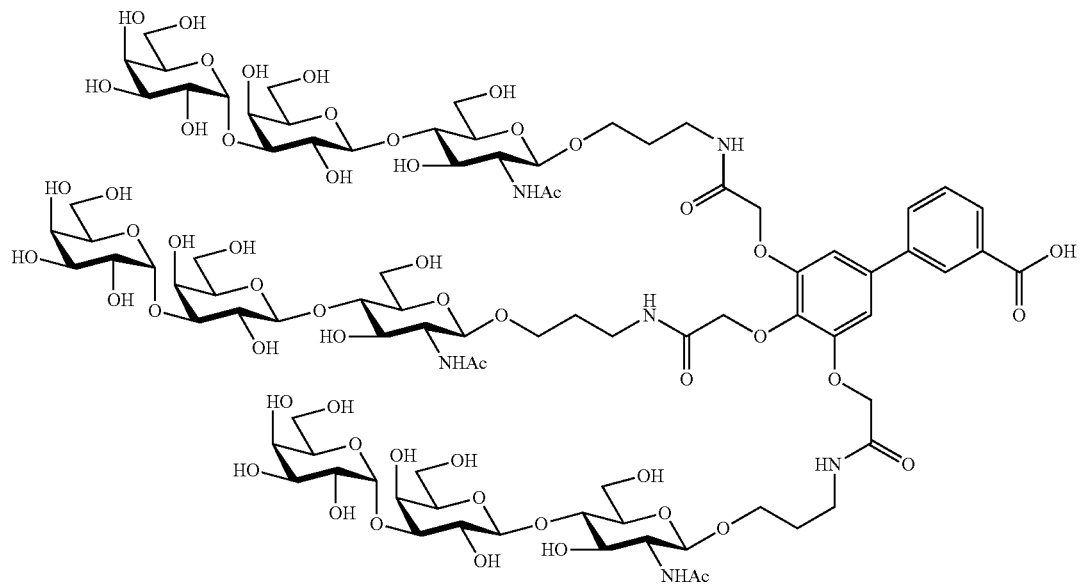

Method: Preparation 83 using 5 eq alpha-Gal, 9 eq TEA and 5 eq HATU.

Isolated yield: 55% over 2 steps, Purification Method 1 with 5-40% MeCN in water with 0.1% NH$_3$ LCMS Method B: Rt=1.26 mins, ES$^-$ MS m/z 1086.4 [M−2H]$^-$/2, theoretical mass: 2174.0

Precursor: Preparation 122

The following Preparations were prepared according to Preparation 83 as above using the benzoic acid precursors above and the corresponding amine-linkers as described below:

Preparation 95

3-((1,6,46-Trioxo-1-(3',5,5'-tris(2-((3-(((2R,3R,4R,5S,6R)-3-acetamido-5-((((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-yl)-9,12,15,18,21,24,27,30,33,36,39,42-dodecaoxa-2,5,45-triazaheptatetracontan-47-yl)oxy)benzoic acid

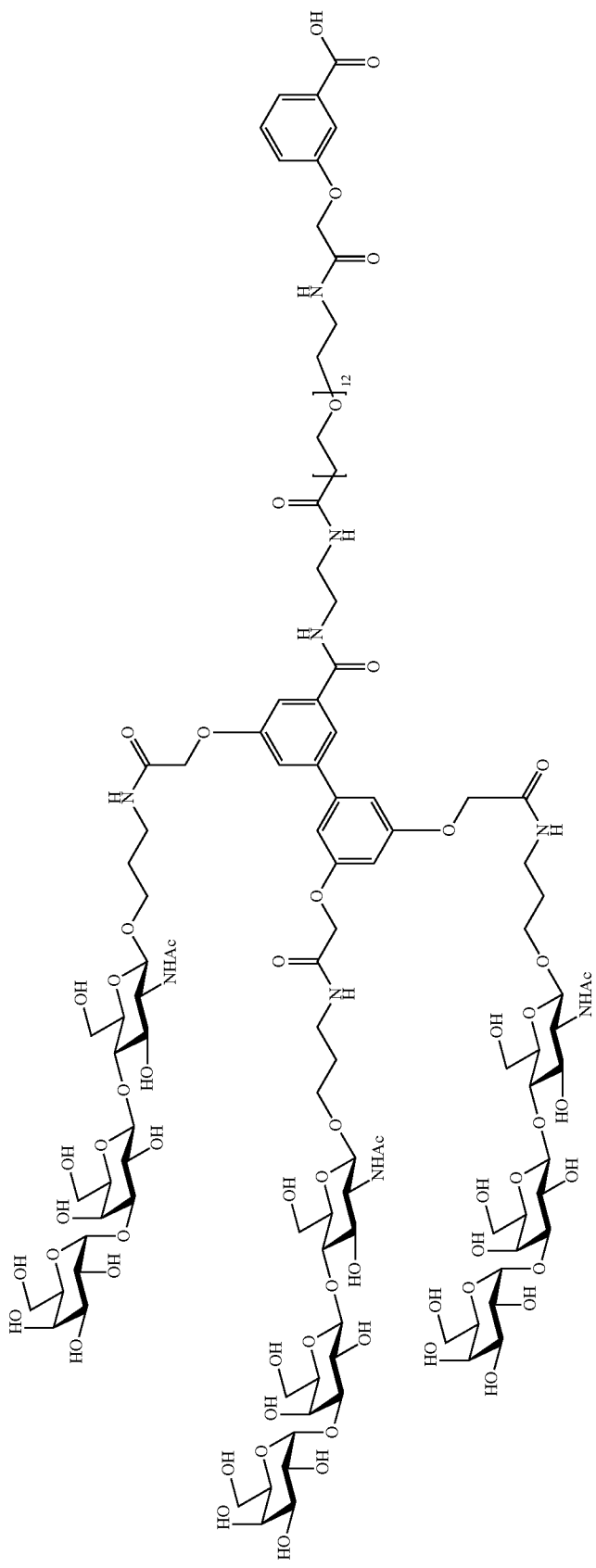

Method: Preparation 83 using 1.2 eq Preparation 134, 2.5 eq TEA and 1.2 eq HATU.

Isolated yield: 57% over 2 steps, Purification Method 1 with 7-60% MeCN in water with 0.1% $NH_3$ LCMS Method A: Rt=1.71 mins, ES$^-$ MS m/z 1495.6 [M−2H]$^-$/2, theoretical mass: 2994.0

Precursor: Preparation 42 and Preparation 134

Preparation 96

3-((1,6,22-Trioxo-1-(3',5,5'-tris(2-((3-(((2R,3R,4R, 5S,6R)-3-acetamido-5-((((2S,3R,4S,5S,6R)-3,5-dihydroxy-6-(hydroxymethyl)-4-((((2R,3R,4S,5R,6R)-3,4, 5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-yl)-9,12,15,18-tetraoxa-2,5,21-triazatricosan-23-yl)oxy)benzoic acid

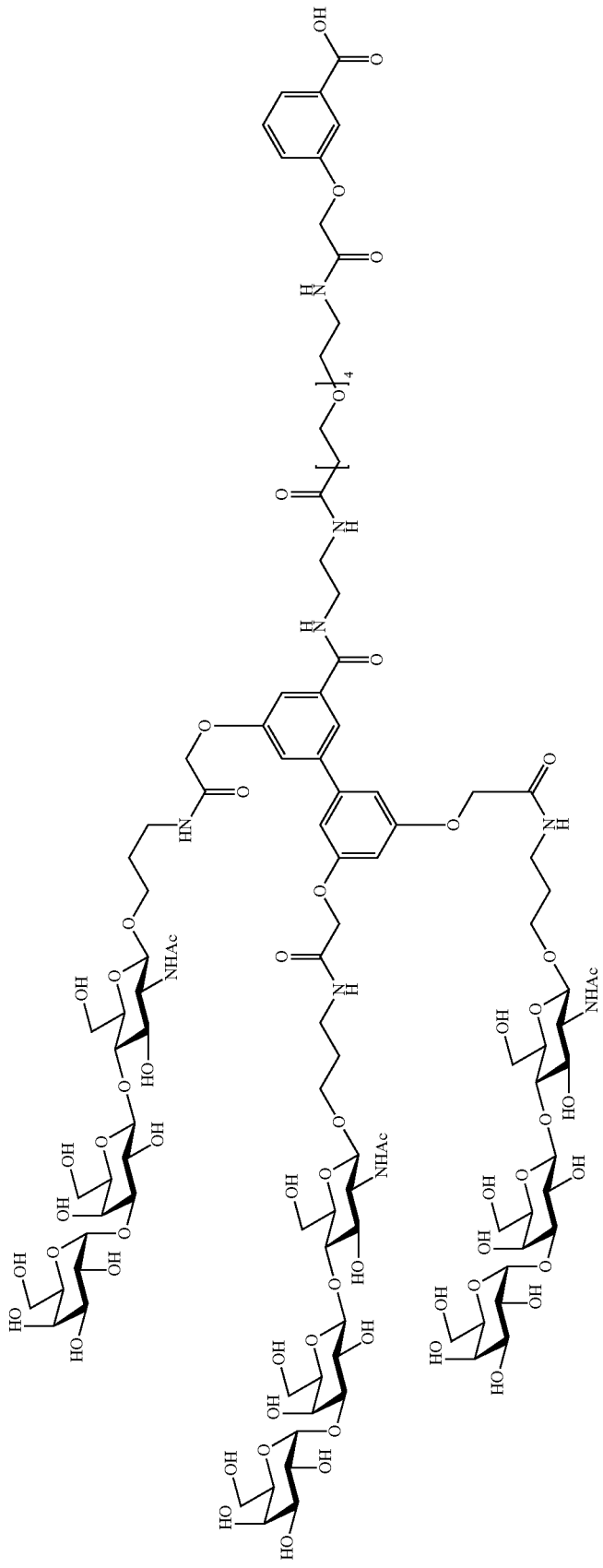

Method: Preparation 83 using 1.2 eq Preparation 130, 4 eq TEA and 1.2 eq HATU.

Isolated yield: 38% over 2 steps, Purification Method 1 with 10-80% MeCN in water with 0.1% $NH_3$ LCMS Method A: Rt=1.57 mins, $ES^-$ MS m/z 1319.5 $[M-2H]^-/2$, theoretical mass: 2641.6

Precursor: Preparation 89 and Preparation 130

Preparation 97

3-((1,6,22-Trioxo-1-(3',5,5'-tris((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-yl)-9,12,15,18-tetraoxa-2,5,21-triazatricosan-23-yl)oxy)benzoic acid

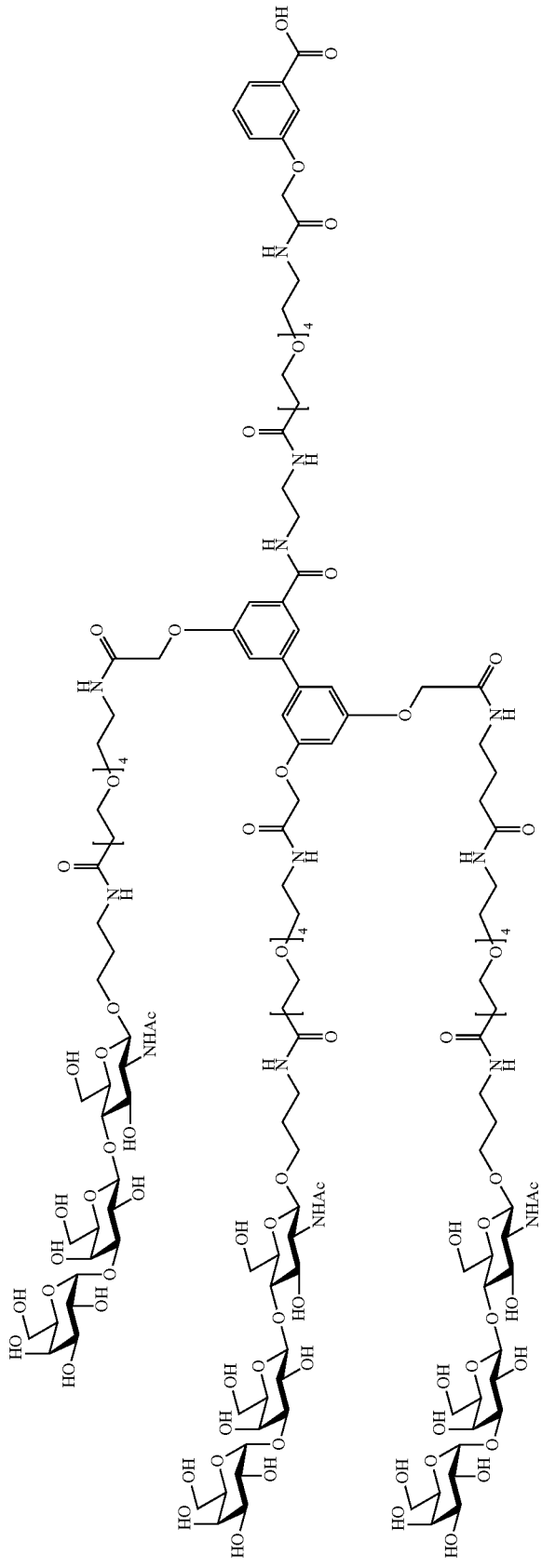

Method: Preparation 83 using 1.2 eq Preparation 130, 4 eq TEA and 1.2 eq HATU.

Isolated yield: 25% over 2 steps, Purification Method 1 with 10-80% MeCN in water with 0.1% $NH_3$ LCMS Method B: Rt=1.48 mins, $ES^-$ MS m/z 1690.4 $[M-2H]^-/2$, theoretical mass: 3383.4

Precursor: Preparation 83 and Preparation 130

Preparation 98

3-(((1,6,46-Trioxo-1-(3',5,5'-tris((22-((((2R,3R,4R,5S,6R)-3-acetamido-5-(((2S,3R,4S,5S,6R)-3,5-dihydroxy-6-(hydroxymethyl)-4-((((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-yl)-9,12,15,18,21,24,27,30,33,36,39,42-dodecaoxa-2,5,45-triazaheptatetracontan-47-yl)oxy)benzoic acid

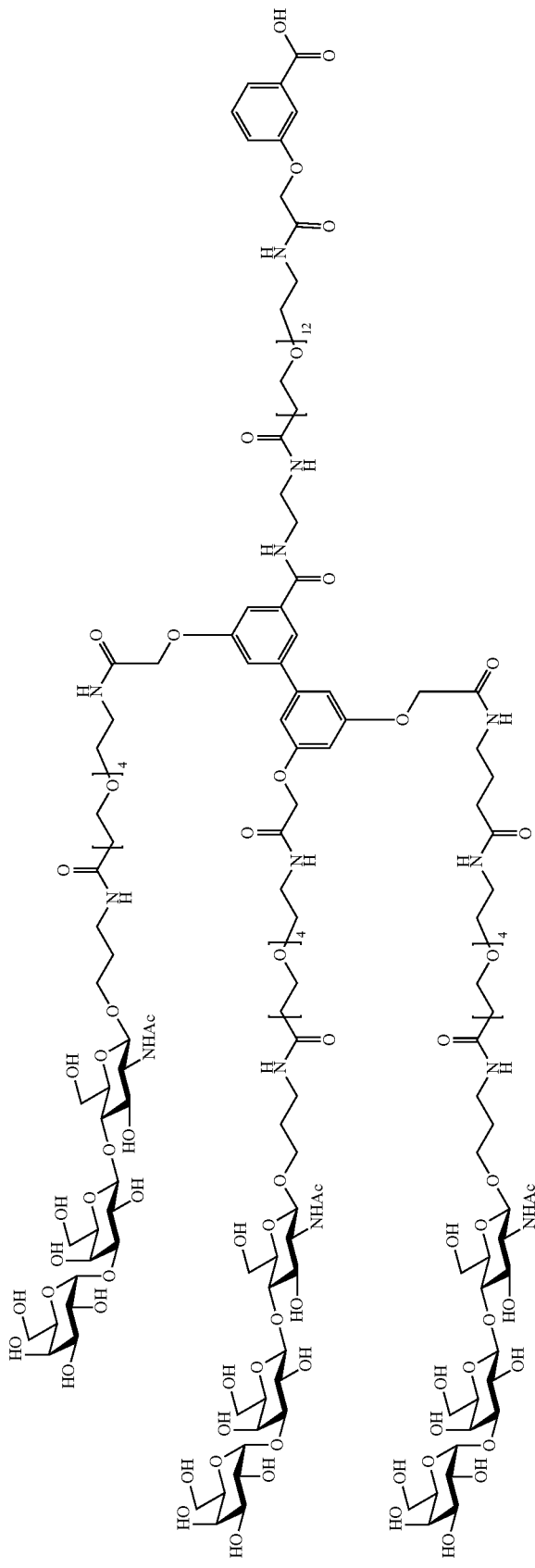

Isolated yield: 76% over 2 steps, Purification Method 1 with 7-60% MeCN in water with 0.1% NH$_3$ LCMS Method A: Rt=1.77 mins, ES$^+$ MS m/z 1868.7 [M+2H]*/2, theoretical mass: 3735.8

Precursor: Preparation 83 and Preparation 134

Preparation 99

6-(6-(3',5,5'-Tris(2-((3-(((2R,3R,4R,5S,6R)-3-acet-amido-5-(((2S,3R,4S,5S,6R)-3,5-dihydroxy-6-(hy-droxymethyl)-4-(((2R,3R,4S,5R,6R)-3,4,5-trihy-droxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-ylcarboxamido)hexanamido)hexanoic acid

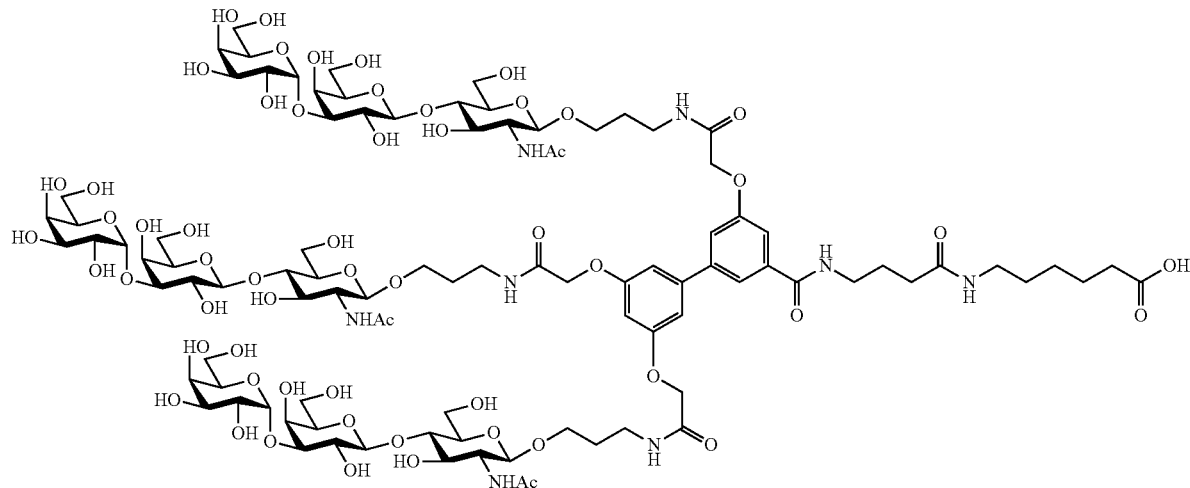

Method: Preparation 83 using 1.2 eq benzyl 6-(6-amino-hexanamide)hexanoate, 2.5 eq TEA and 1.2 eq HATU.

Isolated yield: 71% over 2 steps, Purification Method 1 with 5-40% MeCN in water with 0.1% NH$_3$ LCMS Method B: Rt=1.47 mins, ES$^+$ MS m/z 1201.3 [M+2H]$^+$/2, theoretical mass: 2400.3

Precursor: Preparation 42 and benzyl 6-(6-aminohexana-mide)hexanoate (JACS (2014) 136 (52) 18034-18043).

Preparation 100

1,8,15,22-Tetraoxo-1-(3,3'',5,5''-tetrakis((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1':3',1''-terphenyl]-5'-yl)-2,9,16,23-tetraazanonacosan-29-oic acid

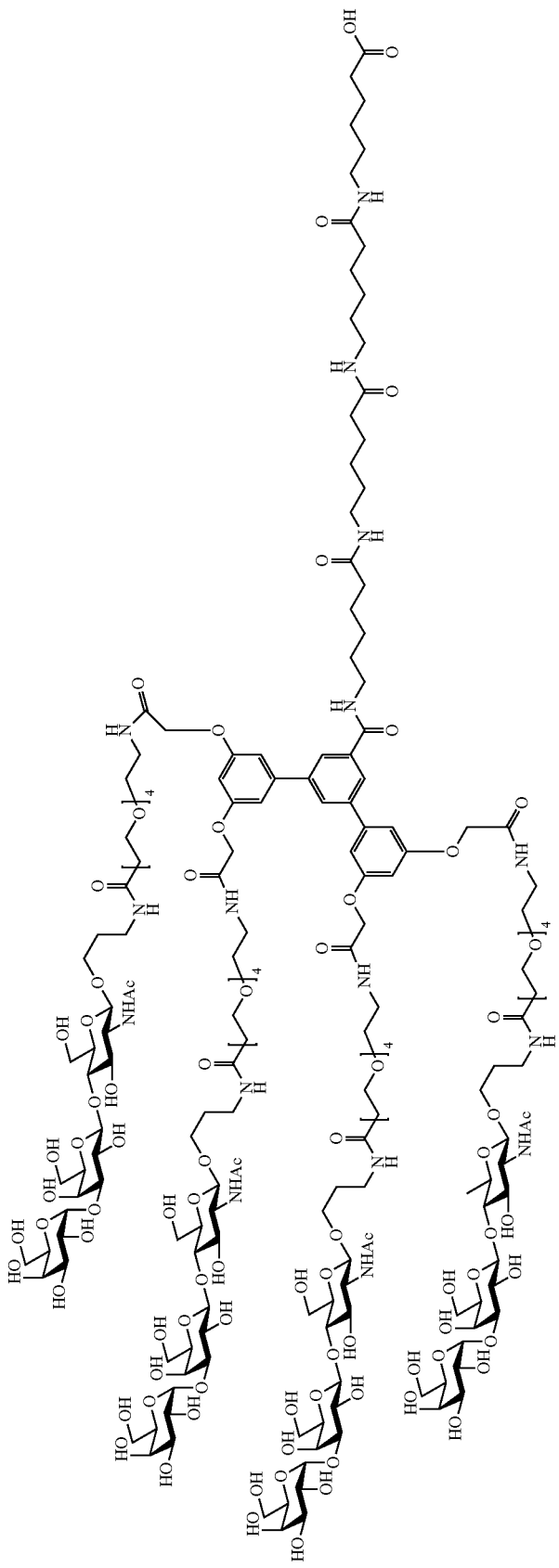

Method: Preparation 83 using 1.2 eq amine, 2.5 eq TEA and 1.2 eq HATU followed by Preparation 42 Method B.

Isolated yield: 59% over 2 steps, Purification Method 1 with 7-60% MeCN in water with 0.1% $NH_3$ followed by Biotage Isolera (10 g, C-18 column, eluting with 5-40% MeCN/water with 0.1% NH3) after the deprotection step.

LCMS Method B: Rt=1.65 mins, $ES^+$ MS m/z 1451.6 $[M+3H]^+/3$, theoretical mass: 4350.5

Precursor: Preparation 93 and Preparation 110

Preparation 101

1-Oxo-1-(3',5,5'-tris((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-yl)-5,8,11,14-tetraoxa-2-azaheptadecan-17-oic acid

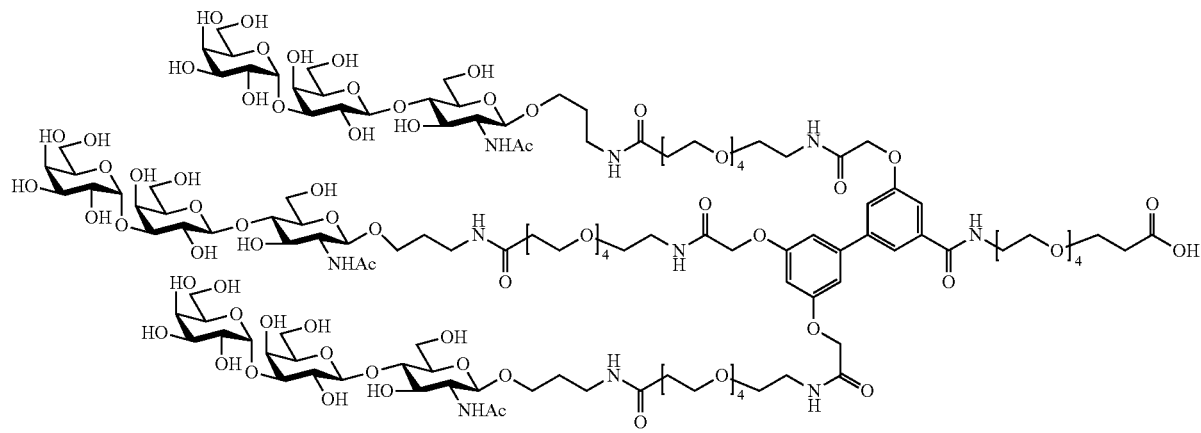

The title compound was prepared according to the method described by Preparation 83 using 3',5,5'-tris((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxylic acid (Preparation 83), 1.3 eq tert-butyl 1-amino-3,6,9,12-tetraoxapentadecan-15-oate, 4 eq TEA and 1.3 eq HATU followed by reverse phase purification using Purification Method 1 (5-60% MeCN in water with 0.1% $NH_3$). The residue was dissolved in DCM (1 mL), treated with 4M HCl in dioxane (5 mL) and stirred at room temperature for 30 minutes followed by heating at 30° C. for 90 minutes. Additional 4M HCl in dioxane was added (25 mL) and the reaction sonicated for 2 hours. The reaction was dissolved in water (2 mL) and freeze-dried to afford the title compound in 99% yield.

LCMS Method A: Rt=1.61 mins, $ES^+$ MS m/z 1582.6 $[M+2H]^+/2$, theoretical mass: 3162.0

Preparation 102

2-({3'-[(2-{5-[(3aS,4S,6aR)-2-Oxo-hexahydro-1H-thieno[3,4-d]imidazol-4-yl]pentanamido}ethyl)carbamoyl]-4,5-bis(carboxymethoxy)-[1,1'-biphenyl]-3-yl}oxy)acetic acid

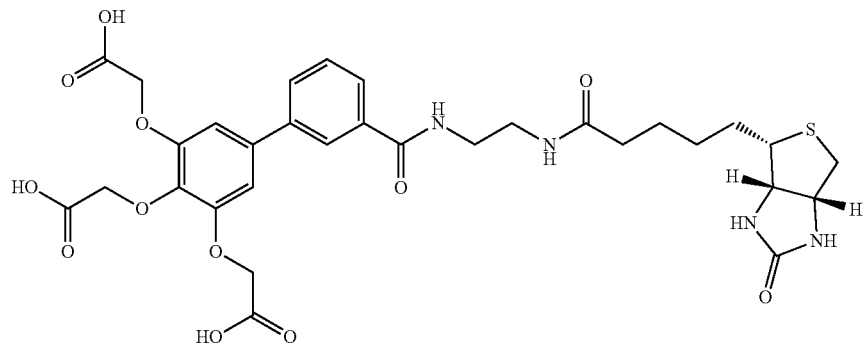 [SMILES: O=C(O)COc1cc(-c2cccc(C(=O)NCCNC(=O)CCCC[C@@H]3SC[C@@H]4NC(=O)N[C@@H]43)c2)cc(OCC(=O)O)c1OCC(=O)O]

To a solution of tert-butyl 2-({3'-[(2-{5-[(3aS,4S,6aR)-2-oxo-hexahydro-1H-thieno[3,4-d]imidazol-4-yl]pentanamido}ethyl)carbamoyl]-4,5-bis[2-(tert-butoxy)-2-oxoethoxy]-[1,1'-biphenyl]-3-yl}oxy)acetate (Preparation 103, 20 mg, 23 µmol) in DCM (1.5 mL) was added 4N HCl in dioxane (0.5 mL, 2 mmol) and the reaction was stirred at room temperature for 1 hour. The reaction was concentrated in vacuo, azeotroped with toluene and taken on directly to the next step.

Preparation 103 tert-Butyl 2-({3'-[(2-{5-[(3aS,4S,6aR)-2-oxo-hexahydro-1H-thieno[3,4-d]imidazol-4-yl]pentanamido}ethyl)carbamoyl]-4,5-bis[2-(tert-butoxy)-2-oxoethoxy]-[1,1'-biphenyl]-3-yl}oxy)acetate

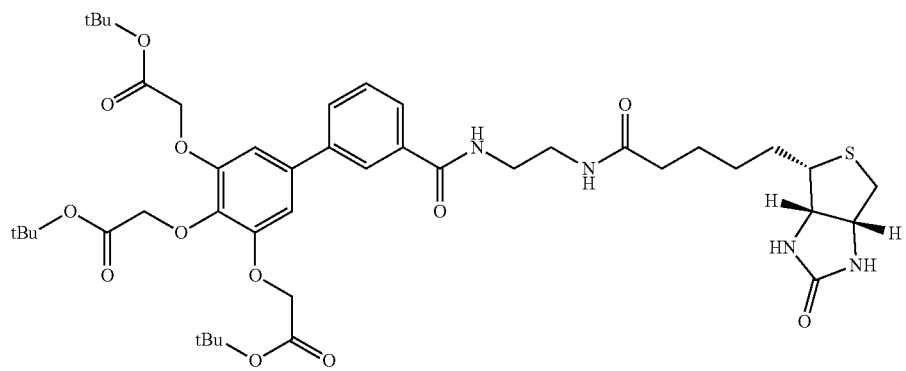 [SMILES: CC(C)(C)OC(=O)COc1cc(-c2cccc(C(=O)NCCNC(=O)CCCC[C@@H]3SC[C@@H]4NC(=O)N[C@@H]43)c2)cc(OCC(=O)OC(C)(C)C)c1OCC(=O)OC(C)(C)C]

The title compound was prepared according to the method described for Preparation 72 using 5-[(3aS,4S,6aR)-2-oxo-hexahydro-1H-thieno[3,4-d]imidazol-4-yl]-N-[2-({3',4',5'-trihydroxy-[1,1'-biphenyl]-3-yl}formamido)ethyl]pentanamide (Preparation 104) and tert-butyl bromo acetate. The residue was purified using silica gel column chromatography eluting with 2-10% MeOH in DCM and taken directly on to the next step.

LCMS Method B: Rt=3.26 mins; ES$^+$ MS m/z 857.4 [M+H]$^+$

Preparation 104

5-[(3aS,4S,6aR)-2-Oxo-hexahydro-1H-thieno[3,4-d]imidazol-4-yl]-N-[2-({3',4',5'-trihydroxy-[1,1'-biphenyl]-3-yl}formamido)ethyl]pentanamide

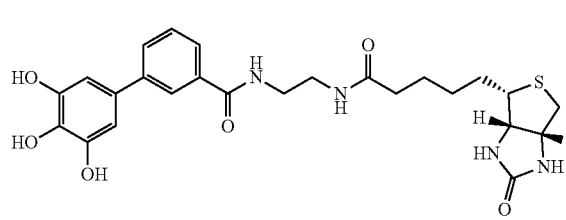

To a suspension 5-[(3aS,4S,6aR)-2-oxo-hexahydro-1H-thieno[3,4-d]imidazol-4-yl]-N-[2-({3',4',5'-trimethoxy-[1,1'-biphenyl]-3-yl}formamido)ethyl]pentanamide (Preparation 105, 142 mg, 0.25 mmol) and some molecular sieves (4 Å) in DCM (15 mL) was added BBr$_3$ (1M in DCM, 5 mL) was added dropwise. The reaction was allowed to warm to room temperature for 1 hour and stirred for 16 hours overnight. The reaction was quenched by the addition of MeOH to afford a 40 mL solution. The reaction was decanted and the solution was heated to reflux before concentrating in vacuo. The residue was partitioned between EtOAc and water, however the product remained in both layers. Hence both layers were combined, concentrated in vacuo and the residue was taken directly on to the next step.

Preparation 105

5-[(3aS,4S,6aR)-2-Oxo-hexahydro-1H-thieno[3,4-d]imidazol-4-yl]-N-[2-({3',4',5'-trimethoxy-[1,1'-biphenyl]-3-yl}formamido)ethyl]pentanamide

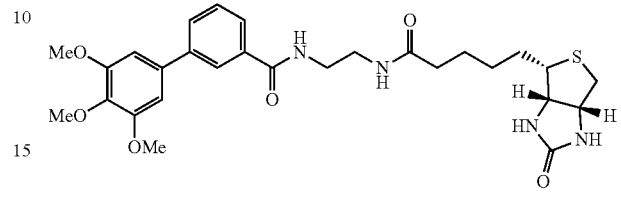

The title compound was prepared according to the method described for Preparation 30 using 3',4',5'-trimethoxy-[1,1'-biphenyl]-3-carboxylic acid (Preparation 125) and N-(2-aminoethyl)-5-((3aS, 4S, 6aR)-2-oxohexahydro-1H-thieno[3,4-d]imidazole-4-yl)pentamide. The residue was purified using silica gel column chromatography eluting with 1-10% MeOH in DCM.

LCMS Method A: Rt=2.22 mins, ES$^+$ MS m/z 557.4 [M+H]$^+$

Preparation 106

1-(3-((4,44-Dioxo-48-((3aS,4S,6aR)-2-oxohexahydro-1H-thieno[3,4-d]imidazol-4-yl)-7,10,13,16,19,22,25,28,31,34,37,40-dodecaoxa-3,43-diazaoctatetracontyl)carbamoyl)phenoxy)-2-oxo-6,9,12,15,18,21,24,27,30,33,36,39-dodecaoxa-3-azadotetracontan-42-oic acid

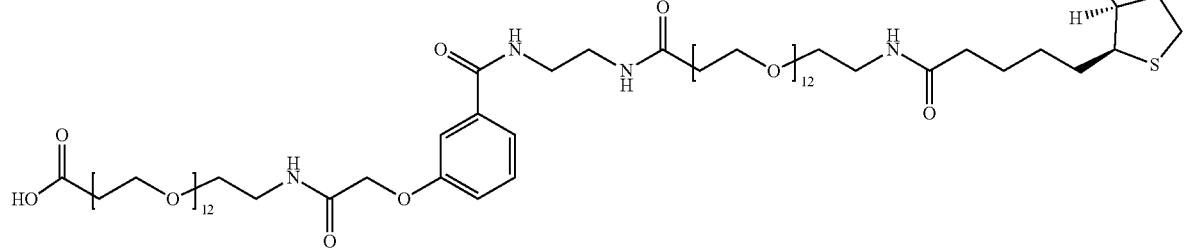

The title compound was prepared according to Preparation 30 followed by Preparation 1 using tert-butyl 1-amino-3,6,9,12,15,18,21,24,27,30,33,36-dodecaoxanonatriacontan-39-oate and 2-(3-{[2-(1-{5-[(3aS,4S,6aR)-2-oxohexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}phenoxy)acetic acid (Preparation 107).

LCMS Method B: Rt=1.98 mins, ES$^+$ MS m/z 1664.9 [M+H]$^+$

Preparation 107

2-(3-{[2-(1-{5-[(3aS,4S,6aR)-2-Oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}phenoxy)acetic acid

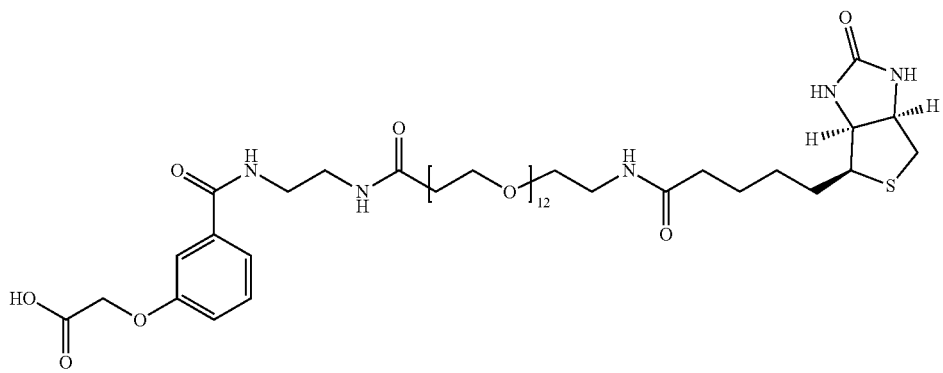

To ethyl 2-(3-{[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}phenoxy)acetate (Preparation 108, 10.0 mg, 9.20 μmol) in MeOH/H$_2$O (500 μL, 1:1 v/v) was added NaOH (2M, 14.0 μL, 27.6 μmol). The reaction mixture was stirred at room temperature for 30 minutes and the solvent was removed under reduced pressure. The residue was dissolved in water (1 mL), and acidified using HCl (2M, 5 drops). The solvent was removed under reduced pressure and azeotroped with toluene (3×2 mL) to afford the crude product as an off white solid. The solid was dissolved in DMF (500 μL) to make a crude stock solution which was used directly in the next step.

LCMS Method A: Rt=1.89 mins, ES$^-$ MS m/z 1062.8 [M+H]$^-$

Preparation 108

Ethyl 2-(3-{[2-(1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}phenoxy)acetate

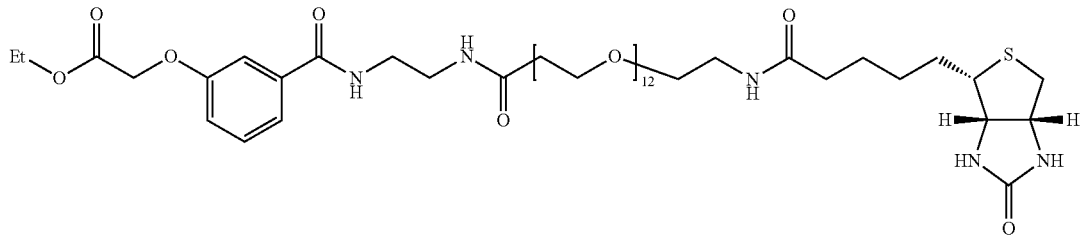

To ethyl 2-(3-((2-aminoethyl)carbamoyl)phenoxy)acetate trifluroacetic acid salt (Preparation 50, 87.0 mg, 229 μmol) dissolved in DMF (500 μL) was added 2,5-dioxopyrrolidin-1-yl 1-{5-[(3aS,4S,6aR)-2-oxo-hexahydro-1H-thieno[3,4-d]imidazolidin-4-yl]pentanamido}-3,6,9,12,15,18,21,24,27,30,33,36-dodecaoxanonatriacontan-39-oate (35.0 mg, 37.0 μmol) and TEA (20.0 μL, 111 μmol). The reaction was stirred at room temperature for 1 hour before concentrating in vacuo. The residue was purifies using silica gel column chromatography (Biotage SP1, eluting with 2-20% MeOH/DCM) to afford the title compound as a colourless oil (29.2 mg, 66%).

LCMS Method A: Rt=2.11 mins, ES$^+$ MS m/z 1092.9 [M+H]$^+$

Preparation 109

1,1',1'',1'''-((5-((2-(5-((3aS,4S,6aR)-2-Oxohexahydro-1H-thieno[3,4-d]imidazol-4-yl)pentanamido)ethyl)carbamoyl)-[1,1'-biphenyl]-2,3',4,5'-tetrayl)tetrakis(oxy))tetrakis(2-oxo-6,9,12,15-tetraoxa-3-azaoctadecan-18-oic acid)

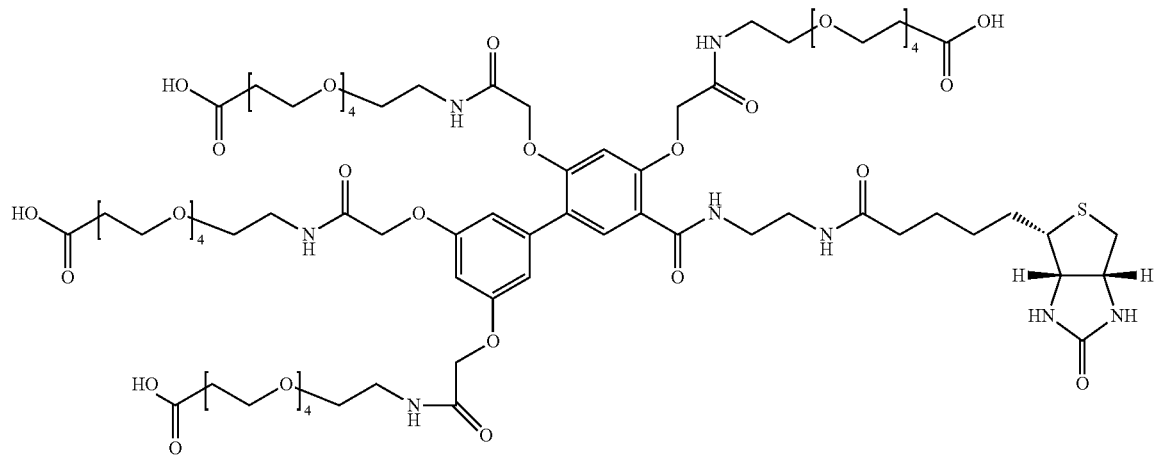

The title compound was prepared according to the method described for Preparation 30 (DIPEA was used in place of TEA) followed by Preparation 1 using tert-butyl 1-amino-3,6,9,12-tetraoxapentadecan-15-oate and 2,2',2'',2'''-((5-((2-(5-((3aS,4S,6aR)-2-oxohexahydro-1H-thieno[3,4-d]imidazole-4-yl)pentamido)ethyl)carbamoyl)-[1,1'-biphenyl]-2,3',4,5'-tetrayl)tetrakis(oxy))tetraacetic acid (Preparation 7).

LCMS Method A: Rt=1.91 mins, no mass ion observed.

Preparation 110

Benzyl 6-(6-(6-(6-aminohexanamido)hexanamido)hexanamido)hexanoate

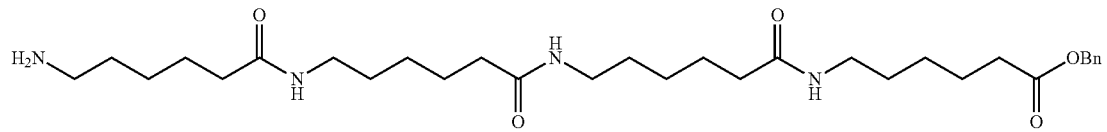 [SMILES: NCCCCCC(=O)NCCCCCC(=O)NCCCCCC(=O)NCCCCCC(=O)OCc1ccccc1]

6-(6-((tert-butoxycarbonyl)amino)hexanamido)hexanoic acid (Pharmazie, 1985, 40, 9, 617-622, 321 mg, 932 mmol) and benzyl 6-(6-aminohexanamido)hexanoate hydrochloride (JACS (2014) 136, 52, 18034-18043, 380 mg, 1.025 mmol) were dissolved in DMF (8.4 mL). TEA (0.46 mL 3.26 mmol) was added followed by HATU (425 mg, 1.118 mmol) and the reaction mixture stirred at room temperature under nitrogen for 60 hours. The resulting solid was filtered, washed with EtOAc and purified by silica gel column chromatography eluting with 2-6% MeOH in DCM. The resulting white solid (338.0 mg, 0.511 mmol) was dissolved in dioxane (6.76 mL) and 4M HCl in dioxane (1.28 mL, 5.12 mmol) was added. The reaction mixture was stirred at room temperature for 18 hours and concentrated in vacuo. The resulting solid was suspended in TBME (10 mL), filtered, washed with TBME and dried for 1 hour under vacuum to afford the title compound as a white solid (271 mg, 89%).

LCMS Method B: Rt=2.32 mins, ES+ MS m/z 561.3 [M+H]+

$^1$H NMR (400 MHz, DMSO-$d_6$): δ ppm 7.90-7.67 (6H, m), 7.38-7.29 (5H, m), 5.10-5.01 (2H, s), 3.01-2.90 (6H, m), 2.45-2.42 (6H, s), 2.36-2.29 (2H, m), 2.37-2.28 (6H, m), 2.08-1.92 (6H, m), 1.56-1.14 (14H, m).

Preparation 111

1,1',1''-((5'-((Benzyloxy)carbonyl)-[1,1'-biphenyl]-3,3',5-triyl)tris(oxy))tris(2-oxo-6,9,12,15-tetraoxa-3-azaoctadecan-18-oic acid)

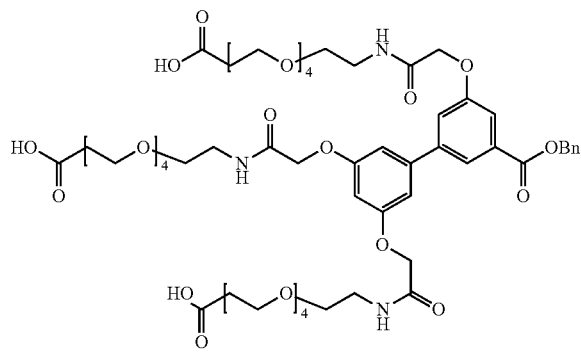

Step 1

To 2,2',2''-((5'-((benzyloxy)carbonyl)-[1,1'-biphenyl]-3,3',5-triyl)tris(oxy))triacetic acid (Preparation 73, 750 mg, 1.47 mmol) dissolved in DMF (30 mL) was added TEA (1.84 mL, 13.2 mmol) and tert-butyl 1-amino-3,6,9,12-tetraoxapentadecan-15-oate (1.89 g, 5.88 mmol). HATU (2.23 g, 5.88 mmol) was added and the reaction was stirred at room temperature under nitrogen for 2 hours. The reaction was concentrated in vacuo and the residue was purified using reverse phase column chromatography (Biotage SP1, 120 g, C-18 column, eluting with 20-80% MeCN/water with 0.1% $NH_3$).

Step 2

The residue was dissolved in DCM/TFA/water (10:10:1 v/v/v, 24 mL) and allowed to stir at room temperature for 2 hours. The reaction was concentrated in vacuo, azeotroped with dioxane/toluene 1:1 v/v, 3×24 mL) and purified using reverse phase column chromatography (Biotage SP1, 30 g, C-8 column, eluting with 5-40% MeCN/water with 0.1% formic acid) to afford the title compound as a colourless gum (1.11 g, 60%).

LCMS Method A: Rt=2.36 mins, ES⁻ MS m/z 1250.8 [M−H]⁻

$^1$H NMR (400 MHz, DMSO-$d_6$): δ ppm 12.20 (3H, br s), 8.25 (1H, t), 8.15-8.10 (2H, m), 7.80 (1H, s), 7.55-7.45 (4H, m), 7.45-7.30 (3H, m), 6.90 (2H, d), 6.65-6.60 (1H, m), 5.40 (2H, s), 4.65 (2H, s), 4.55 (4H, s), 3.55 (6H, t), 3.50-3.40 (42H, m), 3.30-3.25 (6H, m), 2.40 (6H, t).

The following Preparations were prepared according to the methods described by Preparation 111 using either tert-butyl 1-amino-3,6,9,12-tetraoxapentadecan-15-oate or tert-butyl 1-amino-3,6,9,12,15,18,21,24,27,30,33,36-dodecaoxanonatriacontan-39-oate or tert-butyl 4-aminobutanoate and the appropriate carboxylic acid as described below:

Purification after Step 1:
Biotage SP1 (C-18 column, eluting with from between 12-100% MeCN/water with 0.1% formic acid) or Biotage SP1 (C-18 column, eluting with from between 12-100% MeCN/water with 0.1% $NH_3$)

Purification after Step 2:
Biotage SP1 (C-18 column, eluting with from between 2-100% MeCN/water with 0.1% $NH_3$) or Biotage SP1 (C-18 column, eluting with from between 0-80% MeCN/water with 0.1% formic acid).

| Prep No | Name | Structure | Data/Precursor |
|---|---|---|---|
| 112 | 1,1',1'',1'''-((5'-((Benzyloxy)carbonyl)-[1,1':3',1''-terphenyl]-3,3'',5,5''-tetrayl)tetrakis(oxy))tetrakis(2-oxo-6,9,12,15-tetraoxa-3-azaoctadecan-18-oic acid) | 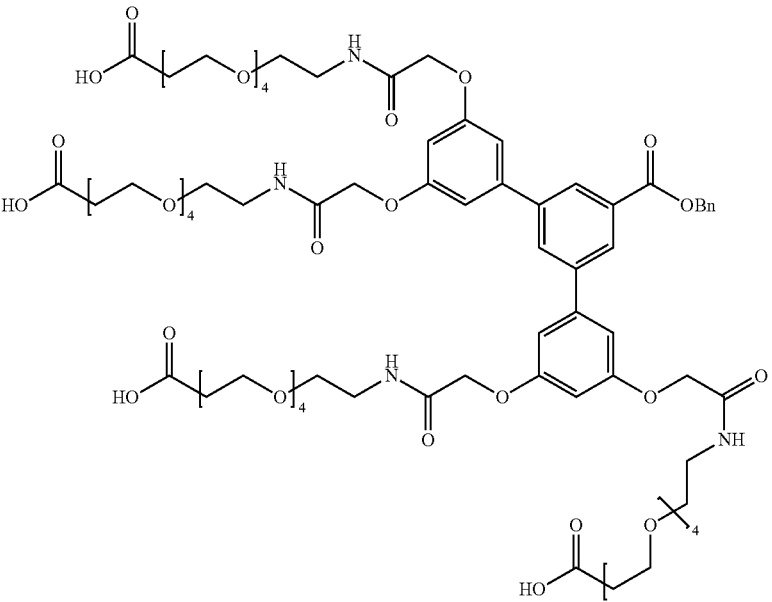 | Using 5 eq amine, 5 eq HATU and 11 eq TEA. LCMS Method A: Rt = 2.39 mins, ES⁺ MS m/z 1648.0 [M + H]⁺ Using Preparation 120 |

-continued

| Prep No | Name | Structure | Data/Precursor |
|---|---|---|---|
| 113 | 1,1'-((5-((Benzyloxy)carbonyl)-[1,1'-biphenyl]-3,4'-diyl)bis(oxy))bis(2-oxo-6,9,12,15,18,21,24,27,30,33,36,39-dodecaoxa-3-azadotetracontan-42-oic acid) | 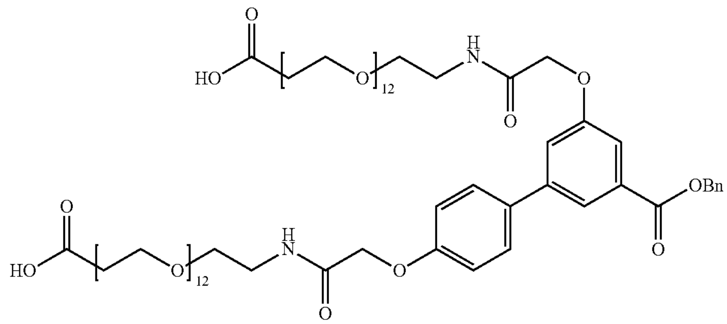 | Using 2.5 eq amine, 2.5 eq HATU and 6 eq TEA LCMS Method A: Rt = 2.53 mins, no mass ion observed. $^1$H NMR (400 MHz, DMSO-d$_6$): δ ppm 12.15 (2H, br s), 8.17 (1H, t), 8.09 (1H, t), 7.78 (1H, m), 7.64 (2H, d), 7.48-7.46 (4H, m), 7.42-7.34 (3H, m), 7.05 (2H, d), 5.37 (2H, s), 4.63 (2H, s), 4.52 (2H, s), 3.58-3.56 (4H, m), 3.49-3.43 (92H, m), 3.30-3.27 (4H, m), 2.40-2.39 (4H, m). Using Preparation 62. |
| 114 | 1-((3'-((Benzyloxy)carbonyl)-[1,1'-biphenyl]-4-yl)oxy)-2-oxo-6,9,12,15-tetraoxa-3-azaoctadecan-18-oic acid | 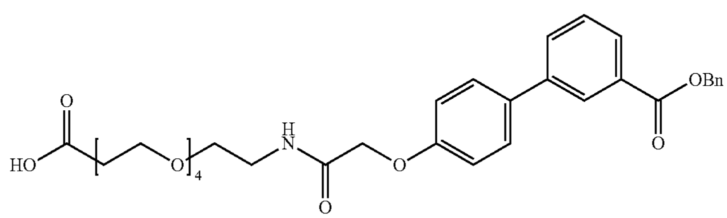 | Using 1.3 eq amine, 1.3 eq HATU and 4 eq TEA. LCMS Method A: Rt = 3.04 mins, ES$^+$ MS m/z 610.6 [M + H]$^+$ $^1$H NMR (400 MHz, DMSO-d$_6$): δ ppm 12.23 (1H, br s), 8.15-8.10 (1H, m), 8.09 (1H, t), 7.94-7.79 (2H, m), 7.65-7.63 (d, 2H), 7.59 (1H, t), 7.48-7.47 (2H, m), 7.42-7.32 (3H, m), 7.06 (2H, d), 5.38 (2H, s), 4.52 (2H, s), 3.56 (2H, t), 3.48-3.43 (14H, m), 3.30-3.28 (2H, m), 2.41 |

| Prep No | Name | Structure | Data/Precursor |
|---|---|---|---|
| | | | (2H, t). Using Preparation 121. |
| 115 | 1,1'-((5-((Benzyloxy)carbonyl)-[1,1'-biphenyl]-3,4'-diyl)bis(oxy))bis(2-oxo-6,9,12,15-tetraoxa-3-azaoctadecan-18-oic acid) | 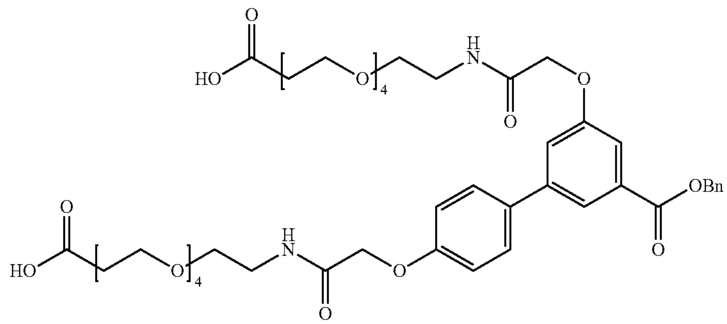 | Using 2.5 eq amine, 2.5 eq HATU and 6 eq TEA. LCMS Method A: Rt = 2.32 mins, ES+ MS m/z 931.6 [M + H]+ 1H NMR (400 MHz, DMSO-d6): δ ppm 12.17 (2H, br s), 8.18 (1H, t), 8.10 (1H, t), 7.78-7.75 (1H, m), 7.64 (2H, d), 7.47-7.46 (4H, m), 7.42-4.32 (3H, m), 7.05 (d, 2H), 5.37 (s, 2H), 4.63 (2H, s), 4.52 (2H, s), 3.57-3.55 (4H, m), 3.49-3.43 (28H, m), 3.30-3.27 (4H, m), 2.41-2.39 (4H, m). Using Preparation 62. |
| 116 | 1,1',1''-((5'-((Benzyloxy)carbonyl)-[1,1'-biphenyl]-3,3',5-triyl)tris(oxy))tris(2-oxo-6,9,12,15,18,21,24,27,30,33,36,39-dodecaoxa-3-azadotetracontan-42-oic acid) | 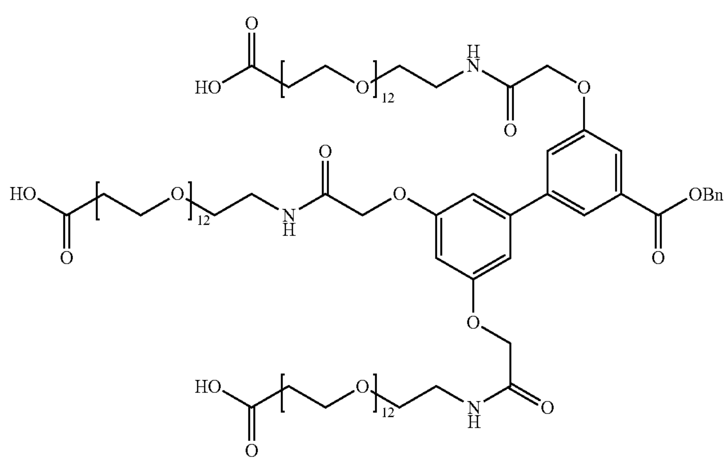 | Using 4 eq amine, 4 eq HATU and 9 eq TEA. LCMS Method A: Rt = 2.24 mins, ES+ MS m/z 1154.1 [M + 2H]+/2, theoretical mass: 2306.0 1H NMR (400 MHz, DMSO-d6): δ ppm 12.15 (3H, br s), 8.19 (1H, t), 8.10 (2H, t), 7.80 (1H, s), 7.55-7.32 (7H, m), 6.90-5.85 (2H, m), 6.94-6.90 (1H, m), 5.38 (2H, s), 4.64 (2H, |

| Prep No | Name | Structure | Data/Precursor |
|---|---|---|---|
| | | | s), 4.54 (4H, s), 3.57 (6H, t), 3.48-3.43 (138H, m), 3.30-3.25 (6H, m), 2.41 (6H, t). Using Preparation 73. |
| 117 | 1,1',1''-((5'-((Benzyloxy)carbonyl)-[1,1'-biphenyl]-3,3',5-triyl)tris(oxy))tris(2,18-dioxo-6,9,12,15-tetraoxa-3,19-diazatricosan-23-oic acid) | 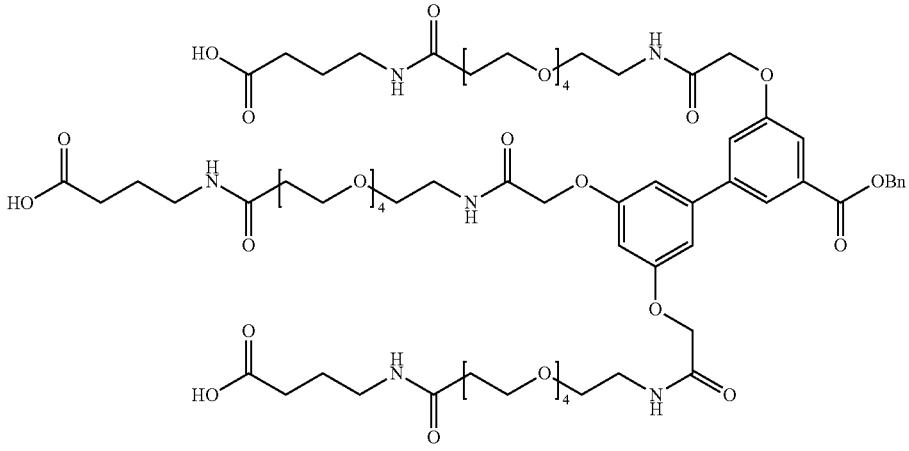 | Using 4 eq amine, 4 eq HATU and 10 eq TEA. LCMS Method A: Rt = 2.21 mins, ES+ MS m/z 1507.8 [M + H]+ 1H NMR (400 MHz, MeOD): δ ppm 7.90-7.85 (1H, m), 7.65-7.60 (1H, m), 7.50-7.30 (6H, m), 6.95 (2H, d), 6.70 (1H, t), 5.40 (2H, s), 4.65 (2H, s), 4.60 (4H, s), 3.65-3.60 (6H, m), 3.60-3.50 (42H, m), 3.50-3.45 (6H, m), 3.25-3.15 (6H, m), 2.40-2.35 (6H, m), 2.30 (6H, t), 1.70-1.65 (6H, m). Using Preparation 111 and 4-aminobutanoic acid. |

| Prep No | Name | Structure | Data/Precursor |
|---|---|---|---|
| 118 | 4,4',4''-((2,2',2''-((5'-((Benzyloxy)carbonyl)-[1,1'-biphenyl]-3,3',5-triyl)tris(oxy))tris(acetyl))tris(azanediyl))tributanoic acid | 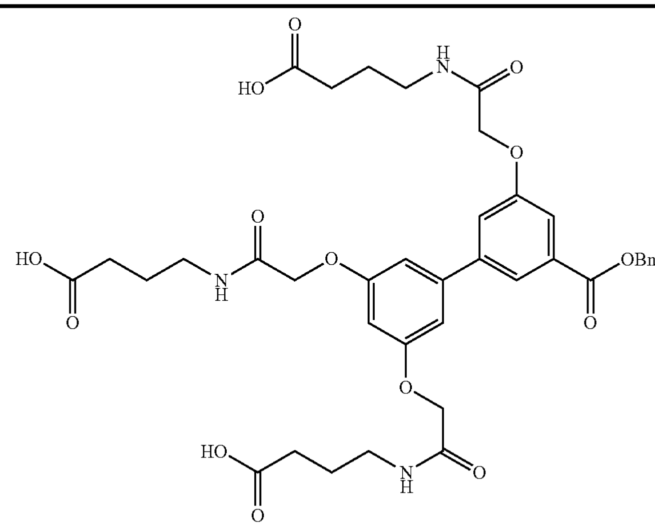 | Using 4 eq amine, 4 eq HATU and 10 eq TEA. LCMS Method A: Rt = 2.36 mins, ES⁺ MS m/z 766.5 [M + H]⁺ ¹H NMR (400 MHz, MeOD): δ ppm 7.90-7.85 (1H, m), 7.65-7.60 (1H, m), 7.50-7.30 (6H, m), 6.90 (2H, d), 6.70 (1H, t), 5.40 (2H, s), 4.65 (2H, s), 4.55 (4H, s), 3.35-3.30 (6H, m), 2.30 (6H, m), 1.90-1.75 (6H, m). Using Preparation 73 and 4-aminobutanoic acid. |

The following Preparations were prepared according to the methods described by Preparation 66 followed by Preparation 61 using the appropriate phenols as described below. Where necessary, the title compound was purified using the following reverse phase chromatography conditions:

Purification Method:
Biotage SP1 (C-18 column, eluting with 5-40% MeCN/water with 0.1% NH₃).

| Prep No | Name | Structure | Data/Precursor |
|---|---|---|---|
| 119 | 2-(3-{3'-[(Benzyloxy)carbonyl)-[1,1'-biphenyl]-3-yl}-5-(carboxymethoxy)phenoxy)acetic acid | 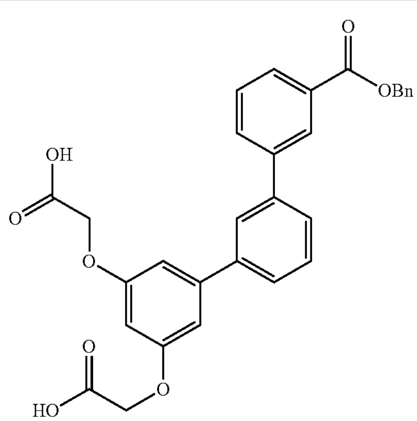 [SMILES: O=C(O)COc1cc(OCC(=O)O)cc(-c2cccc(-c3cccc(C(=O)OCc4ccccc4)c3)c2)c1] | LCMS Method A: Rt = 3.24 mins, ES⁻ MS m/z 511.4 [M − H]⁻ ¹H NMR (400 MHz, DMSO-d₆): δ ppm 8.27 (1H, s), 8.03-7.98 (2H, m), 7.89 (1H, s), 7.64-7.57 (3H, m), 7.47-7.45 (1H, m), 7.27-7.25 (5H, m), 6.87 (2H, s), 6.48 (1H, s), 5.39 (2H, s), 4.76 (4H, s). Using Preparation 129. |

-continued

| Prep No | Name | Structure | Data/Precursor |
|---|---|---|---|
| 120 | 2,2',2'',2'''-((5'-((Benzyloxy)carbonyl)-[1,1':3',1''-terphenyl]-3,3'',5,5''-tetrayl)tetrakis(oxy))tetraacetic acid | 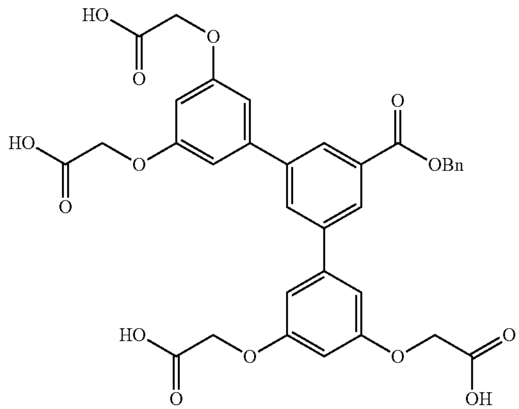 [SMILES: O=C(O)COc1cc(OCC(=O)O)cc(-c2cc(C(=O)OCc3ccccc3)cc(-c3cc(OCC(=O)O)cc(OCC(=O)O)c3)c2)c1] | LCMS Method B: Rt = 1.40 mins, ES⁻ MS m/z 659.4 [M − H]⁻ ¹H NMR (400 MHz, DMSO-d₆): δ ppm 8.20 (2H, s), 8.00 (1H, s), 7.50-7.45 (2H, m), 7.40-7.35 (2H, m), 7.35-7.30 (1H, m), 6.75 (4H, s), 6.40 (2H, s), 5.40 (2H, s), 4.45 (8H, s). Using Preparation 127. |
| 121 | 2-((3'-((Benzyloxy)carbonyl)-[1,1'-biphenyl]-4-yl)oxy)acetic acid | 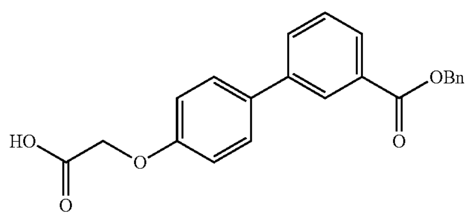 [SMILES: O=C(O)COc1ccc(-c2cccc(C(=O)OCc3ccccc3)c2)cc1] | LCMS Method B: Rt = 2.43 mins, ES⁺ MS m/z 363.2 [M + H]⁺ ¹H NMR (400 MHz, DMSO-d₆): δ ppm 13.00 (1H, s), 8.15 (1H, t), 7.90-7.85 (2H, m), 7.65-55 (3H, m), 7.50-7.45 (2H, m), 7.45-7.30 (3H, m) 7.00-6.95 (2H, m), 5.40 (2H, s), 4.70 (2H, s). Using Preparation 58. |

Preparation 122

2-({3'-[(Benzyloxy)carbonyl]-4,5-bis(carboxymethoxy)-[1,1'-biphenyl]-3-yl}oxy)acetic acid

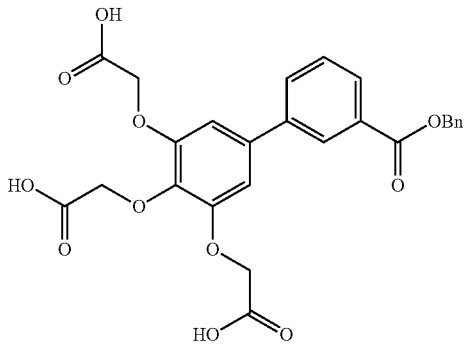 [SMILES: O=C(O)COc1cc(-c2cccc(C(=O)OCc3ccccc3)c2)cc(OCC(=O)O)c1OCC(=O)O]

The title compound was prepared according to the method described for Preparation 61 using Preparation 123.

LCMS Method D: Rt=1.84 mins, ES⁺ MS m/z 528.0 [M+NH₄]+

Preparation 123

Tri-tert-butyl 2,2',2''-((3'-((benzyloxy)carbonyl)-[1,1'-biphenyl]-3,4,5-triyl)tris(oxy))triacetate

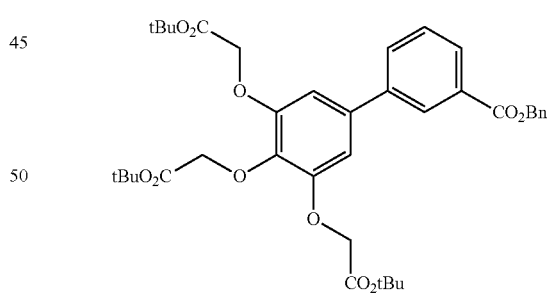

Benzyl 3-bromobenzoate (Bioorganic and Medicinal Chemistry, 2013, 21, 3, 608-617, 308.0 mg, 1.06 mMol), 4,4,4',4',5,5,5',5'-octamethyl-2,2'-bi(1,3,2-dioxaborolane) (403.0 mg, 1.59 mmol) and potassium acetate (311 mg, 3.17 mmol) were suspended in dioxane (10 mL) and thoroughly degassed. [1,1'-Bis(diphenylphosphino)ferrocene]dichloropalladium(II), complex with dichloromethane (86 mg, 0.106 mmol) was added, the reaction mixture degassed again before heating at 100° C. under nitrogen for 4 hours. The reaction mixture was cooled to room temperature and NaHCO₃ (267.0 mg, 3.18 mmol), tri-tert-butyl 2,2',2''-((5-bromobenzene-1,2,3-triyl)tris(oxy))triacetate (580.0 mg, 1.06 mmol) and additional [1,1'-bis(diphenylphosphino)ferrocene]dichloropalladium(II), complex with dichloromethane (86.0 mg, 0.106 mmol) was added. The reaction was heated at 100° C. under nitrogen for 4 hours before cooling to room temperature. The reaction was concentrated in vacuo and the residue was partitioned between EtOAc (25 mL) and water (25 mL). The mixture was filtered through Hyflo and the EtOAc layer separated. The aqueous layer was extracted once more with EtOAc (25 mL) and the combined organic extracts washed with brine (25 mL), dried over magnesium sulphate and concentrated in vacuo. The residue was purified using silica gel column chromatography eluting with 5-30% EtOAc in heptane to afford the title compound (105 mg, 15%).

LCMS Method B: Rt=4.34 mins, ES+ MS m/z 696.3 [M+NH4]+

Preparation 124

Tri-tert-butyl 2,2',2''-((5-bromobenzene-1,2,3-triyl)tris(oxy))triacetate

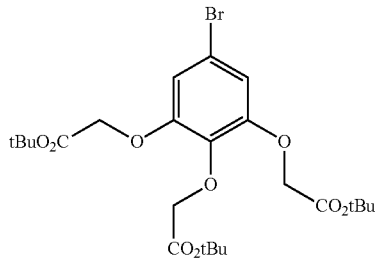 [SMILES: CC(C)(C)OC(=O)COc1cc(Br)cc(OCC(=O)OC(C)(C)C)c1OCC(=O)OC(C)(C)C]

To 5-bromobenzene-1,2,3-triol (JACS, 2011, vol. 133, no. 34, p. 13437-13444, 1.89 g, 9.22 mmol) dissolved in DMF (38 mL) was added potassium carbonate (4.21 g, 30.43 mmol) and tert-butyl bromoacetate (4.49 mL, 30.43 mmol) to give a suspension which was stirred for 16 hours under nitrogen before concentration in vacuo. The residue was partitioned between water (100 mL) and TBME (100 mL). The organic layer was separated and the aqueous layer extracted with TBME (50 mL). The combined organic extracts were dried over magnesium sulphate and concentrated in vacuo. The residue was purified using silica gel column chromatography eluting with 10-20% EtOAc in heptane to afford the title compound (5.0 g, >100%, contains EtOAc).

LCMS Method B: Rt=4.06 mins, ES+ MS m/z 566.3 [M+NH4]+

$^1$H NMR (400 MHz, CDCl$_3$): δ ppm 6.68 (2H, s), 4.61 (2H, s), 4.62 (2H, s), 4.59 (4H, s), 1.47 (27H, s).

Preparation 125

3',4',5'-Trimethoxy-[1,1'-biphenyl]-3-carboxylic acid

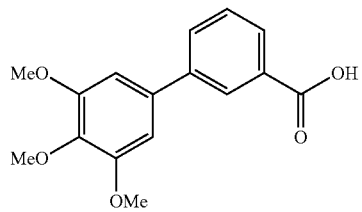 [SMILES: COc1cc(-c2cccc(C(=O)O)c2)cc(OC)c1OC]

The title compound was prepared according to the method described for Preparation 65 using 3-bromobenzoic acid and 3,4,5-trimethoxyphenyl boronic acid.

LCMS Method B: Rt=2.62 mins, ES+ MS m/z 289.4 [M+H]+

$^1$H NMR (400 MHz, CDCl$_3$): δ ppm 8.32 (1H, s), 8.10 (1H, d), 7.81 (1H, d), 7.58-7.54 (1H, m), 6.81 (2H, s), 3.95 (6H, s), 3.90 (3H, s).

Preparation 126

Benzyl 5-{3,5-bis[2-(tert-butoxy)-2-oxoethoxy]phenyl}-3',5'-bis[2-(tert-butoxy)-2-oxoethoxy]-[1,1'-biphenyl]-3-carboxylate

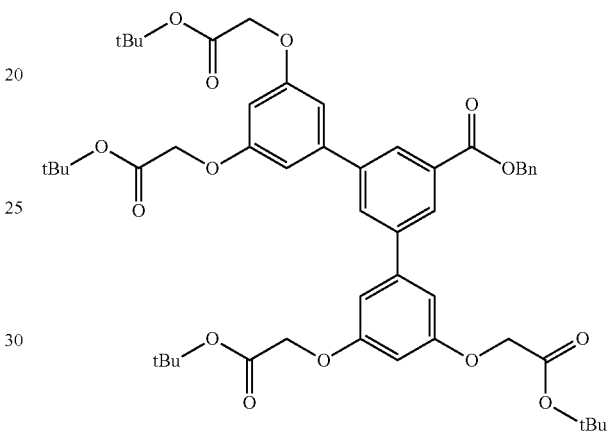

The title compound was prepared according to Preparation 66 using benzyl 5-(3,5-dihydroxyphenyl)-3',5'-dihydroxy-[1,1'-biphenyl]-3-carboxylate (Preparation 127) and tert-butylbromoacetate.

LCMS Method D: Rt=4.57 minutes ES+ MS m/z 903.5 [M+NH4]+

$^1$H NMR (400 MHz, CDCl$_3$): δ ppm 8.22 (2H, s), 7.88 (1H, s), 7.49-7.42 (2H, m), 7.40-7.37 (3H, m), 6.80 (4H, s), 6.52 (2H, s), 5.42 (2H, s), 4.56 (8H, s), 1.49 (36H, s).

Preparation 127

Benzyl 5-(3,5-dihydroxyphenyl)-3',5'-dihydroxy-[1,1'-biphenyl]-3-carboxylate

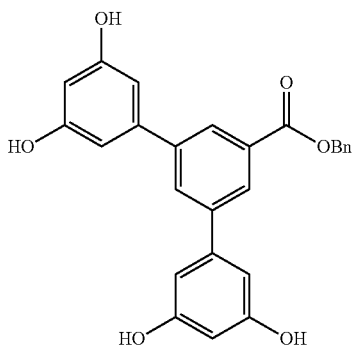 [SMILES: O=C(OCc1ccccc1)c1cc(-c2cc(O)cc(O)c2)cc(-c2cc(O)cc(O)c2)c1]

The title compound was prepared according to the methods described for Preparations 69 and 70 using 2,4-dibromobenzoic acid benzyl ester.

LCMS Method B: Rt=2.73 minutes, ES⁻ MS m/z 427.3 [M−H]⁻

¹H NMR (400 MHz, DMSO-d₆): δ ppm 9.45 (4H, s), 8.02 (2H, s), 7.89 (1H, s), 5.53-5.38 (5H, m), 6.56 (4H, d), 6.28 (2H, s), 5.39 (2H, s).

Preparation 128

Benzyl 3-{3',5'-dihydroxy-[1,1'-biphenyl]-3-yl}benzoate

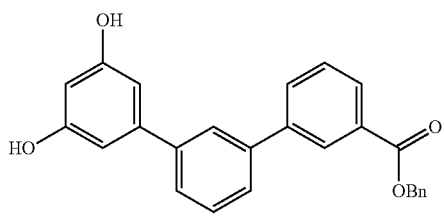 [SMILES: O=C(OCc1ccccc1)c1cccc(-c2cccc(-c3cc(O)cc(O)c3)c2)c1]

The title compound was prepared according to the method described for Preparations 69 and 70 using benzyl 3'-bromo-[1,1'-biphenyl]-3-carboxylate (Preparation 129) and ((5-(4,4,5,5-tetramethyl-1,3,2-dioxaborolan-2-yl)-1,3-phenylene)bis(oxy)) bis(tert-butyldimethylsilane) (Preparation 80). Purified a second time using silica gel column chromatography eluting with TBME:Heptane 1:1.

LCMS Method A: Rt=3.39 mins, ES⁺ MS m/z 397.4 [M+H]⁺

Preparation 129

Benzyl 3'-bromo-[1,1'-biphenyl]-3-carboxylate

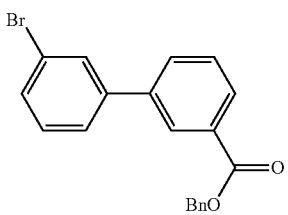 [SMILES: O=C(OCc1ccccc1)c1cccc(-c2cccc(Br)c2)c1]

Benzyl bromide (718 mg, 4.1 mmol) was added slowly to a stirred suspension of 3'-bromobiphenyl-3-carboxylic acid (985 mg, 3.78 mmol) and potassium carbonate (621 mg, 4.49 mmol) in DMF (20 mL). The reaction was stirred at room temperature for 24 hours. The reaction was quenched by the addition of water (50 mL) and extracted with EtOAc (50 mL and 25 mL). The combined organic extracts were washed with brine (3×30 mL) and concentrated in vacuo. The residue was purified using silica gel column chromatography eluting with 0-10% EtOAc in heptanes to afford the title compound as a colourless oil (1.70 g, 100%).

LCMS Method B: Rt=4.22 mins, no mass ion observed.

¹H NMR (400 MHz, CDCl₃): δ ppm 8.26 (1H, s), 8.06-8.01 (1H, m), 7.74-7.69 (2H, m), 7.49-7.45 (5H, m), 7.36-7.3 (4H, m), 5.40 (2H, s).

Preparation 130

Benzyl 3-((21-amino-2,18-dioxo-6,9,12,15-tetraoxa-3,19-diazahenicosyl)oxy)benzoate

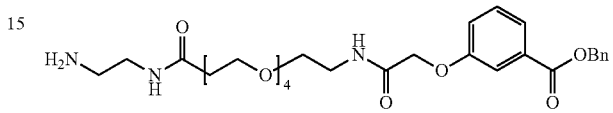

To a solution of benzyl 3-((2,2-dimethyl-4,9,25-trioxo-3,12,15,18,21-pentaoxa-5,8,24-triazahexacosan-26-yl)oxy)benzoate (Preparation 131, 666 mg, 986 μmol) in dioxane (10 mL) was added HCl in dioxane (4.0 N, 5 mL) and the reaction stirred for 2 hours. Further HCl in dioxane (4.0 N, 5 mL) was added and the reaction was stirred for 3 hours before concentration in vacuo. The residue was purified initially by elution through an SCX-2 cartridge (1N NH₃/MeOH) followed by reverse phase column chromatography (Biotage SP1, 30 g, C-18 column, eluting with 7-60% MeCN/water with 0.1% NH₃) followed by a second reverse phase column chromatography (Biotage SP1, 30 g column, 2-40% DCM/MeOH with 1% 7NH₃/MeOH) to afford the title compound as a pale yellow gum (441 mg, 78%).

LCMS Method B: Rt=2.36 mins, ES⁺ MS m/z 576.5 [M+H]⁺

¹H NMR (400 MHz, CDCl₃): δ ppm 7.70-7.60 (3H, m), 7.45-7.30 (7H, m), 7.20-7.15 (1H, m), 5.35 (2H, s), 4.55-4.50 (2H, m), 3.70-3.50 (20H, m), 3.35-3.30 (1H, m), 3.00 (1H, t), 2.40-2.35 (2H, m).

Preparation 131

Benzyl 3-((2,2-dimethyl-4,9,25-trioxo-3,12,15,18,21-pentaoxa-5,8,24-triazahexacosan-26-yl)oxy)benzoate

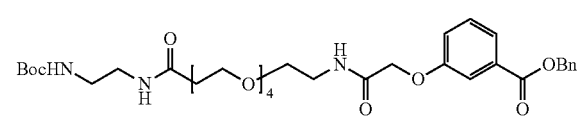

To a solution of 1-(3-((benzyloxy)carbonyl)phenoxy)-2-oxo-6,9,12,15-tetraoxa-3-azaoctadecan-18-oic acid (Preparation 132, 695 mg, 1.30 mmol) in DMF (7 mL) was added TEA (363 μL, 2.61 mmol) followed by a solution of Boc-ethylenediamine (209 mg, 1.30 mmol) in DMF (2 mL). To the reaction mixture was added HATU (743 mg, 1.95 mmol) portionwise over 10 minutes before stirring at room temperature for 30 minutes. The reaction was concentrated in vacuo and purified using reverse phase column chromatography (Biotage SP1, 60 g, C-18 column, eluting with 5-70% MeCN/water with 0.1% formic acid) to afford the title compound as a yellow oil.

LCMS Method B: Rt=2.87 mins, ES+ MS m/z 676.5 [M+H]+

$^1$H NMR (400 MHz, DMSO-d$_6$): δ ppm 8.15 (1H, t), 7.80-7.75 (1H, m), 7.60 (1H, d), 7.55 (1H, s), 7.45-7.30 (6H, m), 7.25 (1H, dd), 6.75-6.70 (1H, m), 5.35 (2H, s), 4.55 (2H, s), 3.55 (2H, t), 3.50-3.35 (14H, m), 3.30-3.25 (2H, m), 3.10-3.05 (2H, m), 3.00-2.95 (2H, m), 2.40 (2H, t), 1.35 (9H, s).

Preparation 132

1-(3-((Benzyloxy)carbonyl)phenoxy)-2-oxo-6,9,12,15-tetraoxa-3-azaoctadecan-18-oic acid

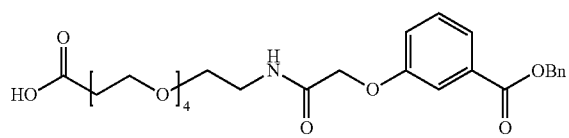

To a solution of tert-butyl 1-(3-((benzyloxy)carbonyl)phenoxy)-2-oxo-6,9,12,15-tetraoxa-3-azaoctadecan-18-oate (Preparation 133, 1.09 g, 1.84 mmol) in DCM (9.5 mL) was added water (1.0 mL) followed by TFA (9.5 mL). The reaction was left to stir at room temperature for 2 hours before concentrating in vacuo. The residue was purified using reverse phase column chromatography (Biotage SP1, 60 g, C-18 column, eluting with 10-70% MeCN/water with 0.1% formic acid) to afford the title compound as a colourless oil (695 mg, 71%).

LCMS Method A: Rt=2.67 mins, ES+ MS m/z 534.5 [M+H]+

$^1$H NMR (400 MHz, DMSO-d$_6$): δ ppm 12.15 (1H, br s), 8.15 (1H, t), 7.60 (1H, d), 7.55-7.50 (1H, m), 7.50-7.35 (6H, m), 7.25 (1H, dd), 5.35 (2H, s), 4.55 (2H, s), 3.60 (2H, t), 3.50-3.40 (14H, m), 3.30-3.25 (2H, m), 2.40 (2H, t).

Preparation 133 tert-Butyl 1-(3-((benzyloxy)carbonyl)phenoxy)-2-oxo-6,9,12,15-tetraoxa-3-azaoctadecan-18-oate

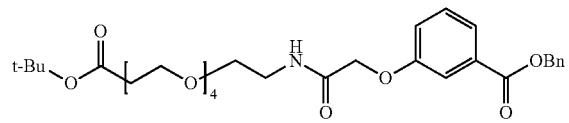

To a solution of 2-(3-((benzyloxy)carbonyl)phenoxy)acetic acid (Preparation 56, 870 mg, 3.04 mmol) in DMF (5.0 mL) was added tert-butyl 1-amino-3,6,9,12-tetraoxapentadecan-15-oate (1.27 g, 3.95 mmol) dissolved in DMF (4.0 mL). To the solution was then added TEA (1.69 mL, 12.2 mmol) followed by HATU (1.50 g, 3.95 mmol) portionwise over 10 minutes. The reaction was stirred at room temperature for 16 hours before concentrating in vacuo. The residue was purified using reverse phase column chromatography (Biotage SP1, 120 g, C-18 column, eluting with 10-30% MeCN/water with 0.1% NH$_3$) to afford the title compound as a colourless oil (1.09 g, 57%).

LCMS Method B: Rt=3.29 mins, ES+ MS m/z 607.6 [M+NH$_4$]+

$^1$H NMR (400 MHz, DMSO-d$_6$): δ ppm 8.15 (1H, t), 7.60 (1H, d), 7.55-7.50 (1H, m), 7.50-7.30 (6H, m), 7.25 (1H, dd), 5.35 (2H, s), 4.55 (2H, s), 3.60 (2H, t), 3.50-3.45 (12H, m), 3.45 (2H, t), 3.25 (2H, q), 2.40 (2H, t), 1.40 (9H, s).

Preparation 134

Benzyl 3-((45-amino-2,42-dioxo-6,9,12,15,18,21,24,27,30,33,36,39-dodecaoxa-3,43-diazapentatetracontyl)oxy)benzoate

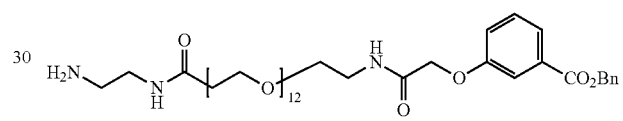

To benzyl 3-((2,2-dimethyl-4,9,49-trioxo-3,12,15,18,21,24,27,30,33,36,39,42,45-tridecaoxa-5,8,48-triazapentacontan-50-yl)oxy)benzoate (Preparation 135, 225 mg, 219 μmol) dissolved in dioxane (4.0 mL) was added 4M HCl in dioxane (4.0 mL, 16.0 mmol). The reaction mixture was stirred at room temperature for 18 hours before concentrating in vacuo. The residue was dissolved in DCM and eluted through a SCX-2 cartridge with MeOH followed by 1N NH$_3$ in MeOH to afford the title compound as a pale yellow gum (190 mg, 94%).

LCMS Method A: Rt=2.56 mins, ES+ MS m/z 929.7 [M+H]+

$^1$H NMR (400 MHz, CDCl$_3$): δ ppm 7.73 (1H, d), 7.60 (1H, d), 7.46-7.32 (6H, m), 7.15-7.06 (3H, m), 5.23 (2H, s), 4.52 (2H, s), 3.74 (2H, t), 3.67-3.52 (48H, m), 3.38-3.30 (2H, m), 2.86 (2H, t), 2.47 (2H, t).

Preparation 135

Benzyl 3-((2,2-di methyl-4,9,49-trioxo-3,12,15,18,21,24,27,30,33,36,39,42,45-tridecaoxa-5,8,48-triazapentacontan-50-yl)oxy)benzoate

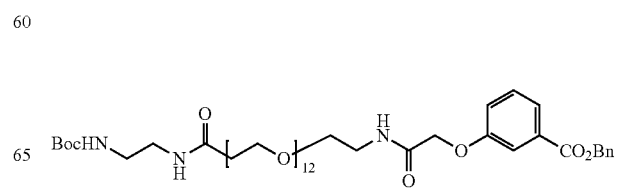

To 1-(3-((benzyloxy)carbonyl)phenoxy)-2-oxo-6,9,12,15,18,21,24,27,30,33,36,39-dodecaoxa-3-azadotetracontan-42-oic acid (Preparation 136, 225.0 mg, 254 μmol) dissolved in DMF (4.50 mL) was added tert-butyl (2-aminoethyl)carbamate (49.0 mg, 305 μmol) and triethylamine (89 μL, 635 μmol), followed by HATU (116.0 mg, 305 μmol). The reaction mixture was stirred at room temperature for 21 hours before concentration in vacuo. The residue was partitioned between EtOAc (40 mL) and brine (25 mL), the aqueous layer was extracted with EtOAc (20 mL) and the combined organic extracts washed with 1M HCl (25 mL), 10% aq. $K_2CO_3$ solution (25 mL) and brine (25 mL) before drying over magnesium sulphate and concentrating in vacuo. The residue was purified by silica gel column chromatography eluting with 2-5% MeOH in DCM to afford the title compound as a pale yellow oil (226 mg, 87%).

LCMS Method A: Rt=2.83 mins, ES$^+$ MS m/z 1028.8 [M+H]$^+$

Preparation 136

1-(3-((Benzyloxy)carbonyl)phenoxy)-2-oxo-6,9,12,15,18,21,24,27,30,33,36,39-dodecaoxa-3-azadotetracontan-42-oic acid

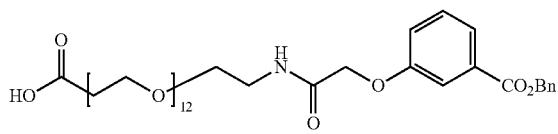

Tert-butyl 1-(3-((benzyloxy)carbonyl)phenoxy)-2-oxo-6,9,12,15,18,21,24,27,30,33,36,39-dodecaoxa-3-azadotetracontan-42-oate (Preparation 137, 241 mg, 256 μmol) was dissolved in a mixture of TFA:DCM:H$_2$O (10:10:1 v/v/v, 10 mL) and stirred at room temperature for 3 hours. The reaction was concentrated in vacuo and azeotroped twice with toluene:dioxane (1:1, 10 mL) to afford the title compound as a pale yellow oil (232 mg, >100%, contains DCM).

LCMS Method A: Rt=2.37 mins, ES$^+$ MS m/z 886.6 [M+H]$^+$ $^1$H NMR (400 MHz, CDCl$_3$): δ ppm 7.72 (1H, d), 7.61 (1H, d), 7.46-7.32 (5H, m), 7.25-7.20 (1H, m), 7.17-7.11 (1H, m), 5.37 (2H, s), 4.58 (2H, s), 3.72-3.56 (52H, m).

Preparation 137 tert-Butyl 1-(3-((benzyloxy)carbonyl)phenoxy)-2-oxo-6,9,12,15,18,21,24,27,30,33,36,39-dodecaoxa-3-azadotetracontan-42-oate

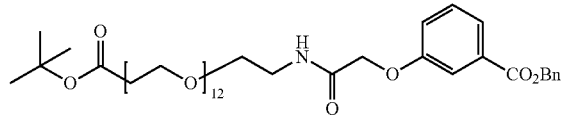

To 2-(3-((benzyloxy)carbonyl)phenoxy)acetic acid (Preparation 56, 96.0 mg, 0.335 mmol), tert-butyl 1-amino-3,6,9,12,15,18,21,24,27,30,33,36-dodecaoxanonatriacontan-39-oate (249.0 mg, 0.369 mmol) and TEA (140 μL, 1.01 mmol) dissolved in DMF (2.0 mL) was added HATU (153 mg, 0.402 mmol). The mixture was stirred at room temperature for 2 hours before concentrating in vacuo. The residue was purified using reverse phase column chromatography (Biotage SP1, 30 g, C-18 column, eluting with 10-80% MeCN/water with 0.1% NH$_3$) to afford the title compound as a yellow oil (241 mg, 76%).

LCMS Method B: Rt=3.12 mins, ES$^+$ MS m/z 942.7 [M+H]$^+$ $^1$H NMR (400 MHz, CDCl$_3$): δ ppm 7.75 (1H, d), 7.60 (1H, s), 7.50-7.30 (2H, m), 7.15 (1H, d), 7.10-7.00 (1H, m), 5.40 (2H, s), 4.55 (2H, s), 3.70 (2H, t), 3.65-3.50 (48H, m), 2.50 (2H, t), 1.40 (9H, s).

Example 1

2,2',2''-((5'-((2-(5-(((3aS,4S,6aR)-2-Oxohexahydro-1H-thieno[3,4-d]imidazol-4-yl)pentanamido)ethyl)carbamoyl)-[1,1'-biphenyl]-3,3',5-triyl)tris(oxy))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide) (E1)

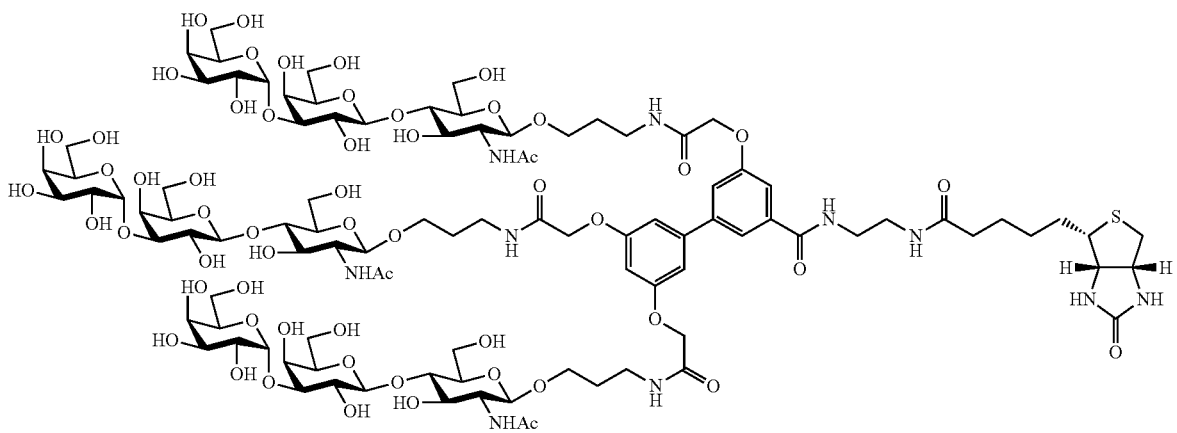

To a solution of 2,2',2''-((5'-((2-(5-((3aS,4S,6aR)-2-oxo-hexahydro-1H-thieno[3,4-d]imidazol-4-yl)pentanamido)ethyl)carbamoyl)-[1,1'-biphenyl]-3,3',5-triyl)tris(oxy))triacetic acid (Preparation 5, 5.72 mg, 8.30 μmol) in DMF (750 μL) was added TEA (10.4 μL, 74.7 μmol) followed by a solution of alpha-Gal (20.0 mg, 33.2 μmol) in DMSO (250 μL). A solution of HATU (12.6 mg, 33.2 μmol) in DMF (250 μL) was added and the reaction was stirred under nitrogen for 1 hour at room temperature. The reaction was concentrated in vacuo and purified using reverse phase column chromatography (TRILUTION™ Lunar 0-18, eluting with 10-40% MeCN/water with 0.1% $NH_3$ over 35 mins, then 40% MeCN/water with 0.1% $NH_3$ for 5 min) to afford the title compound as a colourless solid (10.3 mg, 51%).

LCMS Method B: Rt=1.47 mins, ES$^+$ MS m/z [M+2H]$^+$/2 1222.74, theoretical mass: 2442.7

MALDI-ToF 2463.91 [M+Na]

Examples 2-12 were prepared and purified according to the method described for Example 1 using the appropriate carboxylic acid as described below and a stoichiometric or excess amount of alpha-Gal.

Example 2

3-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-N-(2-(5-((3aS,4S,6aR)-2-oxohexahydro-1H-thieno[3,4-d]imidazol-4-yl)pentanamido)ethyl)benzamide (E2)

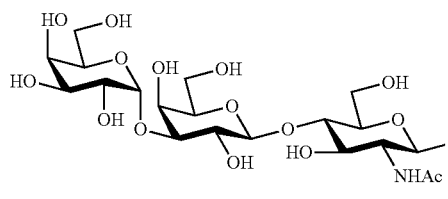
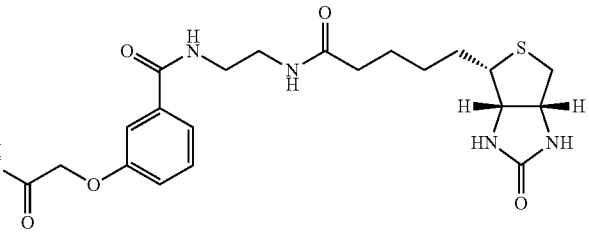

Isolated yield: 22%
LCMS Method A: Rt=1.57 mins, ES$^+$ MS m/z 1049.8 [M+H]$^+$

Precursor: Preparation 11

Example 3

1-{5-[(3aS,4S,6aR)-2-Oxo-hexahydro-1H-thieno[3,4-d]imidazolidin-4-yl]pentanamido}-N-[2-({3-[({14-[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12-tetraoxatetradecan-1-yl}carbamoyl)methoxy]phenyl}formamido)ethyl]-3,6,9,12,15,18,21,24,27,30,33,36-dodecaoxanonatriacontan-39-amide (E3)

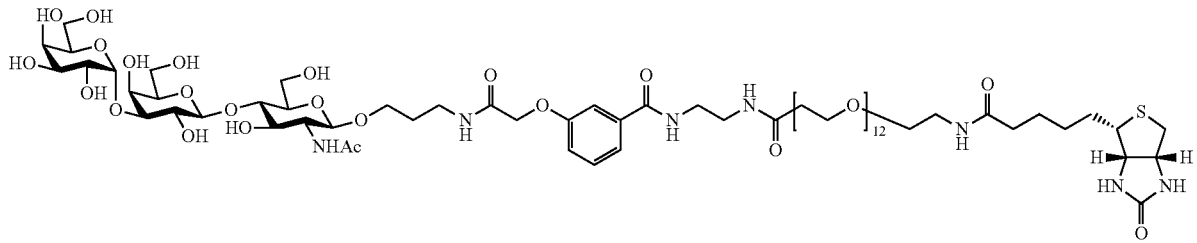

Isolated yield: 36%
LCMS Method A: Rt=1.73 mins, ES$^-$ MS m/z 1647.9 [M-H]$^-$

Precursor: Preparation 12

Example 4

N-(3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)-3-(2-oxo-2-((2-(5-((3aS,4S,6aR)-2-oxohexahydro-1H-thieno[3,4-d]imidazol-4-yl)pentanamido)ethyl)amino)ethoxy)benzamide (E4)

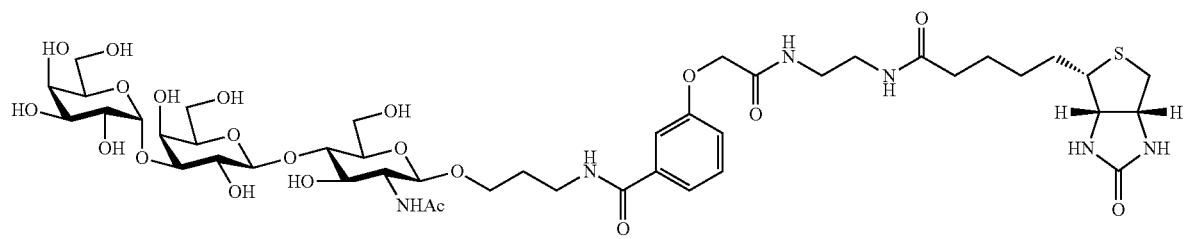

Isolated yield: 35%
LCMS Method B: Rt=1.49 mins, ES$^+$ MS m/z 1049.8 [M+H]$^+$
Precursor: Preparation 3

Example 5

2,2'-((5-((2-(5-((3aS,4S,6aR)-2-Oxohexahydro-1H-thieno[3,4-d]imidazol-4-yl)pentanamido)ethyl)carbamoyl)-1,3-phenylene)bis(oxy))bis(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide) (E5)

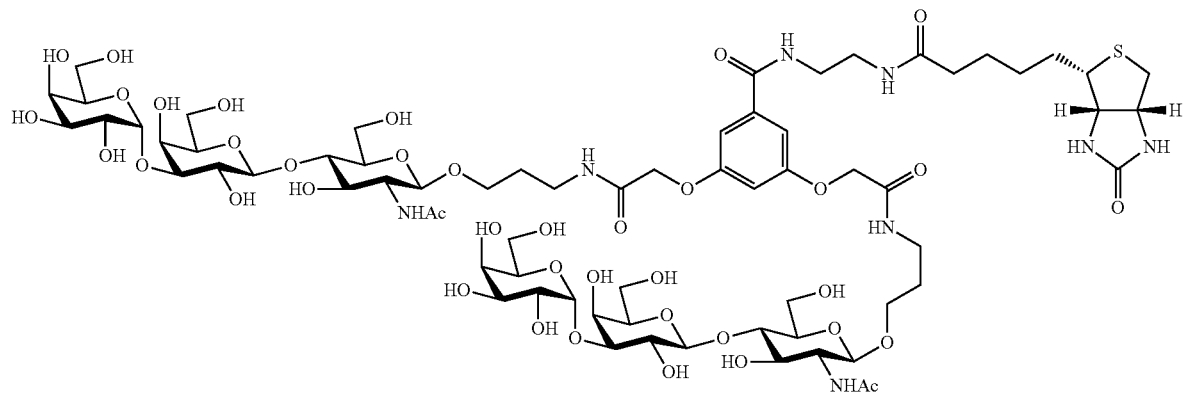

Isolated yield: 17%
LCMS Method B: Rt=1.41 mins, ES$^-$ MS m/z 1706.8 [M−H]$^-$
Precursor: Preparation 13
MALDI-ToF: Monoisotopic mass: 1706.8, observed mass 1729.6 [M+Na]

Example 6

1-{5-[(3aS,4S,6aR)-2-Oxo-hexahydro-1H-thieno[3,4-d]imidazolidin-4-yl]pentanamido}-N-(2-{[3,5-bis({[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]methoxy})phenyl]formamido}ethyl)-3,6,9,12,15,18,21,24,27,30,33,36-dodecaoxanonatriacontan-39-amide (E6)

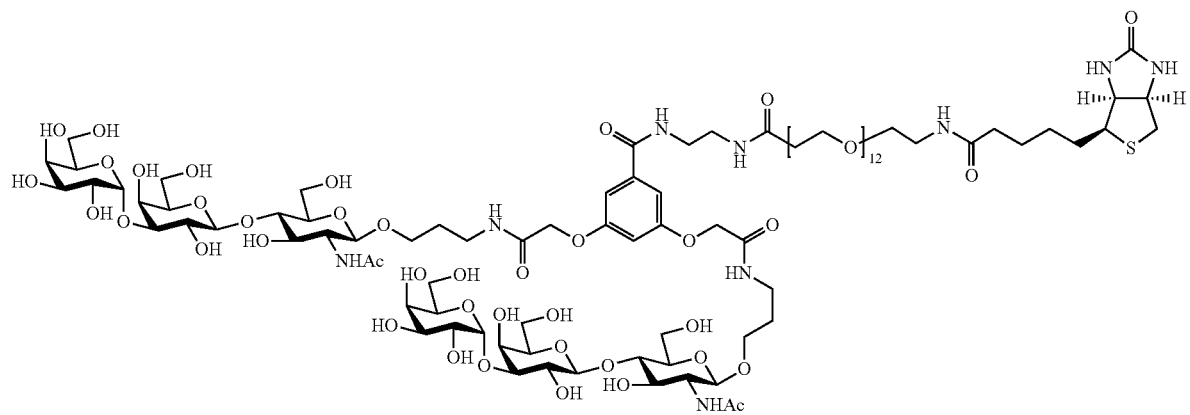

Isolated yield: 33%
LCMS Method B: Rt=1.65 mins, ES$^+$ MS m/z 1155.2 [M+2H]$^+$/2, theoretical mass: 2307.4
Precursor: Preparation 10
MALDI-ToF: Monoisotopic mass: 2306.0, observed mass 2329.0 [M+Na]

Example 7

2,2'-((5-((2-(5-(((3aS,4S,6aR)-2-Oxohexahydro-1H-thieno[3,4-d]imidazol-4-yl)pentanamido)ethyl)carbamoyl)-[1,1'-biphenyl]-3,4'-diyl)bis(oxy))bis(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide) (E7)

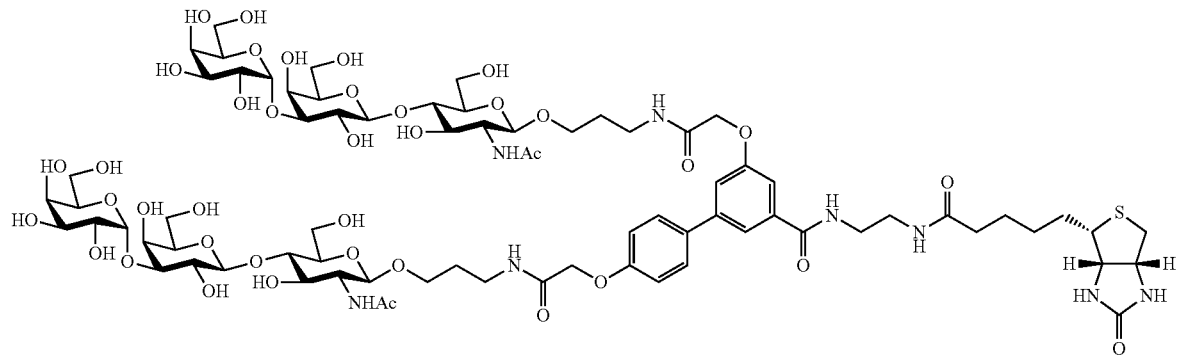

Isolated yield: 10%
LCMS Method B: Rt=1.56 mins, ES⁺ MS m/z 1783.9 [M+H]⁺
Precursor: Preparation 39
MALDI-ToF: Monoisotopic mass: 1882.6, observed mass 1905.6 [M+Na]

Example 8

4-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-N-(2-(5-((3aS,4S,6aR)-2-oxohexahydro-1H-thieno[3,4-d]imidazol-4-yl)pentanamido)ethyl)benzamide (E8)

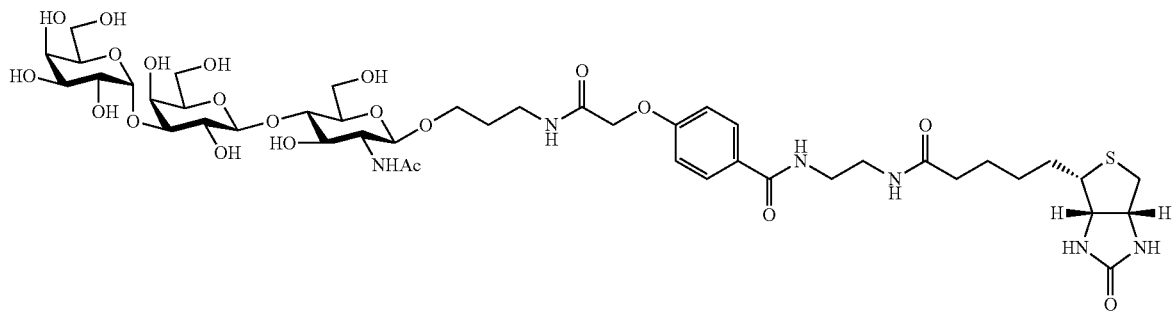

Isolated yield: 42%
LCMS Method B: Rt=1.49 mins, ES⁺ MS m/z 1049.7 [M+H]⁺
Precursor: Preparation 4

Example 9

2,2',2'',2'''-((5-((2-(5-((3aS,4S,6aR)-2-Oxohexahydro-1H-thieno[3,4-d]imidazol-4-yl)pentanamido)ethyl)carbamoyl)-[1,1'-biphenyl]-2,3',4,5'-tetrayl)tetrakis(oxy))tetrakis(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide) (E9)

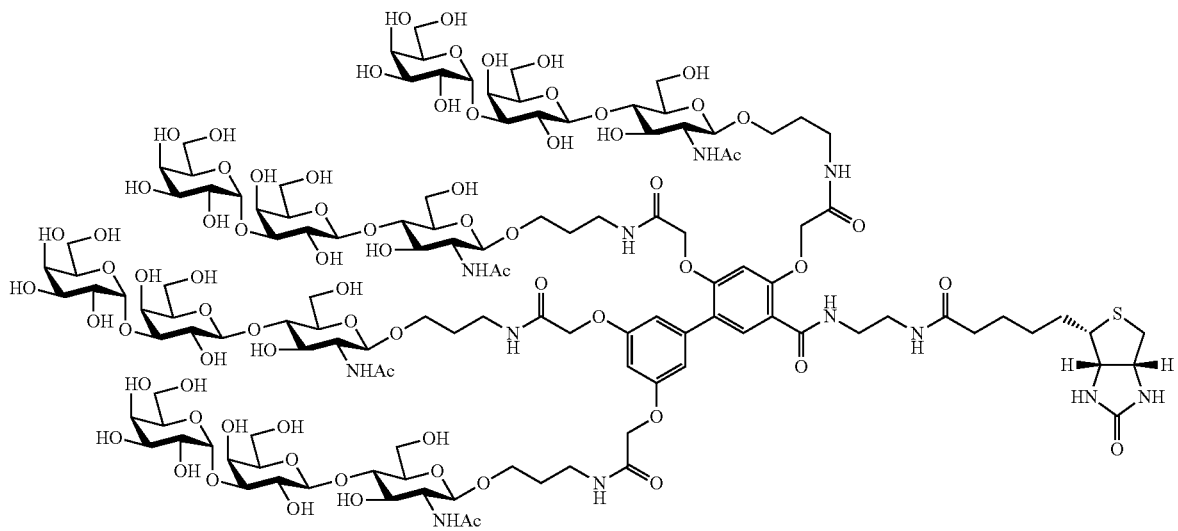

Isolated yield: 23%
LCMS Method A: Rt=1.38 mins, ES+ MS m/z 1552.0 [M+2H]+/2, theoretical mass: 3101.0
Precursor: Preparation 7
MALDI-ToF: Monoisotopic mass: 3099.1, observed mass 3122.1 [M+Na]

Example 10

4-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-N-(2-(5-((3aS,4S,6aR)-2-oxohexahydro-1H-thieno[3,4-d]imidazol-4-yl)pentanamido)ethyl)quinoline-2-carboxamide (E10)

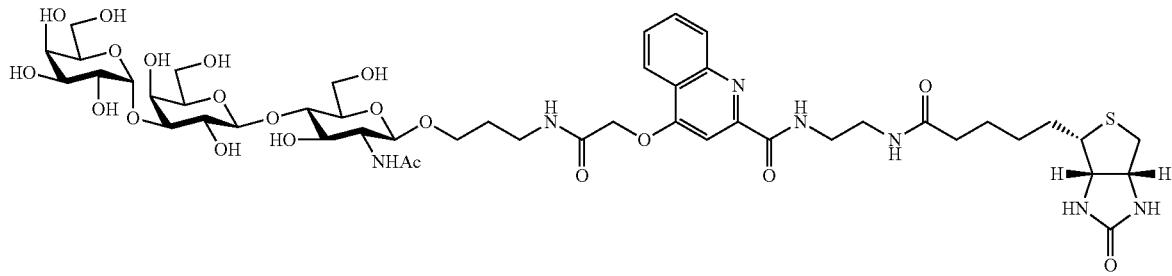

Isolated yield: 50%
LCMS Method B: Rt=1.72 mins, ES+ MS m/z 1100.9 [M+H]+
Precursor: Preparation 8

Example 11

4'-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-N-(2-(5-((3aS,4S,6aR)-2-oxohexahydro-1H-thieno[3,4-d]imidazol-4-yl)pentanamido)ethyl)-[1,1'-biphenyl]-3-carboxamide (E11)

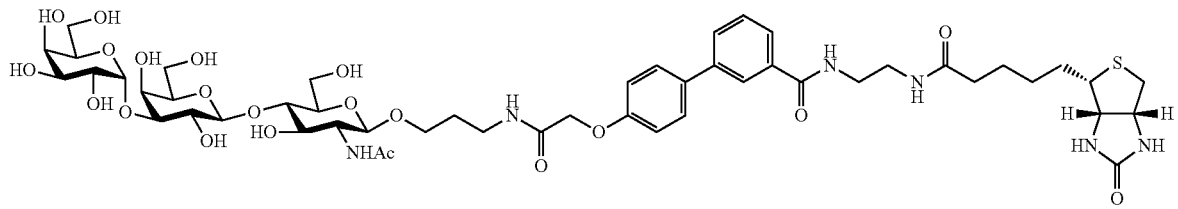

Isolated yield: 74%
LCMS Method B: Rt=1.72 mins, ES+ MS m/z 1125.9 [M+H]+

Precursor: Preparation 9

Example 12

N¹-(3-(2-((3-((((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)benzyl)-N6-(2-(5-((3aS,4S,6aR)-2-oxohexahydro-1H-thieno[3,4-d]imidazol-4-yl)pentanamido)ethyl)adipamide (E12)

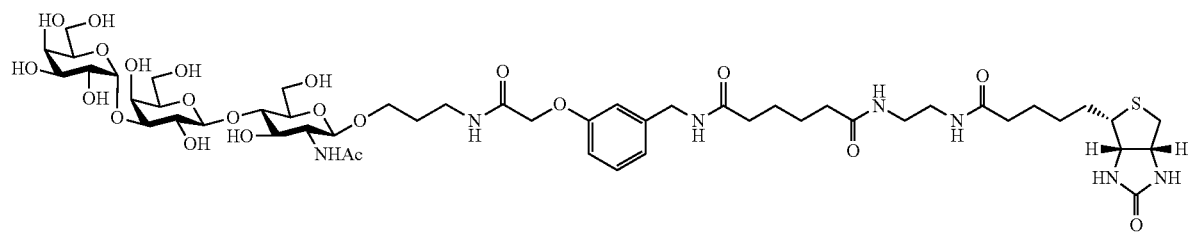

Isolated yield: 15%
LCMS Method B: Rt=1.52 mins, ES⁺ MS m/z 1162.9 [M+H]⁺

Precursor: Preparation 15

Example 13

N¹-(3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)-N6-(3-((2-(5-((3aS,4S,6aR)-2-oxohexahydro-1H-thieno[3,4-d]imidazol-4-yl)pentanamido)ethyl)carbamoyl)benzyl)adipamide (E13)

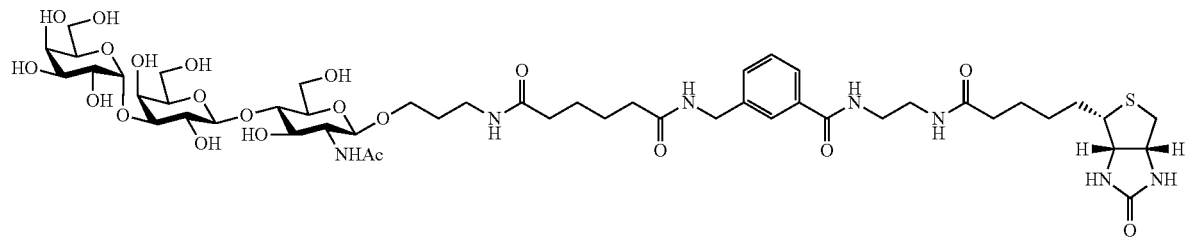

To 2,5-dioxopyrrolidin-1-yl 6-oxo-6-((3-((2-(5-((3aS,4S,6aR)-2-oxohexahydro-1H-thieno[3,4-d]imidazol-4-yl)pentanamido)ethyl)carbamoyl)benzyl)amino)hexanoate (Preparation 14, 13.5 mg, 24.9 μmol) in DMF (500 μL) was added DIPEA (13.0 μL, 74.7 μmol) and a solution of alpha-Gal (15.0 mg, 24.9 μmol) in DMSO (200 μL). The reaction was stirred for 16 hours at room temperature under nitrogen before concentrating in vacuo. The residue was purified using reverse phase column chromatography (Trilution, Magellen C-18, eluting with 5-40% MeCN in water with 0.1% NH₃ over 35 mins, 40% MeCN in water with 0.1% NH₃ for 5 mins) to afford the title compound as a colourless solid (14.8 mg, 55%).

LCMS Method B: Rt=1.46 mins, ES⁺ MS m/z 1132.9 [M+H]⁺

Examples 14-16 were prepared according to the method described for Example 48 using the appropriate benzoic acid and the appropriate amine as described below.

Example 14

2,2'-((5-((2-(5-(((3aS,4S,6aR)-2-Oxohexahydro-1H-thieno[3,4-d]imidazol-4-yl)pentanamido)ethyl)carbamoyl)-[1,1'-biphenyl]-3,3'-diyl)bis(oxy))bis(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide) (E14)

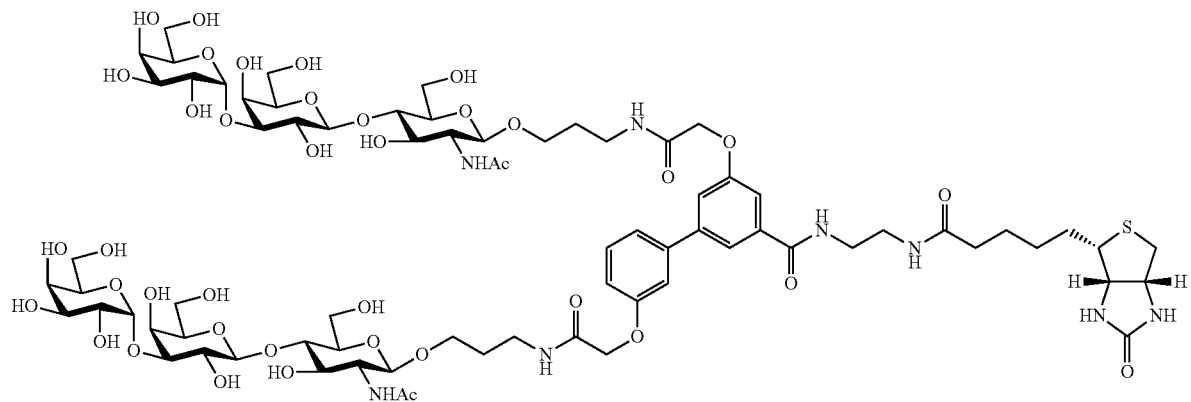

Isolated yield: 40%
LCMS Method B: Rt=1.57 mins, ES⁺ MS m/z 1785.7 [M+H]⁻
Precursors: Preparation 16 and N-(2-aminoethyl)-5-((3aS,4S,6aR)-2-oxohexahydro-1H-thieno[3,4-d]imidazol-4-yl)pentanamide
MALDI-ToF: Monoisotopic mass: 1782.2, observed mass 1805.7 [M+Na]

Example 15

1-{5-[(3aS,4S,6aR)-2-Oxo-hexahydro-1H-thieno[3,4-d]imidazolidin-4-yl]pentanamido}-N-{2-[(3-{[(3-{[(2R,4R,5S)-5-{[(2S,4S,5S)-3,5-dihydroxy-6-(hydroxymethyl)-4-{[(2R,4S,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]methoxy}-5-(4-{[(3-{[(2R,4R,5S)-5-{[(2S,4S,5S)-3,5-dihydroxy-6-(hydroxymethyl)-4-{[(2R,4S,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]methoxy}phenyl)phenyl)formamido]ethyl}-3,6,9,12,15,18,21,24,27,30,33,36-dodecaoxanonatriacontan-39-amide (E15)

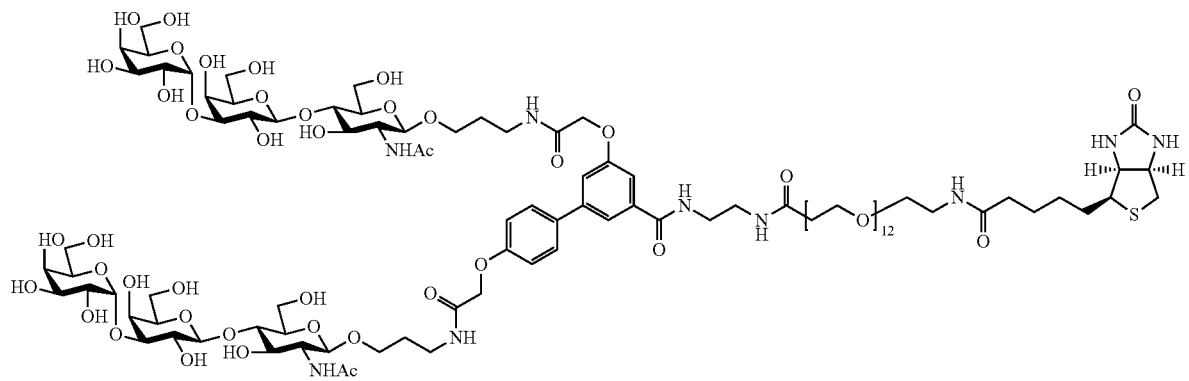

Isolated yield: 22%

LCMS Method B: Rt=1.69 mins, ES+ MS m/z 1193.2 [M+2H]+/2, theoretical mass: 2383.5

Precursor: Preparation 17 and Preparation 41

MALDI-ToF: Monoisotopic mass: 2382.0, observed mass 2405.0 [M+Na]

Example 16

1-{5-[(3aS,4S,6aR)-2-Oxo-hexahydro-1H-thieno[3,4-d]imidazolidin-4-yl]pentanamido}-N-[2-({3-[3,5-bis({[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]methoxy})phenyl]-5-{[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]methoxy}phenyl}formamido)ethyl]-3,6,9,12,15,18,21,24,27,30,33,36-dodecaoxanonatriacontan-39-amide (E16)

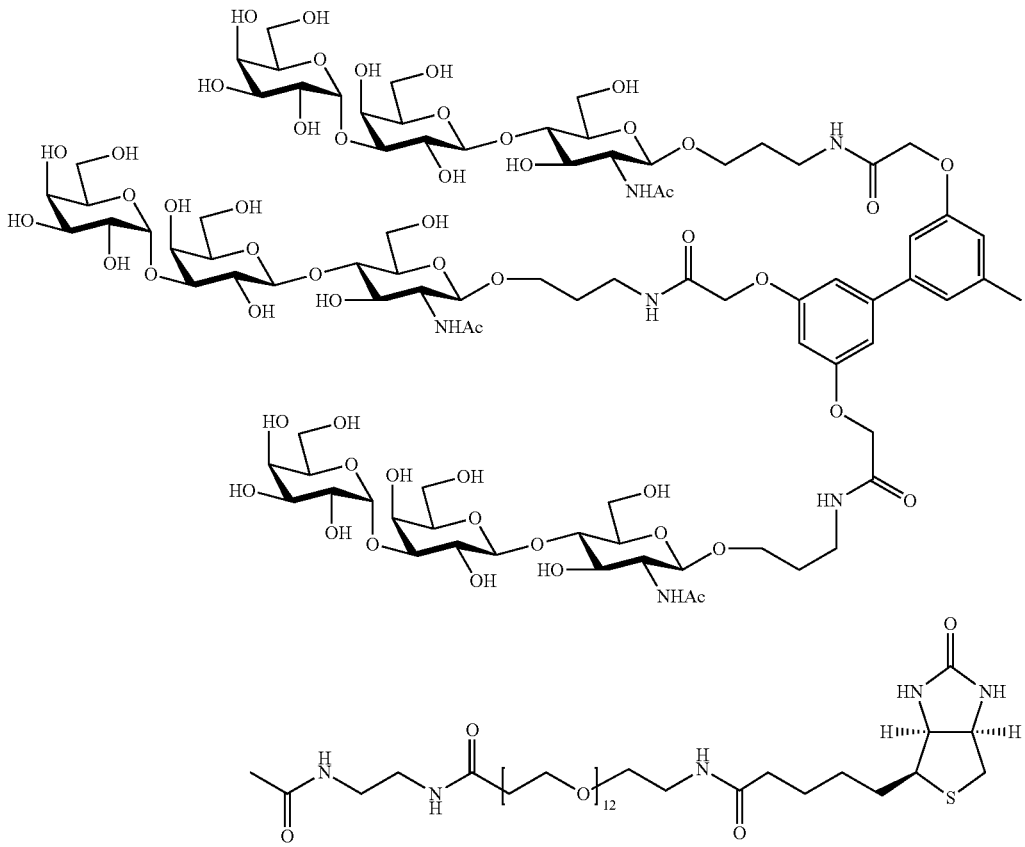

Isolated yield: 32%

LCMS Method A: Rt=1.62 mins, ES+ MS m/z 1522.8 [M+2H]+/2, theoretical mass: 3042.1

Precursor: Preparation 42 and Preparation 41

MALDI-ToF: Monoisotopic mass: 3040.3, observed mass 3063.3 [M+Na]

Example 17

3-(((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)methyl)-N-(2-(5-((3aS,4S,6aR)-2-oxohexahydro-1H-thieno[3,4-d]imidazol-4-yl)pentanamido)ethyl)benzamide (E17)

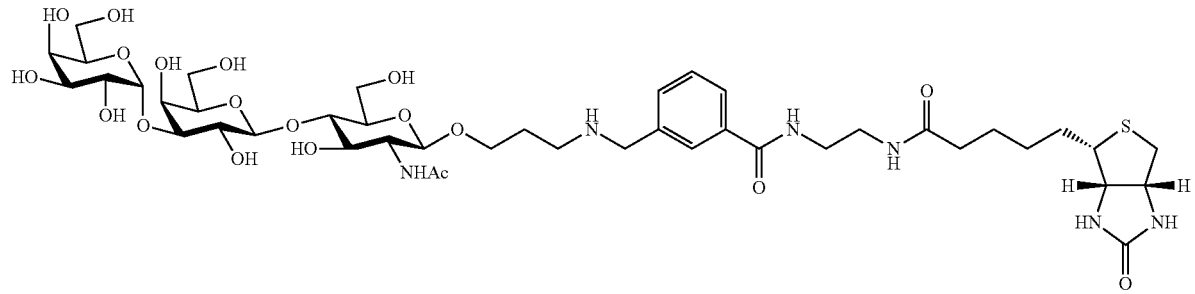

To 3-formyl-N-(2-(5-((3aS,4S,6aR)-2-oxohexahydro-1H-thieno[3,4-d]imidazol-4-yl)pentanamido)ethyl)benzamide (Preparation 35, 20.0 mg, 33.2 μmol) and alpha-Gal (13.9 mg, 33.2 μmol) dissolved in MeOH (1 mL) was added AcOH (7.6 μL, 132 μmol) and picoline-borane complex (3.55 mg, 33.2 μmol). The reaction was stirred for 5 days at room temperature under nitrogen. The reaction was concentrated in vacuo and the residue dissolved in 2M aqueous HCl (2 mL) and stirred for 30 minutes at room temperature. The solvent was concentrated in vacuo and the residue was treated with water (1 mL). The solution was neutralised to pH 7 with TEA dropwise and purified using reverse phase column chromatography (TRILUTION, Magellen C-18, eluting with 10-40% MeCN/water with 0.1% $NH_3$ over 35 mins, 40% MeCN/water with 0.1% $NH_3$ for 5 mins) to afford the title compound as a colourless solid (10.2 mg, 31%).

LCMS Method B: Rt=1.36 mins, $ES^+$ MS m/z 1005.8 $[M+H]^+$

Example 18

1-(2-{3-[(2-{5-[(3aS,4S,6aR)-2-Oxo-hexahydro-1H-thieno[3,4-d]imidazolidin-4-yl]pentanamido}ethyl)carbamoyl]-5-{3,5-bis[({14-[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12-tetraoxatetradecan-1-yl}carbamoyl)methoxy]phenyl}phenoxy}acetamido)-N-(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)-3,6,9,12-tetraoxapentadecan-15-amide (E18)

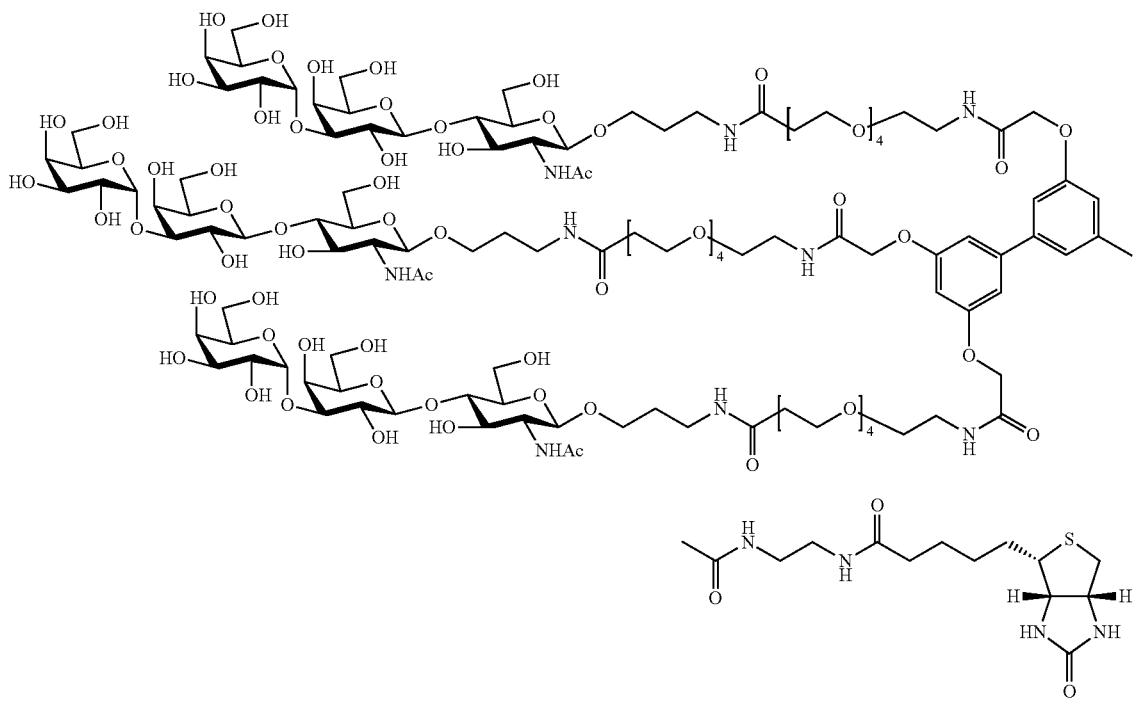

To a crude stock solution of 1-(2-{3-[(2-{5-[(3aS,4S,6aR)-2-oxo-hexahydro-1H-thieno[3,4-d]imidazolidin-4-yl]pentanamido}ethyl)carbamoyl]-5-[3,5-bis({[(14-carboxy-3,6,9,12-tetraoxatetradecan-1-yl)carbamoyl]methoxy})phenyl]phenoxy}acetamido)-3,6,9,12-tetraoxapentadecan-15-oic acid in DMF (Preparation 1, 500 µL, 9.65 µmol) was added DIPEA (13.4 µL, 77.2 µmol) followed by a solution of alpha-Gal (23.3 mg, 38.6 µmol) in DMSO (200 µL). A solution of HATU (14.7 mg, 38.6 µmol) in DMF (200 µL) was added and the reaction mixture stirred under nitrogen for 2 hours at room temperature. The reaction was concentrated in vacuo and the residue was purified using reverse phase column chromatography (TRILUTION, Magellen C-18, eluting with 5-40% MeCN/water with 0.1% NH$_3$ over 35 mins, then 40% MeCN/water with 0.1% NH$_3$ for 5 mins) to afford the title compound as a colourless solid (6.85 mg, 22%).

LCMS Method B: Rt=1.58 mins, ES$^+$ MS m/z 1591.9 [M+2H]$^+$/2, theoretical mass: 3184.3

MALDI-ToF: Monoisotopic mass: 3182.3, observed mass 3205.3 [M+Na]

Examples 19-21 were prepared according to the method described for Example 18 using the appropriate carboxylic acid as described below and a stoichiometric or excess amount of alpha-Gal.

Example 19

1-{5-[(3aS,4S,6aR)-2-Oxo-hexahydro-1H-thieno[3,4-d]imidazolidin-4-yl]pentanamido}-N-[2-({3-[({14-[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12-tetraoxatetradecan-1-yl}carbamoyl)methoxy]phenyl}formamido)ethyl]-3,6,9,12,15,18,21,24,27,30,33,36-dodecaoxanonatriacontan-39-amide (E19)

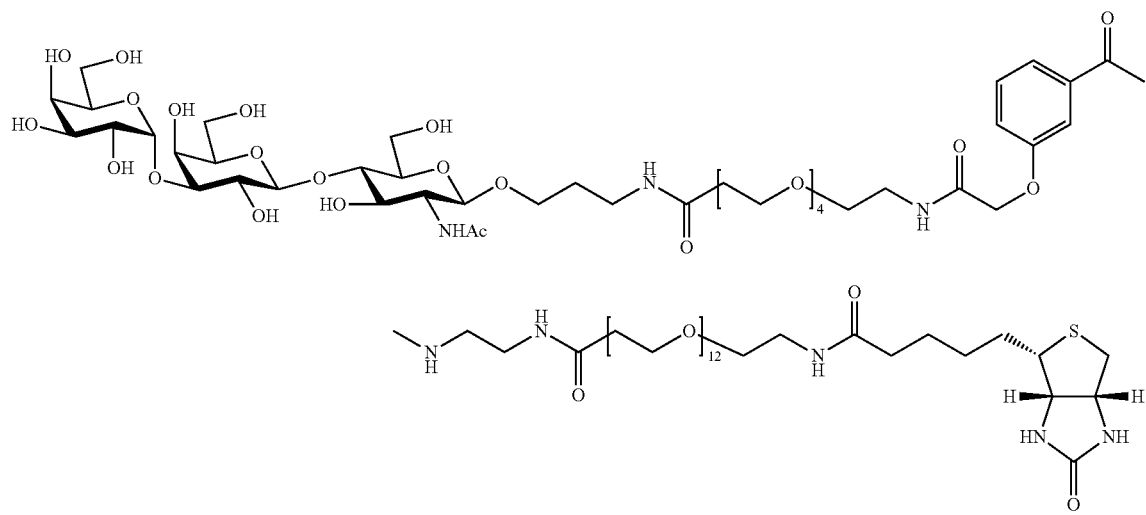

LCMS Method B: Rt=1.87 mins, ES$^+$ MS m/z 1897.6 [M+H]$^+$

Precursor: Preparation 2

MALDI-ToF: Monoisotopic mass: 1894.9, observed mass 1917.9 [M+Na]

Example 20

1-[2-(4-{3-[(2-{5-[(3aS,4S,6aR)-2-Oxo-hexahydro-1H-thieno[3,4-d]imidazolidin-4-yl]pentanamido}ethyl)carbamoyl]-5-[({14-[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12-tetraoxatetradecan-1-yl}carbamoyl)methoxy]phenyl}phenoxy)acetamido]-N-(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)-3,6,9,12-tetraoxapentadecan-15-amide (E20)

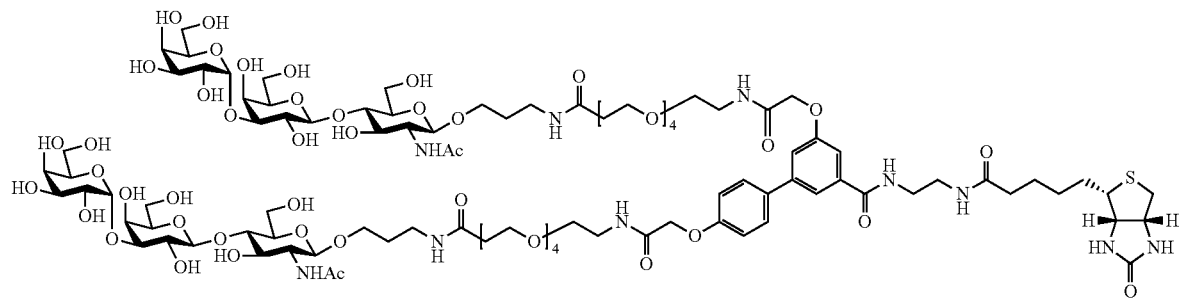

Isolated yield: 7%

LCMS Method B: Rt=1.87 mins, ES$^+$ MS m/z 1140.7 [M+2H]$^+$/2, theoretical mass: 2278.7

Precursor: Preparation 18

MALDI-ToF: Monoisotopic mass: 2276.9, observed mass 2299.9 [M+Na]

Example 21

1-{5-[(3aS,4S,6aR)-2-Oxo-hexahydro-1H-thieno[3,4-d]imidazolidin-4-yl]pentanamido}-N-[2-({3,5-bis[({14-[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12-tetraoxatetradecan-1-yl}carbamoyl)methoxy]phenyl}formamido)ethyl]-3,6,9,12,15,18,21,24,27,30,33,36-dodecaoxanonatriacontan-39-amide (E21)

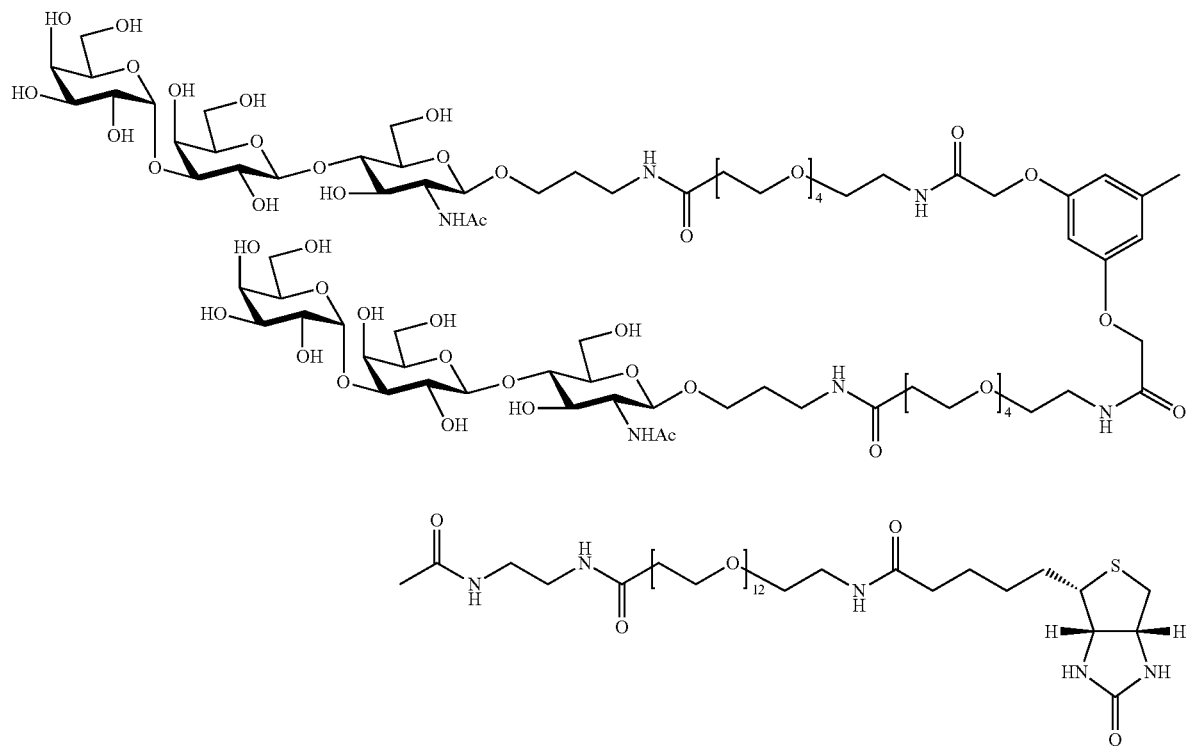

Isolated yield: 9%
LCMS Method B: Rt=1.70 mins, ES$^+$ MS m/z 1400.6 [M+H]$^+$
Precursor: Preparation 6
MALDI-ToF: Monoisotopic mass: 2800.4, observed mass 2823.4 [M+Na]

Example 22

Synthesis of RNA Aptamer Conjugate 1

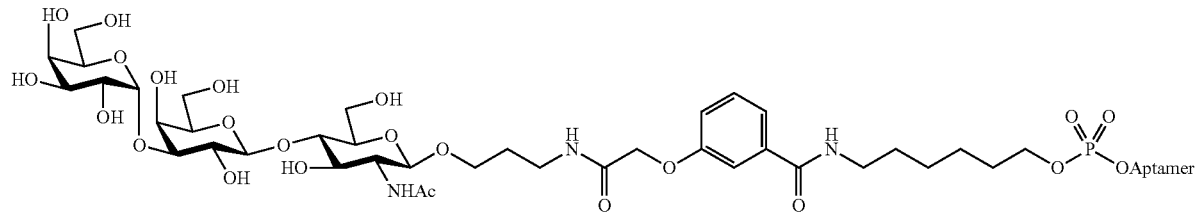

Method 1

To a solution of 3-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)benzoic acid (Preparation 46, 21 eq) in DMF was added a solution of DMTMM chloride (3 eq) in DMF/water 1:1 and the mixture was stirred at room temperature for 20 minutes. This mixture was added to a solution of the RNA aptamer ($C_6$-amino-linked-SEQ ID NO: 79 from International Patent Application No. PCT/GB2015/051812; herein referred to as SEQ ID NO: 1) in aqueous carbonate buffer and the reaction was stirred for 2 hours. The reaction was quenched by the addition of TEAA and purified using reverse phase HPLC using XBridge Prep C18 column (10×50 mm, 5µ) eluting with a gradient of 5-20% TEAA in MeCN in aqueous TEAA. The title compound was collected to afford 260D (1 mg).

LCMS (XBridge OST C18 column (2.1×50 mm, 2.5 µm) eluting with 1-36% solvent B in solvent A over 30 minutes. (Solvent A=100 mmol HFIP, 16.3 mmol TEA and 1% MeOH in water; solvent B=100 mmol HFIP, 16.3 mmol TEA and 95% MeOH), flow rate 0.25 mL/min.

Rt=20.43 minutes; MS $[M+H]^+$ 15073.4

Example 23

Synthesis of RNA Aptamer Conjugate 2

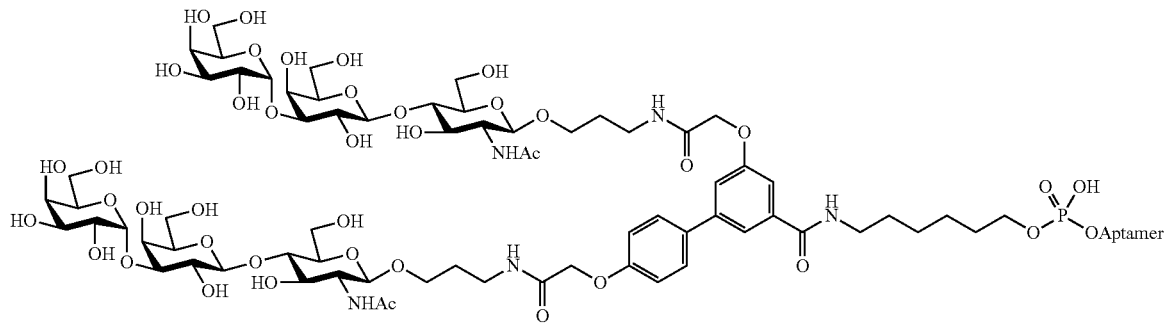

The title compound was prepared according to the method described for Example 22 using 3',5-bis(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid (Preparation 17) and RNA aptamer ($C_6$-amino-linked-SEQ ID NO: 79 from International Patent Application No. PCT/GB2015/051812; herein referred to as SEQ ID NO: 1) to afford 12 OD (0.5 mg).

LCMS conditions used as for Example 22.
Rt=20.81 minutes; MS $[M+H]^+$ 15806.8

Example 24

Synthesis of RNA Aptamer Conjugate 3

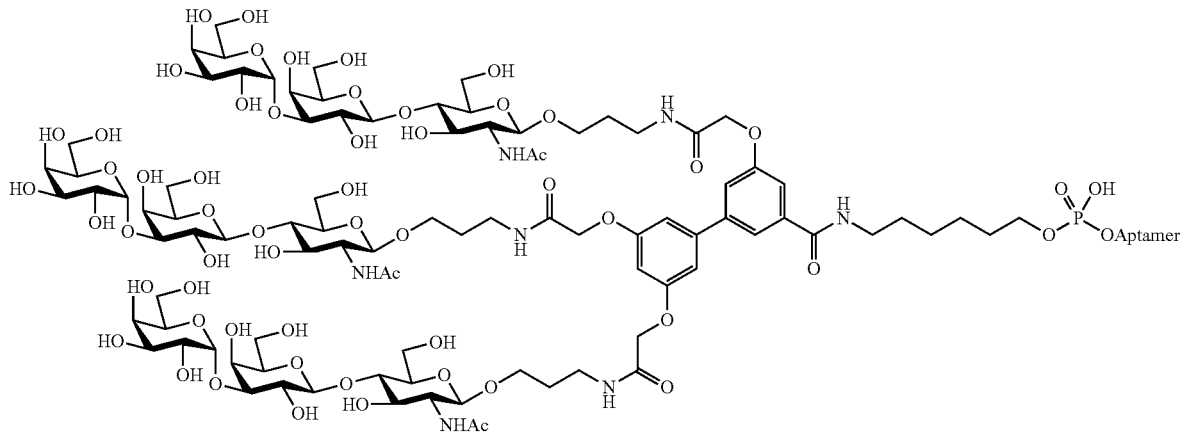

The title compound was prepared according to the method described for Example 22 using 3',5,5'-tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5- trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid (Preparation 42) and RNA aptamer ($C_6$-amino-linked-SEQ ID NO: 79 from International Patent Application No. PCT/GB2015/051812; herein referred to as SEQ ID NO: 1) to afford 10.2 OD (0.41 mg).

LCMS conditions used as for Example 22.

Rt=20.46 minutes; MS [M+H]$^+$ 16465.7

Example 25

Synthesis of DNA Aptamer Conjugate 1

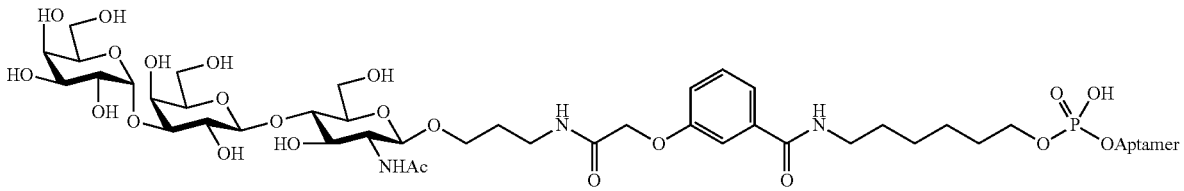

The title compound was prepared according to the method described for Example 22 using 3-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)benzoic acid (Preparation 46) and DNA aptamer ($C_6$-amino-linked-GAS aptamer 20A24P, J. Mol. Med (2015) 93, 619-631; herein referred to as SEQ ID NO: 2).

LCMS conditions used as for Example 22.

Rt=18.41 minutes; MS [M+H]$^+$ 26021.3

Alternative Methods for the Preparation of Aptamer Conjugates

Method 2

To a solution of the desired carboxylic acid (1 mg, 1 eq) in DMF (30 μl) was added N-hydroxysuccinimide (1.1 eq) followed by diisopropylcarbodiimide (1.05 eq) and the reaction was stirred at room temperature overnight. The resultant mixture was added to a solution of the aptamer (1 eq) in aqueous carbonate buffer in two portions separated by 1 hour. The reaction was stirred at room temperature and extra equivalents of NHS-activated acid were added as required to enable formation of the desired reaction product. The resultant solution was purified using preparative reverse phase HPLC as described in Example 22 to afford the aptamer-sugar conjugate.

Method 3

To a solution of the desired carboxylic acid (1 mg, 1 eq) in DMF (30 μL) was added a solution of DMTMM BF$_4$ salt in DMF (2 eq) and the mixture was stirred at room temperature for 40 minutes. 5 eq of the resultant solution was added to a solution of the aptamer (1 eq) in aqueous carbonate buffer and the reaction was stirred for 40 minutes. A further 5 eq of activated acid was added if required and the reaction allowed to stir at room temperature for 1 hour. The resultant solution was purified using preparative reverse phase HPLC as described in Example 22 to afford the desired aptamer-sugar conjugate.

Examples 26-43 were prepared and analysed according to one of Methods 1-3 using RNA aptamer 1 ($C_6$-amino-linked-SEQ ID NO:79, PCT/GB2015/051812; herein referred to as SEQ ID NO: 1) and the appropriate carboxylic acid as described below

Example 26

Synthesis of RNA Aptamer Conjugate 4

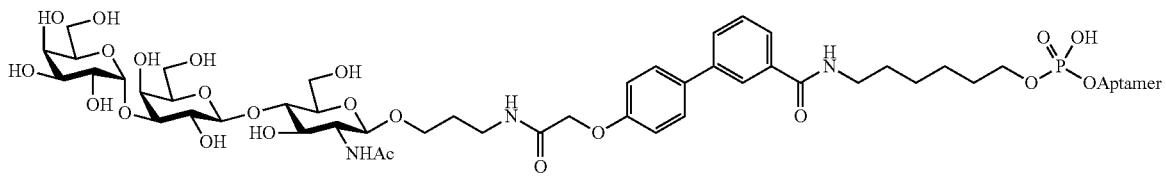

Method: 2
Precursor: Preparation 90
Calculated MWt: 15148
Observed Data: Rt=21.80 minutes; 80.4%; MS 15150
Example 27
Synthesis of RNA Aptamer Conjugate 5
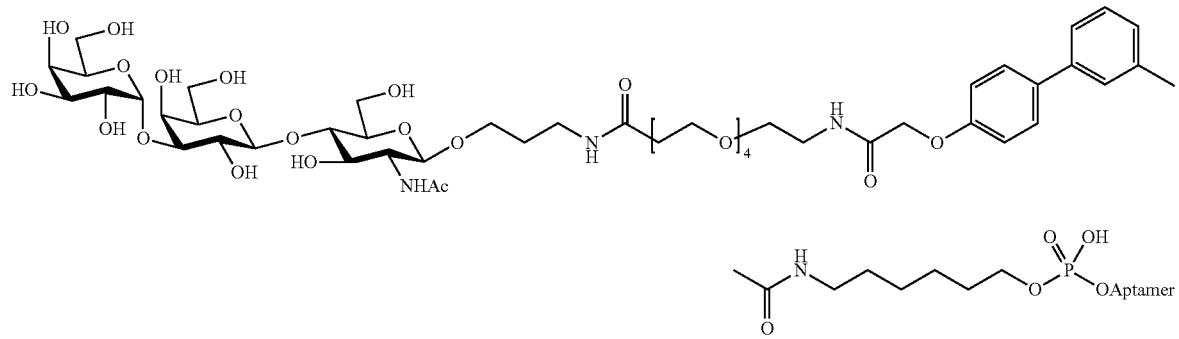
Method: 1
Precursor: Preparation 85
Calculated MWt: 15396
Observed Data: Rt=22.74 minutes; 95.7%; MS 15396
Example 28
Synthesis of RNA Aptamer Conjugate 6
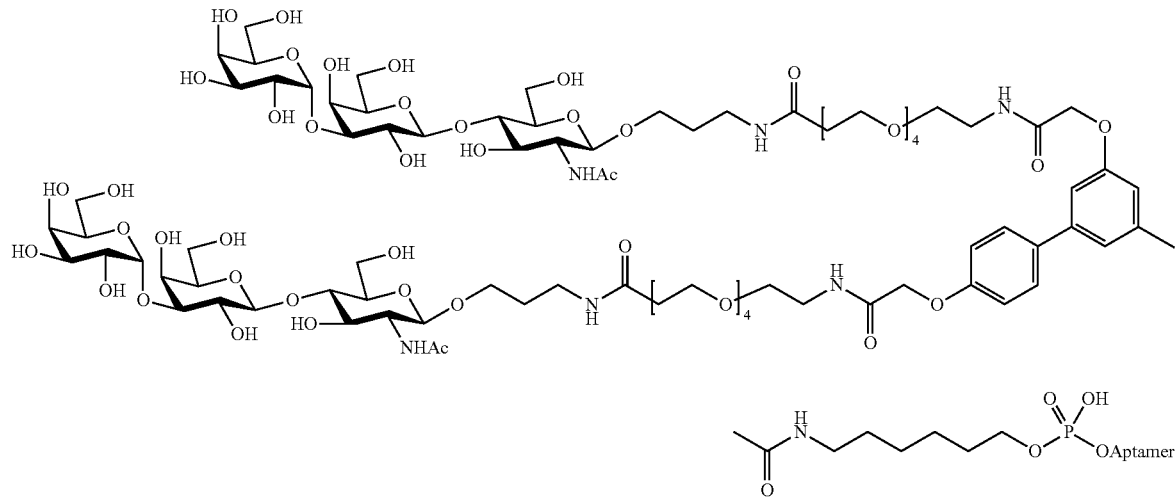
Method: 2
Precursor: Preparation 86
Calculated MWt: 16302
Observed Data: Rt=22.58 minutes; 90.9%; MS 16303

Example 29
Synthesis of RNA Aptamer Conjugate 7
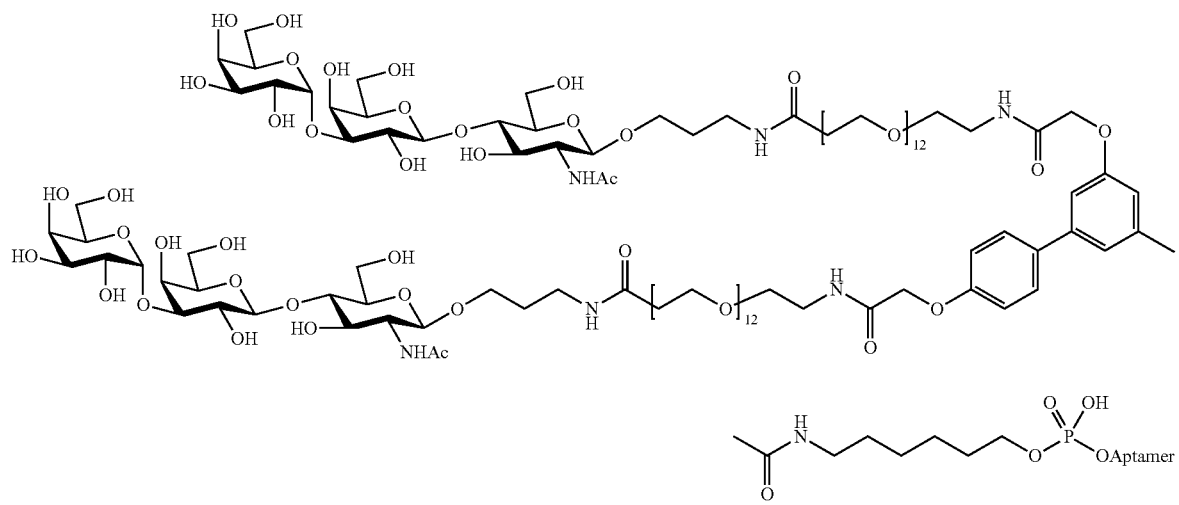
Method: 2
Precursor: Preparation 84
Calculated MWt: 17007
Observed Data: Rt=22.74 minutes; 92.6%; MS 17005
Example 30
Synthesis of RNA Aptamer Conjugate 8
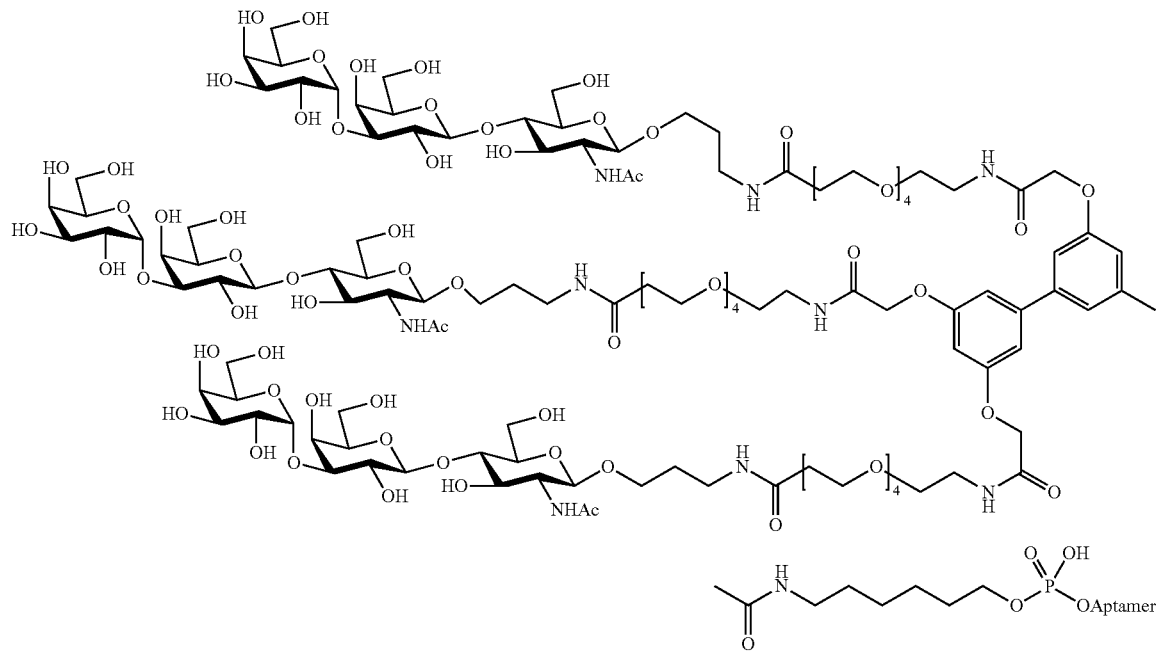
Method: 1
Precursor: Preparation 83
Calculated MWt: 17209
Observed Data: Rt=22.80 minutes; 86.3%; MS 17207

Example 31
Synthesis of RNA Aptamer Conjugate 9
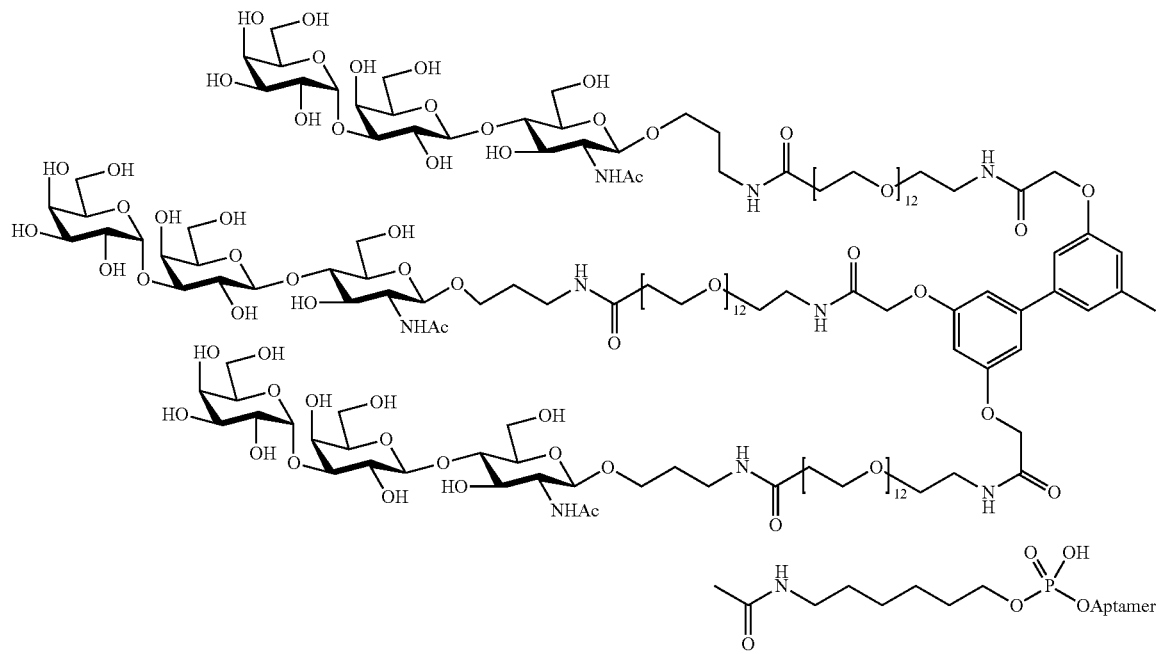
Method: 1
Precursor: Preparation 87
Calculated MWt: 18265
Observed Data: Rt=29.52 minutes; 90.1%; MS 18265
Example 32
Synthesis of RNA Aptamer Conjugate 10
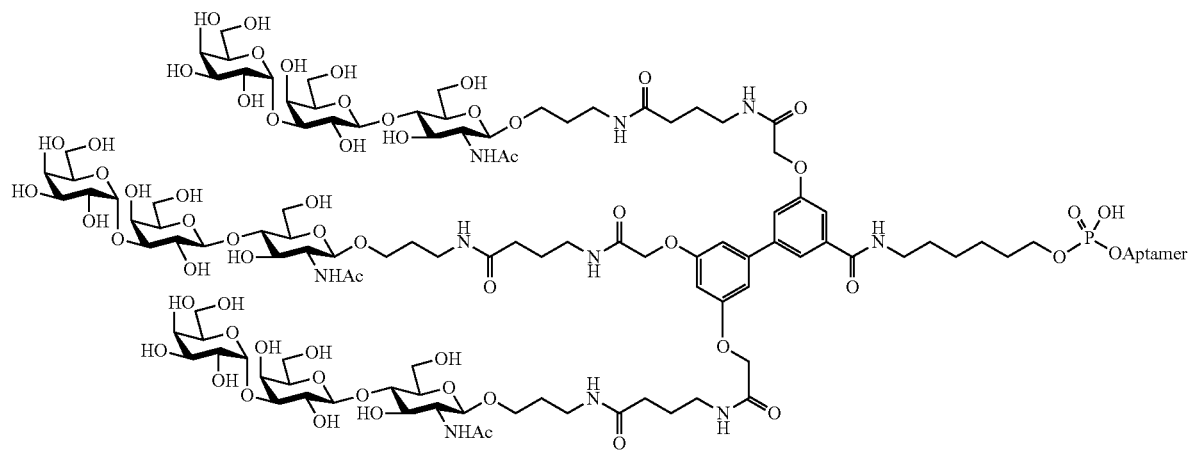
Method: 1
Precursor: Preparation 89
Calculated MWt: 16721
Observed Data: Rt=20.89 minutes; 89.5%; MS 16721
Example 33
Synthesis of RNA Aptamer Conjugate 11

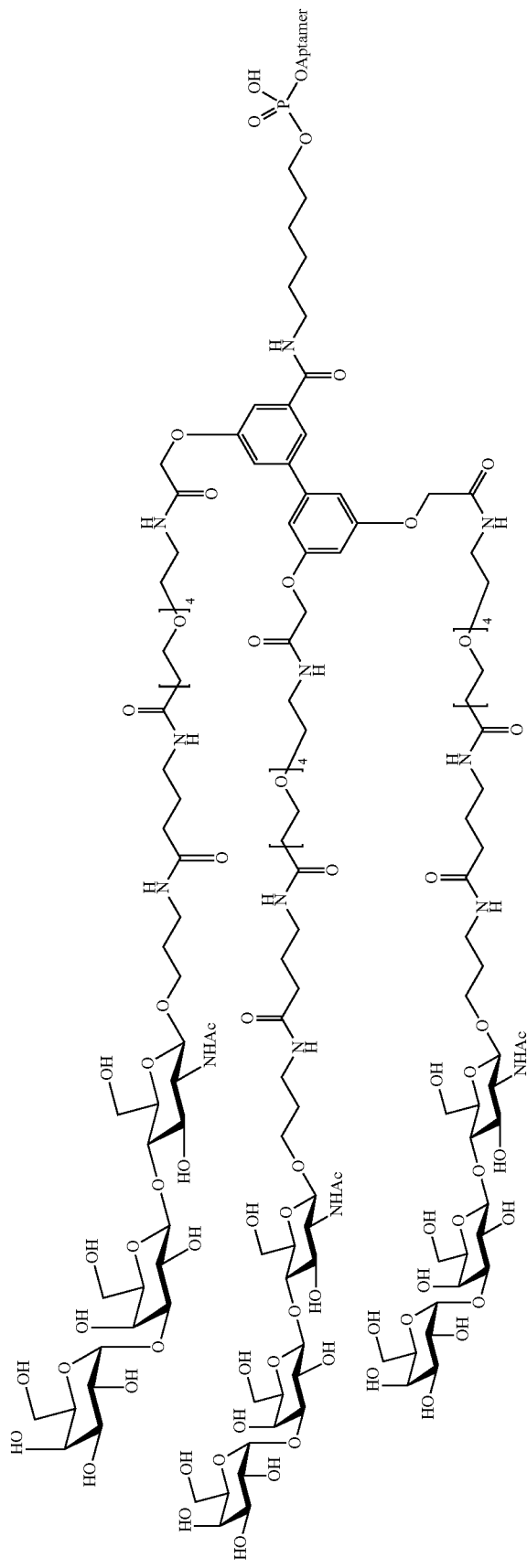

Method: 1
Precursor: Preparation 88
Calculated MWt: 17463
Observed Data: Rt=22.91 minutes; 86.2%; MS 17465
Example 34
Synthesis of RNA Aptamer Conjugate 12
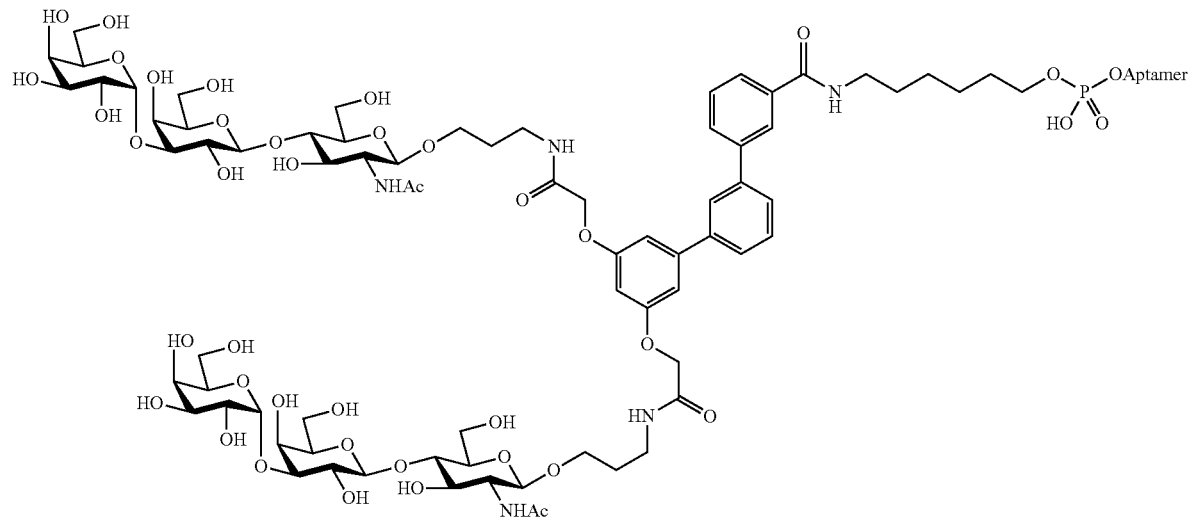
Method: 1
Precursor: Preparation 91
Calculated MWt: 15883
Observed Data: Rt=22.23 minutes; 92.6%; MS 15882
Example 35
Synthesis of RNA Aptamer Conjugate 13
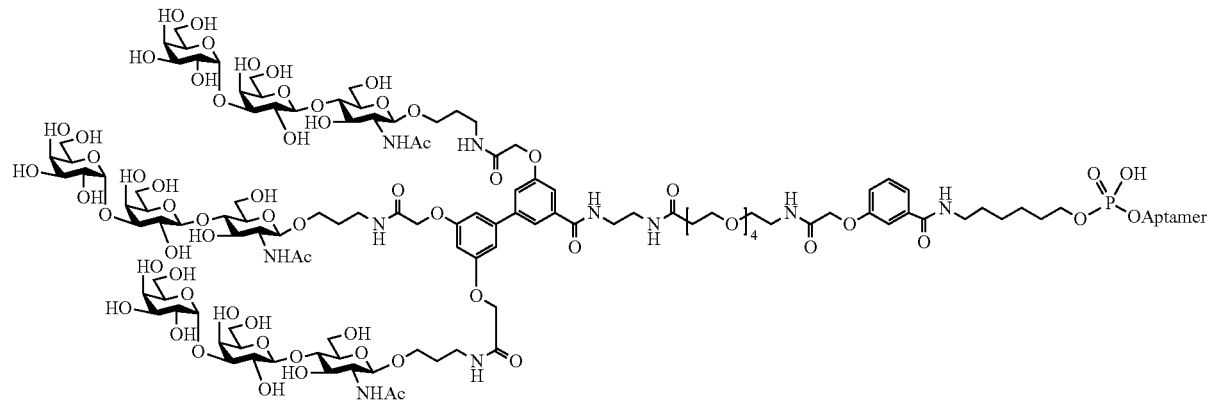
Method: 1
Precursor: Preparation 96
Calculated MWt: 16932
Observed Data: Rt=22.04 minutes; 99.9%; MS 16933

Example 36
Synthesis of RNA Aptamer Conjugate 14
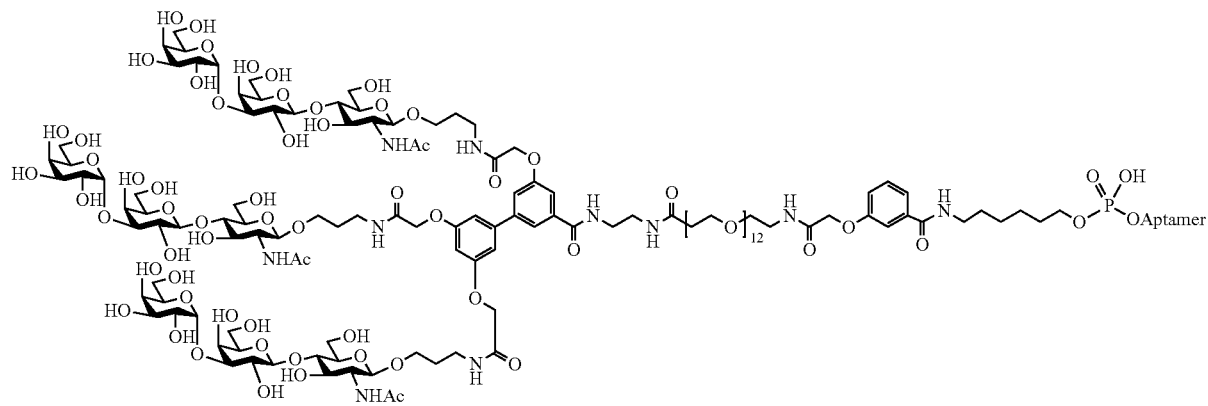
Method: 2
Precursor: Preparation 95
Calculated MWt: 17285
Observed Data: Rt=22.82 minutes; 89.5%; MS 17286
Example 37
Synthesis of RNA Aptamer Conjugate 15
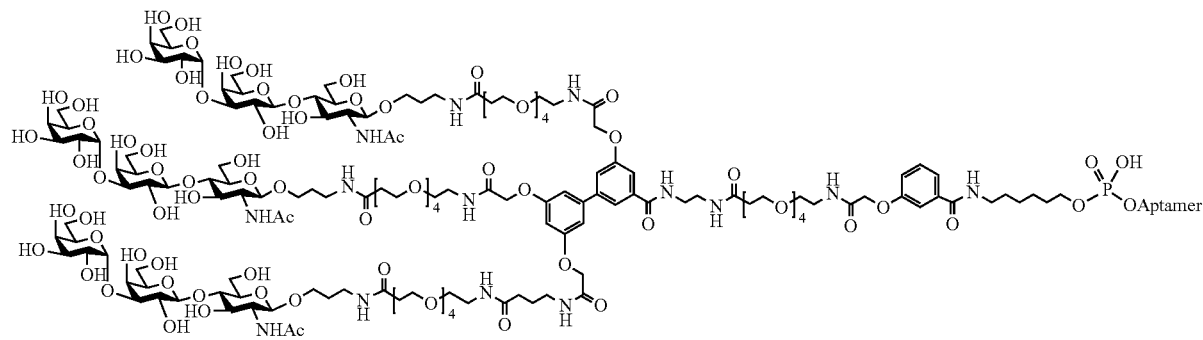
Method: 1
Precursor: Preparation 97
Calculated MWt: 17675
Observed Data: Rt=23.16 minutes; 89.6%; MS 17675
Example 38
Synthesis of RNA Aptamer Conjugate 16
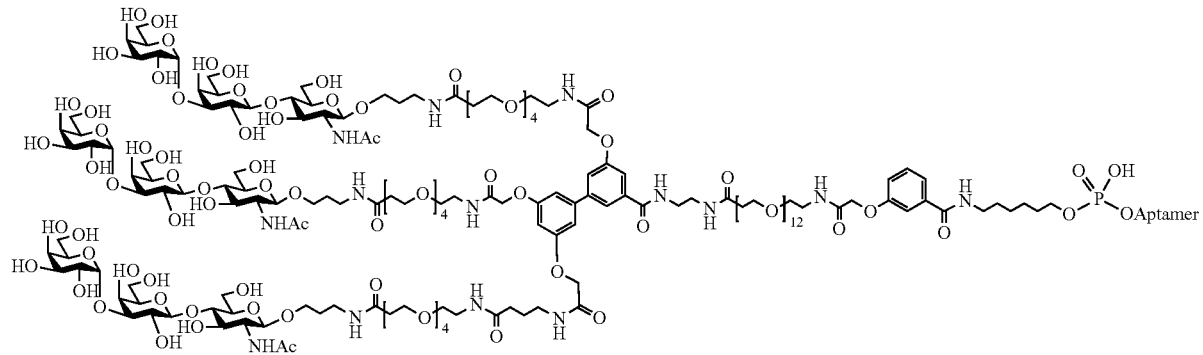

Method: 1
Precursor: Preparation 98
Calculated MWt: 18027
Observed Data: Rt=26.50 minutes; 90.7%; MS 18028
Example 39
Synthesis of RNA Aptamer Conjugate 17
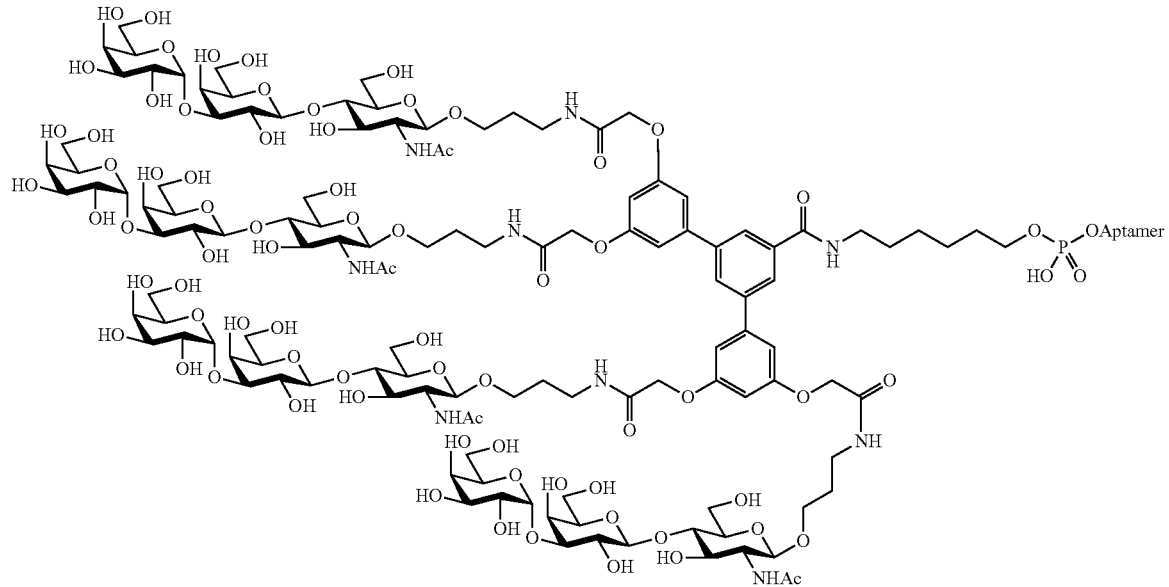
Method: 1
Precursor: Preparation 92
Calculated MWt: 17200
Observed Data: Rt=20.79 minutes; 90.4%; MS 17201
Example 40
Synthesis of RNA Aptamer Conjugate 18
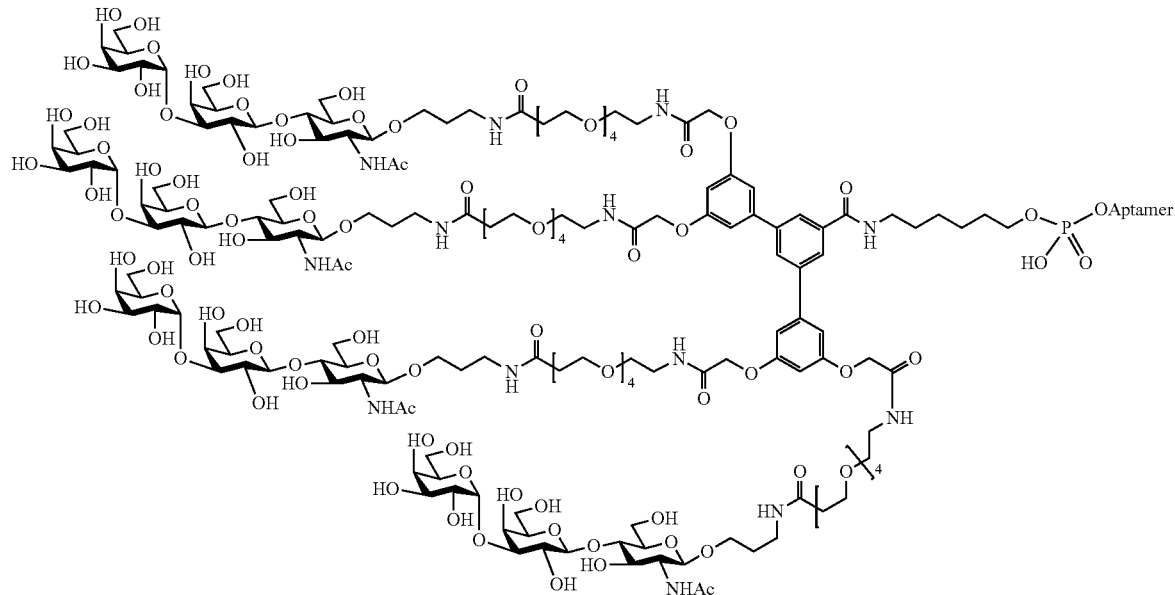

Method: 3
Precursor: Preparation 93
Calculated MWt: 18188
Observed Data: Rt=22.17 minutes; 83.3%; MS 18189
Example 41
Synthesis of RNA Aptamer Conjugate 19
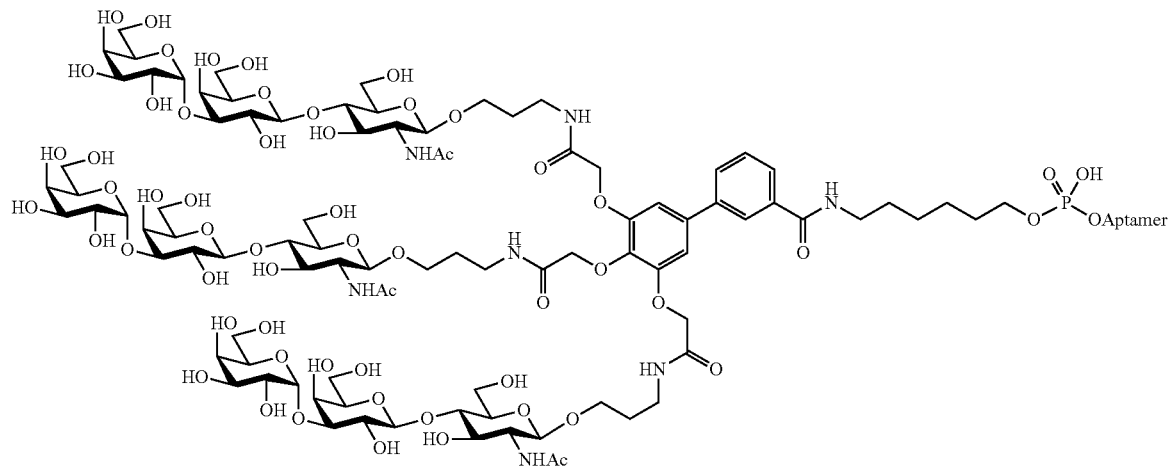
Method: 3
Precursor: Preparation 94
Calculated MWt: 16465
Observed Data: Rt=19.99 minutes; 83.7%; MS 16464
Example 42
Synthesis of RNA Aptamer Conjugate 20
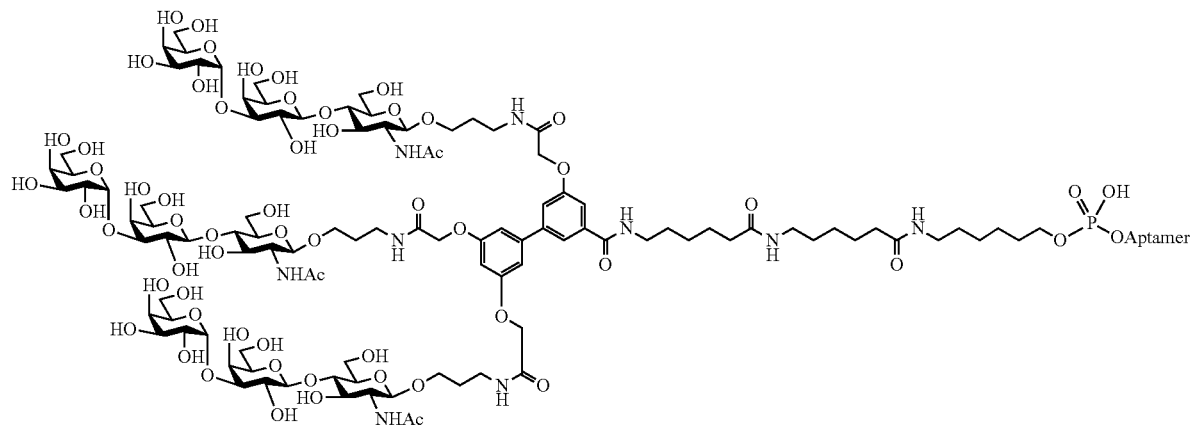
Precursor: Preparation 99
Calculated MWt: 16692
Observed Data: Rt=20.66 minutes; 83.3%; MS 16690

Example 43

Synthesis of RNA Aptamer Conjugate 21

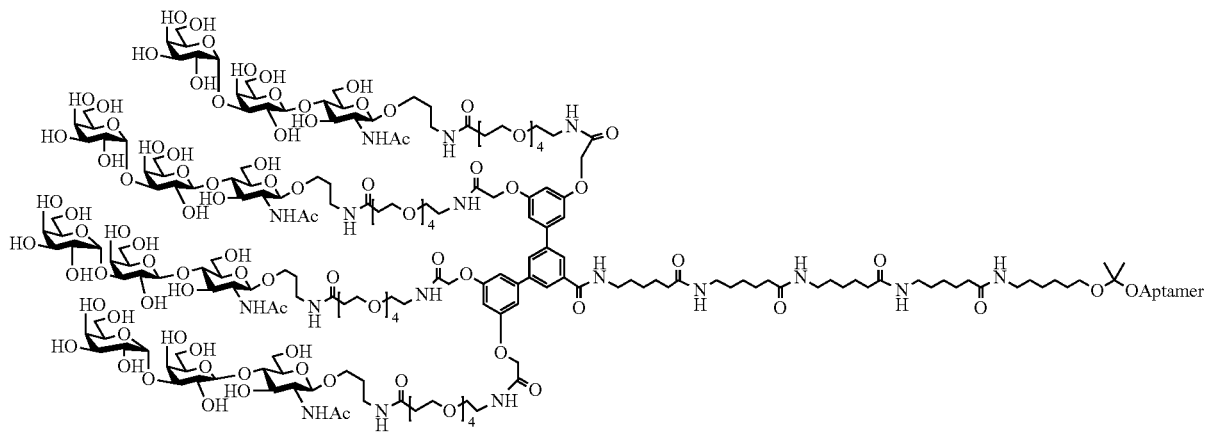

Method: 3
Precursor: Preparation 100
Calculated MWt: 18642
Observed Data: Rt=25.61 minutes; 83.3%; MS 18641

Example 44

Synthesis of RNA Aptamer Conjugate 22

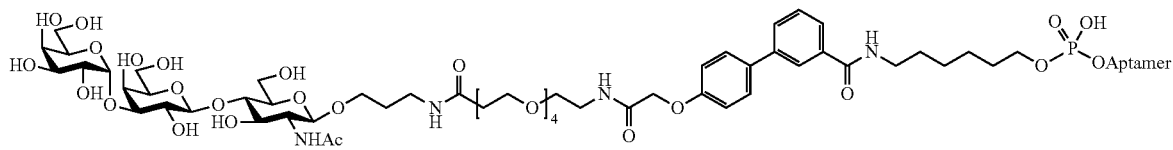

Method: 1
Precursor: Preparation 85
Calculated MWt: 21765
Observed Data: Rt=22.84 minutes; 99.6%; MS 21766

Example 45

Synthesis of RNA Aptamer Conjugate 23

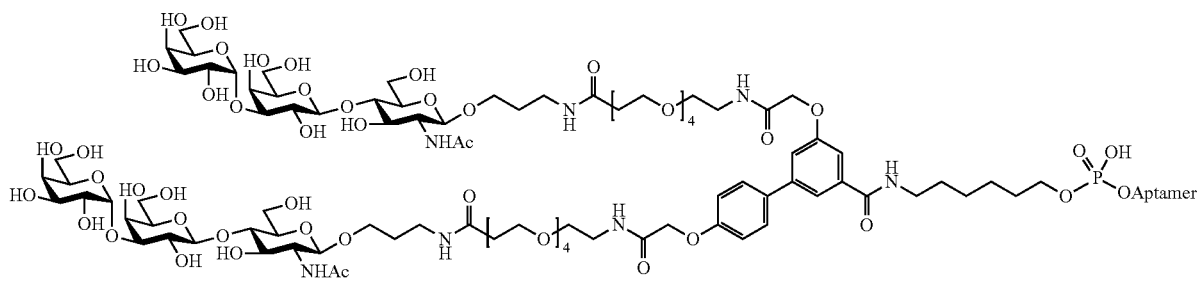

Method: 1
Precursor: Preparation 86
Calculated MWt: 22670
Observed Data: Rt=22.56 minutes; 97.2%; MS 22671

Example 46

Synthesis of RNA Aptamer Conjugate 24

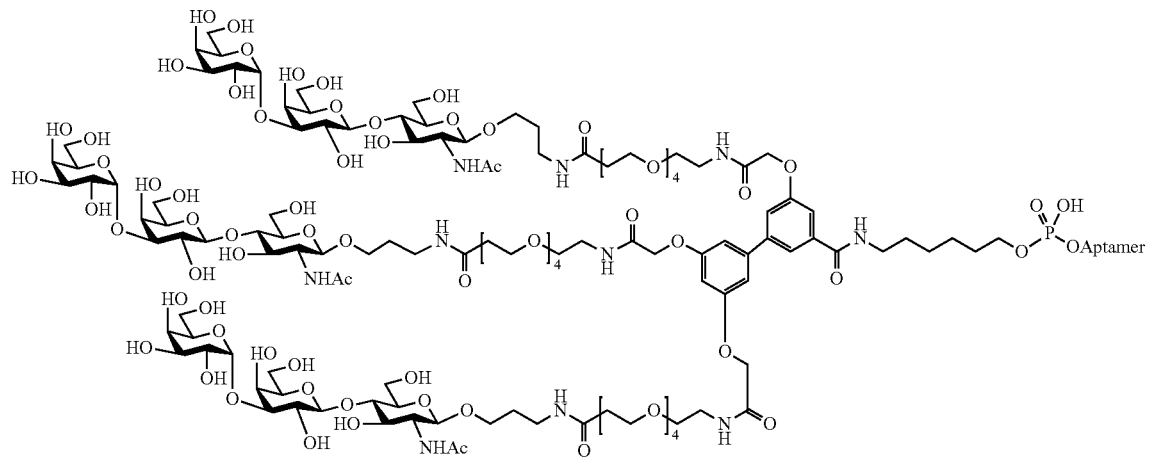

Method: 1
Precursor: Preparation 83
Calculated MWt: 23576
Observed Data: Rt=22.56 minutes; 98.2%; MS 23577

Example 47

Synthesis of RNA Aptamer Conjugate 25

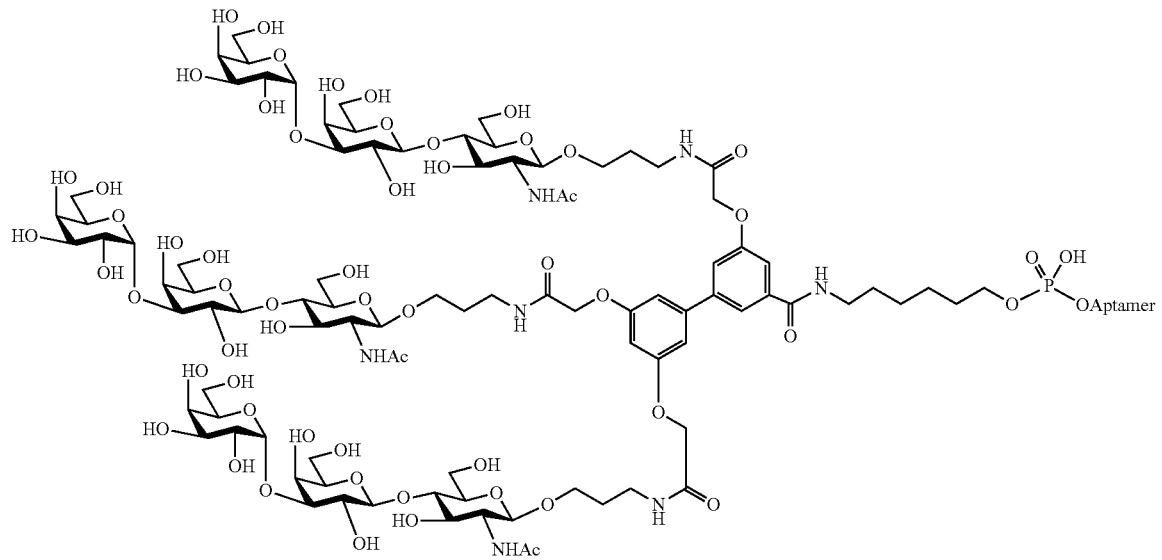

Method: 1
Precursor: Preparation 42
Calculated MWt: 22833
Observed Data: Rt=21.27 minutes; 97.3%; MS 22836

Nucleic Acid Aptamer Synthesis

It will be apparent to the skilled person that the nucleic acid aptamers used herein may be synthesised in accordance with techniques within the common general knowledge, such as solid phase nucleotide synthesis (C R Noe, L Kaufhold; Chemistry of Antisense Oligonucleotides in New Trends in Synthetic Medicinal Chemistry, Ed: F Gualtieri; Wiley-VCH, Weinheim, 2000; pp 261-347. ISBN 3527297995).

Examples 48-62 were prepared according to the methods described for Example 1 or Example 48 using the appropriate carboxylic acid and a stoichiometric or excess amount of alpha-Gal or biotinylated amine, stirring from between 1-24 hours and using the reverse-phase purification conditions as described below unless otherwise specified:

Reverse Phase Conditions:
Method 1:
Trilution (Magellen C-18, eluting with from between 2-50% MeCN/water with 0.1% NH₃ over 35 mins, 40% MeCN/water with 0.1% NH₃ for 5 mins)

Example 48

1-{2-[4-(3-{[2-(1-{5-[(3aS,4S,6aR)-2-Oxo-hexahydro-1H-thieno[3,4-d]imidazolidin-4-yl]pentanamido}-3,6,9,12,15,18,21,24,27,30,33,36-dodecaoxanonatriacontan-39-amido)ethyl]carbamoyl}-5-[({38-[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12,15,18,21,24,27,30,33,36-dodecaoxaoctatriacontan-1-yl}carbamoyl)methoxy]phenyl)phenoxy]acetamido}-N-(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)-3,6,9,12,15,18,21,24,27,30,33,36-dodecaoxanonatriacontan-39-amide

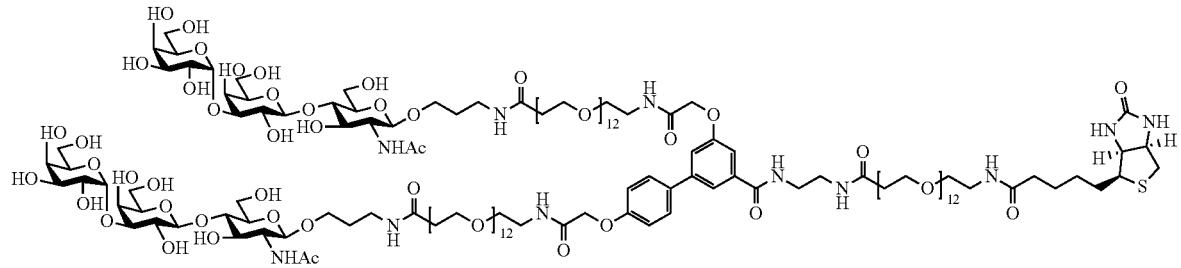

To 4',5-bis((46-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,42-dioxo-6,9,12,15,18,21,24,27,30,33,36,39-dodecaoxa-3,43-diazahexatetracontyl)oxy)-[1,1'-biphenyl]-3-carboxylic acid (Preparation 84, 8.50 mg, 3.13 µmol) in DMSO/DMF (1:5 v/v, 1.5 mL) was added DIPEA (1.64 µL, 9.40 µmol) and 1-{5-[(3aS,4S,6aR)-2-oxo-hexahydro-1H-thieno[3,4-d]imidazolidin-4-yl]pentanamido}-N-(2-aminoethyl)-3,6,9,12,15,18,21,24,27,30,33,36-dodecaoxanonatriacontan-39-amide (Preparation 41, 4.16 mg, 4.70 µmol). HATU (1.79 mg, 4.70 µmol) was added as a solution in DMF (200 µL) and the reaction was stirred for 1 hour at room temperature under nitrogen. The reaction was concentrated in vacuo and purified using reverse phase column chromatography using Purification Method 1 to afford the title compound as a colourless solid (6.25 mg, 56%).

LCMS Method B: Rt=1.86 mins, ES⁻ MS m/z 1791.1 [M−2H]⁻/2, theoretical mass: 3583.0

MALDI-ToF: Monoisotopic mass 3580.8, observed mass 3603.6 [M+Na]

Example 49

1-[2-(4-{3-[(2-{5-[(3aS,4S,6aR)-2-Oxo-hexahydro-1H-thieno[3,4-d]imidazolidin-4-yl]pentanamido}ethyl)carbamoyl]-5-[({38-[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12,15,18,21,24,27,30,33,36-dodecaoxaoctatriacontan-1-yl}carbamoyl)methoxy]phenyl}phenoxy)acetamido]-N-(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)-3,6,9,12,15,18,21,24,27,30,33,36-dodecaoxanonatriacontan-39-amide

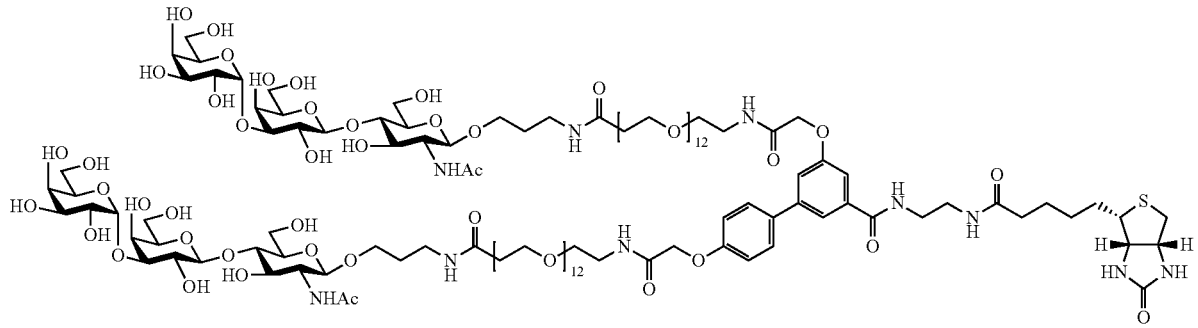

Method: Example 48

Isolated yield: 40%, Purification Method 1

LCMS Method B: Rt=1.80 mins, ES$^+$ MS m/z 1492.9 [M+2H]$^+$/2, theoretical mass: 2983.2

Precursors: Preparation 84 and N-(2-aminoethyl)-5-((3aS, 4S, 6aR)-2-oxohexahydro-1H-thieno[3,4-d]imidazole-4-yl)pentanamide.

MALDI-ToF: Monoisotopic mass 2981.4, observed mass 3004.4 [M+Na]

Example 50

3-((46-(((2R,3R,4R,5S,6R)-3-Acetamido-5-((((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,42-dioxo-6,9,12,15,18,21,24,27,30,33,36,39-dodecaoxa-3,43-diazahexatetracontyl)oxy)-N-(4,44-dioxo-48-((3aS,4S,6aR)-2-oxohexahydro-1H-thieno[3,4-d]imidazol-4-yl)-7,10,13,16,19,22,25,28,31,34,37,40-dodecaoxa-3,43-diazaoctatetracontyl)benzamide

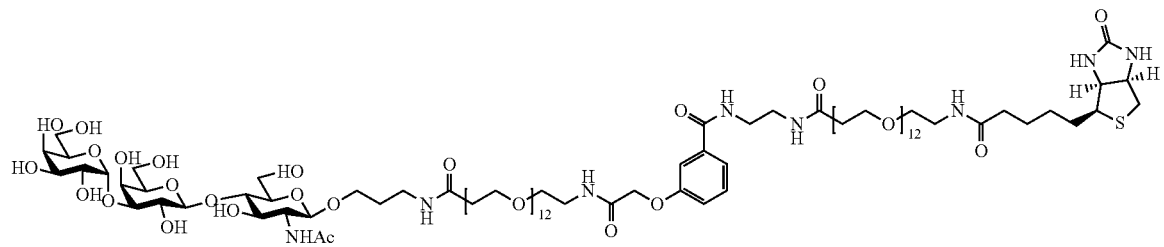

Method: Example 1

Isolated yield: 64%, Purification Method 1

LCMS Method B: Rt=1.85 mins ES$^+$ MS m/z 1125.7 [M+2H]$^+$/2, theoretical mass: 2248.5

Precursors: Preparation 106

MALDI-ToF: Monoisotopic mass 2247.1, observed mass 2270.1 [M+Na]

Example 51

1-(2-{2-[(2-{5-[(3aS,4S,6aR)-2-Oxo-hexahydro-1H-thieno[3,4-d]imidazolidin-4-yl]pentanamido}ethyl)carbamoyl]-4-{3,5-bis[({14-[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12-tetraoxatetradecan-1-yl}carbamoyl)methoxy]phenyl}-5-[({14-[(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12-tetraoxatetradecan-1-yl}carbamoyl)methoxy]phenoxy}acetamido)-N-(3-{[(2R,5S)-5-{[(2S,5S)-3,5-dihydroxy-6-(hydroxymethyl)-4-{[(2R,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)-3,6,9,12-tetraoxapentadecan-15-amide

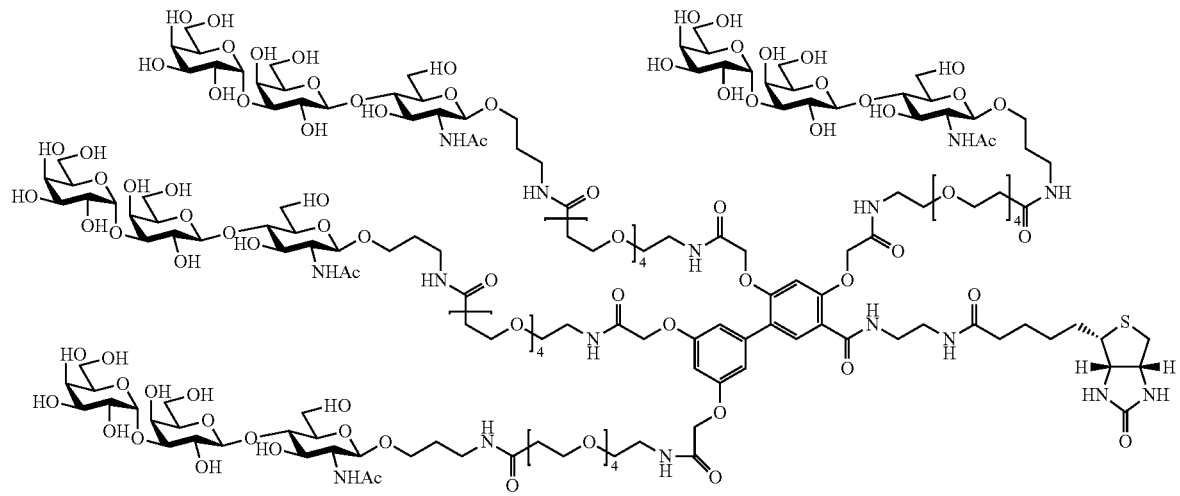

To 1,1',1'',1'''-((5-((2-(5-((3aS,4S,6aR)-2-oxohexahydro-1H-thieno[3,4-d]imidazol-4-yl)pentanamido)ethyl)carbamoyl)-[1,1'-biphenyl]-2,3',4,5'-tetrayl)tetrakis(oxy))tetrakis(2-oxo-6,9,12,15-tetraoxa-3-azaoctadecan-18-oic acid) (Preparation 109, 10.6 mg, 6.7 μmol) dissolved in DMF (1 mL) was added DIPEA (13.9 μL, 75.2 μmol) and alpha-Gal (28.3 mg, 47.0 μmol) as a solution in DMSO (400 μL). HATU (21.4 mg, 56.4 μmol) was added and the reaction was stirred for 2 hours at room temperature under nitrogen. The reaction was concentrated in vacuo and purified according to Method 1 to afford the title compound as a colourless solid (1.33 mg, 5%).

LCMS Method B: Rt=1.54 mins ES$^+$ MS m/z 1364.6 [M+3H]$^+$/3, theoretical mass: 4090.2

MALDI-ToF: Monoisotopic mass 4087.7, observed mass 4111.0 [M+Na]

Example 52

4'-((22-(((2R,3R,4R,5S,6R)-3-Acetamido-5-(((2S,
3R,4S,5S,6R)-3,5-dihydroxy-6-(hydroxymethyl)-4-
(((2R,3R,4S,5R,6R)-3,4,5-trihydroxy-6-(hydroxym-
ethyl)tetrahydro-2H-pyran-2-yl)oxy)tetrahydro-2H-
pyran-2-yl)oxy)-4-hydroxy-6-(hydroxymethyl)
tetrahydro-2H-pyran-2-yl)oxy)-2,18-dioxo-6,9,12,
15-tetraoxa-3,19-diazadocosyl)oxy)-N-(4,44-dioxo-
48-((3aS,4S,6aR)-2-oxohexahydro-1H-thieno[3,4-d]
imidazol-4-yl)-7,10,13,16,19,22,25,28,31,34,37,40-
dodecaoxa-3,43-diazaoctatetracontyl)-[1,1'-
biphenyl]-3-carboxamide

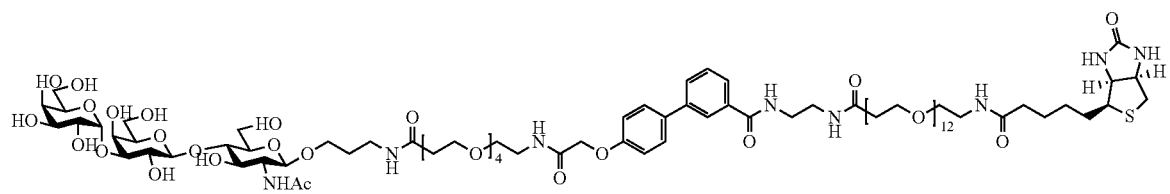

Method: Example 48
Isolated yield: 74%, Purification Method 1
LCMS Method B: Rt=1.90 mins ES$^+$ MS m/z 1973.7
[M+H]+, theoretical mass: 1972.2
Precursors: Preparation 85 and Preparation 41
MALDI-ToF: Monoisotopic mass 1970.9, observed mass 1993.9 [M+Na]

Example 53

1,1'-((2,2'-((5-((4,44-Dioxo-48-((3aS,4S,6aR)-2-
oxohexahydro-1H-thieno[3,4-d]imidazol-4-yl)-7,10,
13,16,19,22,25,28,31,34,37,40-dodecaoxa-3,43-diaz-
aoctatetracontyl)carbamoyl)-[1,1'-biphenyl]-3,4'-
diyl)bis(oxy))bis(acetyl))bis(azanediyl))bis(N-(3-
(((2R,3R,4R,5S,6R)-3-acetamido-5-(((2S,3R,4S,5S,
6R)-3,5-dihydroxy-6-(hydroxymethyl)-4-(((2R,3R,
4S,5R,6R)-3,4,5-trihydroxy-6-(hydroxymethyl)
tetrahydro-2H-pyran-2-yl)oxy)tetrahydro-2H-pyran-
2-yl)oxy)-4-hydroxy-6-(hydroxymethyl)tetrahydro-
2H-pyran-2-yl)oxy)propyl)-3,6,9,12-
tetraoxapentadecan-15-amide)

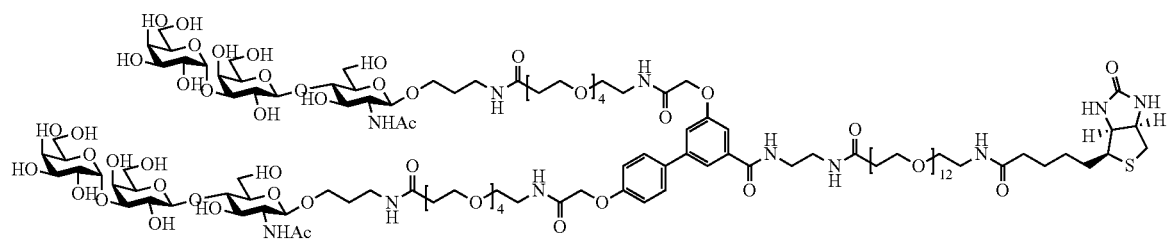

Method: Example 48
Isolated yield: 59%, Purification Method 1
LCMS Method B: Rt=1.77 mins ES$^+$ MS m/z 1438.0
[M−2H]$^-$/2, theoretical mass: 2878.1
Precursors: Preparation 86 and Preparation 41
MALDI-ToF: Monoisotopic mass 2876.3, observed mass 2899.3 [M+Na]

Example 54

1,1',1''-((2,2',2''-((5'-((4,44-Dioxo-48-((3aS,4S,6aR)-2-oxohexahydro-1H-thieno[3,4-d]imidazol-4-yl)-7,10,13,16,19,22,25,28,31,34,37,40-dodecaoxa-3,43-diazaoctatetracontyl)carbamoyl)-[1,1'-biphenyl]-3,3',5-triyl)tris(oxy))tris(acetyl))tris(azanediyl))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)-3,6,9,12-tetraoxapentadecan-15-amide)

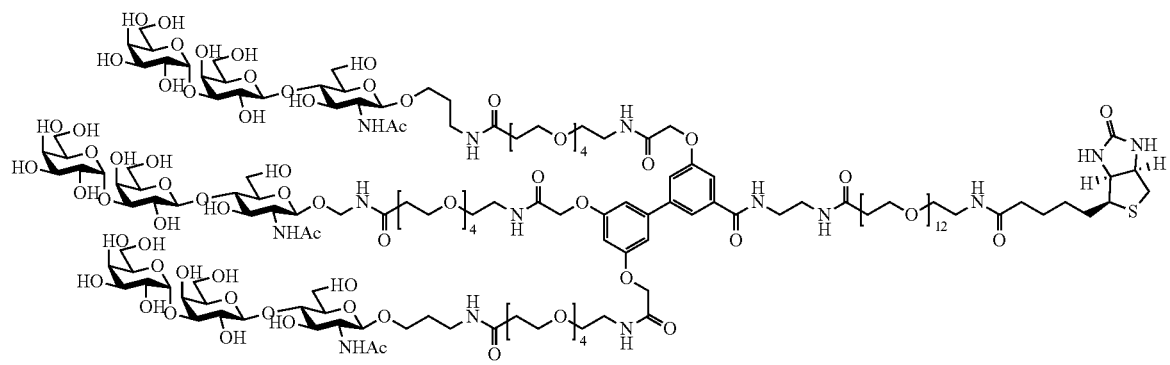

Method: Example 48
Isolated yield: 61%, Purification Method 1
LCMS Method B: Rt=1.70 mins ES$^+$ MS m/z 1890.7 [M−2H]$^−$/2, theoretical mass: 3784.0
Precursors: Preparation 83 and Preparation 41
MALDI-ToF: Monoisotopic mass 3781.7, observed mass 3804.2 [M+Na]

Example 55

2,2',2''-((3'-((2-(5-((3aS,4S,6aR)-2-Oxohexahydro-1H-thieno[3,4-d]imidazol-4-yl)pentanamido)ethyl)carbamoyl)-[1,1'-biphenyl]-3,4,5-triyl)tris(oxy))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide)

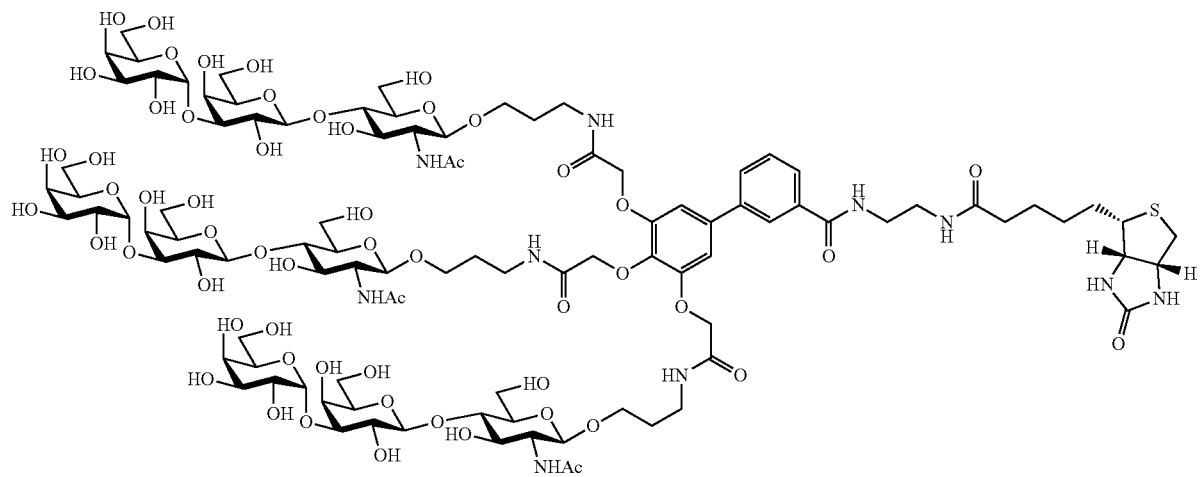

Method: Example 1

Isolated yield: 11%, Purification Method 1

LCMS Method B: Rt=1.43 mins ES⁺ MS m/z 1222.2 [M+2H]⁺/2, theoretical mass: 2442.4

Precursors: Preparation 102

MALDI-ToF: Monoisotopic mass 2440.9, observed mass 2464.0 [M+Na]

Example 56

1-[2-(3-{3-[(2-5-[(3aS,4S,6aR)-2-Oxo-hexahydrothieno[3,4-d]imidazolidin-4-yl]pentanamido}ethyl)carbamoyl]-5-[({38-[(3-{[(2R,5S,6R)-5-{[(2S,5S,6R)-3,5-dihydroxy-6-(hydroxymethyl)-4-{[(2R,5R,6R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12,15,18,21,24,27,30,33,36-dodecaoxaoctatriacontan-1-yl}carbamoyl)methoxy]phenyl}-5-[({38-[(3-{[(2R,5S,6R)-5-{[(2S,5S,6R)-3,5-dihydroxy-6-(hydroxymethyl)-4-{[(2R,5R,6R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12,15,18,21,24,27,30,33,36-dodecaoxaoctatriacontan-1-yl}carbamoyl)methoxy]phenoxy)acetamido]-N-(3-{[(2R,5S,6R)-5-{[(2S,5S,6R)-3,5-dihydroxy-6-(hydroxymethyl)-4-{[(2R,5R,6R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)-3,6,9,12,15,18,21,24,27,30,33,36-dodecaoxanonatriacontan-39-amide

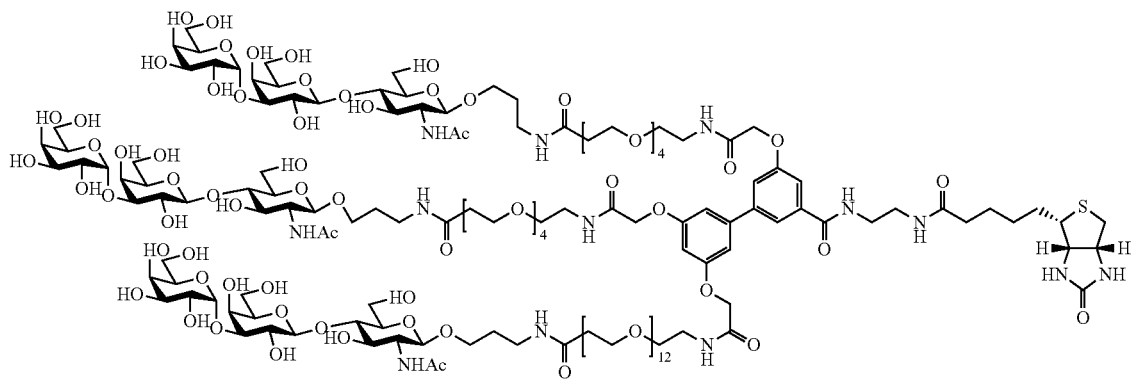

Method: Example 48

Isolated yield: 78%, Purification Method 1

LCMS Method B: Rt=1.76 mins ES⁺ MS m/z 1414.8 [M+3H]⁺/3 and ES⁺ MS m/z 1061.4 [M+4H]⁺/4, theoretical mass: 4241.6

Precursors: Preparation 87 and N-(2-aminoethyl)-5-((3aS,4S,6aR)-2-oxohexahydro-1H-thieno[3,4-d]imidazole-4-yl)pentanamide.

MALDI-ToF: Monoisotopic mass 4239.0, observed mass 4261.7 [M+Na]

Example 57

1-[2-(3-{[2-(1-{5-[(3aS,4S,6aR)-2-Oxo-hexahydrothieno[3,4-d]imidazolidin-4-yl]pentanamido}-3,6,9,12,15,18,21,24,27,30,33,36-dodecaoxanonatriacontan-39-amido)ethyl]carbamoyl}-5-{3,5-bis[({38-[(3-{[(2R,3R,4R,5S,6R)-5-{[(2S,3R,4S,5S,6R)-3,5-dihydroxy-6-(hydroxymethyl)-4-{[(2R,3R,4S,5R,6R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]-3,6,9,12,15,18,21,24,27,30,33,36-dodecaoxaoctatriacontan-1-yl}carbamoyl)methoxy]phenyl}phenoxy)acetamido]-N-(3-{[(2R,3R,4R,5S,6R)-5-{[(2S,3R,4S,5S,6R)-3,5-dihydroxy-6-(hydroxymethyl)-4-{[(2R,3R,4S,5R,6R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)-3,6,9,12,15,18,21,24,27,30,33,36-dodecaoxanonatriacontan-39-amide

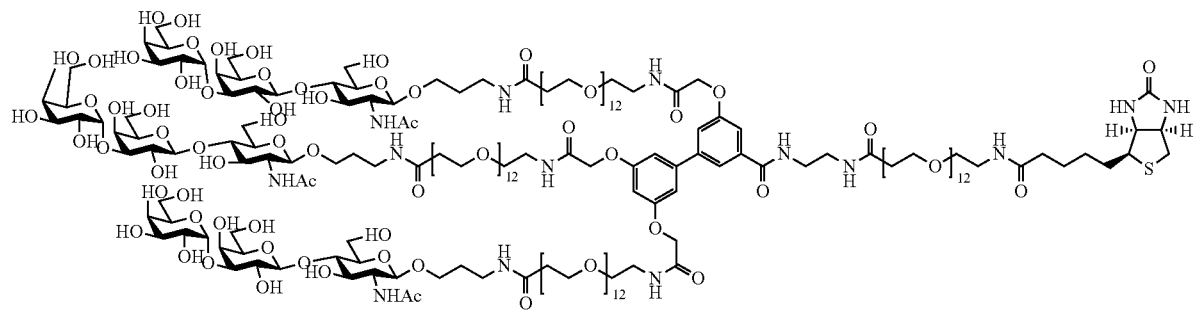

Method: Example 48
Isolated yield: 46%, Purification Method 1
LCMS Method B: Rt=1.81 mins ES$^+$ MS m/z 1211.4 [M+4H]$^+$/4, theoretical mass: 4841.3
Precursors: Preparation 87 and Preparation 41
MALDI-ToF: Monoisotopic mass 4838.3, observed mass 4860.9 [M+Na]

Example 58

1,1',1"-((2,2',2"-((5'-((15,20-Dioxo-24-((3aS,4S,6aR)-2-oxohexahydro-11H-thieno[3,4-d]imidazol-4-yl)-3,6,9,12-tetraoxa-16,19-diazatetracosyl)carbamoyl)-[1,1'-biphenyl]-3,3',5-triyl)tris(oxy))tris(acetyl))tris(azanediyl))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)-3,6,9,12-tetraoxapentadecan-15-amide)

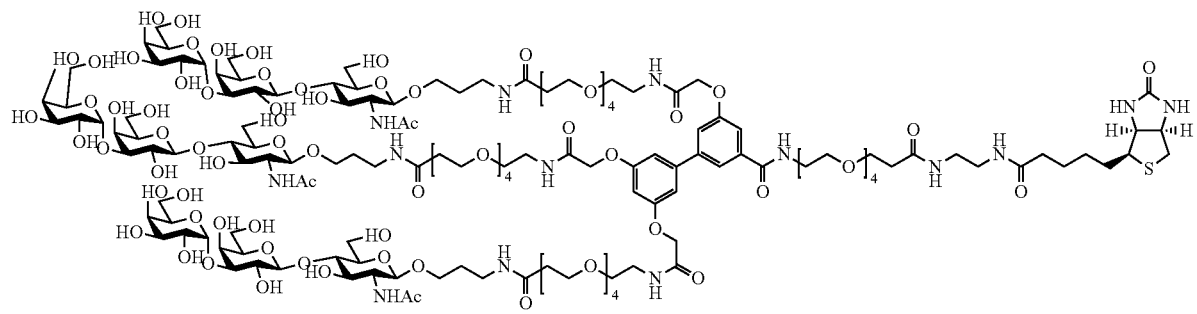

Method: Example 48 with additional equivalents of base (2 eq) and HATU (1.3 eq).

Isolated yield: 10%, Purification Method 1

LCMS Method B: Rt=1.62 mins ES$^+$ MS m/z 1144.9 [M+3H]$^+$/3, theoretical mass: 3431.6

Precursors: Preparation 101 and N-(2-aminoethyl)-5-((3aS, 4S, 6aR)-2-oxohexahydro-1H-thieno[3,4-d]imidazole-4-yl)pentanamide.

MALDI-ToF: Monoisotopic mass 3429.5, observed mass 3452.4 [M+Na]

Example 59

1-(2-{3-[(2-{5-[(3aS,4S,6aR)-2-Oxo-hexahydro-1H-thieno[3,4-d]imidazolidin-4-yl]pentanamido}ethyl)carbamoyl]-5-[3,5-bis({[14-({3-[(3-{[(2R,4R,5S)-5-{[(2S,4S,5S)-3,5-dihydroxy-6-(hydroxymethyl)-4-{[(2R,4S,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]propyl}carbamoyl)-3,6,9,12-tetraoxatetradecan-1-yl]carbamoyl}methoxy)phenyl]phenoxy}acetamido)-N-{3-[(3-{[(2R,4R,5S)-5-{[(2S,4S,5S)-3,5-dihydroxy-6-(hydroxymethyl)-4-{[(2R,4S,5R)-3,4,5-trihydroxy-6-(hydroxymethyl)oxan-2-yl]oxy}oxan-2-yl]oxy}-3-acetamido-4-hydroxy-6-(hydroxymethyl)oxan-2-yl]oxy}propyl)carbamoyl]propyl}-3,6,9,12-tetraoxapentadecan-15-amide

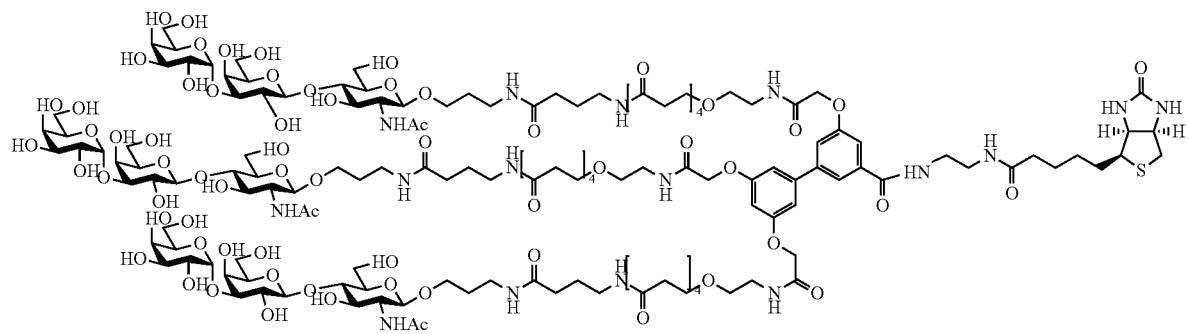

Method: Example 48

Isolated yield: 94%, Purification Method 1

LCMS Method B: Rt=1.47 mins ES$^+$ MS m/z 1147.8 [M+3H]$^+$/3, theoretical mass: 3439.6

Precursors: Preparation 88 and N-(2-aminoethyl)-5-((3aS, 4S, 6aR)-2-oxohexahydro-1H-thieno[3,4-d]imidazole-4-yl)pentanamide.

MALDI-ToF: Monoisotopic mass 3437.5, observed mass 3460.5 [M+Na]

Example 60

4,4',4''-((2,2',2''-((5'-((2-(5-(((3aS,4S,6aR)-2-Oxo-hexahydro-1H-thieno[3,4-d]imidazol-4-yl)pentana-mido)ethyl)carbamoyl)-[1,1'-biphenyl]-3,3',5-triyl)tris(oxy))tris(acetyl))tris(azanediyl))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)butanamide)

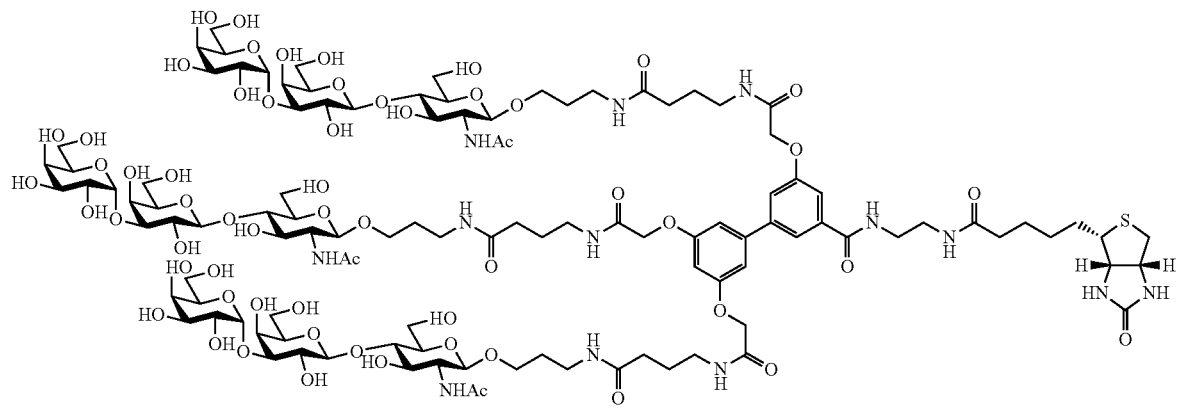

Method: Example 48

Isolated yield: 42%, Purification Method 1

LCMS Method B: Rt=1.47 mins ES$^+$ MS m/z 1349.8 [M+2H]$^+$/2, theoretical mass: 2697.7

Precursors: Preparation 89 and N-(2-aminoethyl)-5-((3aS, 4S, 6aR)-2-oxohexahydro-1H-thieno[3,4-d]imidazole-4-yl)pentanamide.

MALDI-ToF: Monoisotopic mass 2696.1, observed mass 2719.1 [M+Na]

Example 61

2,2'-((3"-((2-(5-((3aS,4S,6aR)-2-Oxohexahydro-1H-thieno[3,4-d]imidazol-4-yl)pentanamido)ethyl)carbamoyl)-[1,1':3',1"-terphenyl]-3,5-diyl)bis(oxy))bis(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide)

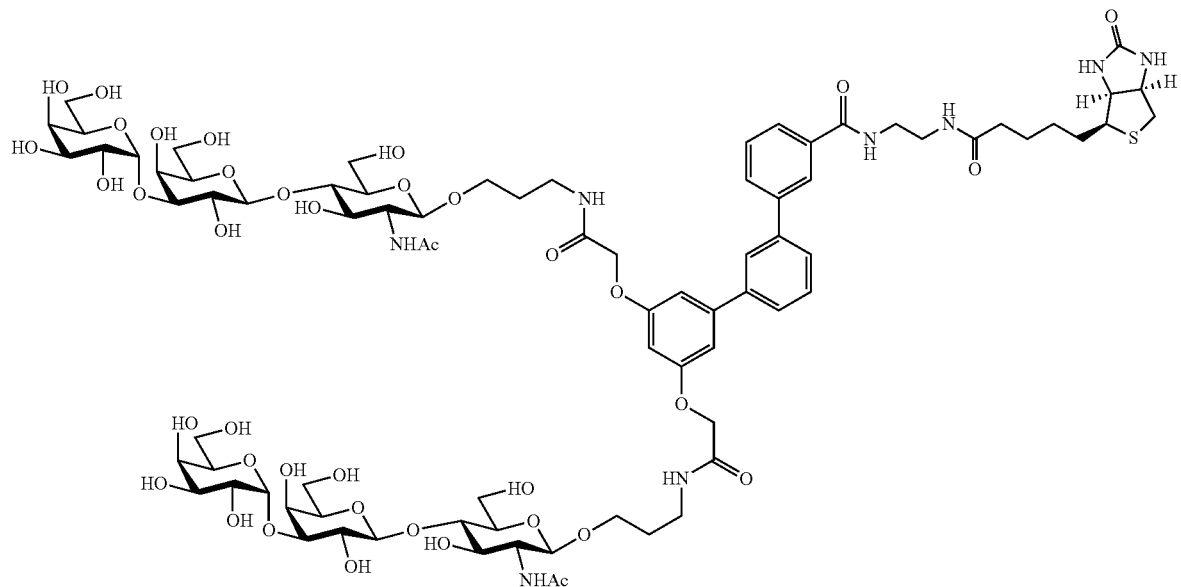

Method: Example 48

Isolated yield: 65%, Purification Method 1

LCMS Method B: Rt=1.78 mins ES+ MS m/z 1860.2 [M+H]+, theoretical mass: 1859.91

Precursors: Preparation 91 and N-(2-aminoethyl)-5-((3aS, 4S, 6aR)-2-oxohexahydro-1H-thieno[3,4-d]imidazole-4-yl) pentanamide.

Example 62

2,2',2'',2'''-((5'-((2-(5-((3aS,4S,6aR)-2-Oxohexahydro-1H-thieno[3,4-d]imidazol-4-yl)pentanamido)ethyl)carbamoyl)-[1,1':3',1''-terphenyl]-3,3'',5,5''-tetrayl)tetrakis(oxy))tetrakis(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide)

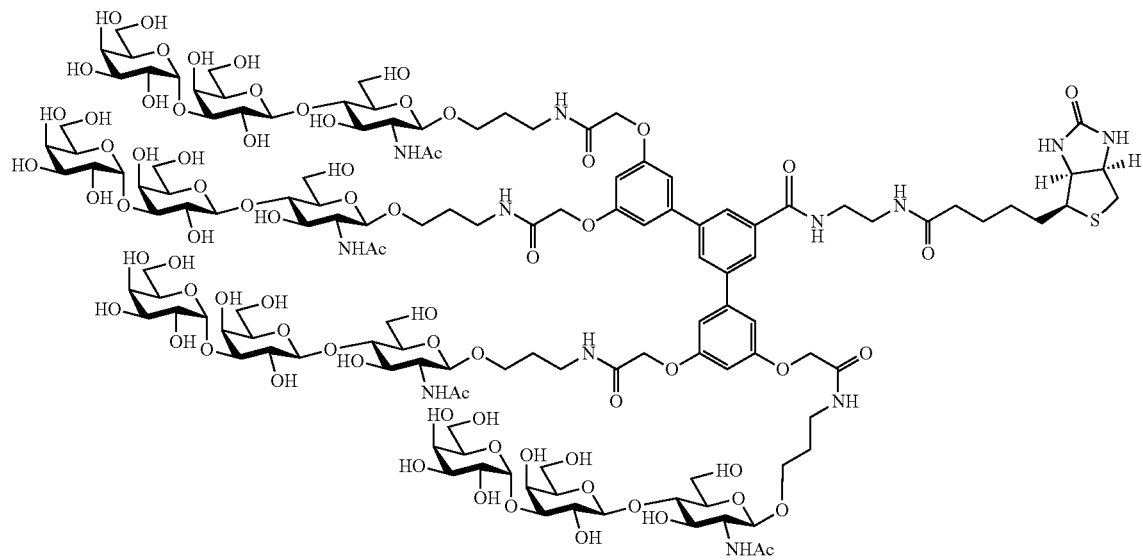

Method: Example 48
Isolated yield: 43%, Purification Method 1
LCMS Method B: Rt=1.48 mins, ES+ MS m/z 1589.6 [M+2H]+/2, theoretical mass: 3177.1
Precursors: Preparation 92 and N-(2-aminoethyl)-5-((3aS, 4S, 6aR)-2-oxohexahydro-1H-thieno[3,4-d]imidazole-4-yl)pentanamide.

Assays
ELISA Assay

Compounds containing F (representing a carbohydrate molecule capable of binding to a human anti-alpha-galactosyl antibody) and L (as biotin) were assayed for binding at both ends of the compound using an enzyme-linked immunosorbent assay (ELISA). Streptavidin-coated plates captured biotin to the surface of the plate and the binding of anti-alpha galactosyl antibodies to the alpha-galactosyl moiety was reported by a secondary antibody labelled with HRP (Horse Radish Peroxidase). The ELISA assay was designed to demonstrate binding of agents to both the F and L component of the compound simultaneously.

Compounds were titrated 1.5 fold from a top dose of 50 nM in phosphate buffered saline (PBS) (Sigma D8537)+ 0.025% DMSO (Dimethyl Sulphoxide, Sigma D8418). Streptavidin immobilizer 96-well plates (nunc 436014) were coated with 100 µL of compound at room temperature for 2 hours shaking at 500 rpm. Plates were washed with 2×200 µL PBS-T (PBS with 0.05% Tween 20 (Sigma P9416)) and 1×200 µL PBS-T with a 5 minute incubation shaking at room temperature, prior to being blocked for 1 hour at room temperature with 1% Bovine Serum Albumin (BSA, Sigma A2153) in PBS-T. After removing the blocking buffer, 50 µL of Anti-alpha galactosyl IgG antibody (Anti-alpha-galactosyl antibody was purified from human IVIG (Gammagard) by affinity purification using an alpha-galactosyl-HSA (Human Serum Albumin) sepharose column by Rockland Immunochemicals Inc.) at 0.5 µg/mL in PBS-T+1% BSA and incubated shaking at room temperature for 1 hour.

Plates were washed 2×200 µL PBS-T and 3×200 µL PBS-T with a 5 minute incubation, shaking at room temperature before the addition of 50 µL 1:5000 Goat Anti-Human IgG-HRP (horseradish peroxidase) conjugate (Abcam ab97175). The plates were incubated shaking at room temperature for 1 hour before a final wash of 2×200 µL PBS-T and 3×200 µl PBS-T with a 5 minute incubation shaking at room temperature. 100 µL TMB buffer (3,3',5, 5'-tetramethylbenzidine, a chromogenic substrate for horseradish peroxidase) (Pierce 34021) was added to the plate and allowed to develop for 5-10 minutes before the samples were quenched with 50 µL 2M sulfuric acid (Sigma 258105). The absorbance was read at 450 nm on an Envision plate reader (Perkin Elmer). Results from wells (duplicate) were averaged and the 50% binding affinity calculated.

Table 1 demonstrates binding activity of Examples using the ELISA described above. The concentration at which half-maximal binding is achieved is reported as a geometric mean with standard error in brackets. The number of independent experiments is also reported. In order to achieve a signal both ends of the molecule are required to bind (biotin to streptavidin and alpha-galactosyl to anti-alpha galactosyl antibodies) simultaneously.

TABLE 1

| Compound | Concentration at half maximal binding (nM) | Number of Tests (n) |
|---|---|---|
| Example 1 | 8.2 (0.2) | n = 2 |
| Example 2 | 21.2 (2.8) | n = 27 |
| Example 3 | 15.0 (2.9) | n = 2 |
| Example 4 | 13.1 (2.2) | n = 2 |
| Example 5 | 9.1 (0.7) | n = 3 |
| Example 6 | 5.8 (0.4) | n = 3 |
| Example 7 | 16.0 (4.4) | n = 2 |
| Example 8 | 28.8 (8.2) | n = 2 |
| Example 9 | 10.1 (1.8) | n = 2 |
| Example 10 | 25.7 (6.1) | n = 2 |
| Example 11 | 19.0 (6.3) | n = 2 |
| Example 12 | 37.3 (10.5) | n = 2 |
| Example 13 | 37.3 (10.8) | n = 2 |
| Example 14 | 11.9 (3.5) | n = 2 |
| Example 15 | 11.5 (1.8) | n = 2 |
| Example 16 | 8.4 (2.8) | n = 2 |
| Example 17 | 17.7 (9.6) | n = 2 |
| Example 18 | 6.7 (0.2) | n = 2 |
| Example 19 | 11.8 (0.6) | n = 3 |
| Example 20 | 14.8 (3.0) | n = 2 |
| Example 21 | 14.8 (5.4) | n = 2 |
| Example 48 | 25.0 (3.5) | n = 2 |
| Example 49 | 26.4 (5.3) | n = 2 |
| Example 50 | 26.1 (4.6) | n = 2 |
| Example 51 | 19.7 (3.7) | n = 2 |
| Example 52 | 34.9 (1.6) | n = 2 |
| Example 53 | 34.9 (1.4) | n = 2 |
| Example 54 | 22.8 (6.8) | n = 2 |
| Example 55 | 27.4 (3.3) | n = 2 |
| Example 56 | 16.3 (2.3) | n = 2 |
| Example 57 | 15.4 (3.2) | n = 2 |
| Example 58 | 37.6 (7.7) | n = 2 |
| Example 59 | 21.3 (6.3) | n = 2 |
| Example 60 | 24.1 (11.1) | n = 2 |
| Example 61 | 29.9 (6.5) | n = 3 |
| Example 62 | 20.7 (5.0) | n = 2 |

Flow Cytometry Assay Using Alpha-Galactosyl IgG Antibody

Flow cytometry was used to demonstrate binding of L (as an EGFR nucleic acid aptamer, RNA aptamer 1, $C_6$-amino-linked-SEQ ID NO:79, PCT/GB2015/051812; herein referred to as SEQ ID NO: 1) to a receptor on a human cell line and F (as the carbohydrate molecule capable of binding to a human anti-alpha-galactosyl antibody). A431 cells are used to capture the EGFR nucleic acid aptamer as it is well known that the cells significantly over-express the EGFR receptor. A secondary phycoerythrin labelled anti-human IgG antibody was used to detect binding of alpha-galactosyl IgG antibody to the compound.

The compounds were used directly in the assay or heated to 70° C. for 10 minutes and cooled to room temperature for 10 minutes prior to use in the assay.

A431 cells (ATCC CRL-1555) were harvested and resuspended at $5\times10^6$ cells/mL in phosphate buffered saline (PBS) (Sigma D8662)+0.1% BSA (Bovine Serum Albumin-Sigma A2153)+0.1 mg/mL Yeast t-RNA (Invitrogen 15401-011)+5 mM $MgCl_2$ (Sigma M1028) and incubated on ice for 30 minutes to block. $5\times10^5$ cells were then incubated with compound at various concentrations as described below or buffer alone at room temperature, shaking at 450 rpm for 1 hour. The cells were washed with 3×200 μL PBS+0.1% BSA, prior to adding 50 μL of Anti-alpha galactosyl IgG antibody (custom purification from human IVIG, Rockland Immunochemicals, Inc.) at 45 μg/mL in PBS+0.1% BSA and incubating at 4° C. for 1 hour. The cells were further washed with 3×200 μL PBS+0.1% BSA before being treated with 100 μL 1:40 dilution of Anti-Human IgG-PE (phycoerythrin) (Biolegend 409303) at 4° C. for 1 hour. After a final wash of 3×200 μL PBS+0.1% BSA the cells were resuspended in 200 μL PBS+0.1% BSA and evaluated on a flow cytometer (FC500 Beckman Coulter). Data from all samples were analysed in the Kaluza software package (Beckman Coulter).

FIG. 1 demonstrates the capture of anti-alpha galactosyl IgG antibodies to the cell surface using Example 22 (FIG. 1A), Example 23 (FIG. 1B) and Example 24 (FIG. 1C). The shift in fluorescence intensity (PE) occurs due to the binding event at each end of the molecule.

Figure 2:
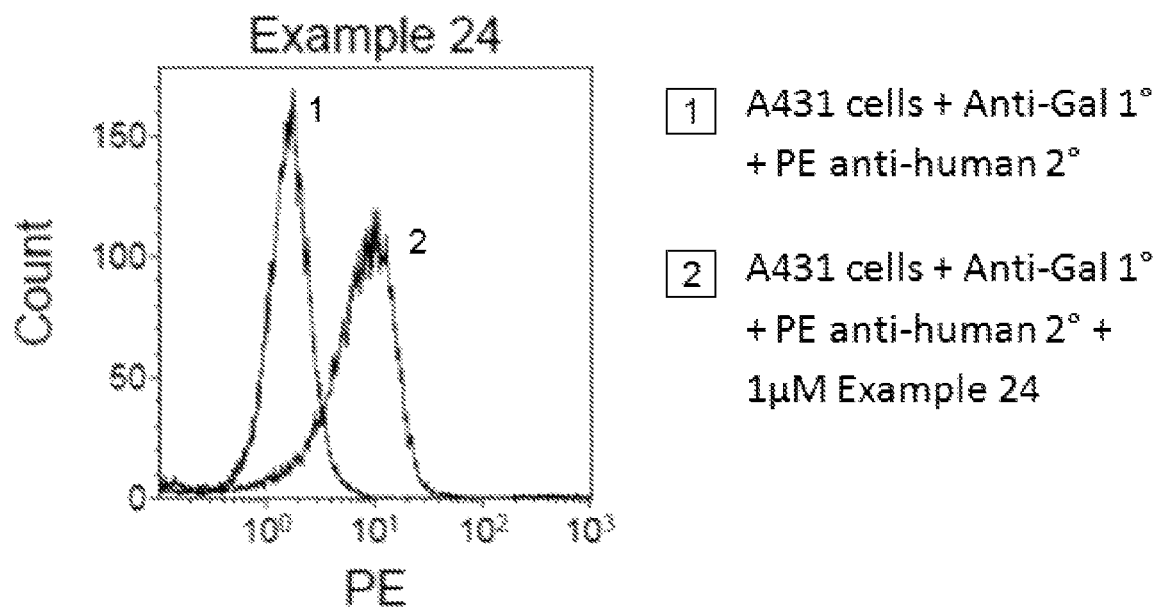
FIG. 2: Dose titration of Examples 22-24 in the Flow Cytometry assay which demonstrate a difference in recruitment of anti-galactosyl antibodies by Examples 22-24 to the human cancer cell line A431.
Figure 2:
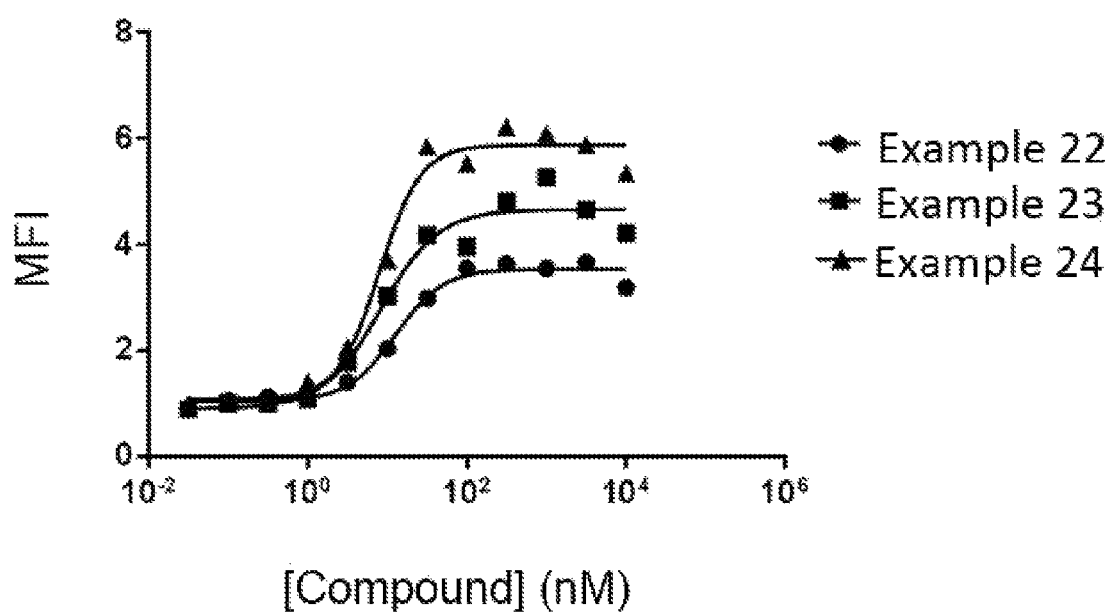

FIG. 2 is a dose titration of Examples 22-24 using the Flow Cytometry assay described. FIG. 2 demonstrates a difference in recruitment of anti-galactosyl antibodies to the human cancer cell line A431 by Examples 22-24. Increasing recruitment is reported by an increase in Mean Fluorescence Intensity (MFI) emanating from the fluorescently labelled secondary antibody.

Table 2 demonstrates binding activity of Examples 26-39 using the flow cytometry assay described above. The fold shift over background was calculated by dividing the Mean Fluorescence Intensity (MFI) obtained in the presence of 10 nM or 1 μM alphamer by the Mean Fluorescence Intensity (MFI) obtained in the absence of alphamer. The fold shift over background is reported as a geometric mean with standard error in brackets. The number of independent experiments is also reported. In order to achieve a signal both ends of the molecule are required to bind (aptamer to EGFR on the cell surface of the A431 cells and alpha-galactosyl to anti-alpha galactosyl antibodies)

TABLE 2

| Compound | Fold Shift in Binding Assay at 10 nM | Fold Shift in Binding Assay at 1 μM | Number of Tests (n) |
|---|---|---|---|
| Example 26 | 1.9 (0.2) | 3.3 (0.4) | n = 2 |
| Example 27 | 2.5 (0.4) | 4.1 (0.5) | n = 2 |
| Example 28 | 4.2 (0.2) | 8.1 (0.5) | n = 2 |
| Example 29 | 3.8 (0.4) | 8.2 (0.7) | n = 2 |
| Example 30 | 5.5 (0.8) | 10.5 (1.8) | n = 2 |
| Example 31 | 5.8 (0.7) | 12.5 (0.9) | n = 2 |
| Example 32 | 5.7 (0.3) | 10.4 (1.1) | n = 2 |
| Example 33 | 5.9 (0.3) | 11.0 (0.6) | n = 2 |
| Example 34 | 4.2 (0.2) | 7.6 (0.1) | n = 3 |
| Example 35 | 6.4 (1.0) | 12.3 (0.8) | n = 2 |
| Example 36 | 7.1 (0.7) | 12.4 (0.6) | n = 2 |
| Example 37 | 6.4 (0.3) | 12.2 (1.3) | n = 2 |
| Example 38 | 7.0 (0.5) | 13.6 (1.0) | n = 2 |
| Example 39 | 6.5 (0.4) | 10.4 (0.8) | n = 3 |

Figure 3:
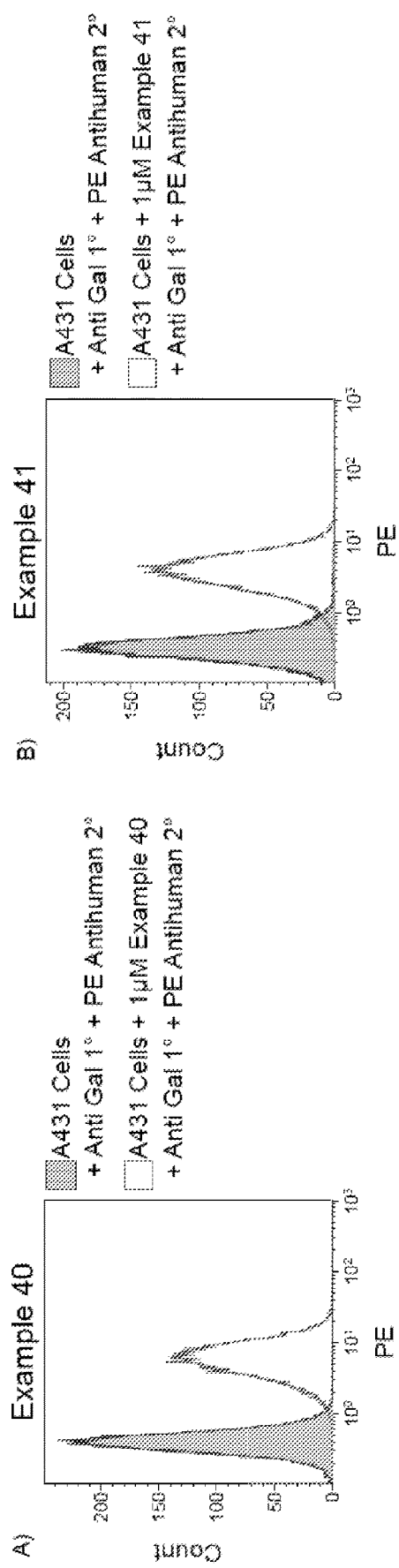
FIG. 3: demonstrates the capture of anti-alpha galactosyl antibodies to the cell surface using Example 40 (FIG. 3A), Example 41 (FIG. 3B), Example 42 (FIG. 3C) and Example 43 (FIG. 3D).

FIG. 3 demonstrates the capture of anti-alpha galactosyl antibodies to the cell surface using Example 40 (FIG. 3A), Example 41 (FIG. 3B), Example 42 (FIG. 3C) and Example 43 (FIG. 3D). The shift in fluorescence intensity (PE) occurs due to the binding event at each end of the molecule.

Figure 4:
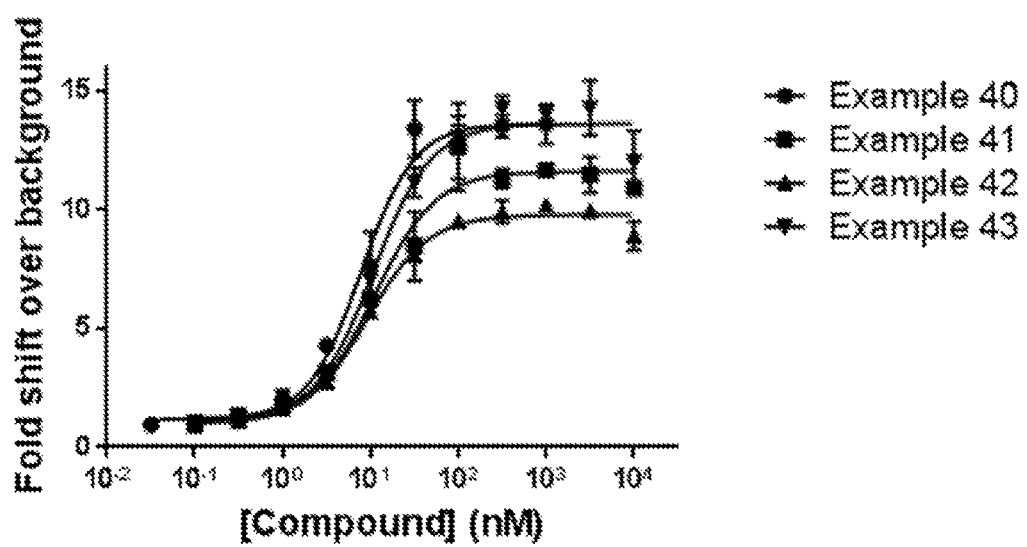
FIG. 4: is a dose titration of Examples 40-43 using the Flow Cytometry assay described.
Figure 5A:
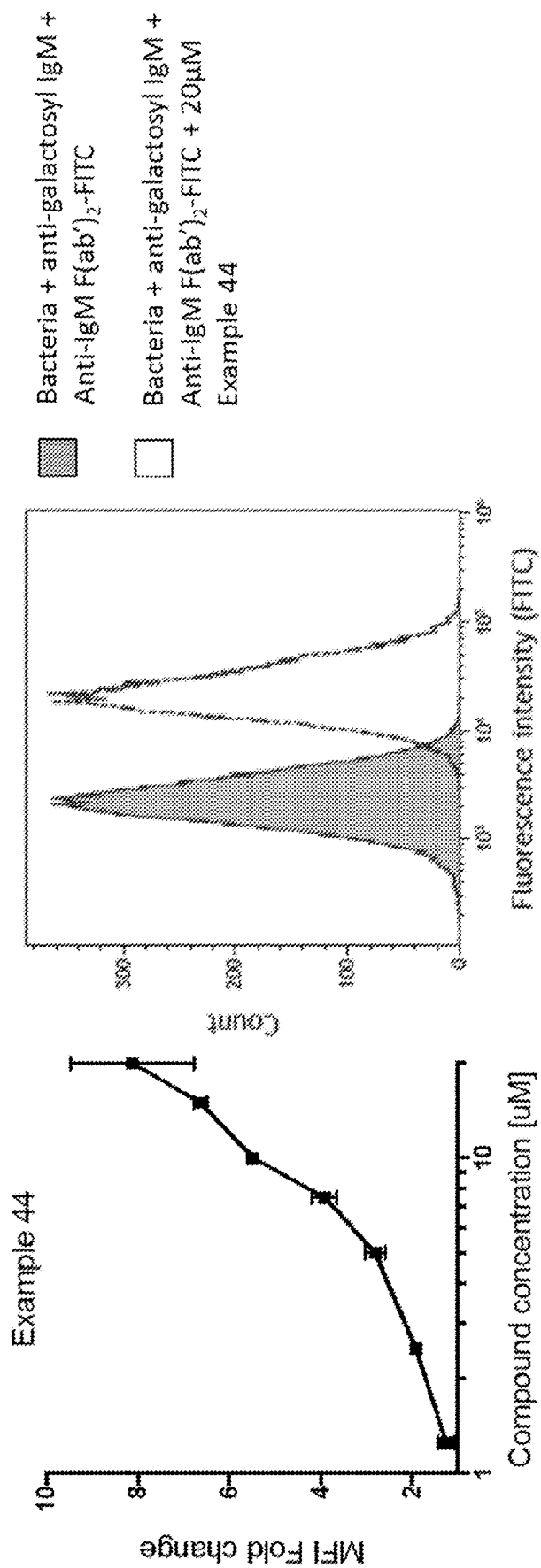
FIG. 5: (left panel) is a dose titration of Examples 44-47 using the Flow Cytometry assay described and demonstrates recruitment of anti-galactosyl antibodies to *S. aureus* of Example 44 (FIG. 5A), Example 45 (FIG. 5B), Examples 46 (FIG. 5C) and Example 47 (FIG. 5D) at concentrations 1.25-20 μM. The right panel of FIG. 5 demonstrates the capture of anti-alpha galactosyl antibodies to the bacteria surface using 20 μM Example 44 (FIG. 5A), Example 45 (FIG. 5B), Example 46 (FIG. 5C) and Example 47 (FIG. 5D).
Figure 5B:
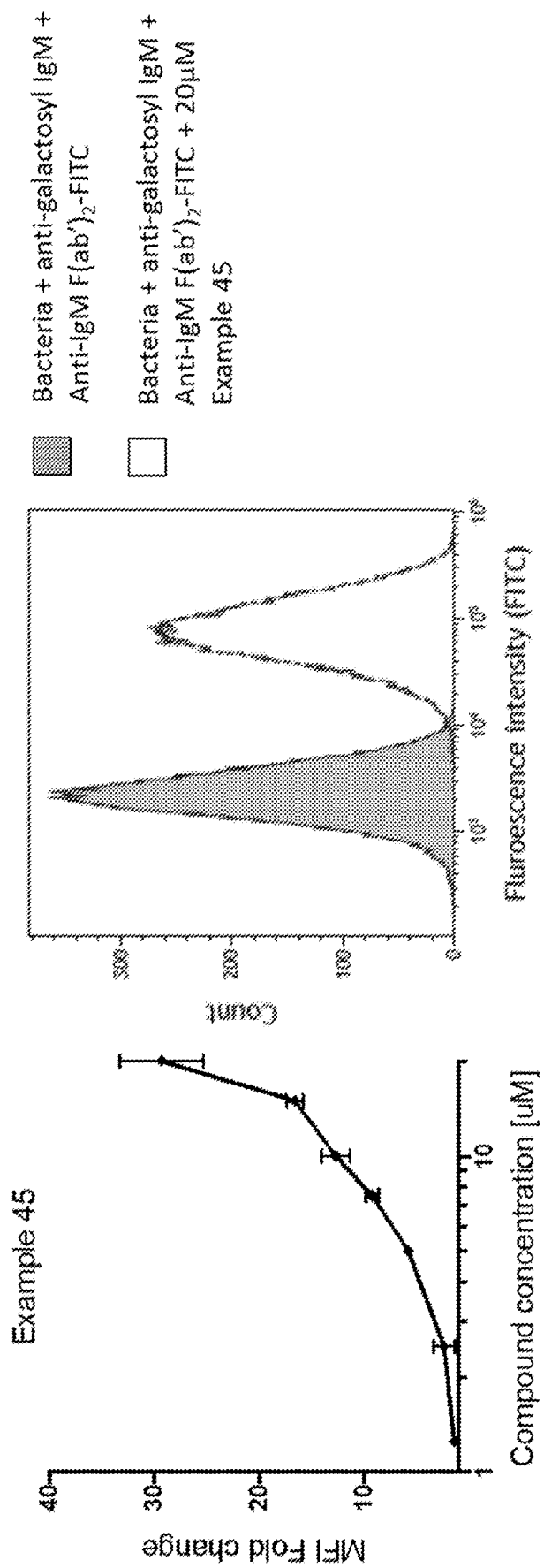
Figure 5C:
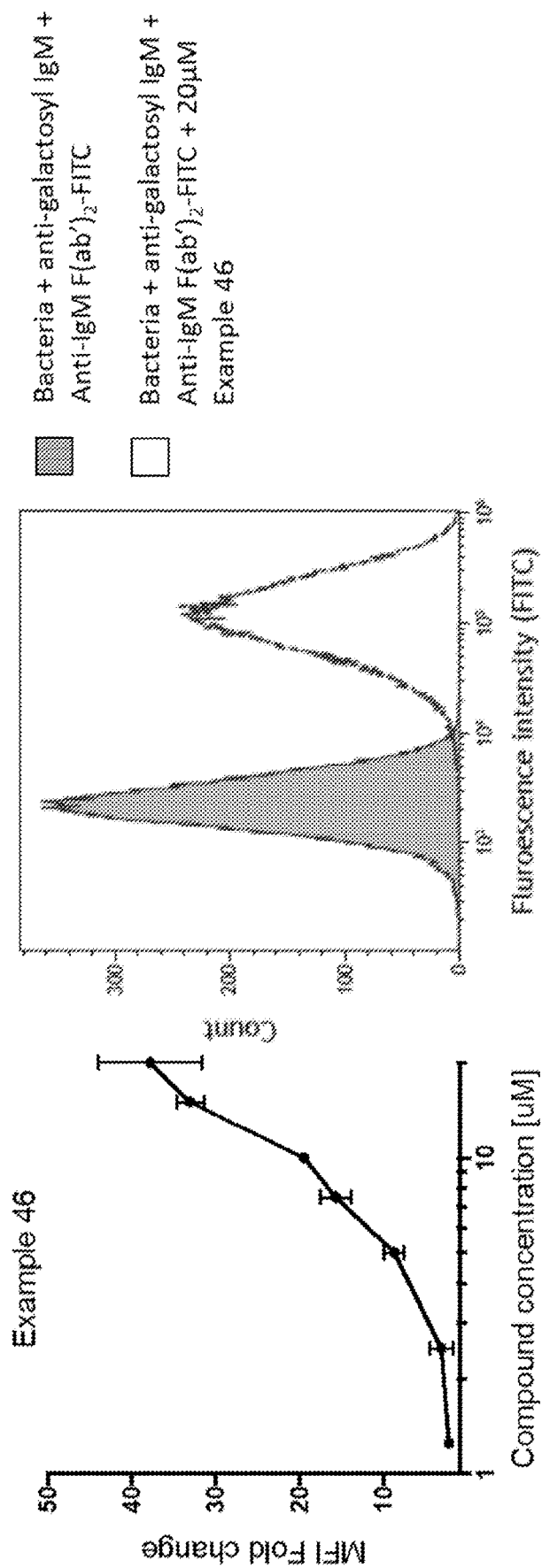
Figure 5D:
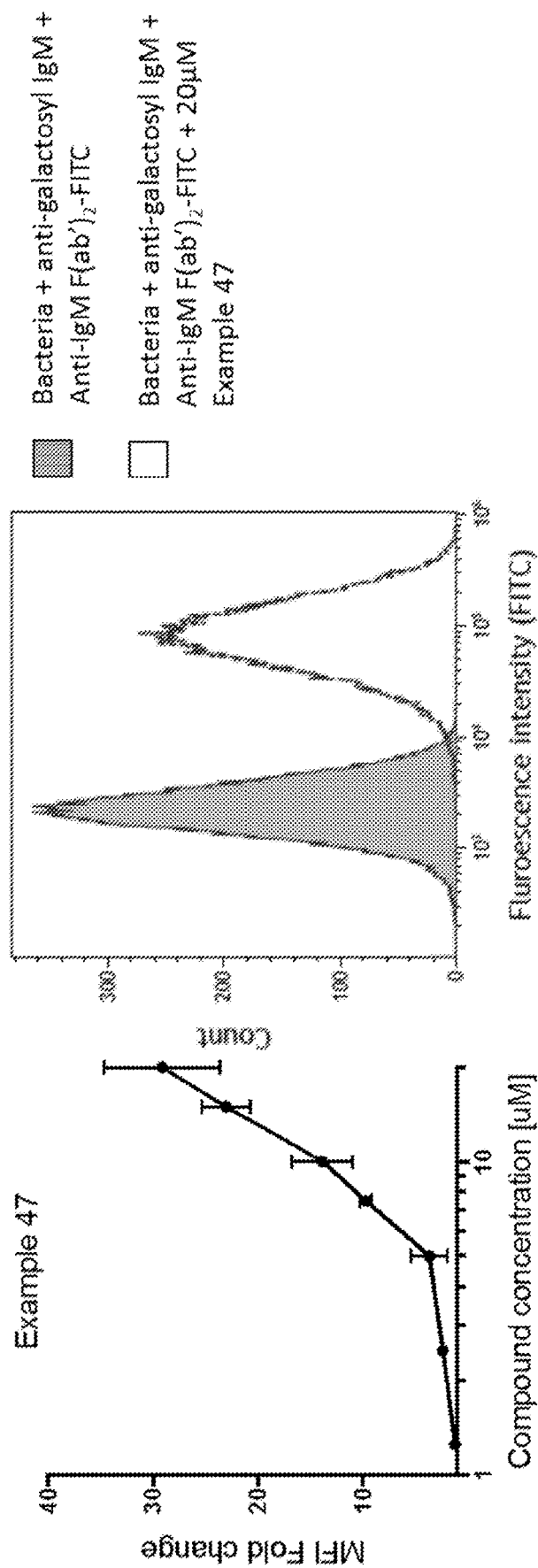

FIG. 4 is a dose titration of Examples 40-43 using the Flow Cytometry assay described. FIG. 4 demonstrates a difference in recruitment of anti-galactosyl antibodies to the human cancer cell line A431 by Examples 40-43. Increasing recruitment is reported by an increase in fold shift over background.

Flow Cytometry Assay Using Anti-Human IgM-F(Ab')$_2$ Fragment Antibody

Flow cytometry was used to demonstrate binding of L (as a protein A nucleic acid aptamer, RNA aptamer 2, $C_6$-amino-linked-SEQ-IDfmA12Δ9, Biomaterials 36 (2016) 110-123; herein referred to as SEQ ID NO: 3) to protein A on *S. aureus* and F (as the carbohydrate molecule capable of binding to a human anti-alpha-galactosyl antibody). Protein A is a surface protein in the cell wall of *S. aureus*. A secondary FITC labelled anti-human IgM-F(ab')₂ fragment antibody was used to detect binding of alpha-galactosyl to the compound.

The compounds were dissolved in nuclease-free dH₂O and used directly in the assay or heated to 70° C. for 10 minutes and cooled to room temperature for 10 minutes prior to use in the assay.

The assays were carried out in polystyrene 96-well U bottom plates (Costar). The 96-well plates were pre-blocked with casein blocking buffer (Thermo Fisher 37528) and then washed three times with (HBSS+/+) (Life Technologies 14025-050) prior to assay. *S. aureus* Newman strain bacteria (Public Health England, NCTC 10833) were grown in LB broth (Fisher BP1426-500) to late exponential phase. Subsequently, the bacteria were centrifuged at 10 000 rpm for 5 minutes and resuspended HBSS+/+ at a bacterial density of 2*10⁹ CFU/mL. Celltrace Far Red Cell staining kit (Thermo Fisher C34564) was added to the bacteria to a final concentration of 1 µM and incubated at room temperature in the dark for 20 minutes. PBS (Sigma D8662)+1% BSA (Sigma A2153) was added to the bacteria (5 times the volume of the original bacteria suspension) and was incubated for 10 minutes at room temperature in the dark. Bacteria were centrifuged (10 000 rpm, 5 minutes) and resuspended in HBSS+/+ at a concentration of 2*10⁹ CFU/mL. 1×10⁸ CFU were then incubated with various concentrations (FIG. 5) of Examples 44-47 or buffer alone, at room temperature, shaking at 450 rpm for 1 hour. The bacteria were washed with 3×200 µL HBSS+/+ (centrifuged at 4000 rpm, 5 minutes), prior to adding 100 µL of Anti-alpha galactosyl human IgM M86 antibody (custom made by Absolute Antibody) at 50 µg/mL in HBSS+/+. The plate was incubated at room temperature for 1 hour. The bacteria were washed with 3×200 µL HBSS+/+(centrifuged for 4000 rpm, 5 minutes), prior to adding 100 µL of Anti-human IgM F(ab')₂-FITC fragment antibody (Jackson ImmunoResearch 109-096-127) at 15 µg/mL in HBSS+/+ and incubated at room temperature for 1 hour. After a final wash of 3×200 µL HBSS+/+ the bacteria were resuspended in 200 µL HBSS+/+ and evaluated on a flow cytometer (FC500 Beckman Coulter). Data from all samples were analysed in the Kaluza software package (Beckman Coulter). Samples were run in triplicates and experiment was repeated twice.

FIG. 5 is a dose titration of Examples 44-47 using the Flow Cytometry assay described and demonstrates recruitment of anti-galactosyl antibodies to *S. aureus* of Example 44 (FIG. 5A), Example 45 (FIG. 5B), Examples 46 (FIG. 5C) and Example 47 (FIG. 5D) at concentrations 1.25-20 µM. Increasing recruitment of anti-galactosyl antibodies is reported by an increase in MFI emanating from the fluorescently labelled secondary antibody. The fold shift over background was calculated by dividing the MFI obtained in the presence of compound by the MFI obtained in the absence of compound, and is reported with standard error in brackets. FIG. 5 (right panel) demonstrates the capture of anti-alpha galactosyl antibodies to the bacteria surface using 20 µM Example 44 (FIG. 5A), Example 45 (FIG. 5B), Example 46 (FIG. 5C) and Example 47 (FIG. 5D). The shift in fluorescence intensity (FITC) occurs due to the binding event at each end of the molecule.

The binding of L (as GAS nucleic acid aptamer, C6-amino-linked-20A24P, J. Mol. Med (2015) 93, 619-631; herein referred to as SEQ ID NO: 2) to a receptor on Group A *Streptococcus* (GAS) bacteria and F (as the carbohydrate molecule capable of binding to a human anti-alpha-galactosyl antibody) as exemplified by Example 25 may be inferred as described by Kristian et al (supra).

Flow Cytometry Assay Using Alpha-Galactosyl IgM Antibody

Flow cytometry was used to demonstrate binding of L (as an EGFR nucleic acid aptamer, RNA aptamer 1, C₆-amino-linked-SEQ ID NO:79, PCT/GB2015/051812; herein referred to as SEQ ID NO: 1) to a receptor on a human cell line and F (as the carbohydrate molecule capable of binding to a human anti-alpha-galactosyl antibody). A431 cells are used to capture the EGFR nucleic acid aptamer as it is well known that the cells significantly over-express the EGFR receptor. A secondary FITC (fluorescein) labelled anti-human IgM antibody was used to detect binding of the alpha-galactosyl IgM antibody to the compound.

The compounds were heated to 70° C. for 10 minutes and cooled to room temperature for 10 minutes prior to use in the assay.

A431 cells (ATCC CRL-1555) were harvested and resuspended at 5×10⁶ cells/mL in phosphate buffered saline (PBS) (Sigma D8662)+0.1% BSA (Bovine Serum Albumin-Sigma A2153)+0.1 mg/mL Yeast t-RNA (Invitrogen 15401-011)+5 mM MgCl₂ (Sigma M1028) and incubated on ice for 30 minutes to block. 5×10⁵ cells were then incubated with compound at 3 µM as described below or buffer alone at room temperature, shaking at 450 rpm for 1 hour.

The cells were washed with 3×200 µL PBS+0.1% BSA, prior to adding 50 µL of an Anti-alpha galactosyl IgM antibody at 32 µg/mL in PBS+0.1% BSA and incubating at 4° C. for 1 hour. The Anti-alpha galactosyl IgM antibody is a custom engineered Human IgM Antibody which uses an M86 anti-alpha galactosyl antibody obtained from Absolute Antibody and has the following variable region amino acid sequences:

```
VH:
                                   (SEQ ID NO: 8)
EVKLDETGGGLVQPGRSMKLSCVASGFIFSDYWMNWVRQSP

EKGLEWIAQIRTNPYNYETYYSDSVKGRFTISRDDSKSSVYLQ

MKNLRSEDMGIYYCTWSHYALDNWGQGTSVTVSS;

VL:
                                   (SEQ ID NO: 9)
DVLVTQNPLSLSVSLGDQASISCRSSQNLVHNDGNTYLHWYL

QKPGQSPKLLIHRISNRFSGVPDRFSGSGSGTDFTLKISRVEAED

LGVYFCSQSTHIPWTFGGGTKLEIK.
```

The cells were further washed with 3×200 µL PBS+0.1% BSA before being treated with 100 µL 1:40 dilution of Anti-Human IgM-FITC (Biolegend 314506) at 4° C. for 1 hour. After a final wash of 3×200 µL PBS+0.1% BSA the cells were resuspended in 200 µL PBS+0.1% BSA and evaluated on a flow cytometer (FC500 Beckman Coulter). Data from all samples were analysed in the Kaluza software package (Beckman Coulter).

Figure 6:
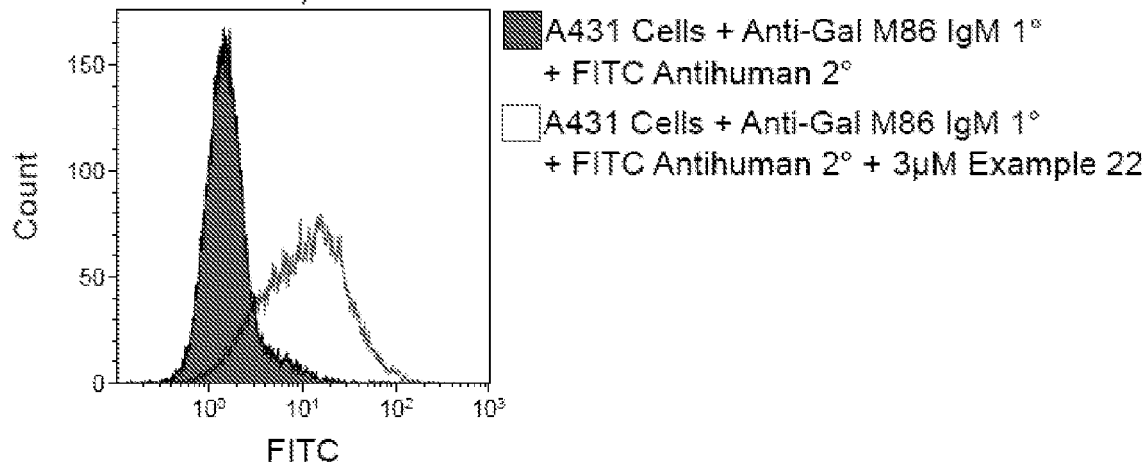
FIG. 6: Flow cytometry assay results which demonstrate the capture of anti-alpha galactosyl IgM antibodies to the cell surface using Example 22 (FIG. 6A), Example 23 (FIG. 6B) and Example 24 (FIG. 6C).
Figure 6:
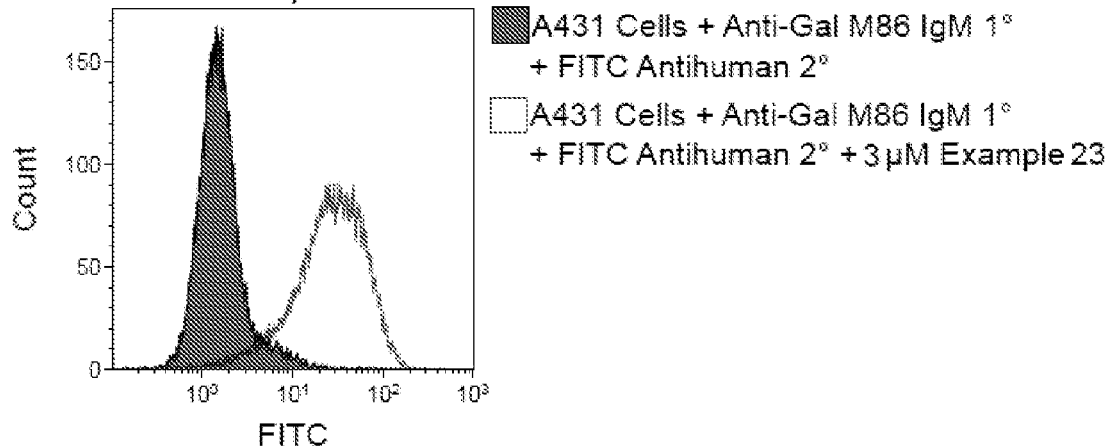

FIG. 6 demonstrates the capture of anti-alpha galactosyl IgM antibodies to the cell surface using Example 22 (FIG. 6A), Example 23 (FIG. 6B) and Example 24 (FIG. 6C). The shift in fluorescence intensity (FITC) occurs due to the binding event at each end of the molecule.

The invention claimed is:
1. A compound of formula (I) or a pharmaceutically acceptable salt thereof:

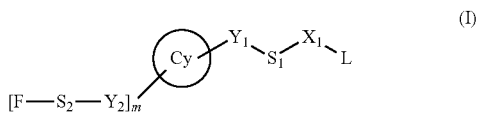

wherein:
- L represents a binding moiety selected from a nucleic acid aptamer or biotin;
- $S_1$ represents a spacer selected from a —$(CH_2)_a$— or —$(CH_2)_b$—$(CH_2$—$CH_2$—$O)_c$—$(CH_2)_d$— group, wherein one to five of said —$CH_2$— groups may optionally be substituted by one or more groups selected from —O—, —C(O)NH—, —NHC(O)— and phenyl;
- a represents an integer selected from 1 to 35;
- b represents an integer selected from 0 to 5;
- c represents an integer selected from 1 to 15;
- d represents an integer selected from 1 to 15;
- $S_2$ represents a spacer selected from a —$(CH_2)_e$— or —$(CH_2)_f$—$(CH_2$—$CH_2$—$O)_g$—$(CH_2)_h$— group, wherein one to three of said —$CH_2$— groups may optionally be substituted by one or more groups selected from —N(H)—, —C(O)NH— and —NHC(O)—;
- e represents an integer selected from 1 to 10;
- f represents an integer selected from 1 to 10;
- g represents an integer selected from 1 to 15;
- h represents an integer selected from 1 to 5;
- $X_1$ represents —O— or —NH—, such that when L represents a nucleic acid aptamer, $X_1$ represents —O— and when L represents biotin, $X_1$ represents —NH—;
- $Y_1$ represents a bond, —C(O)NH— or —O—;
- $Y_2$ represents a bond, —O— or —NHC(O)—;
- F represents a structure as shown in the following formulae:

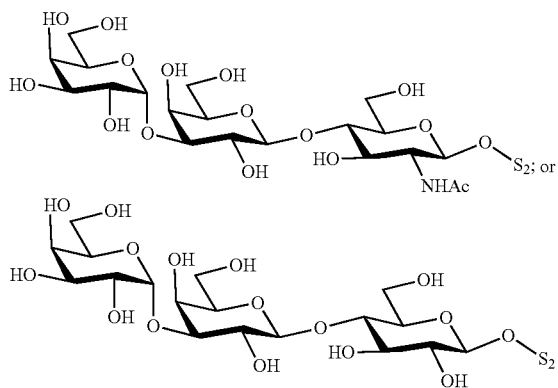

wherein $S_2$ refers to the point of attachment to the $S_2$ group;
- m represents an integer selected from 1 to 4; and
- Cy represents phenyl, biphenyl, triphenyl or quinolinyl, such that when Cy represents biphenyl or triphenyl, said —$Y_1$—$S_1$—$X_1$-L group may be present on any of said phenyl rings and said [F—$S_2$—$Y_2$]$_m$— group or groups may be present on any of said phenyl rings.

2. The compound as defined in claim 1 or a pharmaceutically acceptable salt thereof, wherein $S_1$ represents a spacer selected from:
- —$(CH_2)_a$—, wherein one to four of said —$CH_2$— groups are optionally substituted by one or more groups selected from —C(O)NH— and —NHC(O)— (such as —$(CH_2)_2$—, —$CH_2$—CONH—$(CH_2)_2$—, —$CH_2$—NHCO—$(CH_2)_4$—CONH—$(CH_2)_2$—, —$(CH_2)_6$—, —$(CH_2)_5$—CONH—$(CH_2)_5$—CONH—$(CH_2)_6$— or —$(CH_2)_5$—CONH—$(CH_2)_5$—CONH—$(CH_2)_5$—CONH—$(CH_2)_5$—CONH— $(CH_2)_6$—); or
- —$(CH_2)_b$—$(CH_2$—$CH_2$—$O)_c$—$(CH_2)_d$—, wherein one to five of said —$CH_2$— groups are optionally substituted by one or more groups selected from —O—, —C(O)NH—, —NHC(O)— and phenyl (such as —$(CH_2)_2$—NHCO—$(CH_2CH_2O)_{12}$—$(CH_2)_2$—, —$(CH_2)_2$—NHCO—$(CH_2CH_2O)_4$—$(CH_2)_2$—NHCO—$CH_2$—O-phenyl-CONH—$(CH_2)_6$—, —$(CH_2)_2$—NHCO—$(CH_2CH_2O)_{12}$—$(CH_2)_2$—NHCO—$CH_2$—O-phenyl-CONH—$(CH_2)_6$— or —$(CH_2CH_2O)_4$—$(CH_2)_2$—CONH—$(CH_2)_2$—);

or $S_1$ represents a spacer selected from:
- —$(CH_2)_a$—, wherein two or four of said —$CH_2$— groups are optionally substituted by —C(O)NH— (such as —$(CH_2)_6$—, —$(CH_2)_5$—CONH—$(CH_2)_5$—CONH—$(CH_2)_6$— or —$(CH_2)_5$—CONH—$(CH_2)_5$—CONH—$(CH_2)_5$—CONH—$(CH_2)_5$—CONH—$(CH_2)_6$—); or
- —$(CH_2)_b$—$(CH_2$—$CH_2$—$O)_c$—$(CH_2)_d$—, wherein five of said —$CH_2$— groups are optionally substituted by one or more groups selected from —O—, —C(O)NH—, —NHC(O)— and phenyl (such as —$(CH_2)_2$—NHCO—$(CH_2CH_2O)_4$—$(CH_2)_2$—NHCO—$CH_2$—O-phenyl-CONH—$(CH_2)_6$— or —$(CH_2)_2$—NHCO—$(CH_2CH_2O)_{12}$—$(CH_2)_2$—NHCO—$CH_2$—O-phenyl-CONH—$(CH_2)_6$—).

3. The compound as defined in claim 1 a pharmaceutically acceptable salt thereof, wherein a represents an integer selected from: 1 to 30; or 2 to 30; or 2, 4, 6, 9, 18 or 30; or 6, 18 or 30.

4. The compound as defined in claim 1 or a pharmaceutically acceptable salt thereof, wherein b represents an integer selected from: 0 to 3; or 0 or 3; or 3.

5. The compound as defined in claim 1 or a pharmaceutically acceptable salt thereof, wherein c represents an integer selected from: 1 to 12; or 4 to 12; or 4 or 12; or 12.

6. The compound as defined in claim 1 or a pharmaceutically acceptable salt thereof, wherein d represents an integer selected from: 2 to 13; or 2, 5 or 13; or 13.

7. The compound as defined in claim 1 or a pharmaceutically acceptable salt thereof, wherein $Y_1$ represents —C(O)NH—.

8. The compound as defined in claim 1 or a pharmaceutically acceptable salt thereof, wherein $S_2$ represents a spacer selected from:
- —$(CH_2)_e$—, wherein one or two of said —$CH_2$— groups are optionally substituted by one or two groups selected from —N(H)—, —C(O)NH— and —NHC(O)— (such as —$(CH_2)_3$—NHCO—$CH_2$—, —$(CH_2)_3$—, —$(CH_2)_3$—NHCO—$(CH_2)_4$—CONH—$CH_2$—, —(CH$_2$)$_3$—NH—CH$_2$— or —(CH$_2$)$_3$—NHCO—(CH$_2$)$_3$—NHCO—CH$_2$—); or —(CH$_2$)$_f$—(CH$_2$—CH$_2$—O)$_g$—(CH$_2$)$_h$—, wherein one to three of said —CH$_2$— groups are optionally substituted by one to three —NHC(O)— groups (such as —(CH$_2$)$_3$—NHCO—(CH$_2$CH$_2$O)$_4$—(CH$_2$)$_2$—NHCO—CH$_2$—, —(CH$_2$)$_3$—NHCO—(CH$_2$CH$_2$O)$_{12}$—(CH$_2$)$_2$—NHCO—CH$_2$— or —(CH$_2$)$_3$—NHCO—(CH$_2$)$_3$—NHCO—(CH$_2$CH$_2$O)$_4$—(CH$_2$)$_2$—NHCO—CH$_2$—);

or S$_2$ represents a spacer selected from:

—(CH$_2$)$_e$—, wherein one or two of said —CH$_2$— groups are optionally substituted by one or two —NHC(O)— groups (such as —(CH$_2$)$_3$—NHCO—CH$_2$— or —(CH$_2$)$_3$—NHCO—(CH$_2$)$_3$—NHCO—CH$_2$—); or —(CH$_2$)$_f$—(CH$_2$—CH$_2$—O)$_g$—(CH$_2$)$_h$—, wherein one to three of said —CH$_2$— groups are optionally substituted by one to three —NHC(O)— groups (such as —(CH$_2$)$_3$—NHCO—(CH$_2$CH$_2$O)$_4$—(CH$_2$)$_2$—NHCO—CH$_2$—, —(CH$_2$)$_3$—NHCO—(CH$_2$CH$_2$O)$_{12}$—(CH$_2$)$_2$—NHCO—CH$_2$— or —(CH$_2$)$_3$—NHCO—(CH$_2$)$_3$—NHCO—(CH$_2$CH$_2$O)$_4$—(CH$_2$)$_2$—NHCO—CH$_2$—).

9. The compound as defined in claim 1 or a pharmaceutically acceptable salt thereof, wherein e represents an integer selected from: 3 to 10; or 3, 5, 9 or 10; or 5 or 9.

10. The compound as defined in claim 1 or a pharmaceutically acceptable salt thereof, wherein f represents an integer selected from: 1 to 8; or 2 to 8; or 4 to 8; or 4 or 8.

11. The compound as defined in claim 1 or a pharmaceutically acceptable salt thereof, wherein g represents an integer selected from: 4 to 12; or 4 or 12; or 4.

12. The compound as defined in claim 1 or a pharmaceutically acceptable salt thereof, wherein h represents an integer selected from: 1 to 4; or 4.

13. The compound as defined in claim 1 or a pharmaceutically acceptable salt thereof, wherein: Y$_2$ represents a bond or —O—; or Y$_2$ represents —O—.

14. The compound as defined in claim 1 or a pharmaceutically acceptable salt thereof, wherein m represents an integer selected from: 3 or 4; or 1 to 3; or 2 or 3; or 1 or 2; or 1.

15. The compound as defined in claim 1 or a pharmaceutically acceptable salt thereof, wherein Cy represents phenyl, biphenyl or triphenyl.

16. A compound of formula (I) as defined in claim 1 which is a compound of formula (I)$^b$ or a pharmaceutically acceptable salt thereof:

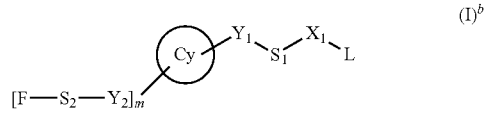

(I)$^b$ wherein:

L represents a binding moiety selected from a nucleic acid aptamer or biotin;

S$_1$ represents a spacer selected from a —(CH$_2$)$_a$— or —(CH$_2$)$_b$—(CH$_2$—CH$_2$—O)$_c$—(CH$_2$)$_d$— group, wherein one to five of said —CH$_2$— groups may optionally be substituted by one or more groups selected from —O—, —C(O)NH—, —NHC(O)— and phenyl;

a represents an integer selected from 2 to 30;
b represents an integer selected from 0 to 3;
c represents an integer selected from 4 to 12;
d represents an integer selected from 2 to 13;
S$_2$ represents a spacer selected from a —(CH$_2$)$_e$— or —(CH$_2$)$_f$—(CH$_2$—CH$_2$—O)$_g$—(CH$_2$)$_h$—group, wherein one to three of said —CH$_2$— groups may optionally be substituted by one or more groups selected from —N(H)—, —C(O)NH— and —NHC(O)—;
e represents an integer selected from 3 to 10;
f represents an integer selected from 4 to 8;
g represents an integer selected from 4 to 12;
h represents an integer selected from 1 to 4;
X$_1$ represents —O— or —NH—, such that when L represents a nucleic acid aptamer, X$_1$ represents —O— and when L represents biotin, X$_1$ represents —NH—;
Y$_1$ represents a bond, —C(O)NH— or —O—;
Y$_2$ represents a bond, —O— or —NHC(O)—;
F represents a structure as shown in the following formulae:

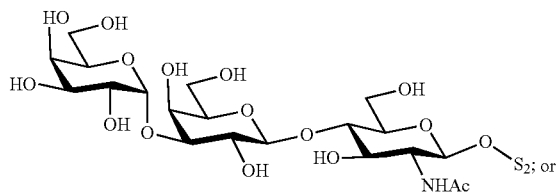

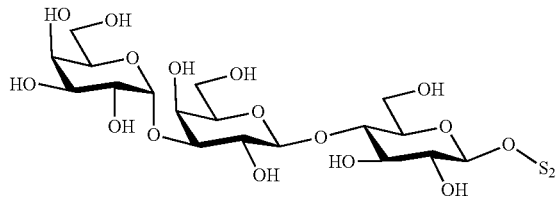

wherein S$_2$ refers to the point of attachment to the S$_2$;
m represents an integer selected from 1 to 4; and
Cy represents phenyl, biphenyl, triphenyl or quinolinyl, such that when Cy represents biphenyl or triphenyl, said —Y$_1$—S$_1$—X$_1$-L group may be present on any of said phenyl rings and said [F—S$_2$—Y$_2$]$_m$— group or groups may be present on any of said phenyl rings.

17. The compound as defined in claim 1 or a pharmaceutically acceptable salt thereof, which is selected from any one of Examples 1-62.

18. The compound as defined in claim 1 or a pharmaceutically acceptable salt thereof, wherein L represents a therapeutic target binding moiety selected from a nucleic acid aptamer.

19. The compound as defined in claim 14, wherein the nucleic acid aptamer is: an EGFR nucleic acid aptamer; or the nucleic acid aptamer of SEQ ID NO: 1 and the compound is selected from any one of Examples 22-24 and 26-43.

20. The compound as defined in claim 18, wherein the nucleic acid aptamer is: a group A *Streptococcus* (GAS) nucleic acid aptamer; or the nucleic acid aptamer of SEQ ID NO: 2 and the compound is selected from Example 25.

21. The compound as defined in claim 18, wherein the nucleic acid aptamer is: a nucleic acid aptamer configured to bind to *Staphylococcus aureus* bacteria, such as protein A (SpA); or the nucleic acid aptamer of SEQ ID NO: 3 and the compound is selected from any one of Examples 44-47.

22. A pharmaceutical composition comprising a compound as defined in claim 18 or a pharmaceutically acceptable salt thereof.

23. A process for preparing a compound of formula (I) as defined in claim 1 which comprises:

(a) preparing a compound of formula (I) wherein $Y_1$ represents —CONH— (i.e. a compound of formula (IA)) by reacting a compound of formula (II) with a compound of formula (III):

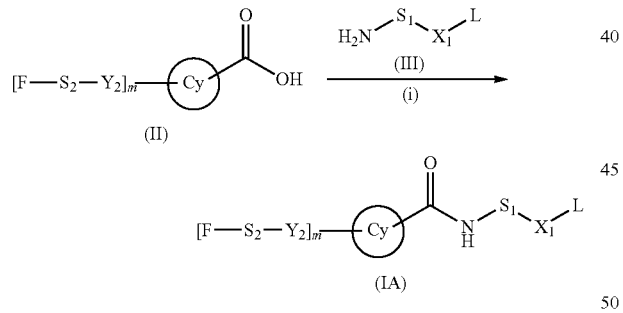

wherein $S_2$, $Y_2$, m, Cy, $S_1$, $X_1$, L and F are as defined in claim 1; or (b) preparing a compound of formula (I) wherein $S_2$ represents —(CH$_2$)$_3$—NHCO—CH$_2$— and $Y_2$ represents —O— (i.e. a compound of formula (IB)) by reacting a compound of formula (IV) with a compound of formula (V):

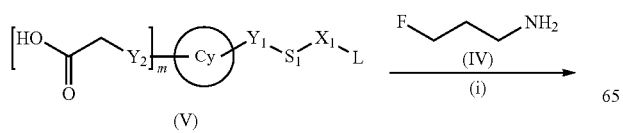

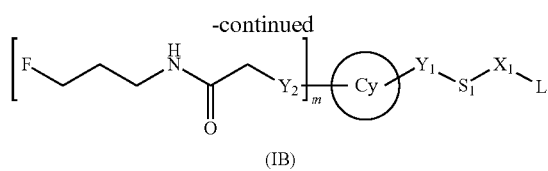

wherein $Y_2$, m, Cy, $Y_1$, $S_1$, $X_1$, L and F are as defined in claim 1; or (c) preparing a compound of formula (I) wherein $S_2$ represents —(CH$_2$)$_3$—NHCO—(CH$_2$)$_2$—(OCH$_2$CH$_2$)$_4$—NHCO—CH$_2$— and $Y_2$ represents —O— (i.e. a compound of formula (IC)) by reacting a compound of formula (IV) with a compound of formula (VI):

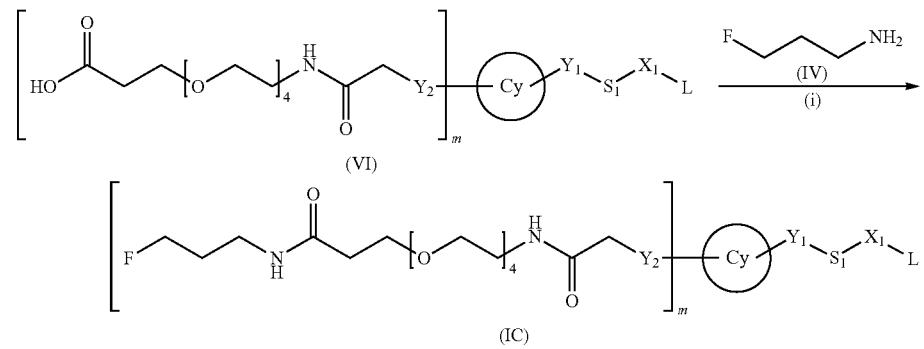

wherein $Y_2$, m, Cy, $Y_1$, $S_1$, $X_1$, L and F are as defined in claim 1; or (d) preparing a compound of formula (I) wherein $S_2$ represents —(CH$_2$)$_3$—NH—CH$_2$— and $Y_2$ represents a bond (i.e. a compound of formula (ID)) by reacting a compound of formula (IV) with a compound of formula (VII):

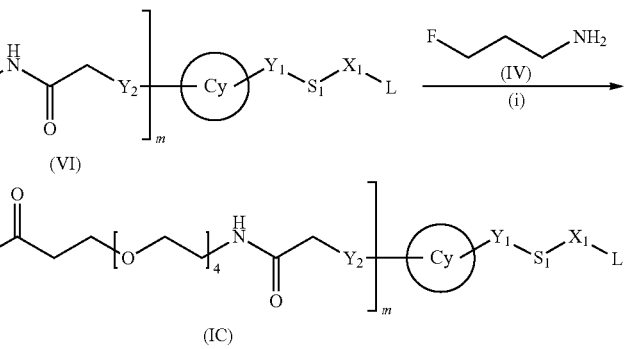

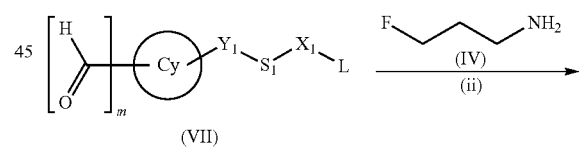

wherein m, Cy, $Y_1$, $S_1$, $X_1$, L and F are as defined in claim 1; or (e) preparing a compound of formula (I) wherein $S_2$ represents —(CH$_2$)$_3$—NHCO—(CH$_2$)$_4$—CONH—CH$_2$— and $Y_2$ represents a bond (i.e. a compound of formula (IE)) by reacting a compound of formula (IV) with a compound of formula (VIII):

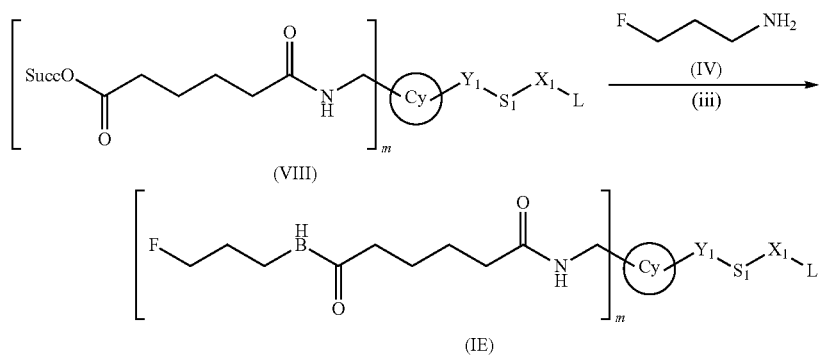

wherein m, Cy, $Y_1$, $S_1$, $X_1$, L and F are as defined in claim 1 and Succ represents succinimide; or (f) preparing a compound of formula (I) wherein $S_2$ represents —$(CH_2)_3$—NHCO— and $Y_2$ represents a bond (i.e. a compound of formula (IF)) by reacting a compound of formula (IV) with a compound of formula (IX):

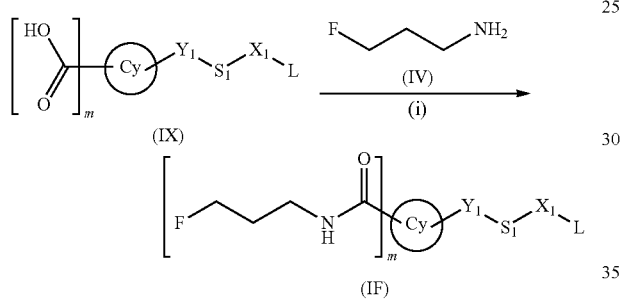

wherein m, Cy, $Y_1$, $S_1$, $X_1$, L and F are as defined in claim 1; or (g) preparing a compound of formula (I) wherein $Y_1$ represents —CONH— and $S_1$ contains a —CONH— group (i.e. a compound of formula (IG)) by reacting a compound of formula (IIA) with a compound of formula (III):

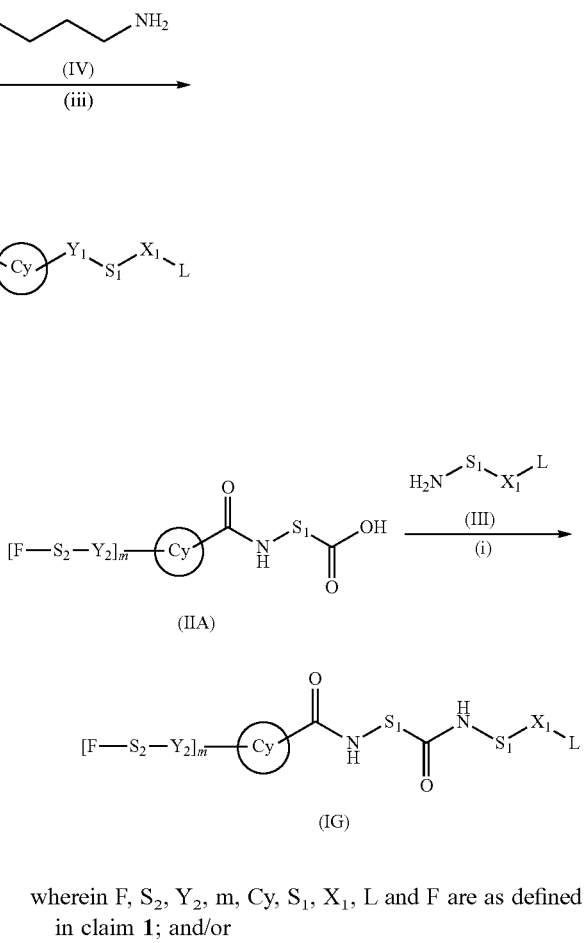

wherein F, $S_2$, $Y_2$, m, Cy, $S_1$, $X_1$, L and F are as defined in claim 1; and/or (h) deprotection of a protected derivative of a compound of formula (I); and/or (i) interconversion of a compound of formula (I) or protected derivative thereof to a further compound of formula (I) or protected derivative thereof.

* * * * *

SEQUENCE LISTING

<160> NUMBER OF SEQ ID NOS: 9

<210> SEQ ID NO 1
<211> LENGTH: 42
<212> TYPE: RNA
<213> ORGANISM: Artificial
<220> FEATURE:
<223> OTHER INFORMATION: Synthetic Aptamer

<400> SEQUENCE: 1
gggauuuaau cgccguagaa aagcauguca aagccggaac cc            42

<210> SEQ ID NO 2
<211> LENGTH: 80
<212> TYPE: DNA
<213> ORGANISM: Artificial
<220> FEATURE:
<223> OTHER INFORMATION: Synthetic Aptamer

<400> SEQUENCE: 2
agcagcacag aggtcagatg gggggaagac acagagaaag gccggggtga agtgtagagg    60
cctatgcgtg ctaccgtgaa                                              80

<210> SEQ ID NO 3
<211> LENGTH: 61
<212> TYPE: RNA
<213> ORGANISM: Artificial
<220> FEATURE:
<223> OTHER INFORMATION: Synthetic Aptamer

<400> SEQUENCE: 3
uguguaauuc ugccauucuu uuuggggcgg aauacaggau gugagugcau ugcaucacgu    60
c                                                                  61

<210> SEQ ID NO 4
<211> LENGTH: 48
<212> TYPE: RNA
<213> ORGANISM: Artificial
<220> FEATURE:
<223> OTHER INFORMATION: Synthetic Aptamer

<400> SEQUENCE: 4
ggacggauuu aaucgccgua gaaaagcaug ucaaagccgg aaccgucc               48

<210> SEQ ID NO 5
<211> LENGTH: 42
<212> TYPE: RNA
<213> ORGANISM: Artificial
<220> FEATURE:
<223> OTHER INFORMATION: Synthetic Aptamer

<400> SEQUENCE: 5
gggauuuaau cgccguagaa aagcauguca aagccggaac cc            42

<210> SEQ ID NO 6
<211> LENGTH: 80
<212> TYPE: DNA
<213> ORGANISM: Artificial
<220> FEATURE:
<223> OTHER INFORMATION: Synthetic Aptamer

<400> SEQUENCE: 6
agcagcacag aggtcagatg gggggaagac acagagaaag gccggggtga agtgtagagg    60
cctatgcgtg ctaccgtgaa                                              80

```
<210> SEQ ID NO 7
<211> LENGTH: 61
<212> TYPE: RNA
<213> ORGANISM: Artificial
<220> FEATURE:
<223> OTHER INFORMATION: Synthetic Aptamer

<400> SEQUENCE: 7
uguguaauuc ugccauucuu uuuggggcgg aauacaggau gugagugcau ugcaucacgu    60
c                                                                   61

<210> SEQ ID NO 8
<211> LENGTH: 118
<212> TYPE: PRT
<213> ORGANISM: Human

<400> SEQUENCE: 8

Glu Val Lys Leu Asp Glu Thr Gly Gly Gly Leu Val Gln Pro Gly Arg
1               5                   10                  15

Ser Met Lys Leu Ser Cys Val Ala Ser Gly Phe Ile Phe Ser Asp Tyr
            20                  25                  30

Trp Met Asn Trp Val Arg Gln Ser Pro Glu Lys Gly Leu Glu Trp Ile
        35                  40                  45

Ala Gln Ile Arg Thr Asn Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Lys Asn Leu Arg Ser Glu Asp Met Gly Ile Tyr
                85                  90                  95

Tyr Cys Thr Trp Ser His Tyr Ala Leu Asp Asn Trp Gly Gln Gly Thr
            100                 105                 110

Ser Val Thr Val Ser Ser
        115

<210> SEQ ID NO 9
<211> LENGTH: 112
<212> TYPE: PRT
<213> ORGANISM: Human

<400> SEQUENCE: 9

Asp Val Leu Val Thr Gln Asn Pro Leu Ser Leu Ser Val Ser Leu Gly
1               5                   10                  15

Asp Gln Ala Ser Ile Ser Cys Arg Ser Ser Gln Asn Leu Val His Asn
            20                  25                  30

Asp Gly Asn Thr Tyr Leu His Trp Tyr Leu Gln Lys Pro Gly Gln Ser
        35                  40                  45

Pro Lys Leu Leu Ile His Arg Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Trp Thr Phe Gly Gly Gly Thr Lys Leu Glu Ile Lys
            100                 105                 110
```